US008000902B2

(12) United States Patent
Khvorova et al.

(10) Patent No.: US 8,000,902 B2
(45) Date of Patent: *Aug. 16, 2011

(54) METHODS AND COMPOSITIONS FOR SELECTING SIRNA OF IMPROVED FUNCTIONALITY

(75) Inventors: Anastasia Khvorova, Boulder, CO (US); Angela Reynolds, Littleton, CO (US); Devin Leake, Denver, CO (US); William Marshall, Boulder, CO (US); Steven Read, Brooklyn, NY (US); Stephen Scaringe, Lafayette, CO (US)

(73) Assignee: Dharmacon, Inc., Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/802,647

(22) Filed: Jun. 11, 2010

(65) Prior Publication Data
US 2010/0291681 A1 Nov. 18, 2010

Related U.S. Application Data

(63) Continuation of application No. 10/940,892, filed on Sep. 14, 2004, which is a continuation of application No. PCT/US2004/014885, filed on May 12, 2004.

(51) Int. Cl.
*G06F 19/00* (2006.01)
*C12N 15/11* (2006.01)
*C12N 15/87* (2006.01)
*C12Q 1/68* (2006.01)

(52) U.S. Cl. .............. 702/20; 536/24.5; 435/6; 435/455

(58) Field of Classification Search .................. None
See application file for complete search history.

(56) References Cited

U.S. PATENT DOCUMENTS

| | | | |
|---|---|---|---|
| 5,958,773 A | 9/1999 | Monia |
| 6,001,992 A | 12/1999 | Ackermann |
| 6,046,319 A | 4/2000 | Power |
| 6,111,086 A | 8/2000 | Scaringe |
| 6,150,092 A | 11/2000 | Uchida |
| 6,172,216 B1 | 1/2001 | Bennett |
| 6,291,642 B1 | 9/2001 | Weinstein |
| 6,506,559 B1 | 1/2003 | Driver et al. |
| 6,566,127 B1 | 5/2003 | Pavco |
| 6,590,093 B1 | 7/2003 | Scaringe |
| 6,965,025 B2 | 11/2005 | Gaarde et al. |
| 6,994,979 B2 | 2/2006 | Reed |
| 7,022,831 B1 | 4/2006 | Reed |
| 7,022,837 B2 | 4/2006 | Harding |
| 7,033,830 B2 | 4/2006 | Karras |
| 7,157,570 B2 | 1/2007 | Yun |
| 7,176,304 B2 | 2/2007 | McSwiggen |
| 7,250,496 B2 | 7/2007 | Bentwich |
| 7,371,735 B2 | 5/2008 | Harel-Bellan |
| 7,399,853 B2 | 7/2008 | Freier |
| 7,459,547 B2 | 12/2008 | Zamore |
| 7,507,811 B2 | 3/2009 | Khvorova |
| 7,511,132 B2 | 3/2009 | Khvorova |
| 7,514,550 B2 | 4/2009 | Khvorova |
| 7,521,191 B2 | 4/2009 | Khvorova |
| 7,541,453 B2 | 6/2009 | Khvorova |
| 7,550,572 B2 | 6/2009 | Khvorova |
| 7,569,684 B2 | 8/2009 | Khvorova |
| 7,576,196 B2 | 8/2009 | Khvorova |
| 7,576,197 B2 | 8/2009 | Khvorova |
| 7,579,457 B2 | 8/2009 | Khvorova |
| 7,579,458 B2 | 8/2009 | Khvorova |
| 7,582,746 B2 | 9/2009 | Khvorova |
| 7,582,747 B2 | 9/2009 | Khvorova |
| 7,589,191 B2 | 9/2009 | Khvorova |
| 7,592,442 B2 | 9/2009 | Khvorova |
| 7,592,443 B2 | 9/2009 | Khvorova |
| 7,592,444 B2 | 9/2009 | Khvorova |
| 7,595,387 B2 | 9/2009 | Leake |
| 7,595,388 B2 | 9/2009 | Khvorova |
| 7,595,389 B2 | 9/2009 | Khvorova |
| 7,598,369 B2 | 10/2009 | Khvorova |
| 7,598,370 B2 | 10/2009 | Khvorova |
| 7,605,250 B2 | 10/2009 | Khvorova |
| 7,605,252 B2 | 10/2009 | Khvorova |
| 7,608,706 B2 | 10/2009 | Khvorova |
| 7,608,707 B2 | 10/2009 | Khvorova |
| 7,612,196 B2 | 11/2009 | Khvorova |
| 7,615,541 B2 | 11/2009 | Khvorova |
| 7,619,081 B2 | 11/2009 | Khvorova |
| 7,632,938 B2 | 12/2009 | Khvorova |
| 7,632,939 B2 | 12/2009 | Khvorova |
| 7,635,770 B2 | 12/2009 | Khvorova |
| 7,635,771 B2 | 12/2009 | Khvorova |
| 7,638,621 B2 | 12/2009 | Khvorova |

(Continued)

FOREIGN PATENT DOCUMENTS

| | | |
|---|---|---|
| EP | 1 637 144 | 3/2006 |
| WO | WO9800532 | 1/1998 |
| WO | WO9938965 | 8/1999 |
| WO | WO9954459 | 10/1999 |

(Continued)

OTHER PUBLICATIONS

Kumar, High-Throughput Selection of Effective RNAi Probes for Gene Silencing (2003).
Laitala et al., Inhibition of Bone Resorption in Vitro by Antisense RNA and DNA Molecules Targeted against Carbonic Anhydrase II or Two Subuntis of Vacuolar H + ATPase, Journal of Clinical Investigation 1994, vol. 93, pp. 2311-2318.
Lapidot-Lifson, et al. (1992) Cloning and Antisense Oligodeoxynucleotide Inhibition of a Human Homolog of cdc2 required in Hematopoiesis, Proc. Natl. Acad. Sci. vol. 89, pp. 579-583.
Levenkova, Gene specific siRNA selector, Bioinofrmatics vol. 20, pp. 430-432 (2004).
Lindgren, et al. (2002) Contribution of Known and Unknown Susceptibility Genes to Early-Onset Diabetes in Scandinavia, Diabetes vol. 51, 1609-1617.

(Continued)

*Primary Examiner* — John Brusca
(74) *Attorney, Agent, or Firm* — Kalow & Springut, LLP; Scott D. Locke, Esq.

(57) ABSTRACT

Efficient sequence specific gene silencing is possible through the use of siRNA technology. By selecting particular siRNAs by rational design, one can maximize the generation of an effective gene silencing reagent, as well as methods for silencing genes. Methods, compositions, and kits generated through rational design of siRNAs are disclosed.

31 Claims, 44 Drawing Sheets

U.S. PATENT DOCUMENTS

| | | |
|---|---|---|
| 7,638,622 B2 | 12/2009 | Khvorova |
| 7,642,349 B2 | 1/2010 | Khvorova |
| 7,645,869 B2 | 1/2010 | Khvorova |
| 7,645,870 B2 | 1/2010 | Khvorova |
| 7,655,788 B2 | 2/2010 | Khvorova |
| 7,655,789 B2 | 2/2010 | Khvorova |
| 7,662,950 B2 | 2/2010 | Khvorova |
| 7,666,853 B2 | 2/2010 | Khvorova |
| 7,674,896 B2 | 3/2010 | Khvorova |
| 7,678,896 B2 | 3/2010 | Khvorova |
| 7,691,997 B2 | 4/2010 | Khvorova |
| 7,691,998 B2 | 4/2010 | Khvorova |
| 7,696,344 B2 | 4/2010 | Khvorova |
| 7,709,629 B2 | 5/2010 | Khvorova |
| 7,737,267 B2 | 6/2010 | Khvorova |
| 7,741,470 B2 | 6/2010 | Khvorova |
| 7,745,610 B2 | 6/2010 | Khvorova |
| 7,745,611 B2 | 6/2010 | Khvorova |
| 7,745,612 B2 | 6/2010 | Khvorova |
| 7,781,575 B2 | 8/2010 | Khvorova |
| 7,795,420 B2 | 9/2010 | Khvorova |
| 7,795,421 B2 | 9/2010 | Khvorova |
| 7,803,933 B2 | 9/2010 | Khvorova |
| 7,807,819 B2 | 10/2010 | Khvorova |
| 7,807,820 B2 | 10/2010 | Khvorova |
| 7,816,512 B2 | 10/2010 | Khvorova |
| 7,820,809 B2 | 10/2010 | Khvorova et al. |
| 7,829,696 B2 | 11/2010 | Khvorova |
| 7,833,989 B2 | 11/2010 | Khvorova |
| 7,834,170 B2 | 11/2010 | Khvorova |
| 2002/0081578 A1 | 6/2002 | Plowman et al. |
| 2002/0086321 A1 | 7/2002 | Craig |
| 2002/0086356 A1 | 7/2002 | Tuschl et al. |
| 2002/0150945 A1 | 10/2002 | Finney |
| 2003/0087259 A1 | 5/2003 | Clancy et al. |
| 2003/0105051 A1 | 6/2003 | McSwiggen |
| 2003/0142597 A1 | 7/2003 | Park et al. |
| 2003/0143732 A1 | 7/2003 | Fosnaugh |
| 2003/0157030 A1 | 8/2003 | Davis et al. |
| 2003/0224512 A1 | 12/2003 | Dobie |
| 2003/0228597 A1 | 12/2003 | Cowsert |
| 2004/0006365 A1 | 1/2004 | Brady |
| 2004/0014956 A1 | 1/2004 | Woolf |
| 2004/0029275 A1 | 2/2004 | Brown et al. |
| 2004/0054155 A1 | 3/2004 | Woolf |
| 2004/0063654 A1 | 4/2004 | Davis et al. |
| 2004/0077574 A1 | 4/2004 | Klinghoffer |
| 2004/0101857 A1 | 5/2004 | Ward |
| 2004/0101915 A1 | 5/2004 | Deveraux |
| 2004/0102391 A1 | 5/2004 | Dean |
| 2004/0180357 A1 | 9/2004 | Reich |
| 2004/0191818 A1 | 9/2004 | O'Toole |
| 2004/0192629 A1 | 9/2004 | Xu et al. |
| 2004/0204380 A1 | 10/2004 | Ackermann |
| 2004/0219671 A1 | 11/2004 | McSwiggen |
| 2004/0248296 A1 | 12/2004 | Beresford |
| 2004/0248299 A1 | 12/2004 | Jayasena |
| 2004/0259247 A1 | 12/2004 | Tuschl et al. |
| 2005/0048529 A1 | 3/2005 | McSwiggen |
| 2005/0106726 A1 | 5/2005 | McSwiggen |
| 2005/0107328 A1 | 5/2005 | Wyatt |
| 2005/0130181 A1 | 6/2005 | McSwiggen |
| 2005/0176025 A1 | 8/2005 | McSwiggen |
| 2005/0181382 A1 | 8/2005 | Zamore |
| 2005/0186586 A1 | 8/2005 | Zamore |
| 2005/0227935 A1 | 10/2005 | McSwiggen |
| 2005/0239731 A1 | 10/2005 | McSwiggen |
| 2005/0245475 A1 | 11/2005 | Khvorova |
| 2005/0261485 A1 | 11/2005 | Uchida |
| 2005/0272680 A1 | 12/2005 | Bhanot |
| 2006/0025372 A1 | 2/2006 | Bhanot |
| 2006/0069056 A1 | 3/2006 | Feinstein et al. |
| 2006/0286575 A1 | 12/2006 | Farrell |
| 2007/0021369 A1 | 1/2007 | Doucette-Stamm et al. |
| 2007/0031844 A1 | 2/2007 | Khvorova |
| 2007/0254850 A1 | 11/2007 | Lieberman |
| 2007/0269395 A1 | 11/2007 | Christiano |
| 2007/0275465 A1 | 11/2007 | Woppmann |
| 2007/0281801 A1 | 12/2007 | Watanabe et al. |
| 2008/0108583 A1 | 5/2008 | Feinstein |
| 2008/0113351 A1 | 5/2008 | Naito |
| 2008/0124370 A1 | 5/2008 | Marx |
| 2008/0287382 A1 | 11/2008 | Feinstein |
| 2009/0082291 A1 | 3/2009 | Feinstein |
| 2009/0105173 A1 | 4/2009 | Feinstein |
| 2010/0029746 A1 | 2/2010 | Feinstein |

FOREIGN PATENT DOCUMENTS

| | | |
|---|---|---|
| WO | WO9955910 | 11/1999 |
| WO | WO0032765 | 12/1999 |
| WO | WO0020645 | 4/2000 |
| WO | WO0044194 | 7/2000 |
| WO | WO0044895 | 8/2000 |
| WO | WO0021559 | 12/2000 |
| WO | WO0076497 | 12/2000 |
| WO | WO0136646 | 5/2001 |
| WO | WO0168836 | 9/2001 |
| WO | WO0244321 | 6/2002 |
| WO | WO02055693 | 7/2002 |
| WO | WO02059300 | 8/2002 |
| WO | WO03035869 | 5/2003 |
| WO | WO03035870 | 5/2003 |
| WO | WO03046176 | 6/2003 |
| WO | WO2004046324 | 6/2003 |
| WO | WO03064625 | 8/2003 |
| WO | WO03064626 | 8/2003 |
| WO | WO03070897 | 8/2003 |
| WO | WO03070910 | 8/2003 |
| WO | WO03070918 | 8/2003 |
| WO | WO03070969 | 8/2003 |
| WO | WO03072704 | 9/2003 |
| WO | WO03074654 | 9/2003 |
| WO | WO03062394 | 10/2003 |
| WO | WO2004111191 | 2/2004 |
| WO | WO2004031237 | 4/2004 |
| WO | WO03064626 | 6/2004 |
| WO | WO2004048511 | 6/2004 |
| WO | WO2004080406 | 9/2004 |
| WO | WO2004090105 | 10/2004 |
| WO | WO2004094636 | 11/2004 |
| WO | WO2005001043 | 1/2005 |
| WO | WO2005062937 | 7/2005 |
| WO | WO2005078095 | 8/2005 |
| WO | WO2005089224 A2 | 9/2005 |
| WO | WO2005117991 | 12/2005 |
| WO | WO2006015389 | 2/2006 |
| WO | WO2006110813 | 10/2006 |
| WO | WO2007087451 | 8/2007 |
| WO | WO2009001359 | 12/2008 |
| WO | WO2009044392 | 4/2009 |

OTHER PUBLICATIONS

Lu, et al., The Human AQP4 gene: Definition of the locus encoding two water channel polypeptides in brain, Proc. Natl Acad. Sci vol. 93, pp. 10908-10912 (Oct. 1996).

Marathi, RAD1, a Human Structural Homolog of the *Schizosaccharomyces pombe* RAD1 Cell Cycle Checkpoint Gene, Genomcs 54, 344-347 (1998).

Miller, V M et al., "Allele-specific silencing of dominant disease genes" Proceedings of the National Acadamy of Sciences of USA, vol. 100, No. 12, Jun. 10, 2003, pp. 7195-7200, XP002276730.

Miyagashi et al. (2003) Comparison of the Suppressive Effects of Antisense Oligonucleotides and siRNAs Directed Against the Same Targets in Mammalian Cells. Antisense and Nucleic Acid Drug Development 13:1-7.

Murphy, et al. (2000) Synucleins are Developmentally Expressed, and Alpha-Synuclein Regulates the Size of the Presynaptic Vesicular Pool in Primary Hippocampal Neurons. The Journal of Neuroscience, vol. 20(9):3214-20.

Naito, siDirect: highly effective, target specific siRNA design software for mammalian RNA interference, Nucleic Acids Research vol. 32, W124-129 (2004).

NCBI Nucleotide Result for NM-002609, http://www.ncbi.nlm.nih.gov/sites/entrez, accessed on Jul. 14, 2008.

NCBI Sequence Viewer v2.0 for NM-004438, http://www.ncbi.nlm.nih.gov/entrez/viewer.fcgi? db=nuccore&id=45439363, accessed on Jul. 3, 2008.

Oishi, et al., Identification and Characterization of PKN Beta, a Novel Isoform of Protein Kinase PKN: Expression and Arachiodonic Acid Dependency Are Different from those of PKN alpha, 1999 Biochemical and Biophysical Research Communcation, 261, pp. 808-814.

Olie et al, A Novel Antisense Oligonucleotide Targeting Survivin Expression Induces Apoptosis and Sensitizes Lung Cancer Cells to Chemotherapy, Cancer Research 2000, vol. 60: pp. 2805-2809.

Pan, et al. (2005) Calmodulin-dependent protein kinase IV regulates nuclear export of Cabin1 during T-cell activation, The EMBO Journal, 24, 2104-2113.

Promega siRNA Target Designer-Version 1.51, http:///www.promega.com/siRNADesigner/prograrn/default.asp. Accessed Jun. 24, 2008.

Promega siRNA Target Designer-Version 1.1, http:///www.promega.com/siRNADesigner/program/default.asp. (2003).

Rabert et al. (1998) A Tetrodextrin-Resistant Voltage-gated Sodium Channel from Human Dorsal Root Ganglia, hPN3/SCN10A. Pain, 78, pp. 107-114.

Reynolds, Rational siRNA design for RNA interference, Nature Biotechnology vol. 22, No. 3, pp. 326-330 (2004).

Ross, et al. (2001) Inhibition of Kirsten-ras Expression in Human Colorectal Cancer Using Rationally Selected Kirsten-ras Antisense Oligonucleotides, Molecular Cancer Therapeutics vol. 1, 29-41.

Shi et al. (2001) Gremlin negatively Modulates BMP-4 Induction of Embryonic Mouse Lung Branching Morphogenesis. Am J Physiol Lung Cell Mol Physiol, 280, pp. L1030-L1039.

Semizarov, Specificity of short interfereing RNA determined through gene expression signatures, Proceedings of the National Acadamy of Sciences USA vol. 100, pp. 6347-6352 (2003).

siRNA Design for RNA Interference (RNAi) Experiments, http://web.archive.org/ web/20010101000000-20021231235959/http://www.ambion.com/techlib/misc/siRNA_design.html. Accessed on Mar. 6, 2008.

siDesign Center for "gene name: src," http://www.dharmacon.com/DesignCenter/DesignCenterPage.aspx, accessed on May 13, 2008.

siRNA Converter, http://web.archive.org/web/20020101-20021231re_/http://www.ambion.com/techlib/misc/siRNA_finder.html. Accessed Mar. 6, 2008. (siRNA Target Finder).

Sorensen, et al. (2003) Gene Silencing by Systemic Delivery of Synthetic siRNAs in Adult Mice, J. Mol. Biol. 327, 761-766.

Tan et al. (2006) Functional Cooperation Between Fact and MCM Helicase Facilitates Initiation of Chromatin DNA Replication. The EMBO Journal, vol. 25, pp. 3975-3985.

Truss, HuSide—the Human siRNA database: an open access database for published functional siRNA sequences and technical details of efficient transfer into recipient cells, Nucleic Acids Research vol. 33, pp. D108-D111 (2005).

Tsuji, et al. (2006) Essential Role of Phosphoorylation of MCM2 by Cdc7/Dbf4 in the Initiation of DNA Replication in Mammalian Cells. Molecular Biology of the Cell, vol. 17, pp. 4459-4472.

Tuschl, Expanding small RNA interference (May 2002), Nature Biotechnology, vol. 20, pp. 446-448.

Tuschl, et al. (2001) The siRNA User Guide. Max Planck Institute for Biophysical Chemistry, pp. 1, 3 and 5, http://www.mpibpc.gwdg.de/abteilungen/100/105/siRNAuserguide.pdf.

Tijsterman, Dicers at RISC, The Mechanism of RNAi, Cell, Apr. 2004, vol. 117, pp. 1-4.

Tuschl et al. (2003) The siRNA User Guide. 6 pages.

Ui-Tei, Guidelines for the selection of highly effective siRNA sequences for mammalian and chick RNA interference, Nucleic Acids Research, Feb. 2004, vol. 32, No. 3 pp. 936-948.

Vankayalapati, et al. (2003) Targeting Aurora2 Kinase in Oncogenesis: A Structural Bioinformatics Approach to Target Validation and Rational Drug Design. Molecular Cancer Therapeutics, v.2:283:94.

Walton, et al. (1999) Prediction of Antisense Oligonucleotide Binding Affinity to a Structured RNA Target. Biotechnol. Bioengineering, v.65(1):1-9. (Abstract Only).

Vickers, Efficient Reduction of Target RNAs by Small Interfereing RNA and Rnase H-dependent Antisense Agents, J. Biol. Chem. vol. 278, No. 9, 7108-7118 (2003).

Wang, et al., (2006) Dexamethasone Represses Signaling through the Mammalian Target of Rapamycin in Muscle Cells by Enhancing Expression of REDD1. The Journal of Biological Chemistry vol. 281, No. 51, pp. 39128-39134. fl.

Yao et al. (2000) Nature Cell Biology 2:484-491.

Yuan, siRNA Selection Server: an automated siRNA oligonucleotide prediction server (2004).

Zender et al., siRNA based strategies for inhibition of apoptotic pathways in vivo—analytical and therapeutic implications, Jan. 2004, vol. 9, pp. 51-54.

Zhang, Physical and Functional Interationc between Myeloid Cell Leukemia 1 Protein (MCL1) ad Fortilin, J. Biol. Chem. 37430-37438 (2002).

Abifadel et al., Mutations in PCSK9 cause autosomal dominant hypercholesterolemia, 2003, Nature Genetics, vol. 34, pp. 154-156.

Ishibashi et al., A Novel Dual Specificity Phosphatase Induced by Setum Stimulation and Heat Shock, (1994) J. Biol. Chem. 47: 29897-2902).

Rashid et al. Decreased plasma cholesterol and hypersensitivity to statins inmice lacking PCSK9, 2005 PNAS, vol. 102, pp. 5374-5379.

Ishimi et al., Enhanced expression of Mcm proteins in cancer cells derived from uterine cervix, 2003, European Journal of Biochemistry, vol. 270, pp. 1089-1101.

Wang et al. Connective Tissue Growth Factor siRNA modulates mRNA levels for a subet of molecules in normaland TFG-Beta1 stimulated porcine skin fibroblasts, 2004, Wound Rep. Reg.12, pp. 205-206.

Nguyen T. el Current Opin. Molec Ther. vol. 10, No. 2, pp. 158-167 (2008).

Shuai, K., Modulation of STAT signaling by STAT interacting proteins, 2000, Oncogene vol. 19, pp. 2638-2644.

Abeliovich, et al. (2000) Mice Lacking Alph-Synuclein Display Functional Deficits in the Nigrostriatal Dopamine System. Neuron v.25:239-52.

Amarzguioui, Secondary structure prediction and in vitro accessibility of mRNA as tools in the selection of target sites for ribozymes (2000) vol. 29, No. 21, 4113-4124.

Amarzguioui M et al, Tolerance for mutations and chemical modifications in a siRNA Nucleic Acids Research vol. 31, No. 2, Jan. 15, 2003 pp. 589-595 , XP002270887 ISSN: 0305-1048.

Bass, B.L., (2001) The Short Answer, Nature V.411:428-29.

Betrand (2002) Comparison of Antisense Oligonucleotides and siRNAs in cell culture and in vivo, Biotechnical and Biophysicial Research Communication 296:1000-1004.

Boutla, Short 5'-phosphorylated double-stranded RNAs induce RNA interference in Drosophila, 1776-1780 (Brief Communication) (2001).

Brown et al. (1997) Identification and cDNA Cloning of a Novel Mammalian C2 Domain-Containing Phosphoinositide 3-kinase, HsC2-PI3K. Biochemical and Biophysical Research Communications. 233, 537-544.

Brummelkarna et al. A System for Stable Expression of Short Intereferring RNAs in Mammalian Cells, Science vol. 295 pp. 550-553 (2002).

Cahill et al. (1999) Characterization of MAD2B and Other Mitotic Spindle Checkpoint Genes. Genomics. 58:181-187.

Caplen et al. Specific inhibition of gene expression by small double-stranded RNAs in invertebrate systems, Proc. Natl. Acad. Sci USA vol. 98, pp. 9742-9747 (2001).

Caplen, dsRNA-mediated gene silencing in cultured Drosophila cells: a tissue culture model for analysis of RNA interference, Jul. 11, 2000; Gene; 252(1-2):95-105.

Caplen, RNAi as a gene therapy approach. Expert Opin. Ther. 3(4):575-586. (2003).

Chalk, siRNA db: a database of siRNA sequences. Nucleic Acids Research. vol. 33 pages, D131-D134 (2004).

Chen et al. (2005) TSSK5, A Novel Member of the Testis-Specific Serine/Threonin Kinase Family, Phosphorylates CRE at Ser-122, and Stimulates the CRE-CREB Responsive Pathway. Biochemical and Biophysical Research Communications. 333: 742-749.

Cherry, Michael J. (1995) Computer Manipulation of DNA and Protein Sequences. Current Protocols in Molecular Biology. 7.7.1-7.7.23.
Chi, Genomewide view of gene silencing by small interfering RNAs. PNAS vol. 100, No. 11, pp. 6343-6346 (2003).
Chinault, Overlap Hybridization Screening: Isolation and Characterization of Overlapping DNA Framgments Surroungin the leu2 Gene on Yeast Chromosome III (1979), 5(2):111-26.
Daniel et al., Specific association of Type I with Ran GTPase in lipopolysacchardie-mediated differentiation, Oncogene 2001, vol. 20: 2618-2625.
Dodelet et al. (2000) Eph Receptors and Ephrin Ligands: embryogenesis to tumorigenesis. Oncogene 19:5614-5619.
Domin et al.(1997) Cloning of Human Phosphoinositide 3-Kinase with a C2 Domain that Displays Reduced Sensitivity to the Inhibitor Wortmannin. Biochem. J., v.325:139-47.
Dottori, et al. (1998) EphA4 (Sek1) receptor tyrosine kinase is required for the development of the corticospinal tract, Proc. Natl. Acad. Sci. vol. 95, pp. 13248-13253, Neurobiology.
Ekholm, et al.(2004) Deregulation of Cyclin E in Human Cells Interferes with Prereplication Complex Assembly. The Journal of Cell Biology. vol. 165, pp. 789-800.
Elbashir et al. (2001) Duplexes of 21-Nucleotide RNAs Mediate RNA Interference in Cultured Mammalian Cells. Nature vol. 411, pp. 494-498.
Elbashir et al. (2002) Analysis of Gene Function in Somatic Mammalian Cells Using Small Interfering RNAs. Methods. 26:199-213.
Elbashir, Functional anatomy of siRNAs for mediating efficient RNAi in Drosophila melaongaster, The EMBO Journal v. 20(23): 6877-6888 (2001).
El Touny, et al. (2006) Identification of Both Myt-I and Wee-I as Necessary Mediators of the P2I-Independent Inactivation of the Cdc-2/Cyclin BI complex and Growth Inhibition of TRAMP Cancer Cells by Genistein. The Prostate, vol. 66:1542-1555.
European Patent Office, European Patent Application No. 03786798.3 Office Action dated Nov. 15, 2007.
Far, R-K, The activity of siRNA in mammalian cells is related to structural target accessibility: a comparison with antisense oligonucleotides (2003) Nucleic Acids Research. vol. 31, No, 15, pp. 4417-4424.
Feng, et al. (2003) Inhibiting the Expression of DNA Replication-Initiation Proteins Induces Apoptosis in Human Cancer Cells. Cancer Research, vol. 63, pp. 7356-7364.
Fox, et al. (1995) cDNA Cloning and Tissue Distribution of Five Human EPH-like Receptor Protein-tyrosine kinases, Oncogene; 10(5): 897-905.
Futami et al. (2002) Induction of Apoptosis in Hela Cells with siRNA Expression Vector Targeted Against BLC-2. Nucleic Acids Research Supplement No. 2:251-2.
Genbank Accession NM 001790 Oct. 10, 2008.
GenBank Accession No. NM_00345, http://www.ncbi.nlm.nih.gov/entrez/viewer.fcgi?db=nuccore&id=6806896. Accessed on Aug. 1, 2008.
Genbank Accession No. NM_002645.2, http://www.ncbi.nlm.nih.gov/entrez/viewer.fcgi?db=nuccore&id=157671928. Accessed on Jul. 31, 2008.
Genbank Accession No. NM_138578, http:/www.ncbi.nlm.nih.gov/entrez/viewer.fcgi?db=nuccore&id=20336334. Accessed on Aug. 11, 2008.
Genbank Accession Z15005.1 (1993).
Hammond et al., Post-transcriptional gene silencing by double-stranded RNA, Nature Reviews, 2001, vol. 2, 110-119 ) MacMilan Magazines Ltd.
Hao, et al. (2004) Expression Analysis of the Human Testis-specific Serine/Threonine Kinase (TSSK) Homologues. A TSSK Member is Present in the Equatorial Segment of Human Sperm. Molecular Human Reproduction, vol. 10, No. 6 pp. 433-444.
Harborth et al. Identification of Essential Genes in Cultured Mammalian Cells Using Small Interfering RNAs. (2001) J. Cell. Sci. 114:4557-4565).

Ho, Potent Antisense Oligunucleotides to the Human Multidrug Resistance-1 mRNA are rationally selected by mapping RNA-accessible sites with Oligonucleotides Libraries. Nucleic Acids Research, vol. 24: 1901-1907 (1996).
Holen, et al. (2002) Positional Effects of Shorts Interfering RNAs Targeting the Human Coagulation Trigger Tissue Factor. Nucleic Acids Research, vol. 30, No. 8, pp. 1757-1766.
Human Neuropeptide Y Blast results, http://www.ncbi.nlm.nih.gov/blast, accessed on Mar. 18, 2008.
International Search Report for PCT/US04, Sep. 24, 2007 (Brusca).
International Search Report for PCT/US03/36787, Feb. 25, 2005 (Epps-Ford).
Iliakis et al. (1990) Induction and Repair of DNA Strand Breaks in Radiation-resistant Cells Obtained by Transformation of Primary Rat Embryo Cells with the Oncogenes H-ras and v-myc. Cancer Research, 50, pp. 6575-6579.
Jackson, et al., Expression profiling reveals off-target gene regulation by RNAi, Nature Biotechnology, vol. 21, pp. 635-637 (2003).
Kalra, Central administration of antisense oligodeoxynucleotides to neuropeptide Y (NPY) mRNA reveals the critical role of newly synthesized NPY in regulation of LHRH release, Regulatory Peptides (1995) 215-220.
Kasif (2002), A computational framework for optimal masking in the synthesis of oligonucleoitde microarrays, University Press, Nucleic Acids Research 2002, No. 30, No. 20 e106.
Khvorova, Functional siRNAs and miRNAs Exhibit Strand Bias vol. 115, pp. 209-216 (2003).
Kretscmer-Kazemei, The Activity of siRNA in mammalian cells is related to structural target accessibility: a comparison with antisense oligonucleoitdes (2003) Nucleic Acids Research. vol. 31, No. 15, 4417-4424.
Jiang, 8c1-2 constitutively suppresses p53-dependent apoptosis in colorectal cancer cells, Genes & Development 1 17:832-837 (2003).
Wacheck, et al., Small Interfering RNA Targeting BcI-2 Sensitizes Malignant Melanoma, Oligonucleotides 13: 2 393-400 (2003).
Final Office Action. United States Patent Office. Mar. 16, 2010. (DHARMA 0100-US2).
Non-Final Office Action. United States Patent Office. Oct. 29, 2010. (DHARMA 0100-US2).
Skalecki et al., Arch. Biochem. Biophys. vol. 365, No. 1 pp. 1-9 (1999).
Tsuruga et al., HsMCM6: a new member of the human MCM/P1 family encodes a protein homologous to fission yeast mis5, 1997 Genes to Cells, vol. 2, pp. 381-399.
Shi et al. (1995), Abl-interactor-1 a novel SH3 protein binding to the carboxy-terminal portion of the Abl protein, suppresses v-abl transforming activity, Genes & Dev. 9:2583-2597.
iHOP [online] [retrieved on Sep. 9, 2008]. Retrieved from the Internet. <http://www.ihop-net.org/UniPub/iHOP/bng/119248.html?list=0>.
Gautam et al. Heparin-binding protein (HBP/CAP37): A missing link in neutrophil-evoked alteration of vascular permeability, Nature Medicine 2001, vol. 7, pp. 1123-1127.
White et al., The nuclear Receptor Co-Repressor Nrip1 (RIP 140) is essential for female fertility. Nature Medicine, 2000, vol. 6, No. 12: 1368-1374.
siRNA Target Finder, Ambion, http://ambion.com/techlib/misc/siRNA_finder.html, (from DHARM 2100-US46 11/811,950) [retrieved on Mar. 6, 2008].
Chalk, et al. (2004) Improved and automated prediction of effective siRNA. Biochem Biophys Res Comm 319:264-274.
Fire et al., (1998) Potent and specific genetic interference by double stranded RNA in *Caenorhabditis elegans*, Nature 391: 806-811.
McManus and Sharp (2002) Gene silencing in mammals by small interfering siRNAs. Nature Reviews Genetics 3:737-747.
Scherer and Rossi. (2003) Approaches for the sequence specific knockdown of mRNA. Nat. Biotechnol. 21—(12):1457-1465.
Scherer and Rossi. (2004) Therapeutic Applications of RNA Inferferences: Recent Advances in siRNA Design. Advances in Genetics 22:1-21.

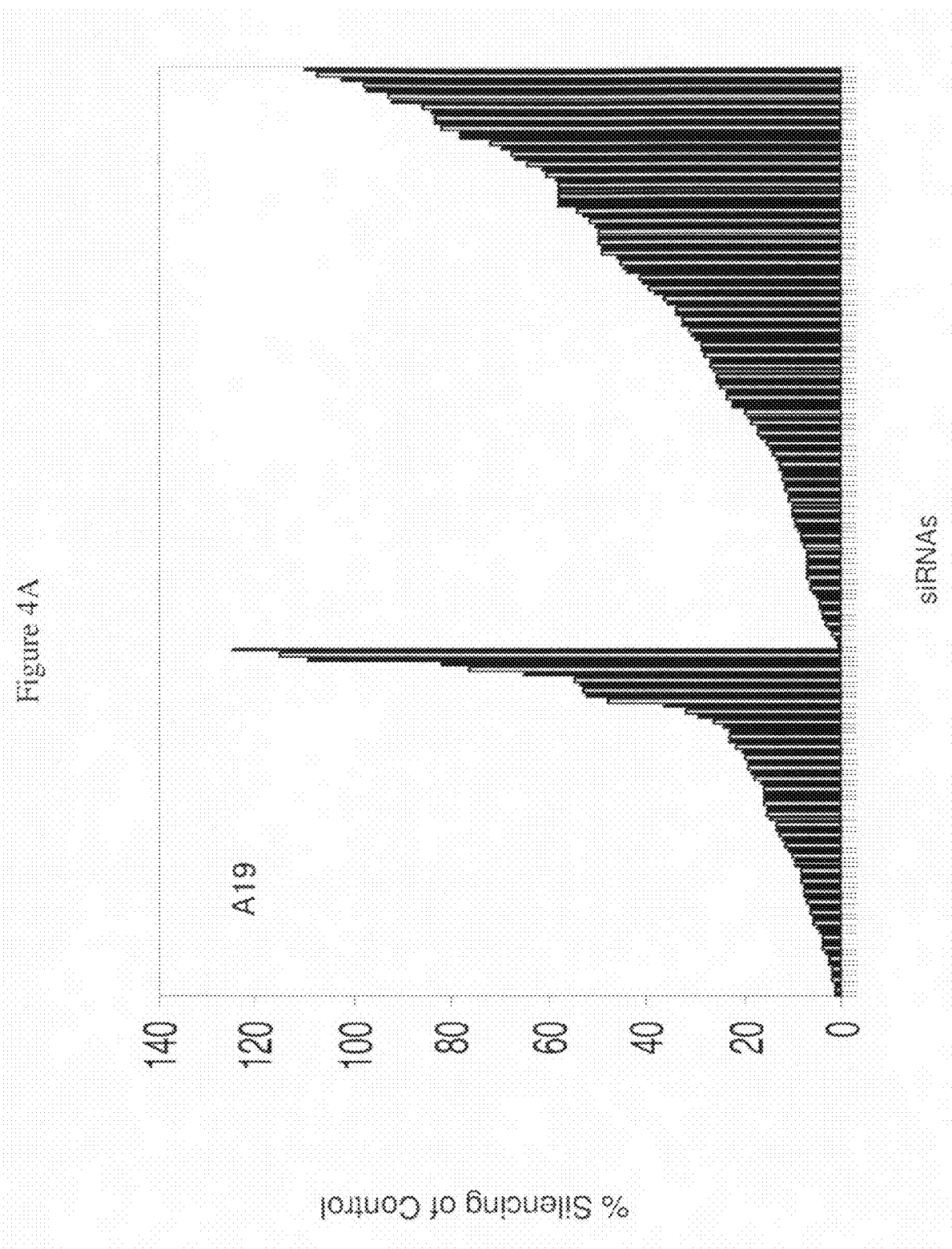

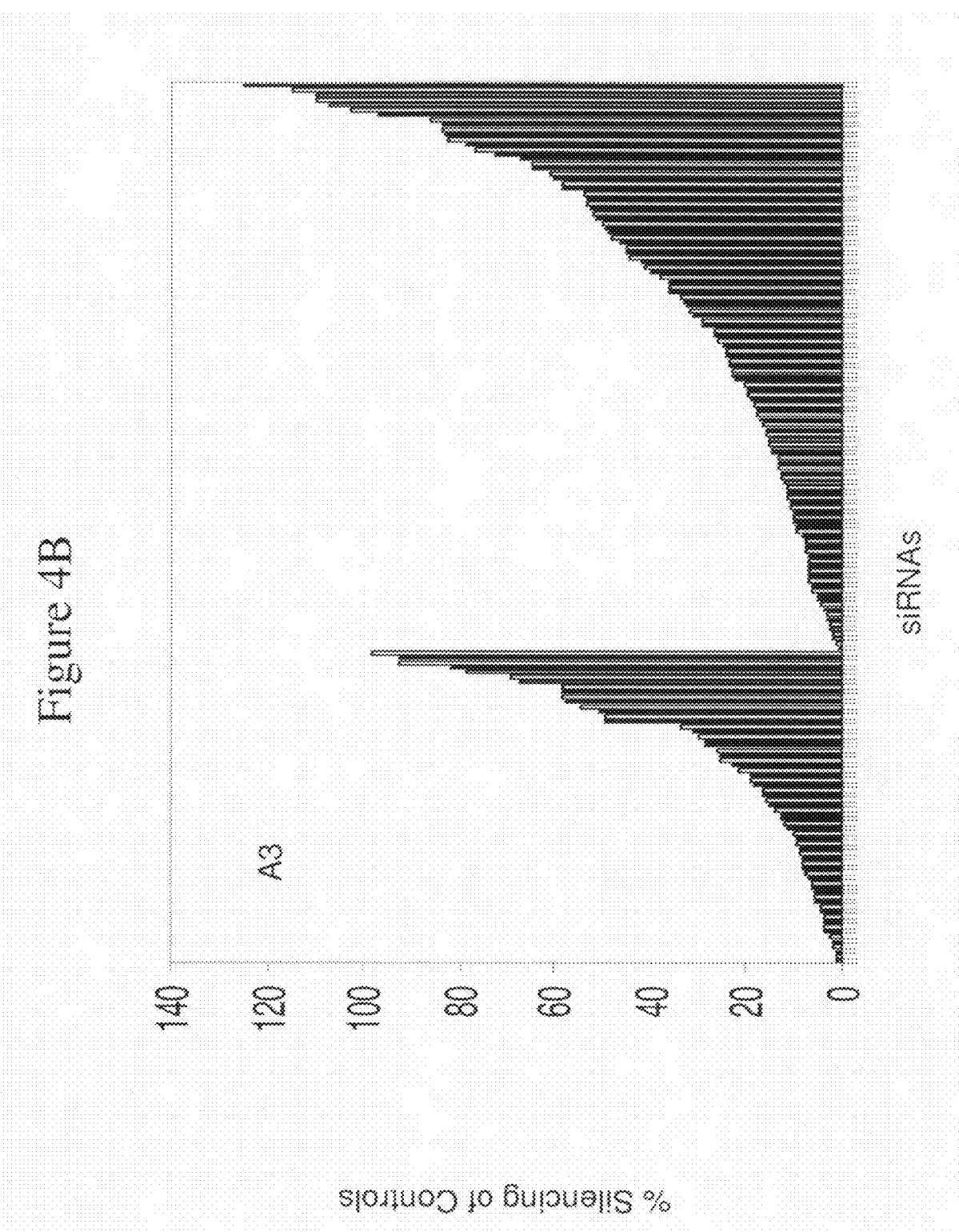

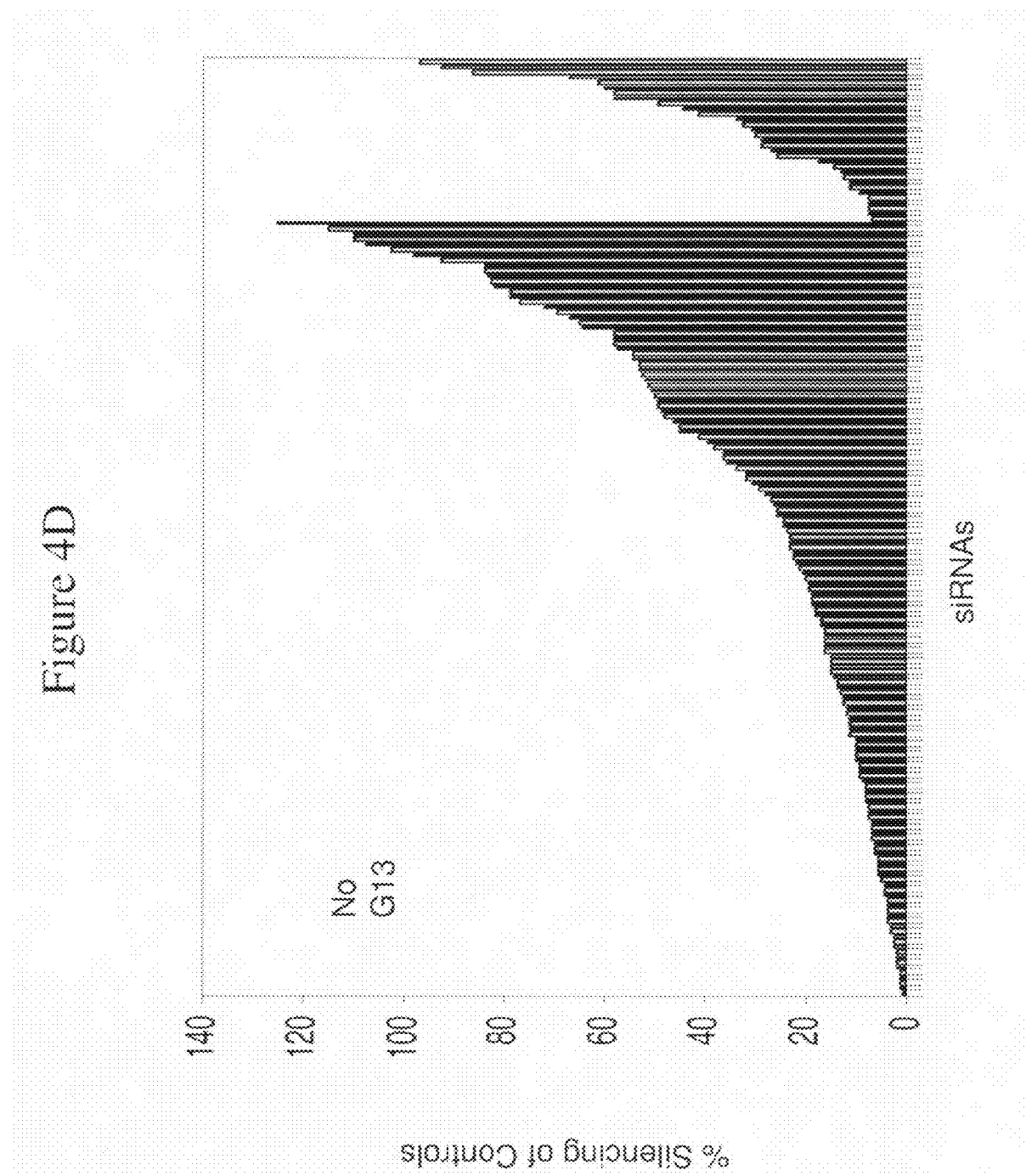

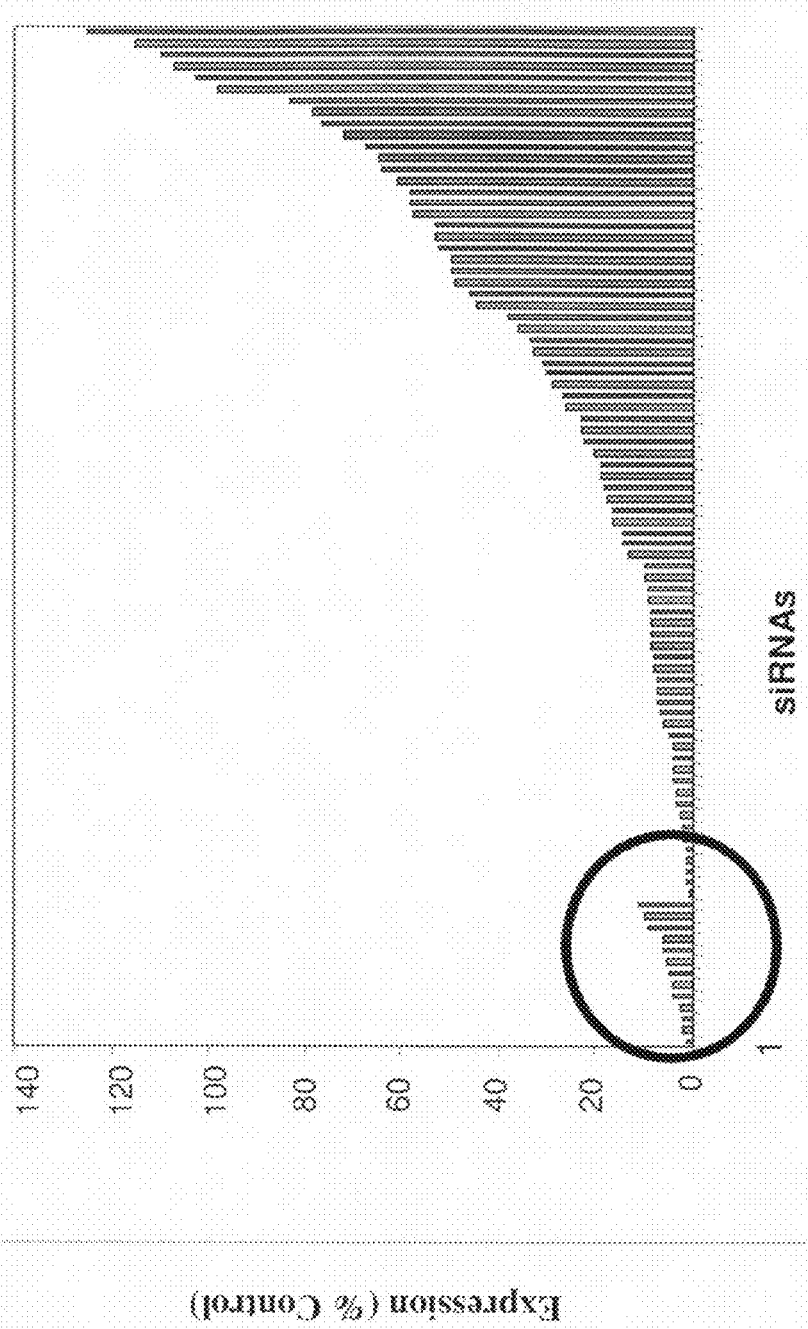

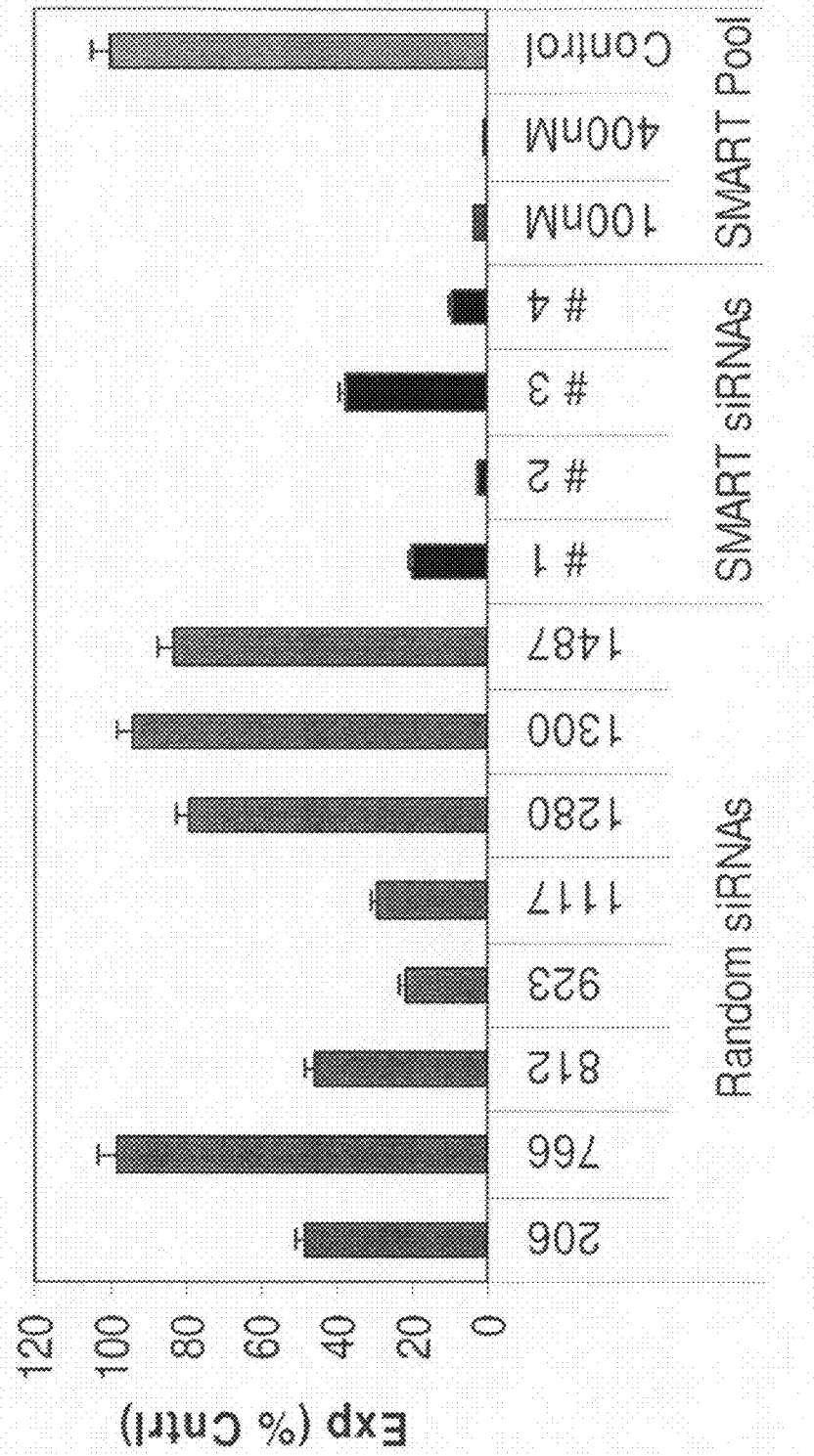

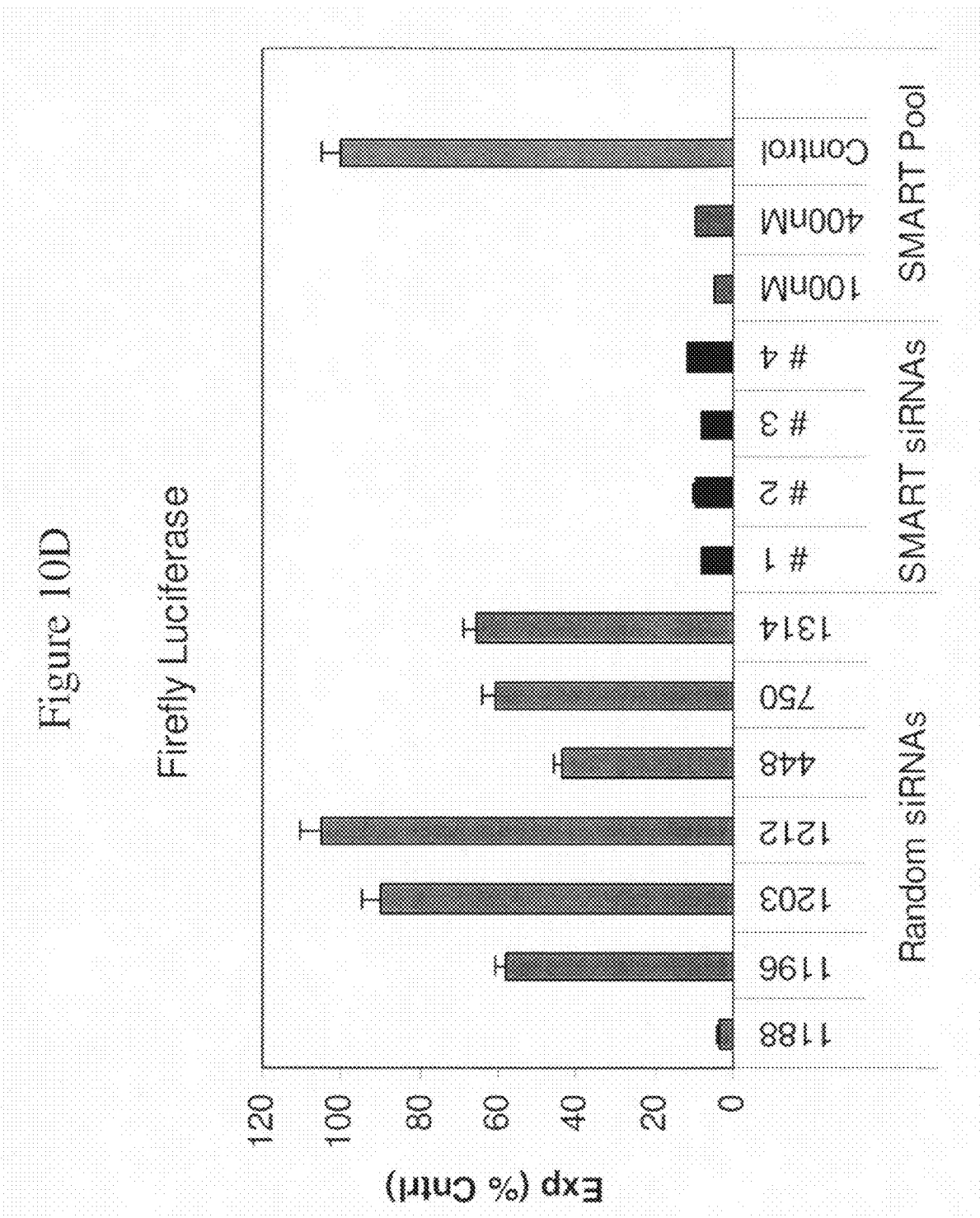

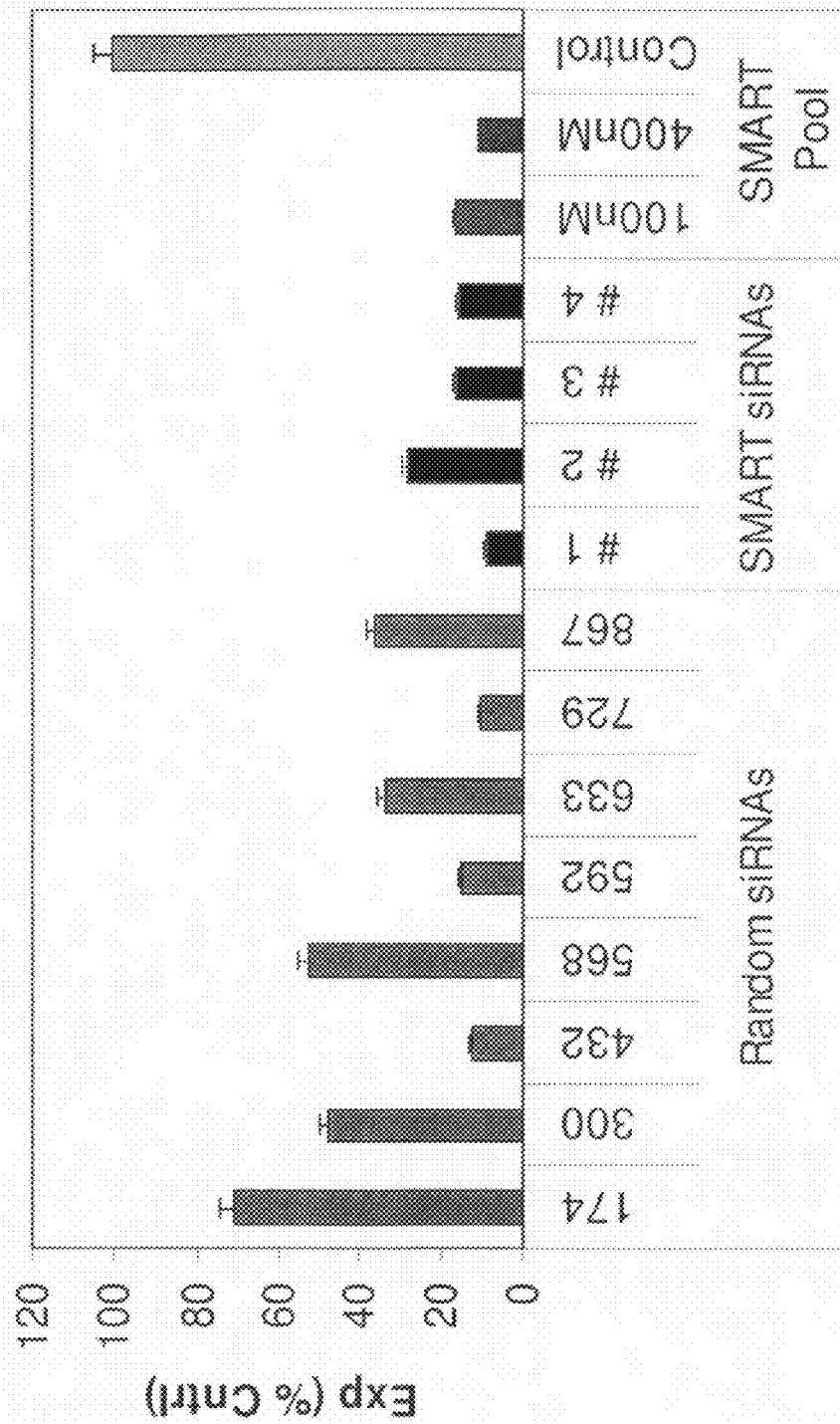

Figure 13 Sequences of top Bcl2

| | | |
|---|---|---|
| siRNA 1 | GGGAGAUAGUGAUGAAGUA | (SEQ. ID NO. 301) |
| siRNA 2 | GAAGUACAUCCAUUAUAAG | (SEQ. ID NO. 302) |
| siRNA 3 | GUACGACAACCGGGAGAUA | (SEQ. ID NO. 303) |
| siRNA 4 | AGAUAGUGAUGAAGUACAU | (SEQ. ID NO. 304) |
| siRNA 5 | UGAAGACUCUGCUCAGUUU | (SEQ. ID NO. 305) |
| siRNA 6 | GCAUGGGCCUCUGUUUGA | (SEQ. ID NO. 306) |
| siRNA 7 | UGCGGCCUCUGUUUGAUUU | (SEQ. ID NO. 307) |
| siRNA 8 | GAGAUAGUGAUGAAGUACA | (SEQ. ID NO. 308) |
| siRNA 9 | GGGAGAUAGUGAUGAAGUAC | (SEQ. ID NO. 309) |
| siRNA 10 | GAAGACUCUGCUCAGUUUG | (SEQ. ID NO. 310) |

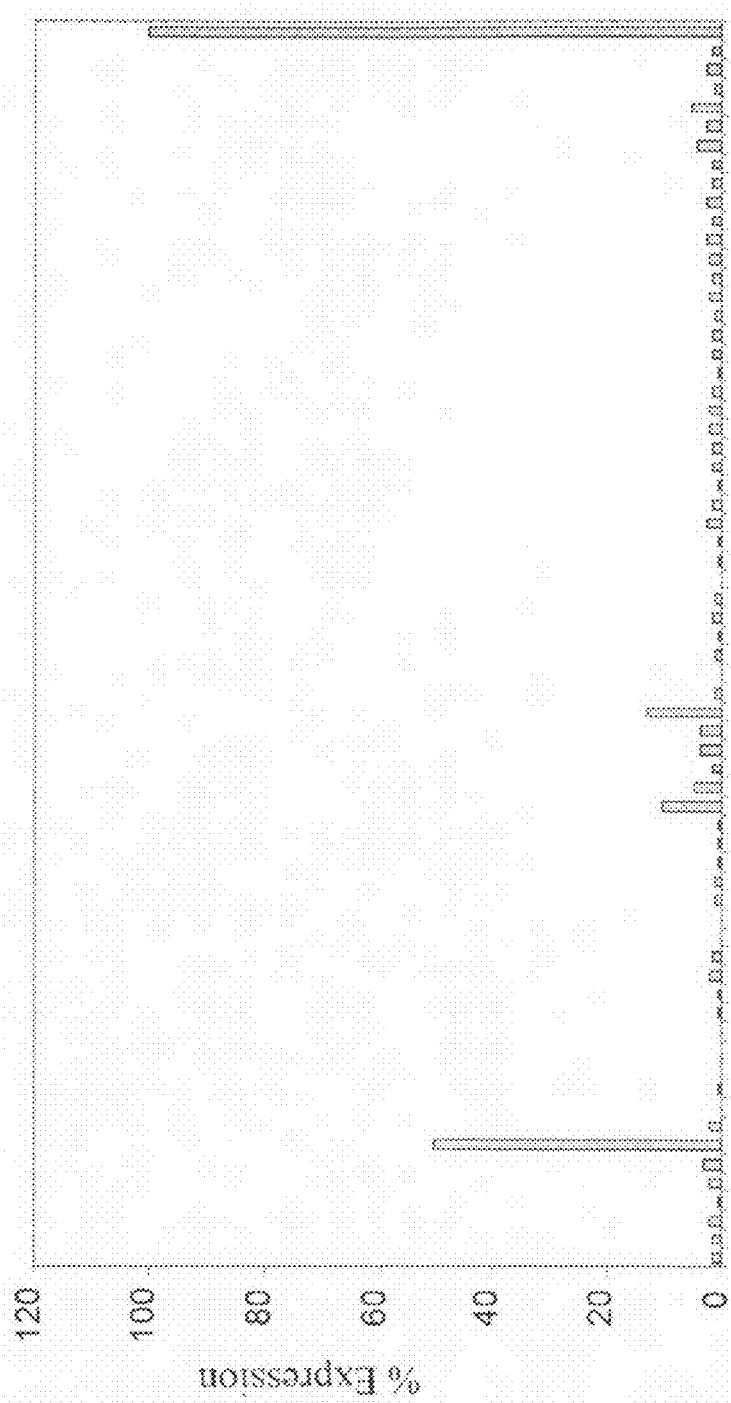

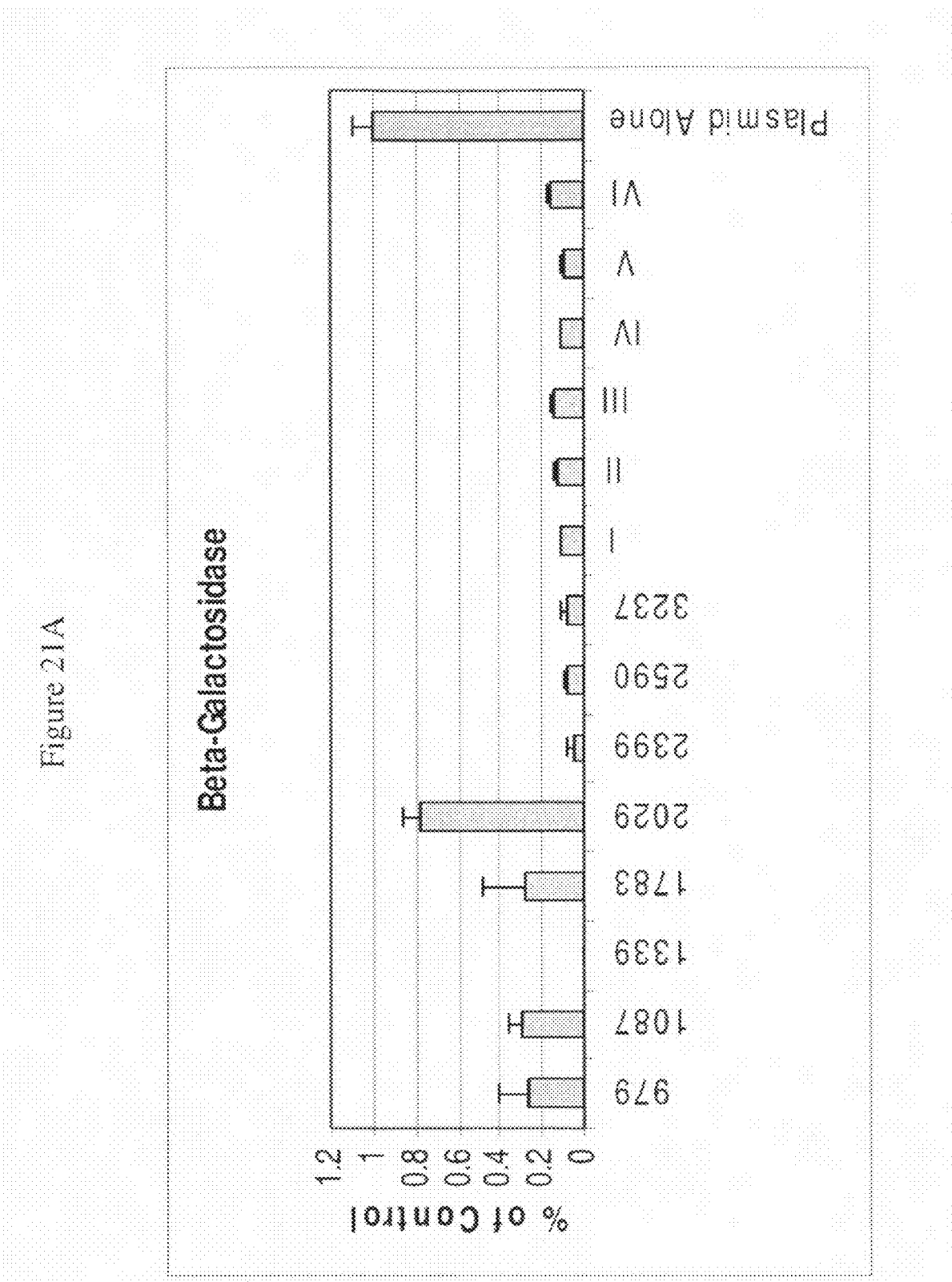

SEQUENCE LISTING

```
<160> NUMBER OF SEQ ID NOS: 437

<210> SEQ ID NO 1
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 1
nnanannnnu cnaannnna                                                  19

<210> SEQ ID NO 2
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 2
nnanannnnu gnaannnna                                                  19

<210> SEQ ID NO 3
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
```

-continued

<223> OTHER INFORMATION: n is any nucleotide

<400> SEQUENCE: 3
nnanannnnu unaannna                                                19

<210> SEQ ID NO 4
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 4
nnanannnnu cncannnna                                               19

<210> SEQ ID NO 5
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 5
nnanannnnu gncannnna                                               19

<210> SEQ ID NO 6
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 6
nnanannnnu uncannnna                                               19

<210> SEQ ID NO 7
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 7
nnanannnnu cnuannnna                                               19

<210> SEQ ID NO 8
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 8
nnanannnnu gnuannnna                                               19

<210> SEQ ID NO 9
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 9
nnanannnnu unuannnna                                                19

<210> SEQ ID NO 10
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 10
nnancnnnnu cnaannnna                                                19

<210> SEQ ID NO 11
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 11
nnancnnnnu gnaannnna                                                19

<210> SEQ ID NO 12
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 12
nnancnnnnu unaannnna                                                19

<210> SEQ ID NO 13
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 13
nnancnnnnu cncannnna                                                19

<210> SEQ ID NO 14
<211> LENGTH: 19
<212> TYPE: RNA

-continued

```
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 14
nnancnnnnu gncannnna                                               19

<210> SEQ ID NO 15
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 15
nnancnnnnu uncannnna                                               19

<210> SEQ ID NO 16
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 16
nnancnnnnu cnuannnna                                               19

<210> SEQ ID NO 17
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 17
nnancnnnnu gnuannnna                                               19

<210> SEQ ID NO 18
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 18
nnancnnnnu unuannnna                                               19

<210> SEQ ID NO 19
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
```

```
<223> OTHER INFORMATION: n is any nucleotide

<400> SEQUENCE: 19
nnangnnnnu cnaannnna                                              19

<210> SEQ ID NO 20
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 20
nnangnnnnu gnaannnna                                              19

<210> SEQ ID NO 21
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 21
nnangnnnnu unaannnna                                              19

<210> SEQ ID NO 22
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 22
nnangnnnnu cncannnna                                              19

<210> SEQ ID NO 23
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 23
nnangnnnnu gncannnna                                              19

<210> SEQ ID NO 24
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 24
nnangnnnnu uncannnna                                              19
```

```
<210> SEQ ID NO 25
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 25
nnangnnnnu cnuannnna                                              19

<210> SEQ ID NO 26
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 26
nnangnnnnu gnuannnna                                              19

<210> SEQ ID NO 27
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1-2, 4, 6-9, 12, 15-18
<223> OTHER INFORMATION: n is any nucleotide

<400> SEQUENCE: 27
nnangnnnnu unuannnna                                              19

<210> SEQ ID NO 28
<211> LENGTH: 22
<212> TYPE: RNA
<213> ORGANISM: Artificial Sequence
<220> FEATURE:
<223> OTHER INFORMATION: Synthetic
<221> NAME/KEY: misc_feature
<222> LOCATION: 4-5,7,9-12,15,18-21
<223> OTHER INFORMATION: n is any nucleotide

<400> SEQUENCE: 28
gucnnanann nnucnaannn na                                          22

<210> SEQ ID NO 29
<211> LENGTH: 208
<212> TYPE: DNA
<213> ORGANISM: Homo sapiens
<220> FEATURE:
<221> NAME/KEY: misc_feature
<222> LOCATION: (1)...(208)
<223> OTHER INFORMATION: human cyclophilin fragment

<400> SEQUENCE: 29
gttccaaaaa cagtggataa ttttgtggcc ttagctacag gagagaaagg atttggctac     60
aaaaacagca aattccatcg tgtaatcaag gacttcatga tccagggcgg agacttcacc    120
aggggagatg gcacaggagg aaagagcatc tacggtgagc gcttccccga tgagaacttc    180
aaactgaagc actacgggcc tggctggg                                       208
```

<210> SEQ ID NO 30
<211> LENGTH: 200
<212> TYPE: DNA
<213> ORGANISM: Photinus pyralis
<220> FEATURE:
<221> NAME/KEY: misc_feature
<222> LOCATION: (1)...(200)
<223> OTHER INFORMATION: firefly luciferase fragment

<400> SEQUENCE: 30
tgaacttccc gccgccgttg ttgttttgga gcacggaaag acgatgacgg aaaaagagat      60
cgtggattac gtcgccagtc aagtaacaac cgcgaaaaag ttgcgcggag gagttgtgtt     120
tgtggacgaa gtaccgaaag gtcttaccgg aaaactcgac gcaagaaaaa tcagagagat     180
cctcataaag gccaagaagg                                                 200

<210> SEQ ID NO 31
<211> LENGTH: 108
<212> TYPE: DNA
<213> ORGANISM: Homo sapiens
<220> FEATURE:
<221> NAME/KEY: misc_feature
<222> LOCATION: (1)...(108)
<223> OTHER INFORMATION: human DBL fragment

<400> SEQUENCE: 31
acgggcaagg ccaagtggga tgcctggaat gagctgaaag ggacttccaa ggaagatgcc      60
atgaaagctt acatcaacaa agtagaagag ctaaagaaaa aatacggg                  108

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
guuccaaaaa caguggaua                                                   19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
cccaaaaaca guggauaau                                                   19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
caaaaacagu ggauaauuu                                                   19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
aaaacagugg auaauuuug                                          19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
aacaguggau aauuugug                                           19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
caguggauaa uuuguggc                                           19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
guggauaauu uuguggccu                                          19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
ggauaauuuu guggccuua                                          19

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
auaauuuugu ggccuuagc                                          19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41 aauuugugg ccuuagcua                                           19

<210> SEQ ID NO 42
<211> LENGTH: 19

```
<212> TYPE: RNA
<213> ORGANISM: Artificial Sequence
<220> FEATURE:
<223> OTHER INFORMATION: Synthetic

<400> SEQUENCE: 42
uuuuguggcc uuagcuaca                                              19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
uuguggccuu agcuacagg                                              19

<210> SEQ ID NO 44
<211> LENGTH: 19
<212> TYPE: RNA
<213> ORGANISM: Artificial Sequence
<220> FEATURE:
<223> OTHER INFORMATION: Synthetic

<400> SEQUENCE: 44
guggccuuag cuacaggag                                              19

<210> SEQ ID NO 45
<211> LENGTH: 19
<212> TYPE: RNA
<213> ORGANISM: Artificial Sequence
<220> FEATURE:
<223> OTHER INFORMATION: Synthetic

<400> SEQUENCE: 45
ggccuuagcu acaggagag                                              19

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
ccuuagcuac aggagagaa                                              19

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
uuagcuacag gagagaaag                                              19

<210> SEQ ID NO 48
<211> LENGTH: 19
<212> TYPE: RNA
<213> ORGANISM: Artificial Sequence
<220> FEATURE:
<223> OTHER INFORMATION: Synthetic

<400> SEQUENCE: 48
agcuacagga gagaaagga                                              19
```

<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
cuacaggaga gaaaggauu                                                   19

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
acaggagaga aaggauuug                                                   19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
aggagagaaa ggauuuggc                                                   19

<210> SEQ ID NO 52
<211> LENGTH: 19
<212> TYPE: RNA
<213> ORGANISM: Artificial Sequence
<220> FEATURE:
<223> OTHER INFORMATION: Synthetic

<400> SEQUENCE: 52
gagagaaagg auuuggcua                                                   19

<210> SEQ ID NO 53
<211> LENGTH: 19
<212> TYPE: RNA
<213> ORGANISM: Artificial Sequence
<220> FEATURE:
<223> OTHER INFORMATION: Synthetic

<400> SEQUENCE: 53
gagaaaggau uuggcuaca                                                   19

<210> SEQ ID NO 54
<211> LENGTH: 19
<212> TYPE: RNA
<213> ORGANISM: Artificial Sequence
<220> FEATURE:
<223> OTHER INFORMATION: Synthetic

<400> SEQUENCE: 54
gaaaggauuu ggcuacaaa                                                   19

<210> SEQ ID NO 55
<211> LENGTH: 19
<212> TYPE: RNA
<213> ORGANISM: Artificial Sequence
<220> FEATURE:
<223> OTHER INFORMATION: Synthetic

```
<400> SEQUENCE: 55
aaggauuugg cuacaaaaa                                               19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
ggauuuggcu acaaaaaca                                               19

<210> SEQ ID NO 57
<211> LENGTH: 19
<212> TYPE: RNA
<213> ORGANISM: Artificial Sequence
<220> FEATURE:
<223> OTHER INFORMATION: Synthetic

<400> SEQUENCE: 57
auuuggcuac aaaaacagc                                               19

<210> SEQ ID NO 58
<211> LENGTH: 19
<212> TYPE: RNA
<213> ORGANISM: Artificial Sequence
<220> FEATURE:
<223> OTHER INFORMATION: Synthetic

<400> SEQUENCE: 58
uuggcuacaa aaacagcaa                                               19

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
ggcuacaaaa acagcaaau                                               19

<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
cuacaaaaac agcaaauuc                                               19

<210> SEQ ID NO 61
<211> LENGTH: 19
<212> TYPE: RNA
<213> ORGANISM: Artificial Sequence
<220> FEATURE:
<223> OTHER INFORMATION: Synthetic

<400> SEQUENCE: 61
acaaaaacag caaauucca                                               19

<210> SEQ ID NO 62
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 62
aaaaacagca aauuccauc                                                    19

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
aaacagcaaa uuccaucgu                                                    19

<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
acagcaaauu ccaucgugu                                                    19

<210> SEQ ID NO 65
<211> LENGTH: 19
<212> TYPE: RNA
<213> ORGANISM: Artificial Sequence
<220> FEATURE:
<223> OTHER INFORMATION: Synthetic

<400> SEQUENCE: 65
agcaaauucc aucguguaa                                                    19

<210> SEQ ID NO 66
<211> LENGTH: 19
<212> TYPE: RNA
<213> ORGANISM: Artificial Sequence
<220> FEATURE:
<223> OTHER INFORMATION: Synthetic

<400> SEQUENCE: 66
caaauuccau cguguaauc                                                    19

<210> SEQ ID NO 67
<211> LENGTH: 19
<212> TYPE: RNA
<213> ORGANISM: Artificial Sequence
<220> FEATURE:
<223> OTHER INFORMATION: Synthetic

<400> SEQUENCE: 67
aauuccaucg uguaaucaa                                                    19

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68
uuccaucgug uaaucaagg                                                    19
```

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69
ccaucgugua aucaaggac                                                19

<210> SEQ ID NO 70
<211> LENGTH: 19
<212> TYPE: RNA
<213> ORGANISM: Artificial Sequence
<220> FEATURE:
<223> OTHER INFORMATION: Synthetic

<400> SEQUENCE: 70
aucguguaau caaggacuu                                                19

<210> SEQ ID NO 71
<211> LENGTH: 19
<212> TYPE: RNA
<213> ORGANISM: Artificial Sequence
<220> FEATURE:
<223> OTHER INFORMATION: Synthetic

<400> SEQUENCE: 71
cguguaauca aggacuuca                                                19

<210> SEQ ID NO 72
<211> LENGTH: 19
<212> TYPE: RNA
<213> ORGANISM: Artificial Sequence
<220> FEATURE:
<223> OTHER INFORMATION: Synthetic

<400> SEQUENCE: 72
uguaaucaag gacuucaug                                                19

<210> SEQ ID NO 73
<211> LENGTH: 19
<212> TYPE: RNA
<213> ORGANISM: Artificial Sequence
<220> FEATURE:
<223> OTHER INFORMATION: Synthetic

<400> SEQUENCE: 73
uaaucaagga cuucaugau                                                19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74
aucaaggacu ucaugaucc                                                19

<210> SEQ ID NO 75
<211> LENGTH: 19
<212> TYPE: RNA
<213> ORGANISM: Artificial Sequence
<220> FEATURE:
<223> OTHER INFORMATION: Synthetic

<400> SEQUENCE: 75
caaggacuuc augauccag					19

<210> SEQ ID NO 76
<211> LENGTH: 19
<212> TYPE: RNA
<213> ORGANISM: Artificial Sequence
<220> FEATURE:
<223> OTHER INFORMATION: Synthetic

<400> SEQUENCE: 76
aggacuucau gauccaggg					19

<210> SEQ ID NO 77
<211> LENGTH: 19
<212> TYPE: RNA
<213> ORGANISM: Artificial Sequence
<220> FEATURE:
<223> OTHER INFORMATION: Synthetic

<400> SEQUENCE: 77
gacuucauga uccagggcg					19

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
cuucaugauc cagggcgga					19

<210> SEQ ID NO 79
<211> LENGTH: 19
<212> TYPE: RNA
<213> ORGANISM: Artificial Sequence
<220> FEATURE:
<223> OTHER INFORMATION: Synthetic

<400> SEQUENCE: 79
ucaugaucca gggcggaga					19

<210> SEQ ID NO 80
<211> LENGTH: 19
<212> TYPE: RNA
<213> ORGANISM: Artificial Sequence
<220> FEATURE:
<223> OTHER INFORMATION: Synthetic

<400> SEQUENCE: 80
augauccagg gcggagacu					19

<210> SEQ ID NO 81
<211> LENGTH: 19
<212> TYPE: RNA
<213> ORGANISM: Artificial Sequence
<220> FEATURE:
<223> OTHER INFORMATION: Synthetic

<400> SEQUENCE: 81
gauccagggc ggagacuuc					19

<210> SEQ ID NO 82
<211> LENGTH: 19

```
<212> TYPE: RNA
<213> ORGANISM: Artificial Sequence
<220> FEATURE:
<223> OTHER INFORMATION: Synthetic

<400> SEQUENCE: 82
uccagggcgg agacuucac                                                    19

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
cagggcggag acuucacca                                                    19

<210> SEQ ID NO 84
<211> LENGTH: 19
<212> TYPE: RNA
<213> ORGANISM: Artificial Sequence
<220> FEATURE:
<223> OTHER INFORMATION: Synthetic

<400> SEQUENCE: 84
gggcggagac uucaccagg                                                    19

<210> SEQ ID NO 85
<211> LENGTH: 19
<212> TYPE: RNA
<213> ORGANISM: Artificial Sequence
<220> FEATURE:
<223> OTHER INFORMATION: Synthetic

<400> SEQUENCE: 85
gcggagacuu caccagggg                                                    19

<210> SEQ ID NO 86
<211> LENGTH: 19
<212> TYPE: RNA
<213> ORGANISM: Artificial Sequence
<220> FEATURE:
<223> OTHER INFORMATION: Synthetic

<400> SEQUENCE: 86
ggagacuuca ccaggggag                                                    19

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87
agacuucacc agggagau                                                     19

<210> SEQ ID NO 88
<211> LENGTH: 19
<212> TYPE: RNA
<213> ORGANISM: Artificial Sequence
<220> FEATURE:
<223> OTHER INFORMATION: Synthetic

<400> SEQUENCE: 88
acuucaccag gggagaugg                                                    19
```

```
<210> SEQ ID NO 89
<211> LENGTH: 19
<212> TYPE: RNA
<213> ORGANISM: Artificial Sequence
<220> FEATURE:
<223> OTHER INFORMATION: Synthetic

<400> SEQUENCE: 89
uucaccaggg gagauggca                                                      19

<210> SEQ ID NO 90
<211> LENGTH: 19
<212> TYPE: RNA
<213> ORGANISM: Artificial Sequence
<220> FEATURE:
<223> OTHER INFORMATION: Synthetic

<400> SEQUENCE: 90
caccagggga gauggcaca                                                      19

<210> SEQ ID NO 91
<211> LENGTH: 19
<212> TYPE: RNA
<213> ORGANISM: Artificial Sequence
<220> FEATURE:
<223> OTHER INFORMATION: Synthetic

<400> SEQUENCE: 91 ccagggggaga uggcacagg                                                     19

<210> SEQ ID NO 92
<211> LENGTH: 19
<212> TYPE: RNA
<213> ORGANISM: Artificial Sequence
<220> FEATURE:
<223> OTHER INFORMATION: Synthetic

<400> SEQUENCE: 92
aggggagaug gcacaggag                                                      19

<210> SEQ ID NO 93
<211> LENGTH: 19
<212> TYPE: RNA
<213> ORGANISM: Artificial Sequence
<220> FEATURE:
<223> OTHER INFORMATION: Synthetic

<400> SEQUENCE: 93
gggagauggc acaggagga                                                      19

<210> SEQ ID NO 94
<211> LENGTH: 19
<212> TYPE: RNA
<213> ORGANISM: Artificial Sequence
<220> FEATURE:
<223> OTHER INFORMATION: Synthetic

<400> SEQUENCE: 94
gagauggcac aggaggaaa                                                      19

<210> SEQ ID NO 95
<211> LENGTH: 19
<212> TYPE: RNA
<213> ORGANISM: Artificial Sequence
<220> FEATURE:
<223> OTHER INFORMATION: Synthetic
```

-continued

<400> SEQUENCE: 95
gauggcacag gaggaaaga					19

<210> SEQ ID NO 96
<211> LENGTH: 19
<212> TYPE: RNA
<213> ORGANISM: Artificial Sequence
<220> FEATURE:
<223> OTHER INFORMATION: Synthetic

<400> SEQUENCE: 96
uggcacagga ggaaagagc					19

<210> SEQ ID NO 97
<211> LENGTH: 19
<212> TYPE: RNA
<213> ORGANISM: Artificial Sequence
<220> FEATURE:
<223> OTHER INFORMATION: Synthetic

<400> SEQUENCE: 97
gcacaggagg aaagagcau					19

<210> SEQ ID NO 98
<211> LENGTH: 19
<212> TYPE: RNA
<213> ORGANISM: Artificial Sequence
<220> FEATURE:
<223> OTHER INFORMATION: Synthetic

<400> SEQUENCE: 98
acaggaggaa agagcaucu					19

<210> SEQ ID NO 99
<211> LENGTH: 19
<212> TYPE: RNA
<213> ORGANISM: Artificial Sequence
<220> FEATURE:
<223> OTHER INFORMATION: Synthetic

<400> SEQUENCE: 99
aggaggaaag agcaucuac					19

<210> SEQ ID NO 100
<211> LENGTH: 19
<212> TYPE: RNA
<213> ORGANISM: Artificial Sequence
<220> FEATURE:
<223> OTHER INFORMATION: Synthetic

<400> SEQUENCE: 100
gaggaaagag caucuacgg					19

<210> SEQ ID NO 101
<211> LENGTH: 19
<212> TYPE: RNA
<213> ORGANISM: Artificial Sequence
<220> FEATURE:
<223> OTHER INFORMATION: Synthetic

<400> SEQUENCE: 101
ggaaagagca ucuacggug					19

<210> SEQ ID NO 102
<211> LENGTH: 19

```
<212> TYPE: RNA
<213> ORGANISM: Artificial Sequence
<220> FEATURE:
<223> OTHER INFORMATION: Synthetic

<400> SEQUENCE: 102
aaagagcauc uacggugag                                                    19

<210> SEQ ID NO 103
<211> LENGTH: 19
<212> TYPE: RNA
<213> ORGANISM: Artificial Sequence
<220> FEATURE:
<223> OTHER INFORMATION: Synthetic

<400> SEQUENCE: 103
agagcaucua cggugagcg                                                    19

<210> SEQ ID NO 104
<211> LENGTH: 19
<212> TYPE: RNA
<213> ORGANISM: Artificial Sequence
<220> FEATURE:
<223> OTHER INFORMATION: Synthetic

<400> SEQUENCE: 104
agcaucuacg gugagcgcu                                                    19

<210> SEQ ID NO 105
<211> LENGTH: 19
<212> TYPE: RNA
<213> ORGANISM: Artificial Sequence
<220> FEATURE:
<223> OTHER INFORMATION: Synthetic

<400> SEQUENCE: 105
caucuacggu gagcgcuuc                                                    19

<210> SEQ ID NO 106
<211> LENGTH: 19
<212> TYPE: RNA
<213> ORGANISM: Artificial Sequence
<220> FEATURE:
<223> OTHER INFORMATION: Synthetic

<400> SEQUENCE: 106
ucuacgguga gcgcuuccc                                                    19

<210> SEQ ID NO 107
<211> LENGTH: 19
<212> TYPE: RNA
<213> ORGANISM: Artificial Sequence
<220> FEATURE:
<223> OTHER INFORMATION: Synthetic

<400> SEQUENCE: 107
uacggugagc gcuuccccg                                                    19

<210> SEQ ID NO 108
<211> LENGTH: 19
<212> TYPE: RNA
<213> ORGANISM: Artificial Sequence
<220> FEATURE:
<223> OTHER INFORMATION: Synthetic

<400> SEQUENCE: 108
cggugagcgc uuccccgau                                                    19
```

<210> SEQ ID NO 109
<211> LENGTH: 19
<212> TYPE: RNA
<213> ORGANISM: Artificial Sequence
<220> FEATURE:
<223> OTHER INFORMATION: Synthetic

<400> SEQUENCE: 109
gugagcgcuu ccccgauga                                                19

<210> SEQ ID NO 110
<211> LENGTH: 19
<212> TYPE: RNA
<213> ORGANISM: Artificial Sequence
<220> FEATURE:
<223> OTHER INFORMATION: Synthetic

<400> SEQUENCE: 110
gagcgcuucc ccgaugaga                                                19

<210> SEQ ID NO 111
<211> LENGTH: 19
<212> TYPE: RNA
<213> ORGANISM: Artificial Sequence
<220> FEATURE:
<223> OTHER INFORMATION: Synthetic

<400> SEQUENCE: 111 gcgcuuccc gaugagaac                                                 19

<210> SEQ ID NO 112
<211> LENGTH: 19
<212> TYPE: RNA
<213> ORGANISM: Artificial Sequence
<220> FEATURE:
<223> OTHER INFORMATION: Synthetic

<400> SEQUENCE: 112
gcuuccccga ugagaacuu                                                19

<210> SEQ ID NO 113
<211> LENGTH: 19
<212> TYPE: RNA
<213> ORGANISM: Artificial Sequence
<220> FEATURE:
<223> OTHER INFORMATION: Synthetic

<400> SEQUENCE: 113
uuccccgaug agaacuuca                                                19

<210> SEQ ID NO 114
<211> LENGTH: 19
<212> TYPE: RNA
<213> ORGANISM: Artificial Sequence
<220> FEATURE:
<223> OTHER INFORMATION: Synthetic

<400> SEQUENCE: 114
ccccgaugag aacuucaaa                                                19

<210> SEQ ID NO 115
<211> LENGTH: 19
<212> TYPE: RNA
<213> ORGANISM: Artificial Sequence
<220> FEATURE:
<223> OTHER INFORMATION: Synthetic -continued

<400> SEQUENCE: 115
ccgaugagaa cuucaaacu                                                      19

<210> SEQ ID NO 116
<211> LENGTH: 19
<212> TYPE: RNA
<213> ORGANISM: Artificial Sequence
<220> FEATURE:
<223> OTHER INFORMATION: Synthetic

<400> SEQUENCE: 116
gaugagaacu ucaaacuga                                                      19

<210> SEQ ID NO 117
<211> LENGTH: 19
<212> TYPE: RNA
<213> ORGANISM: Artificial Sequence
<220> FEATURE:
<223> OTHER INFORMATION: Synthetic

<400> SEQUENCE: 117
ugagaacuuc aaacugaag                                                      19

<210> SEQ ID NO 118
<211> LENGTH: 19
<212> TYPE: RNA
<213> ORGANISM: Artificial Sequence
<220> FEATURE:
<223> OTHER INFORMATION: Synthetic

<400> SEQUENCE: 118
agaacuucaa acugaagca                                                      19

<210> SEQ ID NO 119
<211> LENGTH: 19
<212> TYPE: RNA
<213> ORGANISM: Artificial Sequence
<220> FEATURE:
<223> OTHER INFORMATION: Synthetic

<400> SEQUENCE: 119
aacuucaaac ugaagcacu                                                      19

<210> SEQ ID NO 120
<211> LENGTH: 19
<212> TYPE: RNA
<213> ORGANISM: Artificial Sequence
<220> FEATURE:
<223> OTHER INFORMATION: Synthetic

<400> SEQUENCE: 120
cuucaaacug aagcacuac                                                      19

<210> SEQ ID NO 121
<211> LENGTH: 19
<212> TYPE: RNA
<213> ORGANISM: Artificial Sequence
<220> FEATURE:
<223> OTHER INFORMATION: Synthetic

<400> SEQUENCE: 121
ucaaacugaa gcacuacgg                                                      19

<210> SEQ ID NO 122
<211> LENGTH: 19

```
<212> TYPE: RNA
<213> ORGANISM: Artificial Sequence
<220> FEATURE:
<223> OTHER INFORMATION: Synthetic

<400> SEQUENCE: 122
acgggcaagg ccaaguggg                                                    19

<210> SEQ ID NO 123
<211> LENGTH: 19
<212> TYPE: RNA
<213> ORGANISM: Artificial Sequence
<220> FEATURE:
<223> OTHER INFORMATION: Synthetic

<400> SEQUENCE: 123
cgggcaaggc caaguggga                                                    19

<210> SEQ ID NO 124
<211> LENGTH: 19
<212> TYPE: RNA
<213> ORGANISM: Artificial Sequence
<220> FEATURE:
<223> OTHER INFORMATION: Synthetic

<400> SEQUENCE: 124
gggcaaggcc aagugggau                                                    19

<210> SEQ ID NO 125
<211> LENGTH: 19
<212> TYPE: RNA
<213> ORGANISM: Artificial Sequence
<220> FEATURE:
<223> OTHER INFORMATION: Synthetic

<400> SEQUENCE: 125
ggcaaggcca agugggaug                                                    19

<210> SEQ ID NO 126
<211> LENGTH: 19
<212> TYPE: RNA
<213> ORGANISM: Artificial Sequence
<220> FEATURE:
<223> OTHER INFORMATION: Synthetic

<400> SEQUENCE: 126
gcaaggccaa gugggaugc                                                    19

<210> SEQ ID NO 127
<211> LENGTH: 19
<212> TYPE: RNA
<213> ORGANISM: Artificial Sequence
<220> FEATURE:
<223> OTHER INFORMATION: Synthetic

<400> SEQUENCE: 127
caaggccaag ugggaugcc                                                    19

<210> SEQ ID NO 128
<211> LENGTH: 19
<212> TYPE: RNA
<213> ORGANISM: Artificial Sequence
<220> FEATURE:
<223> OTHER INFORMATION: Synthetic

<400> SEQUENCE: 128
aaggccaagu gggaugccu                                                    19
```

<210> SEQ ID NO 129
<211> LENGTH: 19
<212> TYPE: RNA
<213> ORGANISM: Artificial Sequence
<220> FEATURE:
<223> OTHER INFORMATION: Synthetic

<400> SEQUENCE: 129
aggccaagug ggaugccug                                                  19

<210> SEQ ID NO 130
<211> LENGTH: 19
<212> TYPE: RNA
<213> ORGANISM: Artificial Sequence
<220> FEATURE:
<223> OTHER INFORMATION: Synthetic

<400> SEQUENCE: 130
ggccaagugg gaugccugg                                                  19

<210> SEQ ID NO 131
<211> LENGTH: 19
<212> TYPE: RNA
<213> ORGANISM: Artificial Sequence
<220> FEATURE:
<223> OTHER INFORMATION: Synthetic

<400> SEQUENCE: 131
gccaaguggg augccugga                                                  19

<210> SEQ ID NO 132
<211> LENGTH: 19
<212> TYPE: RNA
<213> ORGANISM: Artificial Sequence
<220> FEATURE:
<223> OTHER INFORMATION: Synthetic

<400> SEQUENCE: 132
ccaaguggga ugccuggaa                                                  19

<210> SEQ ID NO 133
<211> LENGTH: 19
<212> TYPE: RNA
<213> ORGANISM: Artificial Sequence
<220> FEATURE:
<223> OTHER INFORMATION: Synthetic

<400> SEQUENCE: 133
caagugggau gccuggaau                                                  19

<210> SEQ ID NO 134
<211> LENGTH: 19
<212> TYPE: RNA
<213> ORGANISM: Artificial Sequence
<220> FEATURE:
<223> OTHER INFORMATION: Synthetic

<400> SEQUENCE: 134
aagugggaug ccuggaaug                                                  19

<210> SEQ ID NO 135
<211> LENGTH: 19
<212> TYPE: RNA
<213> ORGANISM: Artificial Sequence
<220> FEATURE:
<223> OTHER INFORMATION: Synthetic

```
<400> SEQUENCE: 135
agugggaugc cuggaauga                                              19

<210> SEQ ID NO 136
<211> LENGTH: 19
<212> TYPE: RNA
<213> ORGANISM: Artificial Sequence
<220> FEATURE:
<223> OTHER INFORMATION: Synthetic

<400> SEQUENCE: 136
gugggaugcc uggaaugag                                              19

<210> SEQ ID NO 137
<211> LENGTH: 19
<212> TYPE: RNA
<213> ORGANISM: Artificial Sequence
<220> FEATURE:
<223> OTHER INFORMATION: Synthetic

<400> SEQUENCE: 137
ugggaugccu ggaaugagc                                              19

<210> SEQ ID NO 138
<211> LENGTH: 19
<212> TYPE: RNA
<213> ORGANISM: Artificial Sequence
<220> FEATURE:
<223> OTHER INFORMATION: Synthetic

<400> SEQUENCE: 138
gggaugccug gaaugagcu                                              19

<210> SEQ ID NO 139
<211> LENGTH: 19
<212> TYPE: RNA
<213> ORGANISM: Artificial Sequence
<220> FEATURE:
<223> OTHER INFORMATION: Synthetic

<400> SEQUENCE: 139
ggaugccugg aaugagcug                                              19

<210> SEQ ID NO 140
<211> LENGTH: 19
<212> TYPE: RNA
<213> ORGANISM: Artificial Sequence
<220> FEATURE:
<223> OTHER INFORMATION: Synthetic

<400> SEQUENCE: 140
gaugccugga augagcuga                                              19

<210> SEQ ID NO 141
<211> LENGTH: 19
<212> TYPE: RNA
<213> ORGANISM: Artificial Sequence
<220> FEATURE:
<223> OTHER INFORMATION: Synthetic

<400> SEQUENCE: 141
augccuggaa ugagcugaa                                              19

<210> SEQ ID NO 142
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 142
ugccuggaau gagcugaaa                                                19

<210> SEQ ID NO 143
<211> LENGTH: 19
<212> TYPE: RNA
<213> ORGANISM: Artificial Sequence
<220> FEATURE:
<223> OTHER INFORMATION: Synthetic

<400> SEQUENCE: 143
gccuggaaug agcugaaag                                                19

<210> SEQ ID NO 144
<211> LENGTH: 19
<212> TYPE: RNA
<213> ORGANISM: Artificial Sequence
<220> FEATURE:
<223> OTHER INFORMATION: Synthetic

<400> SEQUENCE: 144
ccuggaauga gcugaaagg                                                19

<210> SEQ ID NO 145
<211> LENGTH: 19
<212> TYPE: RNA
<213> ORGANISM: Artificial Sequence
<220> FEATURE:
<223> OTHER INFORMATION: Synthetic

<400> SEQUENCE: 145
cuggaaugag cugaaaggg                                                19

<210> SEQ ID NO 146
<211> LENGTH: 19
<212> TYPE: RNA
<213> ORGANISM: Artificial Sequence
<220> FEATURE:
<223> OTHER INFORMATION: Synthetic

<400> SEQUENCE: 146
uggaaugagc ugaaaggga                                                19

<210> SEQ ID NO 147
<211> LENGTH: 19
<212> TYPE: RNA
<213> ORGANISM: Artificial Sequence
<220> FEATURE:
<223> OTHER INFORMATION: Synthetic

<400> SEQUENCE: 147
ggaaugagcu gaaagggac                                                19

<210> SEQ ID NO 148
<211> LENGTH: 19
<212> TYPE: RNA
<213> ORGANISM: Artificial Sequence
<220> FEATURE:
<223> OTHER INFORMATION: Synthetic

<400> SEQUENCE: 148
gaaugagcug aaagggacu                                                19
```

```
<210> SEQ ID NO 149
<211> LENGTH: 19
<212> TYPE: RNA
<213> ORGANISM: Artificial Sequence
<220> FEATURE:
<223> OTHER INFORMATION: Synthetic

<400> SEQUENCE: 149
aaugagcuga aagggacuu                                              19

<210> SEQ ID NO 150
<211> LENGTH: 19
<212> TYPE: RNA
<213> ORGANISM: Artificial Sequence
<220> FEATURE:
<223> OTHER INFORMATION: Synthetic

<400> SEQUENCE: 150
augagcugaa agggacuuc                                              19

<210> SEQ ID NO 151
<211> LENGTH: 19
<212> TYPE: RNA
<213> ORGANISM: Artificial Sequence
<220> FEATURE:
<223> OTHER INFORMATION: Synthetic

<400> SEQUENCE: 151
ugagcugaaa gggacuucc                                              19

<210> SEQ ID NO 152
<211> LENGTH: 19
<212> TYPE: RNA
<213> ORGANISM: Artificial Sequence
<220> FEATURE:
<223> OTHER INFORMATION: Synthetic

<400> SEQUENCE: 152
gagcugaaag ggacuucca                                              19

<210> SEQ ID NO 153
<211> LENGTH: 19
<212> TYPE: RNA
<213> ORGANISM: Artificial Sequence
<220> FEATURE:
<223> OTHER INFORMATION: Synthetic

<400> SEQUENCE: 153
agcugaaagg gacuuccaa                                              19

<210> SEQ ID NO 154
<211> LENGTH: 19
<212> TYPE: RNA
<213> ORGANISM: Artificial Sequence
<220> FEATURE:
<223> OTHER INFORMATION: Synthetic

<400> SEQUENCE: 154
gcugaaaggg acuuccaag                                              19

<210> SEQ ID NO 155
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 155
cugaaaggga cuuccaagg                                              19

<210> SEQ ID NO 156
<211> LENGTH: 19
<212> TYPE: RNA
<213> ORGANISM: Artificial Sequence
<220> FEATURE:
<223> OTHER INFORMATION: Synthetic

<400> SEQUENCE: 156
ugaaagggac uuccaagga                                              19

<210> SEQ ID NO 157
<211> LENGTH: 19
<212> TYPE: RNA
<213> ORGANISM: Artificial Sequence
<220> FEATURE:
<223> OTHER INFORMATION: Synthetic

<400> SEQUENCE: 157
gaaagggacu uccaaggaa                                              19

<210> SEQ ID NO 158
<211> LENGTH: 19
<212> TYPE: RNA
<213> ORGANISM: Artificial Sequence
<220> FEATURE:
<223> OTHER INFORMATION: Synthetic

<400> SEQUENCE: 158
aaagggacuu ccaaggaag                                              19

<210> SEQ ID NO 159
<211> LENGTH: 19
<212> TYPE: RNA
<213> ORGANISM: Artificial Sequence
<220> FEATURE:
<223> OTHER INFORMATION: Synthetic

<400> SEQUENCE: 159
aagggacuuc caaggaaga                                              19

<210> SEQ ID NO 160
<211> LENGTH: 19
<212> TYPE: RNA
<213> ORGANISM: Artificial Sequence
<220> FEATURE:
<223> OTHER INFORMATION: Synthetic

<400> SEQUENCE: 160
agggacuucc aaggaagau                                              19

<210> SEQ ID NO 161
<211> LENGTH: 19
<212> TYPE: RNA
<213> ORGANISM: Artificial Sequence
<220> FEATURE:
<223> OTHER INFORMATION: Synthetic

<400> SEQUENCE: 161
gggacuucca aggaagaug                                              19

<210> SEQ ID NO 162
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 162
ggacuuccaa ggaagaugc                                                    19

<210> SEQ ID NO 163
<211> LENGTH: 19
<212> TYPE: RNA
<213> ORGANISM: Artificial Sequence
<220> FEATURE:
<223> OTHER INFORMATION: Synthetic

<400> SEQUENCE: 163
gacuuccaag gaagaugcc                                                    19

<210> SEQ ID NO 164
<211> LENGTH: 19
<212> TYPE: RNA
<213> ORGANISM: Artificial Sequence
<220> FEATURE:
<223> OTHER INFORMATION: Synthetic

<400> SEQUENCE: 164
acuuccaagg aagaugcca                                                    19

<210> SEQ ID NO 165
<211> LENGTH: 19
<212> TYPE: RNA
<213> ORGANISM: Artificial Sequence
<220> FEATURE:
<223> OTHER INFORMATION: Synthetic

<400> SEQUENCE: 165
cuuccaagga agaugccau                                                    19

<210> SEQ ID NO 166
<211> LENGTH: 19
<212> TYPE: RNA
<213> ORGANISM: Artificial Sequence
<220> FEATURE:
<223> OTHER INFORMATION: Synthetic

<400> SEQUENCE: 166
uuccaaggaa gaugccaug                                                    19

<210> SEQ ID NO 167
<211> LENGTH: 19
<212> TYPE: RNA
<213> ORGANISM: Artificial Sequence
<220> FEATURE:
<223> OTHER INFORMATION: Synthetic

<400> SEQUENCE: 167
uccaaggaag augccauga                                                    19

<210> SEQ ID NO 168
<211> LENGTH: 19
<212> TYPE: RNA
<213> ORGANISM: Artificial Sequence
<220> FEATURE:
<223> OTHER INFORMATION: Synthetic

<400> SEQUENCE: 168
ccaaggaaga ugccaugaa                                                    19
```

<210> SEQ ID NO 169
<211> LENGTH: 19
<212> TYPE: RNA
<213> ORGANISM: Artificial Sequence
<220> FEATURE:
<223> OTHER INFORMATION: Synthetic

<400> SEQUENCE: 169
caaggaagau gccaugaaa                                                   19

<210> SEQ ID NO 170
<211> LENGTH: 19
<212> TYPE: RNA
<213> ORGANISM: Artificial Sequence
<220> FEATURE:
<223> OTHER INFORMATION: Synthetic

<400> SEQUENCE: 170
aaggaagaug ccaugaaag                                                   19

<210> SEQ ID NO 171
<211> LENGTH: 19
<212> TYPE: RNA
<213> ORGANISM: Artificial Sequence
<220> FEATURE:
<223> OTHER INFORMATION: Synthetic

<400> SEQUENCE: 171
aggaagaugc caugaaagc                                                   19

<210> SEQ ID NO 172
<211> LENGTH: 19
<212> TYPE: RNA
<213> ORGANISM: Artificial Sequence
<220> FEATURE:
<223> OTHER INFORMATION: Synthetic

<400> SEQUENCE: 172
ggaagaugcc augaaagcu                                                   19

<210> SEQ ID NO 173
<211> LENGTH: 19
<212> TYPE: RNA
<213> ORGANISM: Artificial Sequence
<220> FEATURE:
<223> OTHER INFORMATION: Synthetic

<400> SEQUENCE: 173
gaagaugcca ugaaagcuu                                                   19

<210> SEQ ID NO 174
<211> LENGTH: 19
<212> TYPE: RNA
<213> ORGANISM: Artificial Sequence
<220> FEATURE:
<223> OTHER INFORMATION: Synthetic

<400> SEQUENCE: 174
aagaugccau gaaagcuua                                                   19

<210> SEQ ID NO 175
<211> LENGTH: 19
<212> TYPE: RNA
<213> ORGANISM: Artificial Sequence
<220> FEATURE:
<223> OTHER INFORMATION: Synthetic

```
<400> SEQUENCE: 175
agaugccaug aaagcuuac                                                    19

<210> SEQ ID NO 176
<211> LENGTH: 19
<212> TYPE: RNA
<213> ORGANISM: Artificial Sequence
<220> FEATURE:
<223> OTHER INFORMATION: Synthetic

<400> SEQUENCE: 176
gaugccauga aagcuuaca                                                    19

<210> SEQ ID NO 177
<211> LENGTH: 19
<212> TYPE: RNA
<213> ORGANISM: Artificial Sequence
<220> FEATURE:
<223> OTHER INFORMATION: Synthetic

<400> SEQUENCE: 177
augccaugaa agcuuacau                                                    19

<210> SEQ ID NO 178
<211> LENGTH: 19
<212> TYPE: RNA
<213> ORGANISM: Artificial Sequence
<220> FEATURE:
<223> OTHER INFORMATION: Synthetic

<400> SEQUENCE: 178
ugccaugaaa gcuuacauc                                                    19

<210> SEQ ID NO 179
<211> LENGTH: 19
<212> TYPE: RNA
<213> ORGANISM: Artificial Sequence
<220> FEATURE:
<223> OTHER INFORMATION: Synthetic

<400> SEQUENCE: 179
gccaugaaag cuuacauca                                                    19

<210> SEQ ID NO 180
<211> LENGTH: 19
<212> TYPE: RNA
<213> ORGANISM: Artificial Sequence
<220> FEATURE:
<223> OTHER INFORMATION: Synthetic

<400> SEQUENCE: 180
ccaugaaagc uuacaucaa                                                    19

<210> SEQ ID NO 181
<211> LENGTH: 19
<212> TYPE: RNA
<213> ORGANISM: Artificial Sequence
<220> FEATURE:
<223> OTHER INFORMATION: Synthetic

<400> SEQUENCE: 181
caugaaagcu uacaucaac                                                    19

<210> SEQ ID NO 182
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 182
augaaagcuu acaucaaca                                                19

<210> SEQ ID NO 183
<211> LENGTH: 19
<212> TYPE: RNA
<213> ORGANISM: Artificial Sequence
<220> FEATURE:
<223> OTHER INFORMATION: Synthetic

<400> SEQUENCE: 183
ugaaagcuua caucaacaa                                                19

<210> SEQ ID NO 184
<211> LENGTH: 19
<212> TYPE: RNA
<213> ORGANISM: Artificial Sequence
<220> FEATURE:
<223> OTHER INFORMATION: Synthetic

<400> SEQUENCE: 184
gaaagcuuac aucaacaaa                                                19

<210> SEQ ID NO 185
<211> LENGTH: 19
<212> TYPE: RNA
<213> ORGANISM: Artificial Sequence
<220> FEATURE:
<223> OTHER INFORMATION: Synthetic

<400> SEQUENCE: 185
aaagcuuaca ucaacaaag                                                19

<210> SEQ ID NO 186
<211> LENGTH: 19
<212> TYPE: RNA
<213> ORGANISM: Artificial Sequence
<220> FEATURE:
<223> OTHER INFORMATION: Synthetic

<400> SEQUENCE: 186
aagcuuacau caacaaagu                                                19

<210> SEQ ID NO 187
<211> LENGTH: 19
<212> TYPE: RNA
<213> ORGANISM: Artificial Sequence
<220> FEATURE:
<223> OTHER INFORMATION: Synthetic

<400> SEQUENCE: 187
agcuuacauc aacaaagua                                                19

<210> SEQ ID NO 188
<211> LENGTH: 19
<212> TYPE: RNA
<213> ORGANISM: Artificial Sequence
<220> FEATURE:
<223> OTHER INFORMATION: Synthetic

<400> SEQUENCE: 188
agcuuacauc acaaaguag                                                19
```

```
<210> SEQ ID NO 189
<211> LENGTH: 19
<212> TYPE: RNA
<213> ORGANISM: Artificial Sequence
<220> FEATURE:
<223> OTHER INFORMATION: Synthetic

<400> SEQUENCE: 189
cuuacaucaa caaaguaga                                                  19

<210> SEQ ID NO 190
<211> LENGTH: 19
<212> TYPE: RNA
<213> ORGANISM: Artificial Sequence
<220> FEATURE:
<223> OTHER INFORMATION: Synthetic

<400> SEQUENCE: 190
uuacaucaac aaaguagaa                                                  19

<210> SEQ ID NO 191
<211> LENGTH: 19
<212> TYPE: RNA
<213> ORGANISM: Artificial Sequence
<220> FEATURE:
<223> OTHER INFORMATION: Synthetic

<400> SEQUENCE: 191
uacaucaaca aaguagaag                                                  19

<210> SEQ ID NO 192
<211> LENGTH: 19
<212> TYPE: RNA
<213> ORGANISM: Artificial Sequence
<220> FEATURE:
<223> OTHER INFORMATION: Synthetic

<400> SEQUENCE: 192
acaucaacaa aguagaaga                                                  19

<210> SEQ ID NO 193
<211> LENGTH: 19
<212> TYPE: RNA
<213> ORGANISM: Artificial Sequence
<220> FEATURE:
<223> OTHER INFORMATION: Synthetic

<400> SEQUENCE: 193
caucaacaaa guagaagag                                                  19

<210> SEQ ID NO 194
<211> LENGTH: 19
<212> TYPE: RNA
<213> ORGANISM: Artificial Sequence
<220> FEATURE:
<223> OTHER INFORMATION: Synthetic

<400> SEQUENCE: 194
aucaacaaag uagaagagc                                                  19

<210> SEQ ID NO 195
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 195
ucaacaaagu agaagagcu                                            19

<210> SEQ ID NO 196
<211> LENGTH: 19
<212> TYPE: RNA
<213> ORGANISM: Artificial Sequence
<220> FEATURE:
<223> OTHER INFORMATION: Synthetic

<400> SEQUENCE: 196
caacaaagua gaagagcua                                            19

<210> SEQ ID NO 197
<211> LENGTH: 19
<212> TYPE: RNA
<213> ORGANISM: Artificial Sequence
<220> FEATURE:
<223> OTHER INFORMATION: Synthetic

<400> SEQUENCE: 197
aacaaaguag aagagcuaa                                            19

<210> SEQ ID NO 198
<211> LENGTH: 19
<212> TYPE: RNA
<213> ORGANISM: Artificial Sequence
<220> FEATURE:
<223> OTHER INFORMATION: Synthetic

<400> SEQUENCE: 198
acaaaguaga agagcuaaa                                            19

<210> SEQ ID NO 199
<211> LENGTH: 19
<212> TYPE: RNA
<213> ORGANISM: Artificial Sequence
<220> FEATURE:
<223> OTHER INFORMATION: Synthetic

<400> SEQUENCE: 199
caaaguagaa gagcuaaag                                            19

<210> SEQ ID NO 200
<211> LENGTH: 19
<212> TYPE: RNA
<213> ORGANISM: Artificial Sequence
<220> FEATURE:
<223> OTHER INFORMATION: Synthetic

<400> SEQUENCE: 200
aaaguagaag agcuaaaga                                            19

<210> SEQ ID NO 201
<211> LENGTH: 19
<212> TYPE: RNA
<213> ORGANISM: Artificial Sequence
<220> FEATURE:
<223> OTHER INFORMATION: Synthetic

<400> SEQUENCE: 201
aaguagaaga gcuaaagaa                                            19

<210> SEQ ID NO 202
<211> LENGTH: 19
```

<212> TYPE: RNA
<213> ORGANISM: Artificial Sequence
<220> FEATURE:
<223> OTHER INFORMATION: Synthetic

<400> SEQUENCE: 202
aguagaagag cuaaagaaa                                          19

<210> SEQ ID NO 203
<211> LENGTH: 19
<212> TYPE: RNA
<213> ORGANISM: Artificial Sequence
<220> FEATURE:
<223> OTHER INFORMATION: Synthetic

<400> SEQUENCE: 203
guagaagagc uaaagaaaa                                          19

<210> SEQ ID NO 204
<211> LENGTH: 19
<212> TYPE: RNA
<213> ORGANISM: Artificial Sequence
<220> FEATURE:
<223> OTHER INFORMATION: Synthetic

<400> SEQUENCE: 204
uagaagagcu aaagaaaaa                                          19

<210> SEQ ID NO 205
<211> LENGTH: 19
<212> TYPE: RNA
<213> ORGANISM: Artificial Sequence
<220> FEATURE:
<223> OTHER INFORMATION: Synthetic

<400> SEQUENCE: 205
agaagagcua aagaaaaaa                                          19

<210> SEQ ID NO 206
<211> LENGTH: 19
<212> TYPE: RNA
<213> ORGANISM: Artificial Sequence
<220> FEATURE:
<223> OTHER INFORMATION: Synthetic

<400> SEQUENCE: 206
gaagagcuaa agaaaaaau                                          19

<210> SEQ ID NO 207
<211> LENGTH: 19
<212> TYPE: RNA
<213> ORGANISM: Artificial Sequence
<220> FEATURE:
<223> OTHER INFORMATION: Synthetic

<400> SEQUENCE: 207
aagagcuaaa gaaaaaaua                                          19

<210> SEQ ID NO 208
<211> LENGTH: 19
<212> TYPE: RNA
<213> ORGANISM: Artificial Sequence
<220> FEATURE:
<223> OTHER INFORMATION: Synthetic

<400> SEQUENCE: 208
agagcuaaag aaaaaauac                                          19

<210> SEQ ID NO 209
<211> LENGTH: 19
<212> TYPE: RNA
<213> ORGANISM: Artificial Sequence
<220> FEATURE:
<223> OTHER INFORMATION: Synthetic

<400> SEQUENCE: 209
gagcuaaaga aaaauacg                                              19

<210> SEQ ID NO 210
<211> LENGTH: 19
<212> TYPE: RNA
<213> ORGANISM: Artificial Sequence
<220> FEATURE:
<223> OTHER INFORMATION: Synthetic

<400> SEQUENCE: 210
agcuaaagaa aaauacgg                                              19

<210> SEQ ID NO 211
<211> LENGTH: 19
<212> TYPE: RNA
<213> ORGANISM: Artificial Sequence
<220> FEATURE:
<223> OTHER INFORMATION: Synthetic

<400> SEQUENCE: 211
gcuaaagaaa aaauacggg                                             19

<210> SEQ ID NO 212
<211> LENGTH: 19
<212> TYPE: RNA
<213> ORGANISM: Artificial Sequence
<220> FEATURE:
<223> OTHER INFORMATION: Synthetic

<400> SEQUENCE: 212
auccucauaa aggccaaga                                             19

<210> SEQ ID NO 213
<211> LENGTH: 19
<212> TYPE: RNA
<213> ORGANISM: Artificial Sequence
<220> FEATURE:
<223> OTHER INFORMATION: Synthetic

<400> SEQUENCE: 213
agauccucau aaaggccaa                                             19

<210> SEQ ID NO 214
<211> LENGTH: 19
<212> TYPE: RNA
<213> ORGANISM: Artificial Sequence
<220> FEATURE:
<223> OTHER INFORMATION: Synthetic

<400> SEQUENCE: 214
agagauccuc auaaaggcc                                             19

<210> SEQ ID NO 215
<211> LENGTH: 19
<212> TYPE: RNA
<213> ORGANISM: Artificial Sequence
<220> FEATURE:
<223> OTHER INFORMATION: Synthetic

```
<400> SEQUENCE: 215
agagagaucc ucauaaagg                                                    19

<210> SEQ ID NO 216
<211> LENGTH: 19
<212> TYPE: RNA
<213> ORGANISM: Artificial Sequence
<220> FEATURE:
<223> OTHER INFORMATION: Synthetic

<400> SEQUENCE: 216
ucagagagau ccucauaaa                                                    19

<210> SEQ ID NO 217
<211> LENGTH: 19
<212> TYPE: RNA
<213> ORGANISM: Artificial Sequence
<220> FEATURE:
<223> OTHER INFORMATION: Synthetic

<400> SEQUENCE: 217
aaucagagag auccucaua                                                    19

<210> SEQ ID NO 218
<211> LENGTH: 19
<212> TYPE: RNA
<213> ORGANISM: Artificial Sequence
<220> FEATURE:
<223> OTHER INFORMATION: Synthetic

<400> SEQUENCE: 218
aaaaucagag agauccuca                                                    19

<210> SEQ ID NO 219
<211> LENGTH: 19
<212> TYPE: RNA
<213> ORGANISM: Artificial Sequence
<220> FEATURE:
<223> OTHER INFORMATION: Synthetic

<400> SEQUENCE: 219
gaaaaaucag agagauccu                                                    19

<210> SEQ ID NO 220
<211> LENGTH: 19
<212> TYPE: RNA
<213> ORGANISM: Artificial Sequence
<220> FEATURE:
<223> OTHER INFORMATION: Synthetic

<400> SEQUENCE: 220
aagaaaaauc agagagauc                                                    19

<210> SEQ ID NO 221
<211> LENGTH: 19
<212> TYPE: RNA
<213> ORGANISM: Artificial Sequence
<220> FEATURE:
<223> OTHER INFORMATION: Synthetic

<400> SEQUENCE: 221
gcaagaaaaa ucagagaga                                                    19

<210> SEQ ID NO 222
<211> LENGTH: 19
```

<212> TYPE: RNA
<213> ORGANISM: Artificial Sequence
<220> FEATURE:
<223> OTHER INFORMATION: Synthetic

<400> SEQUENCE: 222
acgcaagaaa aaucagaga                                                    19

<210> SEQ ID NO 223
<211> LENGTH: 19
<212> TYPE: RNA
<213> ORGANISM: Artificial Sequence
<220> FEATURE:
<223> OTHER INFORMATION: Synthetic

<400> SEQUENCE: 223
cgacgcaaga aaaaucaga                                                    19

<210> SEQ ID NO 224
<211> LENGTH: 19
<212> TYPE: RNA
<213> ORGANISM: Artificial Sequence
<220> FEATURE:
<223> OTHER INFORMATION: Synthetic

<400> SEQUENCE: 224
cucgacgcaa gaaaaauca                                                    19

<210> SEQ ID NO 225
<211> LENGTH: 19
<212> TYPE: RNA
<213> ORGANISM: Artificial Sequence
<220> FEATURE:
<223> OTHER INFORMATION: Synthetic

<400> SEQUENCE: 225
aacucgacgc aagaaaaau                                                    19

<210> SEQ ID NO 226
<211> LENGTH: 19
<212> TYPE: RNA
<213> ORGANISM: Artificial Sequence
<220> FEATURE:
<223> OTHER INFORMATION: Synthetic

<400> SEQUENCE: 226
aaaacucgac gcaagaaaa                                                    19

<210> SEQ ID NO 227
<211> LENGTH: 19
<212> TYPE: RNA
<213> ORGANISM: Artificial Sequence
<220> FEATURE:
<223> OTHER INFORMATION: Synthetic

<400> SEQUENCE: 227
ggaaaacucg acgcaagaa                                                    19

<210> SEQ ID NO 228
<211> LENGTH: 19
<212> TYPE: RNA
<213> ORGANISM: Artificial Sequence
<220> FEATURE:
<223> OTHER INFORMATION: Synthetic

<400> SEQUENCE: 228
ccggaaaacu cgacgcaag                                                    19

<210> SEQ ID NO 229
<211> LENGTH: 19
<212> TYPE: RNA
<213> ORGANISM: Artificial Sequence
<220> FEATURE:
<223> OTHER INFORMATION: Synthetic

<400> SEQUENCE: 229
uaccggaaaa cucgacgca                                                19

<210> SEQ ID NO 230
<211> LENGTH: 19
<212> TYPE: RNA
<213> ORGANISM: Artificial Sequence
<220> FEATURE:
<223> OTHER INFORMATION: Synthetic

<400> SEQUENCE: 230
cuuaccggaa aacucgacg                                                19

<210> SEQ ID NO 231
<211> LENGTH: 19
<212> TYPE: RNA
<213> ORGANISM: Artificial Sequence
<220> FEATURE:
<223> OTHER INFORMATION: Synthetic

<400> SEQUENCE: 231
gucuuaccgg aaaacucga                                                19

<210> SEQ ID NO 232
<211> LENGTH: 19
<212> TYPE: RNA
<213> ORGANISM: Artificial Sequence
<220> FEATURE:
<223> OTHER INFORMATION: Synthetic

<400> SEQUENCE: 232
aggucuuacc ggaaaacuc                                                19

<210> SEQ ID NO 233
<211> LENGTH: 19
<212> TYPE: RNA
<213> ORGANISM: Artificial Sequence
<220> FEATURE:
<223> OTHER INFORMATION: Synthetic

<400> SEQUENCE: 233
aaaggucuua ccggaaaac                                                19

<210> SEQ ID NO 234
<211> LENGTH: 19
<212> TYPE: RNA
<213> ORGANISM: Artificial Sequence
<220> FEATURE:
<223> OTHER INFORMATION: Synthetic

<400> SEQUENCE: 234
cgaaaggucu uaccggaaa                                                19

<210> SEQ ID NO 235
<211> LENGTH: 19
<212> TYPE: RNA
<213> ORGANISM: Artificial Sequence
<220> FEATURE:
<223> OTHER INFORMATION: Synthetic

```
<400> SEQUENCE: 235
accgaaaggu cuuaccgga                                            19

<210> SEQ ID NO 236
<211> LENGTH: 19
<212> TYPE: RNA
<213> ORGANISM: Artificial Sequence
<220> FEATURE:
<223> OTHER INFORMATION: Synthetic

<400> SEQUENCE: 236
guaccgaaag gucuuaccg                                            19

<210> SEQ ID NO 237
<211> LENGTH: 19
<212> TYPE: RNA
<213> ORGANISM: Artificial Sequence
<220> FEATURE:
<223> OTHER INFORMATION: Synthetic

<400> SEQUENCE: 237
aaguaccgaa aggucuuac                                            19

<210> SEQ ID NO 238
<211> LENGTH: 19
<212> TYPE: RNA
<213> ORGANISM: Artificial Sequence
<220> FEATURE:
<223> OTHER INFORMATION: Synthetic

<400> SEQUENCE: 238
cgaaguaccg aaaggucuu                                            19

<210> SEQ ID NO 239
<211> LENGTH: 19
<212> TYPE: RNA
<213> ORGANISM: Artificial Sequence
<220> FEATURE:
<223> OTHER INFORMATION: Synthetic

<400> SEQUENCE: 239
gacgaaguac cgaaagguc                                            19

<210> SEQ ID NO 240
<211> LENGTH: 19
<212> TYPE: RNA
<213> ORGANISM: Artificial Sequence
<220> FEATURE:
<223> OTHER INFORMATION: Synthetic

<400> SEQUENCE: 240
uggacgaagu accgaaagg                                            19

<210> SEQ ID NO 241
<211> LENGTH: 19
<212> TYPE: RNA
<213> ORGANISM: Artificial Sequence
<220> FEATURE:
<223> OTHER INFORMATION: Synthetic

<400> SEQUENCE: 241
uguggacgaa guaccgaaa                                            19

<210> SEQ ID NO 242
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 242
uuuguggacg aaguaccga                                               19

<210> SEQ ID NO 243
<211> LENGTH: 19
<212> TYPE: RNA
<213> ORGANISM: Artificial Sequence
<220> FEATURE:
<223> OTHER INFORMATION: Synthetic

<400> SEQUENCE: 243
uguuugugga cgaaguacc                                               19

<210> SEQ ID NO 244
<211> LENGTH: 19
<212> TYPE: RNA
<213> ORGANISM: Artificial Sequence
<220> FEATURE:
<223> OTHER INFORMATION: Synthetic

<400> SEQUENCE: 244
uguguuugug gacgaagua                                               19

<210> SEQ ID NO 245
<211> LENGTH: 19
<212> TYPE: RNA
<213> ORGANISM: Artificial Sequence
<220> FEATURE:
<223> OTHER INFORMATION: Synthetic

<400> SEQUENCE: 245
guuguguuug uggacgaag                                               19

<210> SEQ ID NO 246
<211> LENGTH: 19
<212> TYPE: RNA
<213> ORGANISM: Artificial Sequence
<220> FEATURE:
<223> OTHER INFORMATION: Synthetic

<400> SEQUENCE: 246
gaguuguguu uguggacga                                               19

<210> SEQ ID NO 247
<211> LENGTH: 19
<212> TYPE: RNA
<213> ORGANISM: Artificial Sequence
<220> FEATURE:
<223> OTHER INFORMATION: Synthetic

<400> SEQUENCE: 247
aggaguugug uuuguggac                                               19

<210> SEQ ID NO 248
<211> LENGTH: 19
<212> TYPE: RNA
<213> ORGANISM: Artificial Sequence
<220> FEATURE:
<223> OTHER INFORMATION: Synthetic

<400> SEQUENCE: 248
ggaggaguug uguuugugg                                               19
```

<210> SEQ ID NO 249
<211> LENGTH: 19
<212> TYPE: RNA
<213> ORGANISM: Artificial Sequence
<220> FEATURE:
<223> OTHER INFORMATION: Synthetic

<400> SEQUENCE: 249
gcggaggagu uguguuugu                                              19

<210> SEQ ID NO 250
<211> LENGTH: 19
<212> TYPE: RNA
<213> ORGANISM: Artificial Sequence
<220> FEATURE:
<223> OTHER INFORMATION: Synthetic

<400> SEQUENCE: 250
gcgcggagga guuguguuu                                              19

<210> SEQ ID NO 251
<211> LENGTH: 19
<212> TYPE: RNA
<213> ORGANISM: Artificial Sequence
<220> FEATURE:
<223> OTHER INFORMATION: Synthetic

<400> SEQUENCE: 251
uugcgcggag gaguugugu                                              19

<210> SEQ ID NO 252
<211> LENGTH: 19
<212> TYPE: RNA
<213> ORGANISM: Artificial Sequence
<220> FEATURE:
<223> OTHER INFORMATION: Synthetic

<400> SEQUENCE: 252
aguugcgcgg aggaguugu                                              19

<210> SEQ ID NO 253
<211> LENGTH: 19
<212> TYPE: RNA
<213> ORGANISM: Artificial Sequence
<220> FEATURE:
<223> OTHER INFORMATION: Synthetic

<400> SEQUENCE: 253
aaaguugcgc ggaggaguu                                              19

<210> SEQ ID NO 254
<211> LENGTH: 19
<212> TYPE: RNA
<213> ORGANISM: Artificial Sequence
<220> FEATURE:
<223> OTHER INFORMATION: Synthetic

<400> SEQUENCE: 254
aaaaaguugc gcggaggag                                              19

<210> SEQ ID NO 255
<211> LENGTH: 19
<212> TYPE: RNA
<213> ORGANISM: Artificial Sequence
<220> FEATURE:
<223> OTHER INFORMATION: Synthetic

<400> SEQUENCE: 255
cgaaaaaguu gcgcggagg                                                19

<210> SEQ ID NO 256
<211> LENGTH: 19
<212> TYPE: RNA
<213> ORGANISM: Artificial Sequence
<220> FEATURE:
<223> OTHER INFORMATION: Synthetic

<400> SEQUENCE: 256
cgcgaaaaag uugcgcgga                                                19

<210> SEQ ID NO 257
<211> LENGTH: 19
<212> TYPE: RNA
<213> ORGANISM: Artificial Sequence
<220> FEATURE:
<223> OTHER INFORMATION: Synthetic

<400> SEQUENCE: 257
accgcgaaaa aguugcgcg                                                19

<210> SEQ ID NO 258
<211> LENGTH: 19
<212> TYPE: RNA
<213> ORGANISM: Artificial Sequence
<220> FEATURE:
<223> OTHER INFORMATION: Synthetic

<400> SEQUENCE: 258
caaccgcgaa aaaguugcg                                                19

<210> SEQ ID NO 259
<211> LENGTH: 19
<212> TYPE: RNA
<213> ORGANISM: Artificial Sequence
<220> FEATURE:
<223> OTHER INFORMATION: Synthetic

<400> SEQUENCE: 259
aacaaccgcg aaaaaguug                                                19

<210> SEQ ID NO 260
<211> LENGTH: 19
<212> TYPE: RNA
<213> ORGANISM: Artificial Sequence
<220> FEATURE:
<223> OTHER INFORMATION: Synthetic

<400> SEQUENCE: 260
guaacaaccg cgaaaaagu                                                19

<210> SEQ ID NO 261
<211> LENGTH: 19
<212> TYPE: RNA
<213> ORGANISM: Artificial Sequence
<220> FEATURE:
<223> OTHER INFORMATION: Synthetic

<400> SEQUENCE: 261
aaguaacaac cgcgaaaaa                                                19

<210> SEQ ID NO 262
<211> LENGTH: 19

```
<212> TYPE: RNA
<213> ORGANISM: Artificial Sequence
<220> FEATURE:
<223> OTHER INFORMATION: Synthetic

<400> SEQUENCE: 262
ucaaguaaca accgcgaaa                                                    19

<210> SEQ ID NO 263
<211> LENGTH: 19
<212> TYPE: RNA
<213> ORGANISM: Artificial Sequence
<220> FEATURE:
<223> OTHER INFORMATION: Synthetic

<400> SEQUENCE: 263
agucaaguaa caaccgcga                                                    19

<210> SEQ ID NO 264
<211> LENGTH: 19
<212> TYPE: RNA
<213> ORGANISM: Artificial Sequence
<220> FEATURE:
<223> OTHER INFORMATION: Synthetic

<400> SEQUENCE: 264
ccagucaagu aacaaccgc                                                    19

<210> SEQ ID NO 265
<211> LENGTH: 19
<212> TYPE: RNA
<213> ORGANISM: Artificial Sequence
<220> FEATURE:
<223> OTHER INFORMATION: Synthetic

<400> SEQUENCE: 265
cgccagucaa guaacaacc                                                    19

<210> SEQ ID NO 266
<211> LENGTH: 19
<212> TYPE: RNA
<213> ORGANISM: Artificial Sequence
<220> FEATURE:
<223> OTHER INFORMATION: Synthetic

<400> SEQUENCE: 266
gucgccaguc aaguaacaa                                                    19

<210> SEQ ID NO 267
<211> LENGTH: 19
<212> TYPE: RNA
<213> ORGANISM: Artificial Sequence
<220> FEATURE:
<223> OTHER INFORMATION: Synthetic

<400> SEQUENCE: 267
acgucgccag ucaaguaac                                                    19

<210> SEQ ID NO 268
<211> LENGTH: 19
<212> TYPE: RNA
<213> ORGANISM: Artificial Sequence
<220> FEATURE:
<223> OTHER INFORMATION: Synthetic

<400> SEQUENCE: 268
uuacgucgcc agucaagua                                                    19
```

<210> SEQ ID NO 269
<211> LENGTH: 19
<212> TYPE: RNA
<213> ORGANISM: Artificial Sequence
<220> FEATURE:
<223> OTHER INFORMATION: Synthetic

<400> SEQUENCE: 269
gauuacgucg ccagucaag                                          19

<210> SEQ ID NO 270
<211> LENGTH: 19
<212> TYPE: RNA
<213> ORGANISM: Artificial Sequence
<220> FEATURE:
<223> OTHER INFORMATION: Synthetic

<400> SEQUENCE: 270
uggauuacgu cgccaguca                                          19

<210> SEQ ID NO 271
<211> LENGTH: 19
<212> TYPE: RNA
<213> ORGANISM: Artificial Sequence
<220> FEATURE:
<223> OTHER INFORMATION: Synthetic

<400> SEQUENCE: 271
cguggauuac gucgccagu                                          19

<210> SEQ ID NO 272
<211> LENGTH: 19
<212> TYPE: RNA
<213> ORGANISM: Artificial Sequence
<220> FEATURE:
<223> OTHER INFORMATION: Synthetic

<400> SEQUENCE: 272
aucguggauu acgucgcca                                          19

<210> SEQ ID NO 273
<211> LENGTH: 19
<212> TYPE: RNA
<213> ORGANISM: Artificial Sequence
<220> FEATURE:
<223> OTHER INFORMATION: Synthetic

<400> SEQUENCE: 273
agaucgugga uuacgucgc                                          19

<210> SEQ ID NO 274
<211> LENGTH: 19
<212> TYPE: RNA
<213> ORGANISM: Artificial Sequence
<220> FEATURE:
<223> OTHER INFORMATION: Synthetic

<400> SEQUENCE: 274
agagaucgug gauuacguc                                          19

<210> SEQ ID NO 275
<211> LENGTH: 19
<212> TYPE: RNA
<213> ORGANISM: Artificial Sequence
<220> FEATURE:
<223> OTHER INFORMATION: Synthetic

```
<400> SEQUENCE: 275
aaagagaucg uggauuacg                                               19

<210> SEQ ID NO 276
<211> LENGTH: 19
<212> TYPE: RNA
<213> ORGANISM: Artificial Sequence
<220> FEATURE:
<223> OTHER INFORMATION: Synthetic

<400> SEQUENCE: 276
aaaaagagau cguggauua                                               19

<210> SEQ ID NO 277
<211> LENGTH: 18
<212> TYPE: RNA
<213> ORGANISM: Artificial Sequence
<220> FEATURE:
<223> OTHER INFORMATION: Synthetic

<400> SEQUENCE: 277
gaaaaagaga ucguggau                                                18

<210> SEQ ID NO 278
<211> LENGTH: 19
<212> TYPE: RNA
<213> ORGANISM: Artificial Sequence
<220> FEATURE:
<223> OTHER INFORMATION: Synthetic

<400> SEQUENCE: 278
acggaaaaag agaucgugg                                               19

<210> SEQ ID NO 279
<211> LENGTH: 19
<212> TYPE: RNA
<213> ORGANISM: Artificial Sequence
<220> FEATURE:
<223> OTHER INFORMATION: Synthetic

<400> SEQUENCE: 279
ugacggaaaa agagaucgu                                               19

<210> SEQ ID NO 280
<211> LENGTH: 19
<212> TYPE: RNA
<213> ORGANISM: Artificial Sequence
<220> FEATURE:
<223> OTHER INFORMATION: Synthetic

<400> SEQUENCE: 280
gaugacggaa aaagagauc                                               19

<210> SEQ ID NO 281
<211> LENGTH: 19
<212> TYPE: RNA
<213> ORGANISM: Artificial Sequence
<220> FEATURE:
<223> OTHER INFORMATION: Synthetic

<400> SEQUENCE: 281
acgaugacgg aaaaagaga                                               19

<210> SEQ ID NO 282
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 282
agacgaugac ggaaaaaga                                                      19

<210> SEQ ID NO 283
<211> LENGTH: 19
<212> TYPE: RNA
<213> ORGANISM: Artificial Sequence
<220> FEATURE:
<223> OTHER INFORMATION: Synthetic

<400> SEQUENCE: 283
aaagacgaug acggaaaaa                                                      19

<210> SEQ ID NO 284
<211> LENGTH: 19
<212> TYPE: RNA
<213> ORGANISM: Artificial Sequence
<220> FEATURE:
<223> OTHER INFORMATION: Synthetic

<400> SEQUENCE: 284
ggaaagacga ugacggaaa                                                      19

<210> SEQ ID NO 285
<211> LENGTH: 19
<212> TYPE: RNA
<213> ORGANISM: Artificial Sequence
<220> FEATURE:
<223> OTHER INFORMATION: Synthetic

<400> SEQUENCE: 285
acggaaagac gaugacgga                                                      19

<210> SEQ ID NO 286
<211> LENGTH: 19
<212> TYPE: RNA
<213> ORGANISM: Artificial Sequence
<220> FEATURE:
<223> OTHER INFORMATION: Synthetic

<400> SEQUENCE: 286
gcacggaaag acgaugacg                                                      19

<210> SEQ ID NO 287
<211> LENGTH: 19
<212> TYPE: RNA
<213> ORGANISM: Artificial Sequence
<220> FEATURE:
<223> OTHER INFORMATION: Synthetic

<400> SEQUENCE: 287
gagcacggaa agacgauga                                                      19

<210> SEQ ID NO 288
<211> LENGTH: 19
<212> TYPE: RNA
<213> ORGANISM: Artificial Sequence
<220> FEATURE:
<223> OTHER INFORMATION: Synthetic

<400> SEQUENCE: 288
uggagcacgg aaagacgau                                                      19
```

<210> SEQ ID NO 289
<211> LENGTH: 19
<212> TYPE: RNA
<213> ORGANISM: Artificial Sequence
<220> FEATURE:
<223> OTHER INFORMATION: Synthetic

<400> SEQUENCE: 289
uuuggagcac ggaaagacg                                          19

<210> SEQ ID NO 290
<211> LENGTH: 19
<212> TYPE: RNA
<213> ORGANISM: Artificial Sequence
<220> FEATURE:
<223> OTHER INFORMATION: Synthetic

<400> SEQUENCE: 290 guuuggagc acggaaaga                                           19

<210> SEQ ID NO 291
<211> LENGTH: 19
<212> TYPE: RNA
<213> ORGANISM: Artificial Sequence
<220> FEATURE:
<223> OTHER INFORMATION: Synthetic

<400> SEQUENCE: 291
uuguuuugga gcacggaaa                                          19

<210> SEQ ID NO 292
<211> LENGTH: 19
<212> TYPE: RNA
<213> ORGANISM: Artificial Sequence
<220> FEATURE:
<223> OTHER INFORMATION: Synthetic

<400> SEQUENCE: 292
uguuguuuug gagcacgga                                          19

<210> SEQ ID NO 293
<211> LENGTH: 19
<212> TYPE: RNA
<213> ORGANISM: Artificial Sequence
<220> FEATURE:
<223> OTHER INFORMATION: Synthetic

<400> SEQUENCE: 293
guuguuguuu uggagcacg                                          19

<210> SEQ ID NO 294
<211> LENGTH: 19
<212> TYPE: RNA
<213> ORGANISM: Artificial Sequence
<220> FEATURE:
<223> OTHER INFORMATION: Synthetic

<400> SEQUENCE: 294
ccguuguugu uuuggagca                                          19

<210> SEQ ID NO 295
<211> LENGTH: 19
<212> TYPE: RNA
<213> ORGANISM: Artificial Sequence
<220> FEATURE:
<223> OTHER INFORMATION: Synthetic

```
<400> SEQUENCE: 295
cgccguuguu guuuuggag                                              19

<210> SEQ ID NO 296
<211> LENGTH: 19
<212> TYPE: RNA
<213> ORGANISM: Artificial Sequence
<220> FEATURE:
<223> OTHER INFORMATION: Synthetic

<400> SEQUENCE: 296
gccgccguug uuguuuugg                                              19

<210> SEQ ID NO 297
<211> LENGTH: 19
<212> TYPE: RNA
<213> ORGANISM: Artificial Sequence
<220> FEATURE:
<223> OTHER INFORMATION: Synthetic

<400> SEQUENCE: 297
ccgccgccgu uguuguuuu                                              19

<210> SEQ ID NO 298
<211> LENGTH: 19
<212> TYPE: RNA
<213> ORGANISM: Artificial Sequence
<220> FEATURE:
<223> OTHER INFORMATION: Synthetic

<400> SEQUENCE: 298
ucccgccgcc guuguuguu                                              19

<210> SEQ ID NO 299
<211> LENGTH: 19
<212> TYPE: RNA
<213> ORGANISM: Artificial Sequence
<220> FEATURE:
<223> OTHER INFORMATION: Synthetic

<400> SEQUENCE: 299
cuucccgccg ccguuguug                                              19

<210> SEQ ID NO 300
<211> LENGTH: 19
<212> TYPE: RNA
<213> ORGANISM: Artificial Sequence
<220> FEATURE:
<223> OTHER INFORMATION: Synthetic

<400> SEQUENCE: 300
aacuucccgc cgccguugu                                              19

<210> SEQ ID NO 301
<211> LENGTH: 19
<212> TYPE: RNA
<213> ORGANISM: Artificial Sequence
<220> FEATURE:
<223> OTHER INFORMATION: Synthetic

<400> SEQUENCE: 301
ugaacuuccc gccgccguu                                              19

<210> SEQ ID NO 302
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 302
gggagauagu gaugaagua                                                    19

<210> SEQ ID NO 303
<211> LENGTH: 19
<212> TYPE: RNA
<213> ORGANISM: Artificial Sequence
<220> FEATURE:
<223> OTHER INFORMATION: Synthetic

<400> SEQUENCE: 303
gaaguacauc cauuauaag                                                    19

<210> SEQ ID NO 304
<211> LENGTH: 19
<212> TYPE: RNA
<213> ORGANISM: Artificial Sequence
<220> FEATURE:
<223> OTHER INFORMATION: Synthetic

<400> SEQUENCE: 304
guacgacaac cgggagaua                                                    19

<210> SEQ ID NO 305
<211> LENGTH: 19
<212> TYPE: RNA
<213> ORGANISM: Artificial Sequence
<220> FEATURE:
<223> OTHER INFORMATION: Synthetic

<400> SEQUENCE: 305
agauagugau gaaguacau                                                    19

<210> SEQ ID NO 306
<211> LENGTH: 19
<212> TYPE: RNA
<213> ORGANISM: Artificial Sequence
<220> FEATURE:
<223> OTHER INFORMATION: Synthetic

<400> SEQUENCE: 306
ugaagacucu gcucaguuu                                                    19

<210> SEQ ID NO 307
<211> LENGTH: 19
<212> TYPE: RNA
<213> ORGANISM: Artificial Sequence
<220> FEATURE:
<223> OTHER INFORMATION: Synthetic

<400> SEQUENCE: 307
gcaugcggcc ucuguuuga                                                    19

<210> SEQ ID NO 308
<211> LENGTH: 19
<212> TYPE: RNA
<213> ORGANISM: Artificial Sequence
<220> FEATURE:
<223> OTHER INFORMATION: Synthetic

<400> SEQUENCE: 308
ugcggccucu guuugauuu                                                    19
```

<210> SEQ ID NO 309
<211> LENGTH: 19
<212> TYPE: RNA
<213> ORGANISM: Artificial Sequence
<220> FEATURE:
<223> OTHER INFORMATION: Synthetic

<400> SEQUENCE: 309
gagauaguga ugaaguaca                                                19

<210> SEQ ID NO 310
<211> LENGTH: 19
<212> TYPE: RNA
<213> ORGANISM: Artificial Sequence
<220> FEATURE:
<223> OTHER INFORMATION: Synthetic

<400> SEQUENCE: 310
ggagauagug augaaguac                                                19

<210> SEQ ID NO 311
<211> LENGTH: 19
<212> TYPE: RNA
<213> ORGANISM: Artificial Sequence
<220> FEATURE:
<223> OTHER INFORMATION: Synthetic

<400> SEQUENCE: 311
gaagacucug cucaguuug                                                19

<210> SEQ ID NO 312
<211> LENGTH: 19
<212> TYPE: DNA
<213> ORGANISM: Artificial Sequence
<220> FEATURE:
<223> OTHER INFORMATION: Synthetic

<400> SEQUENCE: 312
gaaagaatct gtagagaaa                                                19

<210> SEQ ID NO 313
<211> LENGTH: 19
<212> TYPE: DNA
<213> ORGANISM: Artificial Sequence
<220> FEATURE:
<223> OTHER INFORMATION: Synthetic

<400> SEQUENCE: 313
gcaatgagct gtttgaaga                                                19

<210> SEQ ID NO 314
<211> LENGTH: 19
<212> TYPE: DNA
<213> ORGANISM: Artificial Sequence
<220> FEATURE:
<223> OTHER INFORMATION: Synthetic

<400> SEQUENCE: 314
tgacaaaggt ggataaatt                                                19

<210> SEQ ID NO 315
<211> LENGTH: 19
<212> TYPE: DNA
<213> ORGANISM: Artificial Sequence
<220> FEATURE:
<223> OTHER INFORMATION: Synthetic

```
<400> SEQUENCE: 315
ggaaatggat ctctttgaa                                              19

<210> SEQ ID NO 316
<211> LENGTH: 19
<212> TYPE: DNA
<213> ORGANISM: Artificial Sequence
<220> FEATURE:
<223> OTHER INFORMATION: Synthetic

<400> SEQUENCE: 316
ggaaagtaat ggtccaaca                                              19

<210> SEQ ID NO 317
<211> LENGTH: 19
<212> TYPE: DNA
<213> ORGANISM: Artificial Sequence
<220> FEATURE:
<223> OTHER INFORMATION: Synthetic

<400> SEQUENCE: 317
agacagttat gcagctatt                                              19

<210> SEQ ID NO 318
<211> LENGTH: 19
<212> TYPE: DNA
<213> ORGANISM: Artificial Sequence
<220> FEATURE:
<223> OTHER INFORMATION: Synthetic

<400> SEQUENCE: 318
ccaattctcg gaagcaaga                                              19

<210> SEQ ID NO 319
<211> LENGTH: 19
<212> TYPE: DNA
<213> ORGANISM: Artificial Sequence
<220> FEATURE:
<223> OTHER INFORMATION: Synthetic

<400> SEQUENCE: 319
gaaagtaatg gtccaacag                                              19

<210> SEQ ID NO 320
<211> LENGTH: 19
<212> TYPE: DNA
<213> ORGANISM: Artificial Sequence
<220> FEATURE:
<223> OTHER INFORMATION: Synthetic

<400> SEQUENCE: 320
gcgccagagt gaacaagta                                              19

<210> SEQ ID NO 321
<211> LENGTH: 19
<212> TYPE: DNA
<213> ORGANISM: Artificial Sequence
<220> FEATURE:
<223> OTHER INFORMATION: Synthetic

<400> SEQUENCE: 321
gaaggtggcc cagctatgt                                              19

<210> SEQ ID NO 322
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 322
ggaaccagcg ccagagtga                                                  19

<210> SEQ ID NO 323
<211> LENGTH: 19
<212> TYPE: DNA
<213> ORGANISM: Artificial Sequence
<220> FEATURE:
<223> OTHER INFORMATION: Synthetic

<400> SEQUENCE: 323
gagcgagatt gcaggcata                                                  19

<210> SEQ ID NO 324
<211> LENGTH: 19
<212> TYPE: DNA
<213> ORGANISM: Artificial Sequence
<220> FEATURE:
<223> OTHER INFORMATION: Synthetic

<400> SEQUENCE: 324
gttagtatct gatgacttg                                                  19

<210> SEQ ID NO 325
<211> LENGTH: 19
<212> TYPE: DNA
<213> ORGANISM: Artificial Sequence
<220> FEATURE:
<223> OTHER INFORMATION: Synthetic

<400> SEQUENCE: 325
gaaatggaac cactaagaa                                                  19

<210> SEQ ID NO 326
<211> LENGTH: 19
<212> TYPE: DNA
<213> ORGANISM: Artificial Sequence
<220> FEATURE:
<223> OTHER INFORMATION: Synthetic

<400> SEQUENCE: 326
ggaaatggaa ccactaaga                                                  19

<210> SEQ ID NO 327
<211> LENGTH: 19
<212> TYPE: DNA
<213> ORGANISM: Artificial Sequence
<220> FEATURE:
<223> OTHER INFORMATION: Synthetic

<400> SEQUENCE: 327
caactacact ttccaatgc                                                  19

<210> SEQ ID NO 328
<211> LENGTH: 19
<212> TYPE: DNA
<213> ORGANISM: Artificial Sequence
<220> FEATURE:
<223> OTHER INFORMATION: Synthetic

<400> SEQUENCE: 328
ccaccaagat ttcatgata                                                  19
```

<210> SEQ ID NO 329
<211> LENGTH: 19
<212> TYPE: DNA
<213> ORGANISM: Artificial Sequence
<220> FEATURE:
<223> OTHER INFORMATION: Synthetic

<400> SEQUENCE: 329
gatcggaact ccaacaaga                                                    19

<210> SEQ ID NO 330
<211> LENGTH: 19
<212> TYPE: DNA
<213> ORGANISM: Artificial Sequence
<220> FEATURE:
<223> OTHER INFORMATION: Synthetic

<400> SEQUENCE: 330
aaacggagct acagattat                                                    19

<210> SEQ ID NO 331
<211> LENGTH: 19
<212> TYPE: DNA
<213> ORGANISM: Artificial Sequence
<220> FEATURE:
<223> OTHER INFORMATION: Synthetic

<400> SEQUENCE: 331
ccacacagca ttcttgtaa                                                    19

<210> SEQ ID NO 332
<211> LENGTH: 19
<212> TYPE: DNA
<213> ORGANISM: Artificial Sequence
<220> FEATURE:
<223> OTHER INFORMATION: Synthetic

<400> SEQUENCE: 332
gaagttacct tgagcaatc                                                    19

<210> SEQ ID NO 333
<211> LENGTH: 19
<212> TYPE: DNA
<213> ORGANISM: Artificial Sequence
<220> FEATURE:
<223> OTHER INFORMATION: Synthetic

<400> SEQUENCE: 333
ggacttggcc gatccagaa                                                    19

<210> SEQ ID NO 334
<211> LENGTH: 19
<212> TYPE: DNA
<213> ORGANISM: Artificial Sequence
<220> FEATURE:
<223> OTHER INFORMATION: Synthetic

<400> SEQUENCE: 334
gcacttggat cgagatgag                                                    19

<210> SEQ ID NO 335
<211> LENGTH: 19
<212> TYPE: DNA
<213> ORGANISM: Artificial Sequence
<220> FEATURE:
<223> OTHER INFORMATION: Synthetic

<400> SEQUENCE: 335
caaagaccaa ttcgcgtta                                                19

<210> SEQ ID NO 336
<211> LENGTH: 19
<212> TYPE: DNA
<213> ORGANISM: Artificial Sequence
<220> FEATURE:
<223> OTHER INFORMATION: Synthetic

<400> SEQUENCE: 336
ccgaatcaat cgcatcttc                                                19

<210> SEQ ID NO 337
<211> LENGTH: 19
<212> TYPE: DNA
<213> ORGANISM: Artificial Sequence
<220> FEATURE:
<223> OTHER INFORMATION: Synthetic

<400> SEQUENCE: 337
gacatgatcc tgcagttca                                                19

<210> SEQ ID NO 338
<211> LENGTH: 19
<212> TYPE: DNA
<213> ORGANISM: Artificial Sequence
<220> FEATURE:
<223> OTHER INFORMATION: Synthetic

<400> SEQUENCE: 338
gagcgaatcg tcaccactt                                                19

<210> SEQ ID NO 339
<211> LENGTH: 19
<212> TYPE: DNA
<213> ORGANISM: Artificial Sequence
<220> FEATURE:
<223> OTHER INFORMATION: Synthetic

<400> SEQUENCE: 339
cctccgagct ggcgtctac                                                19

<210> SEQ ID NO 340
<211> LENGTH: 19
<212> TYPE: DNA
<213> ORGANISM: Artificial Sequence
<220> FEATURE:
<223> OTHER INFORMATION: Synthetic

<400> SEQUENCE: 340
tcacatggtt aacctctaa                                                19

<210> SEQ ID NO 341
<211> LENGTH: 19
<212> TYPE: DNA
<213> ORGANISM: Artificial Sequence
<220> FEATURE:
<223> OTHER INFORMATION: Synthetic

<400> SEQUENCE: 341
gatgagggac gccataatc                                                19

<210> SEQ ID NO 342
<211> LENGTH: 19

```
<212> TYPE: DNA
<213> ORGANISM: Artificial Sequence
<220> FEATURE:
<223> OTHER INFORMATION: Synthetic

<400> SEQUENCE: 342
cctctaacta caaatctta                                                19

<210> SEQ ID NO 343
<211> LENGTH: 19
<212> TYPE: DNA
<213> ORGANISM: Artificial Sequence
<220> FEATURE:
<223> OTHER INFORMATION: Synthetic

<400> SEQUENCE: 343
ggaaggtgct atccaaaat                                                19

<210> SEQ ID NO 344
<211> LENGTH: 19
<212> TYPE: DNA
<213> ORGANISM: Artificial Sequence
<220> FEATURE:
<223> OTHER INFORMATION: Synthetic

<400> SEQUENCE: 344
gcaagcaagt cctaacatt                                                19

<210> SEQ ID NO 345
<211> LENGTH: 19
<212> TYPE: DNA
<213> ORGANISM: Artificial Sequence
<220> FEATURE:
<223> OTHER INFORMATION: Synthetic

<400> SEQUENCE: 345
ggaagaggag tagaccttta                                               19

<210> SEQ ID NO 346
<211> LENGTH: 19
<212> TYPE: DNA
<213> ORGANISM: Artificial Sequence
<220> FEATURE:
<223> OTHER INFORMATION: Synthetic

<400> SEQUENCE: 346
aggaatcagt gttgtagta                                                19

<210> SEQ ID NO 347
<211> LENGTH: 19
<212> TYPE: DNA
<213> ORGANISM: Artificial Sequence
<220> FEATURE:
<223> OTHER INFORMATION: Synthetic

<400> SEQUENCE: 347
gaagaggagt agaccttac                                                19

<210> SEQ ID NO 348
<211> LENGTH: 19
<212> TYPE: DNA
<213> ORGANISM: Artificial Sequence
<220> FEATURE:
<223> OTHER INFORMATION: Synthetic

<400> SEQUENCE: 348
gaaagtcaag cctggtatt                                                19
```

<210> SEQ ID NO 349
<211> LENGTH: 19
<212> TYPE: DNA
<213> ORGANISM: Artificial Sequence
<220> FEATURE:
<223> OTHER INFORMATION: Synthetic

<400> SEQUENCE: 349
aaagtcaagc ctggtatta                                                    19

<210> SEQ ID NO 350
<211> LENGTH: 19
<212> TYPE: DNA
<213> ORGANISM: Artificial Sequence
<220> FEATURE:
<223> OTHER INFORMATION: Synthetic

<400> SEQUENCE: 350
gctatgaacg tgaatgatc                                                    19

<210> SEQ ID NO 351
<211> LENGTH: 19
<212> TYPE: DNA
<213> ORGANISM: Artificial Sequence
<220> FEATURE:
<223> OTHER INFORMATION: Synthetic

<400> SEQUENCE: 351
caagcctggt attacgttt                                                    19

<210> SEQ ID NO 352
<211> LENGTH: 19
<212> TYPE: DNA
<213> ORGANISM: Artificial Sequence
<220> FEATURE:
<223> OTHER INFORMATION: Synthetic

<400> SEQUENCE: 352
ggaacaagat ctgtcaatt                                                    19

<210> SEQ ID NO 353
<211> LENGTH: 19
<212> TYPE: DNA
<213> ORGANISM: Artificial Sequence
<220> FEATURE:
<223> OTHER INFORMATION: Synthetic

<400> SEQUENCE: 353
gcaatgaacg tgaacgaaa                                                    19

<210> SEQ ID NO 354
<211> LENGTH: 19
<212> TYPE: DNA
<213> ORGANISM: Artificial Sequence
<220> FEATURE:
<223> OTHER INFORMATION: Synthetic

<400> SEQUENCE: 354
caatgaacgt gaacgaaat                                                    19

<210> SEQ ID NO 355
<211> LENGTH: 19
<212> TYPE: DNA
<213> ORGANISM: Artificial Sequence
<220> FEATURE:
<223> OTHER INFORMATION: Synthetic

```
<400> SEQUENCE: 355
ggacaggagc ggtatcaca                                               19

<210> SEQ ID NO 356
<211> LENGTH: 19
<212> TYPE: DNA
<213> ORGANISM: Artificial Sequence
<220> FEATURE:
<223> OTHER INFORMATION: Synthetic

<400> SEQUENCE: 356
agacagagct tgagaataa                                               19

<210> SEQ ID NO 357
<211> LENGTH: 19
<212> TYPE: DNA
<213> ORGANISM: Artificial Sequence
<220> FEATURE:
<223> OTHER INFORMATION: Synthetic

<400> SEQUENCE: 357
gagaagatct ttatgcaaa                                               19

<210> SEQ ID NO 358
<211> LENGTH: 19
<212> TYPE: DNA
<213> ORGANISM: Artificial Sequence
<220> FEATURE:
<223> OTHER INFORMATION: Synthetic

<400> SEQUENCE: 358
gaagagaaat cagcagata                                               19

<210> SEQ ID NO 359
<211> LENGTH: 19
<212> TYPE: DNA
<213> ORGANISM: Artificial Sequence
<220> FEATURE:
<223> OTHER INFORMATION: Synthetic

<400> SEQUENCE: 359
gcaagtaact caactaaca                                               19

<210> SEQ ID NO 360
<211> LENGTH: 19
<212> TYPE: DNA
<213> ORGANISM: Artificial Sequence
<220> FEATURE:
<223> OTHER INFORMATION: Synthetic

<400> SEQUENCE: 360
gagctaatct gccacattg                                               19

<210> SEQ ID NO 361
<211> LENGTH: 19
<212> TYPE: DNA
<213> ORGANISM: Artificial Sequence
<220> FEATURE:
<223> OTHER INFORMATION: Synthetic

<400> SEQUENCE: 361
gcagatgagt tactagaaa                                               19

<210> SEQ ID NO 362
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 362
caacttaatt gtccagaaa                                               19

<210> SEQ ID NO 363
<211> LENGTH: 19
<212> TYPE: DNA
<213> ORGANISM: Artificial Sequence
<220> FEATURE:
<223> OTHER INFORMATION: Synthetic

<400> SEQUENCE: 363
caacacagga ttctgataa                                               19

<210> SEQ ID NO 364
<211> LENGTH: 19
<212> TYPE: DNA
<213> ORGANISM: Artificial Sequence
<220> FEATURE:
<223> OTHER INFORMATION: Synthetic

<400> SEQUENCE: 364
agattgtgcc taagtctct                                               19

<210> SEQ ID NO 365
<211> LENGTH: 19
<212> TYPE: DNA
<213> ORGANISM: Artificial Sequence
<220> FEATURE:
<223> OTHER INFORMATION: Synthetic

<400> SEQUENCE: 365
atgaagatct ggaggtgaa                                               19

<210> SEQ ID NO 366
<211> LENGTH: 19
<212> TYPE: DNA
<213> ORGANISM: Artificial Sequence
<220> FEATURE:
<223> OTHER INFORMATION: Synthetic

<400> SEQUENCE: 366
tttgagactt cttgcctaa                                               19

<210> SEQ ID NO 367
<211> LENGTH: 19
<212> TYPE: DNA
<213> ORGANISM: Artificial Sequence
<220> FEATURE:
<223> OTHER INFORMATION: Synthetic

<400> SEQUENCE: 367
agatcaccct ccttaaata                                               19

<210> SEQ ID NO 368
<211> LENGTH: 19
<212> TYPE: DNA
<213> ORGANISM: Artificial Sequence
<220> FEATURE:
<223> OTHER INFORMATION: Synthetic

<400> SEQUENCE: 368
caacggattt ggtcgtatt                                               19
```

<210> SEQ ID NO 369
<211> LENGTH: 19
<212> TYPE: DNA
<213> ORGANISM: Artificial Sequence
<220> FEATURE:
<223> OTHER INFORMATION: Synthetic

<400> SEQUENCE: 369
gaaatcccat caccatctt                                                    19

<210> SEQ ID NO 370
<211> LENGTH: 19
<212> TYPE: DNA
<213> ORGANISM: Artificial Sequence
<220> FEATURE:
<223> OTHER INFORMATION: Synthetic

<400> SEQUENCE: 370
gacctcaact acatggttt                                                    19

<210> SEQ ID NO 371
<211> LENGTH: 19
<212> TYPE: DNA
<213> ORGANISM: Artificial Sequence
<220> FEATURE:
<223> OTHER INFORMATION: Synthetic

<400> SEQUENCE: 371
tggtttacat gttccaata                                                    19

<210> SEQ ID NO 372
<211> LENGTH: 19
<212> TYPE: DNA
<213> ORGANISM: Artificial Sequence
<220> FEATURE:
<223> OTHER INFORMATION: Synthetic

<400> SEQUENCE: 372
gaagaaatcg atgttgttt                                                    19

<210> SEQ ID NO 373
<211> LENGTH: 19
<212> TYPE: DNA
<213> ORGANISM: Artificial Sequence
<220> FEATURE:
<223> OTHER INFORMATION: Synthetic

<400> SEQUENCE: 373
acacaaactt gaacagcta                                                    19

<210> SEQ ID NO 374
<211> LENGTH: 19
<212> TYPE: DNA
<213> ORGANISM: Artificial Sequence
<220> FEATURE:
<223> OTHER INFORMATION: Synthetic

<400> SEQUENCE: 374
ggaagaaatc gatgttgtt                                                    19

<210> SEQ ID NO 375
<211> LENGTH: 19
<212> TYPE: DNA
<213> ORGANISM: Artificial Sequence
<220> FEATURE:
<223> OTHER INFORMATION: Synthetic

<400> SEQUENCE: 375
gaaacgacga gaacagttg                                              19

<210> SEQ ID NO 376
<211> LENGTH: 19
<212> TYPE: DNA
<213> ORGANISM: Artificial Sequence
<220> FEATURE:
<223> OTHER INFORMATION: Synthetic

<400> SEQUENCE: 376
gcacatggat ggaggttct                                              19

<210> SEQ ID NO 377
<211> LENGTH: 19
<212> TYPE: DNA
<213> ORGANISM: Artificial Sequence
<220> FEATURE:
<223> OTHER INFORMATION: Synthetic

<400> SEQUENCE: 377
gcagagagag cagatttga                                              19

<210> SEQ ID NO 378
<211> LENGTH: 19
<212> TYPE: DNA
<213> ORGANISM: Artificial Sequence
<220> FEATURE:
<223> OTHER INFORMATION: Synthetic

<400> SEQUENCE: 378
gaggttctct ggatcaagt                                              19

<210> SEQ ID NO 379
<211> LENGTH: 19
<212> TYPE: DNA
<213> ORGANISM: Artificial Sequence
<220> FEATURE:
<223> OTHER INFORMATION: Synthetic

<400> SEQUENCE: 379
gagcagattt gaagcaact                                              19

<210> SEQ ID NO 380
<211> LENGTH: 19
<212> TYPE: DNA
<213> ORGANISM: Artificial Sequence
<220> FEATURE:
<223> OTHER INFORMATION: Synthetic

<400> SEQUENCE: 380
caaagacgat gacttcgaa                                              19

<210> SEQ ID NO 381
<211> LENGTH: 19
<212> TYPE: DNA
<213> ORGANISM: Artificial Sequence
<220> FEATURE:
<223> OTHER INFORMATION: Synthetic

<400> SEQUENCE: 381
gatcagcatt tgcatggaa                                              19

<210> SEQ ID NO 382
<211> LENGTH: 19

<212> TYPE: DNA
<213> ORGANISM: Artificial Sequence
<220> FEATURE:
<223> OTHER INFORMATION: Synthetic

<400> SEQUENCE: 382
tccaggagtt tgtcaataa					19

<210> SEQ ID NO 383
<211> LENGTH: 19
<212> TYPE: DNA
<213> ORGANISM: Artificial Sequence
<220> FEATURE:
<223> OTHER INFORMATION: Synthetic

<400> SEQUENCE: 383
ggaagctgat ccaccttga					19

<210> SEQ ID NO 384
<211> LENGTH: 19
<212> TYPE: DNA
<213> ORGANISM: Artificial Sequence
<220> FEATURE:
<223> OTHER INFORMATION: Synthetic

<400> SEQUENCE: 384
gcagaaatct aaggatata					19

<210> SEQ ID NO 385
<211> LENGTH: 19
<212> TYPE: DNA
<213> ORGANISM: Artificial Sequence
<220> FEATURE:
<223> OTHER INFORMATION: Synthetic

<400> SEQUENCE: 385
caacaaggat gaagtctat					19

<210> SEQ ID NO 386
<211> LENGTH: 19
<212> TYPE: DNA
<213> ORGANISM: Artificial Sequence
<220> FEATURE:
<223> OTHER INFORMATION: Synthetic

<400> SEQUENCE: 386
cagcagaaat ctaaggata					19

<210> SEQ ID NO 387
<211> LENGTH: 19
<212> TYPE: DNA
<213> ORGANISM: Artificial Sequence
<220> FEATURE:
<223> OTHER INFORMATION: Synthetic

<400> SEQUENCE: 387
ctagatggct ttctcagta					19

<210> SEQ ID NO 388
<211> LENGTH: 19
<212> TYPE: DNA
<213> ORGANISM: Artificial Sequence
<220> FEATURE:
<223> OTHER INFORMATION: Synthetic

<400> SEQUENCE: 388
agacaaggtc ccaaagaca					19

<210> SEQ ID NO 389
<211> LENGTH: 19
<212> TYPE: DNA
<213> ORGANISM: Artificial Sequence
<220> FEATURE:
<223> OTHER INFORMATION: Synthetic

<400> SEQUENCE: 389
ggaatggcaa gaccagcaa                                              19

<210> SEQ ID NO 390
<211> LENGTH: 19
<212> TYPE: DNA
<213> ORGANISM: Artificial Sequence
<220> FEATURE:
<223> OTHER INFORMATION: Synthetic

<400> SEQUENCE: 390
agaattattc cagggttta                                              19

<210> SEQ ID NO 391
<211> LENGTH: 19
<212> TYPE: DNA
<213> ORGANISM: Artificial Sequence
<220> FEATURE:
<223> OTHER INFORMATION: Synthetic

<400> SEQUENCE: 391
gcagacaagg tcccaaaga                                              19

<210> SEQ ID NO 392
<211> LENGTH: 19
<212> TYPE: DNA
<213> ORGANISM: Artificial Sequence
<220> FEATURE:
<223> OTHER INFORMATION: Synthetic

<400> SEQUENCE: 392
agaagcagct tcaggatga                                              19

<210> SEQ ID NO 393
<211> LENGTH: 19
<212> TYPE: DNA
<213> ORGANISM: Artificial Sequence
<220> FEATURE:
<223> OTHER INFORMATION: Synthetic

<400> SEQUENCE: 393
gagcttgact tccagaaga                                              19

<210> SEQ ID NO 394
<211> LENGTH: 19
<212> TYPE: DNA
<213> ORGANISM: Artificial Sequence
<220> FEATURE:
<223> OTHER INFORMATION: Synthetic

<400> SEQUENCE: 394
ccaccgaagt tcaccctaa                                              19

<210> SEQ ID NO 395
<211> LENGTH: 19
<212> TYPE: DNA
<213> ORGANISM: Artificial Sequence
<220> FEATURE:
<223> OTHER INFORMATION: Synthetic

```
<400> SEQUENCE: 395
gagaagagct cctccatca                                                19

<210> SEQ ID NO 396
<211> LENGTH: 19
<212> TYPE: DNA
<213> ORGANISM: Artificial Sequence
<220> FEATURE:
<223> OTHER INFORMATION: Synthetic

<400> SEQUENCE: 396
gaaagagcat ctacggtga                                                19

<210> SEQ ID NO 397
<211> LENGTH: 19
<212> TYPE: DNA
<213> ORGANISM: Artificial Sequence
<220> FEATURE:
<223> OTHER INFORMATION: Synthetic

<400> SEQUENCE: 397
gaaaggattt ggctacaaa                                                19

<210> SEQ ID NO 398
<211> LENGTH: 19
<212> TYPE: DNA
<213> ORGANISM: Artificial Sequence
<220> FEATURE:
<223> OTHER INFORMATION: Synthetic

<400> SEQUENCE: 398
acagcaaatt ccatcgtgt                                                19

<210> SEQ ID NO 399
<211> LENGTH: 19
<212> TYPE: DNA
<213> ORGANISM: Artificial Sequence
<220> FEATURE:
<223> OTHER INFORMATION: Synthetic

<400> SEQUENCE: 399
ggaaagactg ttccaaaaa                                                19

<210> SEQ ID NO 400
<211> LENGTH: 19
<212> TYPE: DNA
<213> ORGANISM: Artificial Sequence
<220> FEATURE:
<223> OTHER INFORMATION: Synthetic

<400> SEQUENCE: 400
caacacgcct catcctcta                                                19

<210> SEQ ID NO 401
<211> LENGTH: 19
<212> TYPE: DNA
<213> ORGANISM: Artificial Sequence
<220> FEATURE:
<223> OTHER INFORMATION: Synthetic

<400> SEQUENCE: 401
catgaaagct tacatcaac                                                19

<210> SEQ ID NO 402
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 402
aagatgccat gaaagctta                                                   19

<210> SEQ ID NO 403
<211> LENGTH: 19
<212> TYPE: DNA
<213> ORGANISM: Artificial Sequence
<220> FEATURE:
<223> OTHER INFORMATION: Synthetic

<400> SEQUENCE: 403
gcacataccg cctgagtct                                                   19

<210> SEQ ID NO 404
<211> LENGTH: 19
<212> TYPE: DNA
<213> ORGANISM: Artificial Sequence
<220> FEATURE:
<223> OTHER INFORMATION: Synthetic

<400> SEQUENCE: 404
gatcaaatct gaagaagga                                                   19

<210> SEQ ID NO 405
<211> LENGTH: 19
<212> TYPE: DNA
<213> ORGANISM: Artificial Sequence
<220> FEATURE:
<223> OTHER INFORMATION: Synthetic

<400> SEQUENCE: 405
gccaagaagt ttcctaata                                                   19

<210> SEQ ID NO 406
<211> LENGTH: 19
<212> TYPE: DNA
<213> ORGANISM: Artificial Sequence
<220> FEATURE:
<223> OTHER INFORMATION: Synthetic

<400> SEQUENCE: 406
cagcatatct tgaaccatt                                                   19

<210> SEQ ID NO 407
<211> LENGTH: 19
<212> TYPE: DNA
<213> ORGANISM: Artificial Sequence
<220> FEATURE:
<223> OTHER INFORMATION: Synthetic

<400> SEQUENCE: 407
gaacaaagga aacggatga                                                   19

<210> SEQ ID NO 408
<211> LENGTH: 19
<212> TYPE: DNA
<213> ORGANISM: Artificial Sequence
<220> FEATURE:
<223> OTHER INFORMATION: Synthetic

<400> SEQUENCE: 408
cggaaacggt ccaggctat                                                   19
```

<210> SEQ ID NO 409
<211> LENGTH: 19
<212> TYPE: DNA
<213> ORGANISM: Artificial Sequence
<220> FEATURE:
<223> OTHER INFORMATION: Synthetic

<400> SEQUENCE: 409
gcttcgagca gacatgata                                               19

<210> SEQ ID NO 410
<211> LENGTH: 19
<212> TYPE: DNA
<213> ORGANISM: Artificial Sequence
<220> FEATURE:
<223> OTHER INFORMATION: Synthetic

<400> SEQUENCE: 410
cctacacggt cctcctata                                               19

<210> SEQ ID NO 411
<211> LENGTH: 19
<212> TYPE: DNA
<213> ORGANISM: Artificial Sequence
<220> FEATURE:
<223> OTHER INFORMATION: Synthetic

<400> SEQUENCE: 411
gccaagaacc tcatcatct                                               19

<210> SEQ ID NO 412
<211> LENGTH: 19
<212> TYPE: DNA
<213> ORGANISM: Artificial Sequence
<220> FEATURE:
<223> OTHER INFORMATION: Synthetic

<400> SEQUENCE: 412
gatatgggct gaatacaaa                                               19

<210> SEQ ID NO 413
<211> LENGTH: 19
<212> TYPE: DNA
<213> ORGANISM: Artificial Sequence
<220> FEATURE:
<223> OTHER INFORMATION: Synthetic

<400> SEQUENCE: 413
gcactctgat tgacaaata                                               19

<210> SEQ ID NO 414
<211> LENGTH: 19
<212> TYPE: DNA
<213> ORGANISM: Artificial Sequence
<220> FEATURE:
<223> OTHER INFORMATION: Synthetic

<400> SEQUENCE: 414
tgaagtctct gattaagta                                               19

<210> SEQ ID NO 415
<211> LENGTH: 19
<212> TYPE: DNA
<213> ORGANISM: Artificial Sequence
<220> FEATURE:
<223> OTHER INFORMATION: Synthetic

<400> SEQUENCE: 415
tcagagagat cctcataaa                                                      19

<210> SEQ ID NO 416
<211> LENGTH: 19
<212> TYPE: DNA
<213> ORGANISM: Artificial Sequence
<220> FEATURE:
<223> OTHER INFORMATION: Synthetic

<400> SEQUENCE: 416
gcaagaagat caccatttc                                                      19

<210> SEQ ID NO 417
<211> LENGTH: 19
<212> TYPE: DNA
<213> ORGANISM: Artificial Sequence
<220> FEATURE:
<223> OTHER INFORMATION: Synthetic

<400> SEQUENCE: 417
gagagaaatt tgaggatga                                                      19

<210> SEQ ID NO 418
<211> LENGTH: 19
<212> TYPE: DNA
<213> ORGANISM: Artificial Sequence
<220> FEATURE:
<223> OTHER INFORMATION: Synthetic

<400> SEQUENCE: 418
gaaaggattt ggctataag                                                      19

<210> SEQ ID NO 419
<211> LENGTH: 19
<212> TYPE: DNA
<213> ORGANISM: Artificial Sequence
<220> FEATURE:
<223> OTHER INFORMATION: Synthetic

<400> SEQUENCE: 419
gaaagaaggc atgaacatt                                                      19

<210> SEQ ID NO 420
<211> LENGTH: 19
<212> TYPE: DNA
<213> ORGANISM: Artificial Sequence
<220> FEATURE:
<223> OTHER INFORMATION: Synthetic

<400> SEQUENCE: 420
gggagatagt gatgaagta                                                      19

<210> SEQ ID NO 421
<211> LENGTH: 19
<212> TYPE: DNA
<213> ORGANISM: Artificial Sequence
<220> FEATURE:
<223> OTHER INFORMATION: Synthetic

<400> SEQUENCE: 421
gaagtacatc cattataag                                                      19

<210> SEQ ID NO 422
<211> LENGTH: 19

```
<212> TYPE: DNA
<213> ORGANISM: Artificial Sequence
<220> FEATURE:
<223> OTHER INFORMATION: Synthetic

<400> SEQUENCE: 422
gtacgacaac cgggagata                                                     19

<210> SEQ ID NO 423
<211> LENGTH: 19
<212> TYPE: DNA
<213> ORGANISM: Artificial Sequence
<220> FEATURE:
<223> OTHER INFORMATION: Synthetic

<400> SEQUENCE: 423
agatagtgat gaagtacat                                                     19

<210> SEQ ID NO 424
<211> LENGTH: 19
<212> TYPE: DNA
<213> ORGANISM: Artificial Sequence
<220> FEATURE:
<223> OTHER INFORMATION: Synthetic

<400> SEQUENCE: 424
tgaagactct gctcagttt                                                     19

<210> SEQ ID NO 425
<211> LENGTH: 19
<212> TYPE: DNA
<213> ORGANISM: Artificial Sequence
<220> FEATURE:
<223> OTHER INFORMATION: Synthetic

<400> SEQUENCE: 425
gcatgcggcc tctgtttga                                                     19

<210> SEQ ID NO 426
<211> LENGTH: 19
<212> TYPE: RNA
<213> ORGANISM: Artificial Sequence
<220> FEATURE:
<223> OTHER INFORMATION: Synthetic

<400> SEQUENCE: 426
gcacacagcu uacuacauc                                                     19

<210> SEQ ID NO 427
<211> LENGTH: 19
<212> TYPE: RNA
<213> ORGANISM: Artificial Sequence
<220> FEATURE:
<223> OTHER INFORMATION: Synthetic

<400> SEQUENCE: 427
gaaaugcccu gguaucuca                                                     19

<210> SEQ ID NO 428
<211> LENGTH: 19
<212> TYPE: RNA
<213> ORGANISM: Artificial Sequence
<220> FEATURE:
<223> OTHER INFORMATION: Synthetic

<400> SEQUENCE: 428
gaaggaacgu gaugugauc                                                     19
```

<210> SEQ ID NO 429
<211> LENGTH: 19
<212> TYPE: RNA
<213> ORGANISM: Artificial Sequence
<220> FEATURE:
<223> OTHER INFORMATION: Synthetic

<400> SEQUENCE: 429
gcacuacucc uguguguga                                              19

<210> SEQ ID NO 430
<211> LENGTH: 19
<212> TYPE: RNA
<213> ORGANISM: Artificial Sequence
<220> FEATURE:
<223> OTHER INFORMATION: Synthetic

<400> SEQUENCE: 430
gaacccagcu ggagaacuu                                              19

<210> SEQ ID NO 431
<211> LENGTH: 19
<212> TYPE: RNA
<213> ORGANISM: Artificial Sequence
<220> FEATURE:
<223> OTHER INFORMATION: Synthetic

<400> SEQUENCE: 431
gauauacagu gugaucuua                                              19

<210> SEQ ID NO 432
<211> LENGTH: 19
<212> TYPE: RNA
<213> ORGANISM: Artificial Sequence
<220> FEATURE:
<223> OTHER INFORMATION: Synthetic

<400> SEQUENCE: 432
guacuacgau ccugauuau                                              19

<210> SEQ ID NO 433
<211> LENGTH: 19
<212> TYPE: RNA
<213> ORGANISM: Artificial Sequence
<220> FEATURE:
<223> OTHER INFORMATION: Synthetic

<400> SEQUENCE: 433
gugccgaccu uuacaauuu                                              19

<210> SEQ ID NO 434
<211> LENGTH: 19
<212> TYPE: DNA
<213> ORGANISM: Artificial Sequence
<220> FEATURE:
<223> OTHER INFORMATION: Synthetic

<400> SEQUENCE: 434
gaaggaaact gaattcaaa                                              19

<210> SEQ ID NO 435
<211> LENGTH: 19
<212> TYPE: DNA
<213> ORGANISM: Artificial Sequence
<220> FEATURE:
<223> OTHER INFORMATION: Synthetic

```
<400> SEQUENCE: 435
ggaaatatgt actacgaaa                                                  19

<210> SEQ ID NO 436
<211> LENGTH: 19
<212> TYPE: DNA
<213> ORGANISM: Artificial Sequence
<220> FEATURE:
<223> OTHER INFORMATION: Synthetic

<400> SEQUENCE: 436
ccacaaagca gtgaattta                                                  19

<210> SEQ ID NO 437
<211> LENGTH: 19
<212> TYPE: DNA
<213> ORGANISM: Artificial Sequence
<220> FEATURE:
<223> OTHER INFORMATION: Synthetic

<400> SEQUENCE: 437
gtaacaagct cacgcagtt                                                  19
```

METHODS AND COMPOSITIONS FOR SELECTING SIRNA OF IMPROVED FUNCTIONALITY

CROSS-REFERENCE TO RELATED APPLICATIONS

This application is a continuation application of U.S. Ser. No. 10/940,892, filed Sep. 14, 2004, which is a continuation of PCT Application No. PCT/US 04/14885, international filing date May 12, 2004. The disclosures of the priority applications, including the sequence listings and tables submitted in electronic form in lieu of paper, are incorporated by reference into the instant specification.

SEQUENCE LISTING

The sequence listing for this application has been submitted in accordance with 37 CFR §1.52(e) and 37 CFR §1.821 on CD-ROM in lieu of paper on a disk containing the sequence listing file entitled "DHARMA_2100-US144_CRF.txt" created May 28, 2010, 408 kb. Applicants hereby incorporate by reference the sequence listing provided on CD-ROM in lieu of paper into the instant specification.

FIELD OF INVENTION

The present invention relates to RNA interference ("RNAi").

BACKGROUND OF THE INVENTION

Relatively recently, researchers observed that double stranded RNA ("dsRNA") could be used to inhibit protein expression. This ability to silence a gene has broad potential for treating human diseases, and many researchers and commercial entities are currently investing considerable resources in developing therapies based on this technology.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation.

It is generally considered that the major mechanism of RNA induced silencing (RNA interference, or RNAi) in mammalian cells is mRNA degradation. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al., *Ribonuclease Activity and RNA Binding of Recombinant Human Dicer*, E.M.B.O. J., 2002 November 1; 21(21): 5864-5874; Tabara et al., *The dsRNA Binding Protein RDE-4 Interacts with RDE-1, DCR-1 and a DexH-box Helicase to Direct RNAi in C. elegans*, Cell 2002, June 28; 109(7):861-71; Ketting et al., *Dicer Functions in RNA Interference and in Synthesis of Small RNA Involved in Developmental Timing in C. elegans*; Martinez et al., *Single-Stranded Antisense siRNAs Guide Target RNA Cleavage in RNAi*, Cell 2002, September 6; 110(5): 563; Hutvagner & Zamore, *A microRNA in a multiple-turnover RNAi enzyme complex*, Science 2002, 297:2056.

From a mechanistic perspective, introduction of long double stranded RNA into plants and invertebrate cells is broken down into siRNA by a Type III endonuclease known as Dicer. Sharp, *RNA interference—2001*, Genes Dev. 2001, 15:485. Dicer, a ribonuclease-III-like enzyme, processes the dsRNA into 19-23 base pair short interfering RNAs with characteristic two base 3' overhangs. Bernstein, Caudy, Hammond, & Hannon, *Role for a bidentate ribonuclease in the initiation step of RNA interference*, Nature 2001, 409:363. The siRNAs are then incorporated into an RNA-induced silencing complex (RISC) where one or more helicases unwind the siRNA duplex, enabling the complementary antisense strand to guide target recognition. Nykanen, Haley, & Zamore, *ATP requirements and small interfering RNA structure in the RNA interference pathway*, Cell 2001, 107:309. Upon binding to the appropriate target mRNA, one or more endonucleases within the RISC cleaves the target to induce silencing. Elbashir, Lendeckel, & Tuschl, *RNA interference is mediated by 21- and 22-nucleotide RNAs*, Genes Dev 2001, 15:188, FIG. 1.

The interference effect can be long lasting and may be detectable after many cell divisions. Moreover, RNAi exhibits sequence specificity. Kisielow, M. et al. (2002) *Isoform-specific knockdown and expression of adaptor protein ShcA using small interfering RNA*, J. of Biochemistry 363: 1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Successful siRNA-dependent gene silencing depends on a number of factors. One of the most contentious issues in RNAi is the question of the necessity of siRNA design, i.e., considering the sequence of the siRNA used. Early work in *C. elegans* and plants circumvented the issue of design by introducing long dsRNA (see, for instance, Fire, A. et al. (1998) Nature 391:806-811). In this primitive organism, long dsRNA molecules are cleaved into siRNA by Dicer, thus generating a diverse population of duplexes that can potentially cover the entire transcript. While some fraction of these molecules are non-functional (i.e., induce little or no silencing) one or more have the potential to be highly functional, thereby silencing the gene of interest and alleviating the need for siRNA design. Unfortunately, due to the interferon response, this same approach is unavailable for mammalian systems. While this effect can be circumvented by bypassing the Dicer cleavage step and directly introducing siRNA, this tactic carries with it the risk that the chosen siRNA sequence may be non-functional or semi-functional.

A number of researches have expressed the view that siRNA design is not a crucial element of RNAi. On the other hand, others in the field have begun to explore the possibility that RNAi can be made more efficient by paying attention to the design of the siRNA. Unfortunately, none of the reported methods have provided a satisfactory scheme for reliably selecting siRNA with acceptable levels of functionality. Accordingly, there is a need to develop rational criteria by which to select siRNA with an acceptable level of functionality, and to identify siRNA that have this improved level of functionality, as well as to identify siRNAs that are hyperfunctional.

SUMMARY OF THE INVENTION

The present invention is directed to increasing the efficiency of RNAi, particularly in mammalian systems. Accordingly, the present invention provides kits, siRNAs and methods for increasing siRNA efficacy.

According to a first embodiment, the present invention provides a kit for gene silencing, wherein said kit is comprised of a pool of at least two siRNA duplexes, each of which is comprised of a sequence that is complementary to a portion of the sequence of one or more target messenger RNA, and each of which is selected using non-target specific criteria.

According to a second embodiment, the present invention provides a method for selecting an siRNA, said method comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; and determining the relative functionality of the at least two siRNAs.

In one embodiment, the present invention also provides a method wherein said selection criteria are embodied in a formula comprising:

$$(-14)*G_{13} - 13*A_1 - 12*U_7 - 11*U_2 - 10*A_{11} - 10*U_4 - 10*C_3 - 10*C_5 - 10*C_6 - 9*A_{10} - 9*U_9 - 9*C_{18} - 8*G_{10} - 7*U_1 - 7*U_{16} - 7*C_{17} - 7*C_{19} + 7*U_{17} + 8*A_2 + 8*A_4 + 8*A_5 + 8*C_4 + 9*G_8 + 10*A_7 + 10*U_{18} + 11*A_{19} + 11*C_9 + 15*G_1 + 18*A_3 + 19*U_{10} - Tm - 3*(GC_{total}) - 6*(GC_{15-19}) - 30*X \quad \text{Formula VIII; or}$$

$$(-8)*A1 + (-1)*A2 + (12)*A3 + (7)*A4 + (18)*A5 + (12)*A6 + (19)*A7 + (6)*A8 + (-4)*A9 + (-5)*A10 + (-2)*A11 + (-5)*A12 + (17)*A13 + (-3)*A14 + (4)*A15 + (2)*A16 + (8)*A17 + (11)*A18 + (30)*A19 + (-13)*U1 + (-10)*U2 + (2)*U3 + (-2)*U4 + (-5)*U5 + (5)*U6 + (-2)*U7 + (-10)*U8 + (-5)*U9 + (15)*U10 + (-1)*U11 + (0)*U12 + (10)*U13 + (-9)*U14 + (-13)*U15 + (-10)*U16 + (3)*U17 + (9)*U18 + (9)*U19 + (7)*C1 + (3)*C2 + (-21)*C3 + (5)*C4 + (-9)*C5 + (-20)*C6 + (-18)*C7 + (-5)*C8 + (5)*C9 + (1)*C10 + (2)*C11 + (-5)*C12 + (-3)*C13 + (-6)*C14 + (-2)*C15 + (-5)*C16 + (-3)*C17 + (-12)*C18 + (-18)*C19 + (14)*G1 + (8)*G2 + (7)*G3 + (-10)*G4 + (-4)*G5 + (2)*G6 + (1)*G7 + (9)*G8 + (5)*G9 + (-11)*G10 + (1)*G11 + (9)*G12 + (-24)*G13 + (18)*G14 + (11)*G15 + (13)*G16 + (-7)*G17 + (-9)*G18 + (-22)*G19 + 6*(\text{number of A+U in position 15-19}) - 3*(\text{number of G+C in whole siRNA}), \quad \text{Formula X}$$

wherein position numbering begins at the 5'-most position of a sense strand, and $A_1=1$ if A is the base at position 1 of the sense strand, otherwise its value is 0;
$A_2=1$ if A is the base at position 2 of the sense strand, otherwise its value is 0;
$A_3=1$ if A is the base at position 3 of the sense strand, otherwise its value is 0;
$A_4=1$ if A is the base at position 4 of the sense strand, otherwise its value is 0;
$A_5=1$ if A is the base at position 5 of the sense strand, otherwise its value is 0;
$A_6=1$ if A is the base at position 6 of the sense strand, otherwise its value is 0;
$A_7=1$ if A is the base at position 7 of the sense strand, otherwise its value is 0;
$A_{10}=1$ if A is the base at position 10 of the sense strand, otherwise its value is 0;
$A_{11}=1$ if A is the base at position 11 of the sense strand, otherwise its value is 0;
$A_{13}=1$ if A is the base at position 13 of the sense strand, otherwise its value is 0;
$A_{19}=1$ if A is the base at position 19 of the sense strand, otherwise if another base is present or the sense strand is only 18 base pairs in length, its value is 0;
$C_3=1$ if C is the base at position 3 of the sense strand, otherwise its value is 0;
$C_4=1$ if C is the base at position 4 of the sense strand, otherwise its value is 0;
$C_5=1$ if C is the base at position 5 of the sense strand, otherwise its value is 0;
$C_6=1$ if C is the base at position 6 of the sense strand, otherwise its value is 0;
$C_7=1$ if C is the base at position 7 of the sense strand, otherwise its value is 0;
$C_9=1$ if C is the base at position 9 of the sense strand, otherwise its value is 0;
$C_{17}=1$ if C is the base at position 17 of the sense strand, otherwise its value is 0;
$C_{18}=1$ if C is the base at position 18 of the sense strand, otherwise its value is 0;
$C_{19}=1$ if C is the base at position 19 of the sense strand, otherwise if another base is present or the sense strand is only 18 base pairs in length, its value is 0;
$G_1=1$ if G is the base at position 1 on the sense strand, otherwise its value is 0;
$G_2=1$ if G is the base at position 2 of the sense strand, otherwise its value is 0;
$G_8=1$ if G is the base at position 8 on the sense strand, otherwise its value is 0;
$G_{10}=1$ if G is the base at position 10 on the sense strand, otherwise its value is 0;
$G_{13}=1$ if G is the base at position 13 on the sense strand, otherwise its value is 0;
$G_{19}=1$ if G is the base at position 19 of the sense strand, otherwise if another base is present or the sense strand is only 18 base pairs in length, its value is 0;
$U_1=1$ if U is the base at position 1 on the sense strand, otherwise its value is 0;
$U_2=1$ if U is the base at position 2 on the sense strand, otherwise its value is 0;
$U_3=1$ if U is the base at position 3 on the sense strand, otherwise its value is 0;
$U_4=1$ if U is the base at position 4 on the sense strand, otherwise its value is 0;
$U_7=1$ if U is the base at position 7 on the sense strand, otherwise its value is 0;
$U_9=1$ if U is the base at position 9 on the sense strand, otherwise its value is 0;
$U_{10}=1$ if U is the base at position 10 on the sense strand, otherwise its value is 0;
$U_{15}=1$ if U is the base at position 15 on the sense strand, otherwise its value is 0;
$U_{16}=1$ if U is the base at position 16 on the sense strand, otherwise its value is 0;
$U_{17}=1$ if U is the base at position 17 on the sense strand, otherwise its value is 0;
$U_{18}=1$ if U is the base at position 18 on the sense strand, otherwise its value is 0.
$GC_{15-19}$=the number of G and C bases within positions 15-19 of the sense strand, or within positions 15-18 if the sense strand is only 18 base pairs in length;
$GC_{total}$=the number of G and C bases in the sense strand;

Tm=100 if the siRNA oligo has the internal repeat longer then 4 base pairs, otherwise its value is 0; and X=the number of times that the same nucleotide repeats four or more times in a row.

According to a third embodiment, the invention provides a method for developing an algorithm for selecting siRNA, said method comprising: (a) selecting a set of siRNA; (b) measuring gene silencing ability of each siRNA from said set; (c) determining relative functionality of each siRNA; (d) determining improved functionality by the presence or absence of at least one variable selected from the group consisting of the presence or absence of a particular nucleotide at a particular position, the total number of As and Us in positions 15-19, the number of times that the same nucleotide repeats within a given sequence, and the total number of Gs and Cs; and (e) developing an algorithm using the information of step (d).

According to a fourth embodiment, the present invention provides a kit, wherein said kit is comprised of at least two siRNAs, wherein said at least two siRNAs comprise a first optimized siRNA and a second optimized siRNA, wherein said first optimized siRNA and said second optimized siRNA are optimized according a formula comprising Formula X.

According to a fifth embodiment, the present invention provides a method for identifying a hyperfunctional siRNA, comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; determining the relative functionality of the at least two siRNAs and assigning each of the at least two siRNAs a functionality score; and selecting siRNAs from the at least two siRNAs that have a functionality score that reflects greater than 80 percent silencing at a concentration in the picomolar range, wherein said greater than 80 percent silencing endures for greater than 120 hours.

According to a sixth embodiment, the present invention provides a hyperfunctional siRNA that is capable of silencing Bcl2.

According to a seventh embodiment, the present invention provides a method for developing an siRNA algorithm for selecting functional and hyperfunctional siRNAs for a given sequence. The method comprises:

(a) selecting a set of siRNAs;

(b) measuring the gene silencing ability of each siRNA from said set;

(c) determining the relative functionality of each siRNA;

(d) determining the amount of improved functionality by the presence or absence of at least one variable selected from the group consisting of the total GC content, melting temperature of the siRNA, GC content at positions 15-19, the presence or absence of a particular nucleotide at a particular position, relative thermodynamic stability at particular positions in a duplex, and the number of times that the same nucleotide repeats within a given sequence; and (e) developing an algorithm using the information of step (d).

According to this embodiment, preferably the set of siRNAs comprises at least 90 siRNAs from at least one gene, more preferably at least 180 siRNAs from at least two different genes, and most preferably at least 270 and 360 siRNAs from at least three and four different genes, respectively. Additionally, in step (d) the determination is made with preferably at least two, more preferably at least three, even more preferably at least four, and most preferably all of the variables. The resulting algorithm is not target sequence specific.

In another embodiment, the present invention provides rationally designed siRNAs identified using the formulas above.

In yet another embodiment, the present invention is directed to hyperfunctional siRNA.

The ability to use the above algorithms, which are not sequence or species specific, allows for the cost-effective selection of optimized siRNAs for specific target sequences. Accordingly, there will be both greater efficiency and reliability in the use of siRNA technologies.

For a better understanding of the present invention together with other and further advantages and embodiments, reference is made to the following description taken in conjunction with the examples, the scope of which is set forth in the appended claims.

BRIEF DESCRIPTION OF THE FIGURES

FIGS. 5A and 5B are representations of firefly luciferase and cyclophilin siRNA panels sorted according to functionality and predicted values using Formula VIII. The siRNA found within the circle represent those that have Formula VIII values (SMARTscores™) above zero. siRNA outside the indicated area have calculated Formula VIII values that are below zero. Y-axis is "Expression (% Control)." Each position on the X-axis represents a unique siRNA.

FIG. 13 is the sequence of the top ten Bcl2 siRNAs as determined by Formula VIII. Sequences are listed 5' to 3'.

FIG. 16 is a histogram demonstrating the inhibition of target gene expression by pools of 2 and 3 siRNAs duplexes taken from the walk described in FIG. 15. The Y-axis represents the percent expression relative to control. The X-axis represents the position of the first siRNA in paired pools, or trios of siRNA. For instance, the first paired pool contains siRNA 1 and 3. The second paired pool contains siRNA 3 and 5. Pool 3 (of paired pools) contains siRNA 5 and 7, and so on.

DETAILED DESCRIPTION

Definitions

Figure 1:
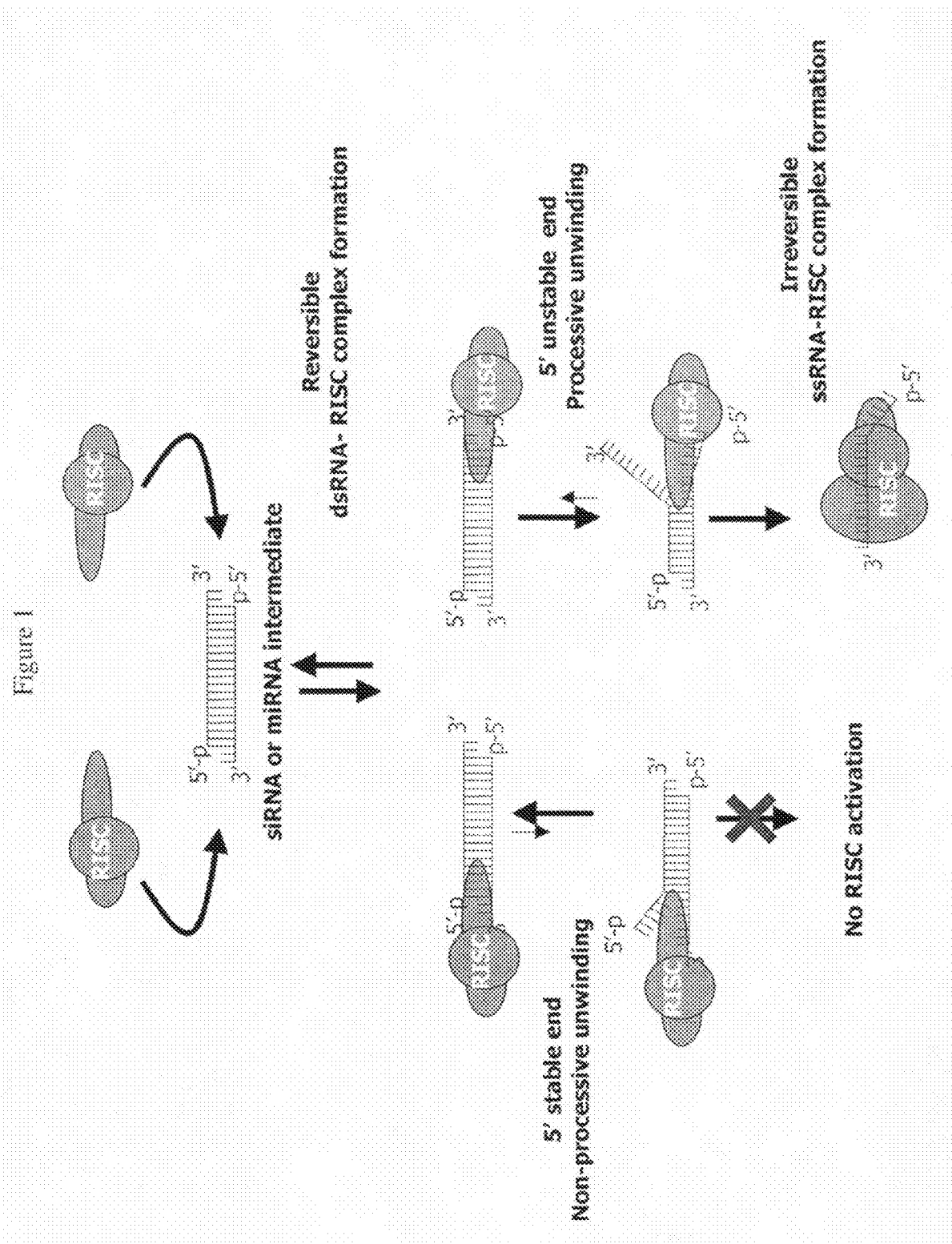
FIG. 1 shows a model for siRNA-RISC interactions. RISC has the ability to interact with either end of the siRNA or miRNA molecule. Following binding, the duplex is unwound, and the relevant target is identified, cleaved, and released.

Unless stated otherwise, the following terms and phrases have the meanings provided below:

siRNA

The term "siRNA" refers to small inhibitory RNA duplexes that induce the RNA interference (RNAi) pathway. These molecules can vary in length (generally 18-30 basepairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

siRNA may be divided into five (5) groups (non-functional, semi-functional, functional, highly functional, and hyperfunctional) based on the level or degree of silencing that they induce in cultured cell lines. As used herein, these definitions are based on a set of conditions where the siRNA is transfected into said cell line at a concentration of 100nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

miRNA

The term "miRNA" refers to microRNA.

Gene Silencing

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

Filters

The term "filter" refers to one or more procedures that are performed on sequences that are identified by the algorithm. In some instances, filtering includes in silico procedures where sequences identified by the algorithm can be screened to identify duplexes carrying desirable or undesirable motifs. Sequences carrying such motifs can be selected for, or selected against, to obtain a final set with the preferred properties. In other instances, filtering includes wet lab experiments. For instance, sequences identified by one or more versions of the algorithm can be screened using any one of a number of procedures to identify duplexes that have hyperfunctional traits (e.g., they exhibit a high degree of silencing at subnanomolar concentrations and/or exhibit high degrees of silencing longevity).

Transfection

The term "transfection" refers to a process by which agents are introduced into a cell. The list of agents that can be transfected is large and includes, but is not limited to, siRNA, sense and/or anti-sense sequences, DNA encoding one or more genes and organized into an expression plasmid, proteins, protein fragments, and more. There are multiple methods for transfecting agents into a cell including, but not limited to, electroporation, calcium phosphate-based transfections, DEAF-dextran-based transfections, lipid-based transfections, molecular conjugate-based transfections (e.g., polylysine-DNA conjugates), microinjection and others.

Target

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

Off-Target Silencing and Off-Target Interference

The phrases "off-target silencing" and "off-target interference" are defined as degradation of mRNA other than the intended target mRNA due to overlapping and/or partial homology with secondary mRNA messages.

SMARTscore™

The term "SMARTscore™" refers to a number determined by applying any of the Formulas I-Formula X to a given siRNA sequence. The phrases "SMART-selected" or "rationally selected" or "rational selection" refer to siRNA that have been selected on the basis of their SMARTscores™.

Complementary

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. "Substantial complementarity" refers to polynucleotide strands exhibiting 79% or greater complementarity, excluding regions of the polynucleotide strands, such as overhangs, that are selected so as to be noncomplementary. ("Substantial similarity" refers to polynucleotide strands exhibiting 79% or greater similarity, excluding regions of the polynucleotide strands, such as overhangs, that are selected so as not to be similar.) Thus, for example, two polynucleotides of 29 nucleotide units each, wherein each comprises a di-dT at the 3' terminus such that the duplex region spans 27 bases, and wherein 26 of the 27 bases of the duplex region on each strand are complementary, are substantially complementary since they are 96.3% complementary when excluding the di-dT overhangs.

Deoxynucleotide

The term "deoxynucleotide" refers to a nucleotide or polynucleotide lacking a hydroxyl group (OH group) at the 2' and/or 3' position of a sugar moiety. Instead, it has a hydrogen bonded to the 2' and/or 3' carbon. Within an RNA molecule that comprises one or more deoxynucleotides, "deoxynucleotide" refers to the lack of an OH group at the 2' position of the sugar moiety, having instead a hydrogen bonded directly to the 2' carbon.

Deoxyribonucleotide

The terms "deoxyribonucleotide" and "DNA" refer to a nucleotide or polynucleotide comprising at least one sugar moiety that has an H, rather than an OH, at its 2' and/or 3' position.

Substantially Similar

The phrase "substantially similar" refers to a similarity of at least 90% with respect to the identity of the bases of the sequence.

Duplex Region

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" has 19 base pairs. The remaining bases may, for example, exist as 5' and 3' overhangs. Further, within the duplex region, 100% complementarity is not required; substantial complementarity is allowable within a duplex region. Substantial complementarity refers to 79% or greater complementarity. For example, a mismatch in a duplex region consisting of 19 base pairs results in 94.7% complementarity, rendering the duplex region substantially complementary.

Nucleotide

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza -adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

Further, the term nucleotide also includes those species that have a detectable label, such as for example a radioactive or fluorescent moiety, or mass label attached to the nucleotide.

Polynucleotide

The term "polynucleotide" refers to polymers of nucleotides, and includes but is not limited to DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

Polyribonucleotide

The term "polyribonucleotide" refers to a polynucleotide comprising two or more modified or unmodified ribonucleotides and/or their analogs. The term "polyribonucleotide" is used interchangeably with the term "oligoribonucleotide."

Ribonucleotide and Ribonucleic Acid

The term "ribonucleotide" and the phrase "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

DETAILED DESCRIPTION OF THE INVENTION

The present invention is directed to improving the efficiency of gene silencing by siRNA. Through the inclusion of multiple siRNA sequences that are targeted to a particular gene and/or selecting an siRNA sequence based on certain defined criteria, improved efficiency may be achieved.

The present invention will now be described in connection with preferred embodiments. These embodiments are presented in order to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

Furthermore, this disclosure is not a primer on RNA interference. Basic concepts known to persons skilled in the art have not been set forth in detail.

The present invention is directed to increasing the efficiency of RNAi, particularly in mammalian systems. Accordingly, the present invention provides kits, siRNAs and methods for increasing siRNA efficacy.

According to a first embodiment, the present invention provides a kit for gene silencing, wherein said kit is comprised of a pool of at least two siRNA duplexes, each of which is comprised of a sequence that is complementary to a portion of the sequence of one or more target messenger RNA, and each of which is selected using non-target specific criteria. Each of the at least two siRNA duplexes of the kit complementary to a portion of the sequence of one or more target mRNAs is preferably selected using Formula X.

According to a second embodiment, the present invention provides a method for selecting an siRNA, said method comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; and determining the relative functionality of the at least two siRNAs.

In one embodiment, the present invention also provides a method wherein said selection criteria are embodied in a formula comprising:

$$(-14)*G_{13}-13*A_1-12*U_7-11*U_2-10*A_{11}-10*U_4-$$
$$10*C_3-10*C_5-10*C_6-9*A_{10}-9*U_9-9*C_{18}-$$
$$8*G_{10}-7*U_1-7*U_{16}-7*C_{17}-7*C_{19}+7*U_{17}+$$
$$8*A_2+8*A_4+8*A_5+8*C_4+9*G_8+10*A_7+$$
$$10*U_{18}+11*A_{19}+11*C_9+15*G_1+18*A_3+$$
$$19*U_{10}-Tm-3*(GC_{total})-6*(GC_{15-19})-30*X \quad \text{Formula VIII; or}$$

$$(-8)*A1+(-1)*A2+(12)*A3+(7)*A4+(18)*A5+$$
$$(12)*A6+(19)*A7+(6)*A8+(-4)*A9+(-5)*A10+$$
$$(-2)*A11+(-5)*A12+(17)*A13+(-3)*A14+$$
$$(4)*A15+(2)*A16+(8)*A17+(11)*A18+$$
$$(30)*A19+(-13)*U1+(-10)*U2+(2)*U3+$$
$$(-2)*U4+(-5)*U5+(5)*U6+(-2)*U7+$$
$$(-10)*U8+(-5)*U9+(15)*U10+(-1)*U11+$$
$$(0)*U12+(10)*U13+(-9)*U14+(-13)*U15+(-10)*U16+(3)*U17+(9)*U18+(9)*U19+(7)*C1+$$
$$(3)*C2+(-21)*C3+(5)*C4+(-9)*C5+(-20)*C6+$$
$$(-18)*C7+(-5)*C8+(5)*C9+(1)*C10+(2)*C11+$$
$$(-5)*C12+(-3)*C13+(-6)*C14+(-2)*C15+$$
$$(-5)*C16+(-3)*C17+(-12)*C18+(-18)*C19+$$
$$(14)*G1+(8)*G2+(7)*G3+(-10)*G4+(-4)*G5+$$
$$(2)*G6+(1)*G7+(9)*G8+(5)*G9+(-11)*G10+$$
$$(1)*G11+(9)*G12+(-24)*G13+(18)*G14+$$
$$(11)*G15+(13)*G16+(-7)*G17+(-9)*G18+(-22)*G19+6*(\text{number of A+U in position 15-19})-$$
$$3*(\text{number of G+C in whole siRNA}), \quad \text{Formula X}$$

wherein position numbering begins at the 5'-most position of a sense strand, and $A_1=1$ if A is the base at position 1 of the sense strand, otherwise its value is 0;

$A_2=1$ if A is the base at position 2 of the sense strand, otherwise its value is 0;

$A_3=1$ if A is the base at position 3 of the sense strand, otherwise its value is 0;

$A_4=1$ if A is the base at position 4 of the sense strand, otherwise its value is 0;

$A_5=1$ if A is the base at position 5 of the sense strand, otherwise its value is 0;

$A_6=1$ if A is the base at position 6 of the sense strand, otherwise its value is 0;

$A_7=1$ if A is the base at position 7 of the sense strand, otherwise its value is 0;

$A_{10}=1$ if A is the base at position 10 of the sense strand, otherwise its value is 0;

$A_{11}=1$ if A is the base at position 11 of the sense strand, otherwise its value is 0;

$A_{13}=1$ if A is the base at position 13 of the sense strand, otherwise its value is 0;

$A_{19}=1$ if A is the base at position 19 of the sense strand, otherwise if another base is present or the sense strand is only 18 base pairs in length, its value is 0;

$C_3=1$ if C is the base at position 3 of the sense strand, otherwise its value is 0;

$C_4=1$ if C is the base at position 4 of the sense strand, otherwise its value is 0;

$C_5=1$ if C is the base at position 5 of the sense strand, otherwise its value is 0;

$C_6=1$ if C is the base at position 6 of the sense strand, otherwise its value is 0;

$C_7=1$ if C is the base at position 7 of the sense strand, otherwise its value is 0;

$C_9=1$ if C is the base at position 9 of the sense strand, otherwise its value is 0;

$C_{17}=1$ if C is the base at position 17 of the sense strand, otherwise its value is 0;

$C_{18}=1$ if C is the base at position 18 of the sense strand, otherwise its value is 0;

$C_{19}=1$ if C is the base at position 19 of the sense strand, otherwise if another base is present or the sense strand is only 18 base pairs in length, its value is 0;

$G_1=1$ if G is the base at position 1 on the sense strand, otherwise its value is 0;

$G_2=1$ if G is the base at position 2 of the sense strand, otherwise its value is 0;

$G_8=1$ if G is the base at position 8 on the sense strand, otherwise its value is 0;

$G_{10}=1$ if G is the base at position 10 on the sense strand, otherwise its value is 0;

$G_{13}=1$ if G is the base at position 13 on the sense strand, otherwise its value is 0;

$G_{19}=1$ if G is the base at position 19 of the sense strand, otherwise if another base is present or the sense strand is only 18 base pairs in length, its value is 0;

$U_1=1$ if U is the base at position 1 on the sense strand, otherwise its value is 0;

$U_2=1$ if U is the base at position 2 on the sense strand, otherwise its value is 0;

$U_3=1$ if U is the base at position 3 on the sense strand, otherwise its value is 0;

$U_4=1$ if U is the base at position 4 on the sense strand, otherwise its value is 0;

$U_7=1$ if U is the base at position 7 on the sense strand, otherwise its value is 0;

$U_9=1$ if U is the base at position 9 on the sense strand, otherwise its value is 0;

$U_{10}=1$ if U is the base at position 10 on the sense strand, otherwise its value is 0;

$U_{15}=1$ if U is the base at position 15 on the sense strand, otherwise its value is 0;

$U_{16}=1$ if U is the base at position 16 on the sense strand, otherwise its value is 0;

$U_{17}=1$ if U is the base at position 17 on the sense strand, otherwise its value is 0;

$U_{18}=1$ if U is the base at position 18 on the sense strand, otherwise its value is 0.

$GC_{15-19}$=the number of G and C bases within positions 15-19 of the sense strand, or within positions 15-18 if the sense strand is only 18 base pairs in length;

$GC_{total}$=the number of G and C bases in the sense strand;

Tm=100 if the siRNA oligo has the internal repeat longer then 4 base pairs, otherwise its value is 0; and X=the number of times that the same nucleotide repeats four or more times in a row.

Any of the methods of selecting siRNA in accordance with the invention can further comprise comparing the internal stability profiles of the siRNAs to be selected, and selecting those siRNAs with the most favorable internal stability profiles. Any of the methods of selecting siRNA can further comprise selecting either for or against sequences that contain motifs that induce cellular stress. Such motifs include, for example, toxicity motifs. Any of the methods of selecting siRNA can further comprise either selecting for or selecting against sequences that comprise stability motifs.

In another embodiment, the present invention provides a method of gene silencing, comprising introducing into a cell at least one siRNA selected according to any of the methods of the present invention. The siRNA can be introduced by allowing passive uptake of siRNA, or through the use of a vector.

According to a third embodiment, the invention provides a method for developing an algorithm for selecting siRNA, said method comprising: (a) selecting a set of siRNA; (b) measuring gene silencing ability of each siRNA from said set; (c) determining relative functionality of each siRNA; (d) determining improved functionality by the presence or absence of at least one variable selected from the group consisting of the presence or absence of a particular nucleotide at a particular position, the total number of As and Us in positions 15-19, the number of times that the same nucleotide repeats within a given sequence, and the total number of Gs and Cs; and (e) developing an algorithm using the information of step (d).

In another embodiment, the invention provides a method for selecting an siRNA with improved functionality, comprising using the above-mentioned algorithm to identify an siRNA of improved functionality.

According to a fourth embodiment, the present invention provides a kit, wherein said kit is comprised of at least two siRNAs, wherein said at least two siRNAs comprise a first optimized siRNA and a second optimized siRNA, wherein said first optimized siRNA and said second optimized siRNA are optimized according a formula comprising Formula X.

According to a fifth embodiment, the present invention provides a method for identifying a hyperfunctional siRNA, comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; determining the relative functionality of the at least two siRNAs and assigning each of the at least two siRNAs a functionality score; and selecting siRNAs from the at least two siRNAs that have a functionality score that reflects greater than 80 percent silencing at a concentration in the picomolar range, wherein said greater than 80 percent silencing endures for greater than 120 hours.

In other embodiments, the invention provides kits and/or methods wherein the siRNA are comprised of two separate polynucleotide strands; wherein the siRNA are comprised of a single contiguous molecule such as, for example, a unimolecular siRNA (comprising, for example, either a nucleotide or non-nucleotide loop); wherein the siRNA are expressed from one or more vectors; and wherein two or more genes are silenced by a single administration of siRNA.

According to a sixth embodiment, the present invention provides a hyperfunctional siRNA that is capable of silencing Bcl2.

According to a seventh embodiment, the present invention provides a method for developing an siRNA algorithm for selecting functional and hyperfunctional siRNAs for a given sequence. The method comprises:

(a) selecting a set of siRNAs;

(b) measuring the gene silencing ability of each siRNA from said set;

(c) determining the relative functionality of each siRNA;

(d) determining the amount of improved functionality by the presence or absence of at least one variable selected from the group consisting of the total GC content, melting temperature of the siRNA, GC content at positions 15-19, the presence or absence of a particular nucleotide at a particular position, relative thermodynamic stability at particular positions in a duplex, and the number of times that the same nucleotide repeats within a given sequence; and (e) developing an algorithm using the information of step (d).

According to this embodiment, preferably the set of siRNAs comprises at least 90 siRNAs from at least one gene, more preferably at least 180 siRNAs from at least two different genes, and most preferably at least 270 and 360 siRNAs from at least three and four different genes, respectively. Additionally, in step (d) the determination is made with preferably at least two, more preferably at least three, even more preferably at least four, and most preferably all of the variables. The resulting algorithm is not target sequence specific.

In another embodiment, the present invention provides rationally designed siRNAs identified using the formulas above.

In yet another embodiment, the present invention is directed to hyperfunctional siRNA.

The ability to use the above algorithms, which are not sequence or species specific, allows for the cost-effective selection of optimized siRNAs for specific target sequences. Accordingly, there will be both greater efficiency and reliability in the use of siRNA technologies.

The methods disclosed herein can be used in conjunction with comparing internal stability profiles of selected siRNAs, and designing an siRNA with a desirable internal stability profile; and/or in conjunction with a selection either for or against sequences that contain motifs that induce cellular stress, for example, cellular toxicity.

Any of the methods disclosed herein can be used to silence one or more genes by introducing an siRNA selected, or designed, in accordance with any of the methods disclosed herein. The siRNA(s) can be introduced into the cell by any method known in the art, including passive uptake or through the use of one or more vectors.

Any of the methods and kits disclosed herein can employ either unimolecular siRNAs, siRNAs comprised of two separate polynucleotide strands, or combinations thereof. Any of the methods disclosed herein can be used in gene silencing, where two or more genes are silenced by a single administration of siRNA(s). The siRNA(s) can be directed against two or more target genes, and administered in a single dose or single transfection, as the case may be.

Optimizing siRNA

According to one embodiment, the present invention provides a method for improving the effectiveness of gene silencing for use to silence a particular gene through the selection of an optimal siRNA. An siRNA selected according to this method may be used individually, or in conjunction with the first embodiment, i.e., with one or more other siRNAs, each of which may or may not be selected by this criteria in order to maximize their efficiency.

The degree to which it is possible to select an siRNA for a given mRNA that maximizes these criteria will depend on the sequence of the mRNA itself. However, the selection criteria will be independent of the target sequence. According to this method, an siRNA is selected for a given gene by using a rational design. That said, rational design can be described in a variety of ways. Rational design is, in simplest terms, the application of a proven set of criteria that enhance the probability of identifying a functional or hyperfunctional siRNA. In one method, rationally designed siRNA can be identified by maximizing one or more of the following criteria:

1. A low GC content, preferably between about 30-52%.
2. At least 2, preferably at least 3 A or U bases at positions 15-19 of the siRNA on the sense strand.
3. An A base at position 19 of the sense strand.
4. An A base at position 3 of the sense strand.
5. A U base at position 10 of the sense strand.
6. An A base at position 14 of the sense strand.
7. A base other than C at position 19 of the sense strand.
8. A base other than G at position 13 of the sense strand.
9. A Tm, which refers to the character of the internal repeat that results in inter- or intramolecular structures for one strand of the duplex, that is preferably not stable at greater than 50° C., more preferably not stable at greater than 37° C., even more preferably not stable at greater than 30° C. and most preferably not stable at greater than 20° C.
10. A base other than U at position 5 of the sense strand.
11. A base other than A at position 11 of the sense strand.
12. A base other than an A at position 1 of the sense strand.
13. A base other than an A at position 2 of the sense strand.
14. An A base at position 4 of the sense strand.
15. An A base at position 5 of the sense strand.
16. An A base at position 6 of the sense strand.
17. An A base at position 7 of the sense strand.
18. An A base at position 8 of the sense strand.
19. A base other than an A at position 9 of the sense strand.
20. A base other than an A at position 10 of the sense strand.
21. A base other than an A at position 11 of the sense strand.
22. A base other than an A at position 12 of the sense strand.
23. An A base at position 13 of the sense strand.
24. A base other than an A at position 14 of the sense strand.
25. An A base at position 15 of the sense strand
26. An A base at position 16 of the sense strand.
27. An A base at position 17 of the sense strand.
28. An A base at position 18 of the sense strand.
29. A base other than a U at position 1 of the sense strand.
30. A base other than a U at position 2 of the sense strand.
31. A U base at position 3 of the sense strand.
32. A base other than a U at position 4 of the sense strand.
33. A base other than a U at position 5 of the sense strand.
34. A U base at position 6 of the sense strand.
35. A base other than a U at position 7 of the sense strand.
36. A base other than a U at position 8 of the sense strand.
37. A base other than a U at position 9 of the sense strand.
38. A base other than a U at position 11 of the sense strand.
39. A U base at position 13 of the sense strand.
40. A base other than a U at position 14 of the sense strand.
41. A base other than a U at position 15 of the sense strand.
42. A base other than a U at position 16 of the sense strand.
43. A U base at position 17 of the sense strand.
44. A U base at position 18 of the sense strand.
45. A U base at position 19 of the sense strand.
46. A C base at position 1 of the sense strand.
47. A C base at position 2 of the sense strand.
48. A base other than a C at position 3 of the sense strand.
49. A C base at position 4 of the sense strand.
50. A base other than a C at position 5 of the sense strand.
51. A base other than a C at position 6 of the sense strand.
52. A base other than a C at position 7 of the sense strand.
53. A base other than a C at position 8 of the sense strand.
54. A C base at position 9 of the sense strand.
55. A C base at position 10 of the sense strand.
56. A C base at position 11 of the sense strand.
57. A base other than a C at position 12 of the sense strand.
58. A base other than a C at position 13 of the sense strand.
59. A base other than a C at position 14 of the sense strand.
60. A base other than a C at position 15 of the sense strand.
61. A base other than a C at position 16 of the sense strand.
62. A base other than a C at position 17 of the sense strand.
63. A base other than a C at position 18 of the sense strand.
64. A G base at position 1 of the sense strand.
65. A G base at position 2 of the sense strand.
66. A G base at position 3 of the sense strand.
67. A base other than a G at position 4 of the sense strand.
68. A base other than a G at position 5 of the sense strand.
69. A G base at position 6 of the sense strand.
70. A G base at position 7 of the sense strand.
71. A G base at position 8 of the sense strand.
72. A G base at position 9 of the sense strand.
73. A base other than a G at position 10 of the sense strand.
74. A G base at position 11 of the sense strand.
75. A G base at position 12 of the sense strand.
76. A G base at position 14 of the sense strand.
77. A G base at position 15 of the sense strand.
78. A G base at position 16 of the sense strand.
79. A base other than a G at position 17 of the sense strand.
80. A base other than a G at position 18 of the sense strand.
81. A base other than a G at position 19 of the sense strand.

The importance of various criteria can vary greatly. For instance, a C base at position 10 of the sense strand makes a minor contribution to duplex functionality. In contrast, the absence of a C at position 3 of the sense strand is very important. Accordingly, preferably an siRNA will satisfy as many of the aforementioned criteria as possible.

With respect to the criteria, GC content, as well as a high number of AU in positions 15-19 of the sense strand, may be important for easement of the unwinding of double stranded siRNA duplex. Duplex unwinding has been shown to be crucial for siRNA functionality in vivo.

With respect to criterion 9, the internal structure is measured in terms of the melting temperature of the single strand of siRNA, which is the temperature at which 50% of the molecules will become denatured. With respect to criteria 2-8 and 10-11, the positions refer to sequence positions on the sense strand, which is the strand that is identical to the mRNA.

In one preferred embodiment, at least criteria 1 and 8 are satisfied. In another preferred embodiment, at least criteria 7 and 8 are satisfied. In still another preferred embodiment, at least criteria 1, 8 and 9 are satisfied.

It should be noted that all of the aforementioned criteria regarding sequence position specifics are with respect to the 5' end of the sense strand. Reference is made to the sense strand, because most databases contain information that describes the information of the mRNA. Because according to the present invention a chain can be from 18 to 30 bases in length, and the aforementioned criteria assumes a chain 19 base pairs in length, it is important to keep the aforementioned criteria applicable to the correct bases.

When there are only 18 bases, the base pair that is not present is the base pair that is located at the 3' of the sense strand. When there are twenty to thirty bases present, then additional bases are added at the 5' end of the sense chain and occupy positions −1 to −11. Accordingly, with respect to SEQ. ID NO. 0001 NNANANNNNUCNAANNNA and SEQ. ID NO. 0028 GUCNNANANNNNUCNAANNNNA, both would have A at position 3, A at position 5, U at position 10, C at position 11, A and position 13, A and position 14 and A at position 19. However, SEQ. ID NO. 0028 would also have C at position −1, U at position −2 and G at position −3.

For a 19 base pair siRNA, an optimal sequence of one of the strands may be represented below, where N is any base, A, C, G, or U:

SEQ. ID NO. 0001.    NNANANNNNUCNAANNNNA
    SEQ. ID NO. 0001.    NNANANNNNUGNAANNNNA
    SEQ. ID NO. 0002.    NNANANNNNUUNAANNNNA
    SEQ. ID NO. 0003.    NNANANNNNUCNCANNNNA
    SEQ. ID NO. 0004.    NNANANNNNUGNCANNNNA
    SEQ. ID NO. 0005.    NNANANNNNUUNCANNNNA
    SEQ. ID NO. 0006.    NNANANNNNUCNUANNNNA
    SEQ. ID NO. 0007.    NNANANNNNUGNUANNNNA
    SEQ. ID NO. 0008.    NNANANNNNUUNUANNNNA
    SEQ. ID NO. 0010.    NNANCNNNNUCNAANNNNA
    SEQ. ID NO. 0011.    NNANCNNNNUGNAANNNNA
    SEQ. ID NO. 0012.    NNANCNNNNUUNAANNNNA
    SEQ. ID NO. 0013.    NNANCNNNNUCNCANNNNA
    SEQ. ID NO. 0014.    NNANCNNNNUGNCANNNNA
    SEQ. ID NO. 0015.    NNANCNNNNUUNCANNNNA
    SEQ. ID NO. 0016.    NANCNNNNUCNUANNNNA
    SEQ. ID NO. 0017.    NNANCNNNNUGNUANNNNA
    SEQ. ID NO. 0018.    NNANCNNNNUUNUANNNNA
    SEQ. ID NO. 0019.    NNANGNNNNUCNAANNNNA
    SEQ. ID NO. 0020.    NNANGNNNNUGNAANNNNA
    SEQ. ID NO. 0021.    NNANGNNNNUUNAANNNNA
    SEQ. ID NO. 0022.    NNANGNNNNUCNCANNNNA
    SEQ. ID NO. 0023.    NNANGNNNNUGNCANNNNA
    SEQ. ID NO. 0024.    NNANGNNNNUUNCANNNNA
    SEQ. ID NO. 0025.    NNANGNNNNUCNUANNNNA
    SEQ. ID NO. 0026.    NNANGNNNNUGNUANNNNA
    SEQ. ID NO. 0027.    NNANGNNNNUUNUANNNNA

In one embodiment, the sequence used as an siRNA is selected by choosing the siRNA that score highest according to one of the following seven algorithms that are represented by Formulas I-VII:

Relative functionality of siRNA=−(GC/3)+($AU_{15-19}$)−($Tm_{20° C.}$)*3−($G_{13}$)*3−($C_{19}$)+($A_{19}$)*2+($A_3$)+($U_{10}$)+($A_{14}$)−($U_5$)−($A_{11}$)    Formula I Relative functionality of siRNA=−(GC/3)−($AU_{15-19}$)*3−($G_{13}$)*3−($C_{19}$)+($A_{19}$)*2+($A_3$)    Formula II Relative functionality of siRNA=−(GC/3)+($AU_{15-19}$)−($Tm_{20° C.}$)*3    Formula III Relative functionality of siRNA=−GC/2+($AU_{15-19}$)/2−($Tm_{20° C.}$)*2−($G_{13}$)*3−($C_{19}$)+($A_{19}$)*2+($A_3$)+($U_{10}$)+($A_{14}$)−($U_5$)−($A_{11}$)    Formula IV Relative functionality of siRNA=−($G_{13}$)*3−($C_{19}$)+($A_{19}$)*2+($A_3$)+($U_{10}$)+($A_{14}$)−($U_5$)−($A_{11}$)    Formula V Relative functionality of siRNA=−($G_{13}$)*3−($C_{19}$)+($A_{19}$)*2+($A_3$)    Formula VI Relative functionality of siRNA=−(GC/2)+($AU_{15-19}$)/2−($Tm_{20° C.}$)*1−($G_{13}$)*3−($C_{19}$)+($A_{19}$)*3+($A_3$)*3+($U_{10}$)/2+($A_{14}$)/2−($U_5$)/2−($A_{11}$)/2    Formula VII In Formulas I-VII:

wherein $A_{19}$=1 if A is the base at position 19 on the sense strand, otherwise its value is 0, $AU_{15-19}$=0-5 depending on the number of A or U bases on the sense strand at positions 15-19;

$G_{13}$=1 if G is the base at position 13 on the sense strand, otherwise its value is 0;

$C_{19}$=1 if C is the base at position 19 of the sense strand, otherwise its value is 0;

GC=the number of G and C bases in the entire sense strand;

$Tm_{20° C.}$=1 if the Tm is greater than 20° C.;

$A_3$=1 if A is the base at position 3 on the sense strand, otherwise its value is 0;

$U_{10}$=1 if U is the base at position 10 on the sense strand, otherwise its value is 0;

$A_{14}$=1 if A is the base at position 14 on the sense strand, otherwise its value is 0;

$U_5$=1 if U is the base at position 5 on the sense strand, otherwise its value is 0; and $A_{11}$=1 if A is the base at position 11 of the sense strand, otherwise its value is 0.

Formulas I-VII provide relative information regarding functionality. When the values for two sequences are compared for a given formula, the relative functionality is ascertained; a higher positive number indicates a greater functionality. For example, in many applications a value of 5 or greater is beneficial.

Additionally, in many applications, more than one of these formulas would provide useful information as to the relative functionality of potential siRNA sequences. However, it is beneficial to have more than one type of formula, because not every formula will be able to help to differentiate among potential siRNA sequences. For example, in particularly high GC mRNAs, formulas that take that parameter into account would not be useful and application of formulas that lack GC elements (e.g., formulas V and VI) might provide greater insights into duplex functionality. Similarly, formula II might by used in situations where hairpin structures are not observed in duplexes, and formula IV might be applicable for sequences that have higher AU content. Thus, one may consider a particular sequence in light of more than one or even all of these algorithms to obtain the best differentiation among sequences. In some instances, application of a given algorithm may identify an unusually large number of potential siRNA sequences, and in those cases, it may be appropriate to re-analyze that sequence with a second algorithm that is, for instance, more stringent. Alternatively, it is conceivable that analysis of a sequence with a given formula yields no acceptable siRNA sequences (i.e., low SMARTscores™). In this instance, it may be appropriate to re-analyze that sequences with a second algorithm that is, for instance, less stringent. In still other instances, analysis of a single sequence with two separate formulas may give rise to conflicting results (i.e., one formula generates a set of siRNA with high SMARTscores™ while the other formula identifies a set of siRNA with low SMARTscores™). In these instances, it may be necessary to determine which weighted factor(s) (e.g., GC content) are contributing to the discrepancy and assessing the sequence to decide whether these factors should or should not be included. Alternatively, the sequence could be analyzed by a third, fourth, or fifth algorithm to identify a set of rationally designed siRNA.

The above-referenced criteria are particularly advantageous when used in combination with pooling techniques as depicted in Table I:

TABLE I

|  | Functional Probability | | | | | |
|---|---|---|---|---|---|---|
|  | Oligos | | | Pools | | |
| Criteria | >95% | >80% | <70% | >95% | >80% | <70% |
| Current | 33.0 | 50.0 | 23.0 | 79.5 | 97.3 | 0.3 |
| New | 50.0 | 88.5 | 8.0 | 93.8 | 99.98 | 0.005 |
| (GC) | 28.0 | 58.9 | 36.0 | 72.8 | 97.1 | 1.6 |

The term "current" used in Table I refers to Tuschl's conventional siRNA parameters (Elbashir, S. M. et al. (2002) "Analysis of gene function in somatic mammalian cells using small interfering RNAs" Methods 26: 199-213). "New" refers to the design parameters described in Formulas I-VII. "GC" refers to criteria that select siRNA solely on the basis of GC content.

As Table I indicates, when more functional siRNA duplexes are chosen, siRNAs that produce <70% silencing drops from 23% to 8% and the number of siRNA duplexes that produce >80% silencing rises from 50% to 88.5%. Further, of the siRNA duplexes with >80% silencing, a larger portion of these siRNAs actually silence >95% of the target expression (the new criteria increases the portion from 33% to 50%). Using this new criteria in pooled siRNAs, shows that, with pooling, the amount of silencing >95% increases from 79.5% to 93.8% and essentially eliminates any siRNA pool from silencing less than 70%.

Table II similarly shows the particularly beneficial results of pooling in combination with the aforementioned criteria. However, Table II, which takes into account each of the aforementioned variables, demonstrates even a greater degree of improvement in functionality.

TABLE II

|  | Functional Probability | | | | | |
|---|---|---|---|---|---|---|
|  | Oligos | | | Pools | | |
|  | Functional | Average | Non-functional | Functional | Average | Non-functional |
| Random | 20 | 40 | 50 | 67 | 97 | 3 |
| Criteria 1 | 52 | 99 | 0.1 | 97 | 93 | 0.0040 |
| Criteria 4 | 89 | 99 | 0.1 | 99 | 99 | 0.0000 |

The terms "functional," "Average," and "Non-functional" used in Table II, refer to siRNA that exhibit >80%, >50%, and <50% functionality, respectively. Criteria 1 and 4 refer to specific criteria described above.

The above-described algorithms may be used with or without a computer program that allows for the inputting of the sequence of the mRNA and automatically outputs the optimal siRNA. The computer program may, for example, be accessible from a local terminal or personal computer, over an internal network or over the Internet.

In addition to the formulas above, more detailed algorithms may be used for selecting siRNA. Preferably, at least one RNA duplex of 18-30 base pairs is selected such that it is optimized according a formula selected from:

$(-14)*G_{13}-13*A_1-12*U_7-11*U_2-10*A_{11}-10*U_4-$
$10*C_3-10*C_5-10*C_6-9*A_{10}-9*U_9-9*C_{18}-$
$8*G_{10}-7*U_1-7*U_{16}-7*C_{17}-7*C_{19}+7*U_{17}+$
$8*A_2+8*A_4+8*A_5+8*C_4+9*G_8+10*A_7+$
$10*U_{18}+11*A_{19}+11*C_9+15*G_1+18*A_3+$
$19*U_{10}-Tm-3*(GC_{total})-6*(GC_{15-19})-30*X$  Formula VIII; and $(14.1)*A_3+(14.9)*A_6+(17.6)*A_{13}+(24.7)*A_{10}+$
$(14.2)*U_{10}+(10.5)*C_9+(23.9)*G_1+(16.3)*G_2+(-$
$12.3)*A_{11}+(-19.3)*U_1+(-12.1)*U_2+(-11)*U_3+$
$(-15.2)*U_{15}+(-11.3)*U_{16}+(-11.8)*C_3+$
$(-17.4)*C_6+(-10.5)*C_7+(-13.7)*G_{13}+$
$(-25.9)*G_{19}-Tm-3*(GC_{total})-6*(GC_{15-19})-$
$30*X$  Formula IX; and $(-8)*A1+(-1)*A2+(12)*A3+(7)*A4+(18)*A5+$
$(12)*A6+(19)*A7+(6)*A8+(-4)*A9+(-5)*A10+$
$(-2)*A11+(-5)*A12+(17)*A13+(-3)*A14+$
$(4)*A15+(2)*A16+(8)*A17+(11)*A18+$
$(30)*A19+(-13)*U1+(-10)*U2+(2)*U3+$
$(-2)*U4+(-5)*U5+(5)*U6+(-2)*U7+$
$(-10)*U8+(-5)*U9+(15)*U10+(-1)*U11+$
$(0)*U12+(10)*U13+(-9)*U14+(-13)*U15+(-$
$10)*U16+(3)*U17+(9)*U18+(9)*U19+(7)*C1+$
$(3)*C2+(-21)*C3+(5)*C4+(-9)*C5+(-20)*C6+$
$(-18)*C7+(-5)*C8+(5)*C9+(1)*C10+(2)*C11+$
$(-5)*C12+(-3)*C13+(-6)*C14+(-2)*C15+$
$(-5)*C16+(-3)*C17+(-12)*C18+(-18)*C19+$
$(14)*G1+(8)*G2+(7)*G3+(-10)*G4+(-4)*G5+$
$(2)*G6+(1)*G7+(9)*G8+(5)*G9+(-11)*G10+$
$(1)*G11+(9)*G12+(-24)*G13+(18)*G14+$
$(11)*G15+(13)*G16+(-7)*G17+(-9)*G18+(-$
$22)*G19+6*(\text{number of A+U in position 15-19})-$
$3*(\text{number of G+C in whole siRNA}).$  Formula X:

wherein $A_1$=1 if A is the base at position 1 of the sense strand, otherwise its value is 0;

$A_2$=1 if A is the base at position 2 of the sense strand, otherwise its value is 0;

$A_3$=1 if A is the base at position 3 of the sense strand, otherwise its value is 0;

$A_4$=1 if A is the base at position 4 of the sense strand, otherwise its value is 0;

$A_5$=1 if A is the base at position 5 of the sense strand, otherwise its value is 0;

$A_6$=1 if A is the base at position 6 of the sense strand, otherwise its value is 0;

$A_7$=1 if A is the base at position 7 of the sense strand, otherwise its value is 0;

$A_{10}$=1 if A is the base at position 10 of the sense strand, otherwise its value is 0;

$A_{11}$=1 if A is the base at position 11 of the sense strand, otherwise its value is 0;

$A_{13}$=1 if A is the base at position 13 of the sense strand, otherwise its value is 0;

$A_{19}$=1 if A is the base at position 19 of the sense strand, otherwise if another base is present or the sense strand is only 18 base pairs in length, its value is 0;

$C_3$=1 if C is the base at position 3 of the sense strand, otherwise its value is 0;

$C_4$=1 if C is the base at position 4 of the sense strand, otherwise its value is 0;

$C_5$=1 if C is the base at position 5 of the sense strand, otherwise its value is 0;

$C_6$=1 if C is the base at position 6 of the sense strand, otherwise its value is 0;

$C_7$=1 if C is the base at position 7 of the sense strand, otherwise its value is 0;

$C_9$=1 if C is the base at position 9 of the sense strand, otherwise its value is 0;

$C_{17}$=1 if C is the base at position 17 of the sense strand, otherwise its value is 0;

$C_{18}$=1 if C is the base at position 18 of the sense strand, otherwise its value is 0;

$C_{19}$=1 if C is the base at position 19 of the sense strand, otherwise if another base is present or the sense strand is only 18 base pairs in length, its value is 0;

$G_1$=1 if G is the base at position 1 on the sense strand, otherwise its value is 0;

$G_2$=1 if G is the base at position 2 of the sense strand, otherwise its value is 0;

$G_8$=1 if G is the base at position 8 on the sense strand, otherwise its value is 0;

$G_{10}$=1 if G is the base at position 10 on the sense strand, otherwise its value is 0;

$G_{13}$=1 if G is the base at position 13 on the sense strand, otherwise its value is 0;

$G_{19}$=1 if G is the base at position 19 of the sense strand, otherwise if another base is present or the sense strand is only 18 base pairs in length, its value is 0;

$U_1$=1 if U is the base at position 1 on the sense strand, otherwise its value is 0;

$U_2$=1 if U is the base at position 2 on the sense strand, otherwise its value is 0;

$U_3$=1 if U is the base at position 3 on the sense strand, otherwise its value is 0;

$U_4$=1 if U is the base at position 4 on the sense strand, otherwise its value is 0;

$U_7$=1 if U is the base at position 7 on the sense strand, otherwise its value is 0;

$U_9$=1 if U is the base at position 9 on the sense strand, otherwise its value is 0;

$U_{10}$=1 if U is the base at position 10 on the sense strand, otherwise its value is 0;

$U_{15}$=1 if U is the base at position 15 on the sense strand, otherwise its value is 0;

$U_{16}$=1 if U is the base at position 16 on the sense strand, otherwise its value is 0;

$U_{17}$=1 if U is the base at position 17 on the sense strand, otherwise its value is 0;

$U_{18}$=1 if U is the base at position 18 on the sense strand, otherwise its value is 0;

$GC_{15-19}$=the number of G and C bases within positions 15-19 of the sense strand, or within positions 15-18 if the sense strand is only 18 base pairs in length;

$GC_{total}$=the number of G and C bases in the sense strand;

Tm=100 if the siRNA oligo has the internal repeat longer then 4 base pairs, otherwise its value is 0; and X=the number of times that the same nucleotide repeats four or more times in a row.

The above formulas VIII, IX, and X, as well as formulas I-VII, provide methods for selecting siRNA in order to increase the efficiency of gene silencing. A subset of variables of any of the formulas may be used, though when fewer variables are used, the optimization hierarchy becomes less reliable.

With respect to the variables of the above-referenced formulas, a single letter of A or C or G or U followed by a subscript refers to a binary condition. The binary condition is that either the particular base is present at that particular position (wherein the value is "1") or the base is not present (wherein the value is "0"). Because position 19 is optional, i.e., there might be only 18 base pairs, when there are only 18 base pairs, any base with a subscript of 19 in the formulas above would have a zero value for that parameter. Before or after each variable is a number followed by *, which indicates that the value of the variable is to be multiplied or weighed by that number.

The numbers preceding the variables A, or G, or C, or U in Formulas VIII, IX, and X (or after the variables in Formula I-VII) were determined by comparing the difference in the frequency of individual bases at different positions in functional siRNA and total siRNA. Specifically, the frequency in which a given base was observed at a particular position in functional groups was compared with the frequency that that same base was observed in the total, randomly selected siRNA set. If the absolute value of the difference between the functional and total values was found to be greater than 6%, that parameter was included in the equation. Thus, for instance, if the frequency of finding a "G" at position 13 ($G_{13}$) is found to be 6% in a given functional group, and the frequency of $G_{13}$ in the total population of siRNAs is 20%, the difference between the two values is 6%−20%=−14%. As the absolute value is greater than six (6), this factor (−14) is included in the equation. Thus, in Formula VIII, in cases where the siRNA under study has a G in position 13, the accrued value is (−14)*(1)=−14. In contrast, when a base other than G is found at position 13, the accrued value is (−14)*(0)=0.

When developing a means to optimize siRNAs, the inventors observed that a bias toward low internal thermodynamic stability of the duplex at the 5'-antisense (AS) end is characteristic of naturally occurring miRNA precursors. The inventors extended this observation to siRNAs for which functionality had been assessed in tissue culture.

With respect to the parameter $GC_{15-19}$, a value of 0-5 will be ascribed depending on the number of G or C bases at positions 15 to 19. If there are only 18 base pairs, the value is between 0 and 4.

With respect to the criterion $GC_{total}$ content, a number from 0-30 will be ascribed, which correlates to the total number of G and C nucleotides on the sense strand, excluding overhangs. Without wishing to be bound by any one theory, it is postulated that the significance of the GC content (as well as AU content at positions 15-19, which is a parameter for formulas III-VII) relates to the easement of the unwinding of a double-stranded siRNA duplex. Duplex unwinding is believed to be crucial for siRNA functionality in vivo and overall low internal stability, especially low internal stability of the first unwound base pair is believed to be important to maintain sufficient processivity of RISC complex-induced duplex unwinding. If the duplex has 19 base pairs, those at positions 15-19 on the sense strand will unwind first if the molecule exhibits a sufficiently low internal stability at that position. As persons skilled in the art are aware, RISC is a complex of approximately twelve proteins; Dicer is one, but not the only, helicase within this complex. Accordingly, although the GC parameters are believed to relate to activity with Dicer, they are also important for activity with other RISC proteins.

The value of the parameter Tm is 0 when there are no internal repeats longer than (or equal to) four base pairs present in the siRNA duplex; otherwise the value is 1. Thus for example, if the sequence ACGUACGU, or any other four nucleotide (or more) palindrome exists within the structure, the value will be one (1). Alternatively if the structure ACGGACG, or any other 3 nucleotide (or less) palindrome exists, the value will be zero (0).

The variable "X" refers to the number of times that the same nucleotide occurs contiguously in a stretch of four or more units. If there are, for example, four contiguous As in one part of the sequence and elsewhere in the sequence four contiguous Cs, X=2. Further, if there are two separate contiguous stretches of four of the same nucleotides or eight or more of the same nucleotides in a row, then X=2. However, X does not increase for five, six or seven contiguous nucleotides.

Again, when applying Formula VIII, Formula IX, or Formula X, to a given mRNA, (the "target RNA" or "target molecule"), one may use a computer program to evaluate the criteria for every sequence of 18-30 base pairs or only sequences of a fixed length, e.g., 19 base pairs. Preferably the computer program is designed such that it provides a report ranking of all of the potential siRNAs 18-30 base pairs, ranked according to which sequences generate the highest value. A higher value refers to a more efficient siRNA for a particular target gene. The computer program that may be used may be developed in any computer language that is known to be useful for scoring nucleotide sequences, or it may be developed with the assistance of commercially available product such as Microsoft's product.net. Additionally, rather than run every sequence through one and/or another formula, one may compare a subset of the sequences, which may be desirable if for example only a subset are available. For instance, it may be desirable to first perform a BLAST (Basic Local Alignment Search Tool) search and to identify sequences that have no homology to other targets. Alternatively, it may be desirable to scan the sequence and to identify regions of moderate GC context, then perform relevant calculations using one of the above-described formulas on these regions. These calculations can be done manually or with the aid of a computer.

As with Formulas I-VII, either Formula VIII, Formula IX, or Formula X may be used for a given mRNA target sequence. However, it is possible that according to one or the other formula more than one siRNA will have the same value. Accordingly, it is beneficial to have a second formula by which to differentiate sequences. Formulas IX and X were derived in a similar fashion as Formula VIII, yet used a larger data set and thus yields sequences with higher statistical correlations to highly functional duplexes. The sequence that has the highest value ascribed to it may be referred to as a "first optimized duplex." The sequence that has the second highest value ascribed to it may be referred to as a "second optimized duplex." Similarly, the sequences that have the third and fourth highest values ascribed to them may be referred to as a third optimized duplex and a fourth optimized duplex, respectively. When more than one sequence has the same value, each of them may, for example, be referred to as first optimized duplex sequences or co-first optimized duplexes. Formula X is similar to Formula IX, yet uses a greater numbers of variables and for that reason, identifies sequences on the basis of slightly different criteria.

It should also be noted that the output of a particular algorithm will depend on several of variables including: (1) the size of the data base(s) being analyzed by the algorithm, and (2) the number and stringency of the parameters being applied to screen each sequence. Thus, for example, in U.S. patent application Ser. No. 10/714,333, entitled "Functional and Hyperfunctional siRNA," filed Nov. 14, 2003, Formula VIII was applied to the known human genome (ncbi refseq database) through Entrez (efetch). As a result of these procedures, roughly 1.6 million siRNA sequences were identified. Application of Formula VIII to the same database in March of 2004 yielded roughly 2.2 million sequences, a difference of approximately 600,000 sequences resulting from the growth of the database over the course of the months that span this period of time. Application of other formulas (e.g., Formula X) that change the emphasis of, include, or eliminate different variables can yield unequal numbers of siRNAs. Alternatively, in cases where application of one formula to one or more genes fails to yield sufficient numbers of siRNAs with scores that would be indicative of strong silencing, said genes can be reassessed with a second algorithm that is, for instance, less stringent.

siRNA sequences identified using Formula VIII and Formula X (minus sequences generated by Formula VIII) are contained within the enclosed compact disks. The data included on the enclosed compact disks is described more fully below. The sequences identified by Formula VIII and Formula X that are disclosed in the compacts disks may be used in gene silencing applications.

It should be noted that for Formulas VIII, IX, and X all of the aforementioned criteria are identified as positions on the sense strand when oriented in the 5' to 3' direction as they are identified in connection with Formulas I-VII unless otherwise specified.

Formulas I-X, may be used to select or to evaluate one, or more than one, siRNA in order to optimize silencing. Preferably, at least two optimized siRNAs that have been selected according to at least one of these formulas are used to silence a gene, more preferably at least three and most preferably at least four. The siRNAs may be used individually or together in a pool or kit. Further, they may be applied to a cell simultaneously or separately. Preferably, the at least two siRNAs are applied simultaneously. Pools are particularly beneficial for many research applications. However, for therapeutics, it may be more desirable to employ a single hyperfunctional siRNA as described elsewhere in this application.

When planning to conduct gene silencing, and it is necessary to choose between two or more siRNAs, one should do so by comparing the relative values when the siRNA are subjected to one of the formulas above. In general a higher scored siRNA should be used.

Useful applications include, but are not limited to, target validation, gene functional analysis, research and drug discovery, gene therapy and therapeutics. Methods for using siRNA in these applications are well known to persons of skill in the art.

Because the ability of siRNA to function is dependent on the sequence of the RNA and not the species into which it is introduced, the present invention is applicable across a broad range of species, including but not limited to all mammalian species, such as humans, dogs, horses, cats, cows, mice, hamsters, chimpanzees and gorillas, as well as other species and organisms such as bacteria, viruses, insects, plants and *C. elegans*.

The present invention is also applicable for use for silencing a broad range of genes, including but not limited to the roughly 45,000 genes of a human genome, and has particular relevance in cases where those genes are associated with diseases such as diabetes, Alzheimer's, cancer, as well as all genes in the genomes of the aforementioned organisms.

The siRNA selected according to the aforementioned criteria or one of the aforementioned algorithms are also, for example, useful in the simultaneous screening and functional analysis of multiple genes and gene families using high throughput strategies, as well as in direct gene suppression or silencing.

Development of the Algorithms

To identify siRNA sequence features that promote functionality and to quantify the importance of certain currently accepted conventional factors—such as G/C content and target site accessibility—the inventors synthesized an siRNA panel consisting of 270 siRNAs targeting three genes, Human Cyclophilin, Firefly Luciferase, and Human DBI. In all three cases, siRNAs were directed against specific regions of each gene. For Human Cyclophilin and Firefly Luciferase, ninety siRNAs were directed against a 199 by segment of each respective mRNA. For DBI, 90 siRNAs were directed against a smaller, 109 base pair region of the mRNA. The sequences to which the siRNAs were directed are provided below.

It should be noted that in certain sequences, "t" is present. This is because many databases contain information in this manner. However, the t denotes a uracil residue in mRNA and siRNA. Any algorithm will, unless otherwise specified, process at in a sequence as a u.

```
Human cyclophilin: 193-390, M60857
SEQ. ID NO. 29:
gttccaaaaacagtggataattttgtggccttagctacaggagagaaagg atttggctacaaaaacagcaaattccatcgtgtaatcaaggacttcatga tccagggcggagacttcaccagggagatggcacaggaggaaagagcatc tacggtgagcgcttccccgatgagaacttcaaactgaagcactacgggcc tggctggg Firefly luciferase: 1434-1631, U47298 (pGL3,
Promega)
SEQ. ID NO. 30:
tgaacttcccgccgccgttgttgttttggagcacggaaagacgatgacgg aaaaagagatcgtggattacgtcgccagtcaagtaacaaccgcgaaaaag ttgcgcggaggagttgtgtttgtggacgaagtaccgaaaggtcttaccgg aaaactcgacgcaagaaaaatcagagagatcctcataaaggccaagaagg DBI, NM_020548 (202-310) (every position)
SEQ. ID NO. 0031:
acgggcaaggccaagtgggatgcctggaatgagctgaaagggacttccaa ggaagatgccatgaaagcttacatcaacaaagtagaagagctaaagaaaa aatacggg
```

A list of the siRNAs appears in Table III (see Examples Section, Example II)

The set of duplexes was analyzed to identify correlations between siRNA functionality and other biophysical or thermodynamic properties. When the siRNA panel was analyzed in functional and non-functional subgroups, certain nucleotides were much more abundant at certain positions in functional or non-functional groups. More specifically, the frequency of each nucleotide at each position in highly functional siRNA duplexes was compared with that of non-functional duplexes in order to assess the preference for or against any given nucleotide at every position. These analyses were used to determine important criteria to be included in the siRNA algorithms (Formulas VIII, IX, and X).

The data set was also analyzed for distinguishing biophysical properties of siRNAs in the functional group, such as optimal percent of GC content, propensity for internal structures and regional thermodynamic stability. Of the presented criteria, several are involved in duplex recognition, RISC activation/duplex unwinding, and target cleavage catalysis.

Figure 2:
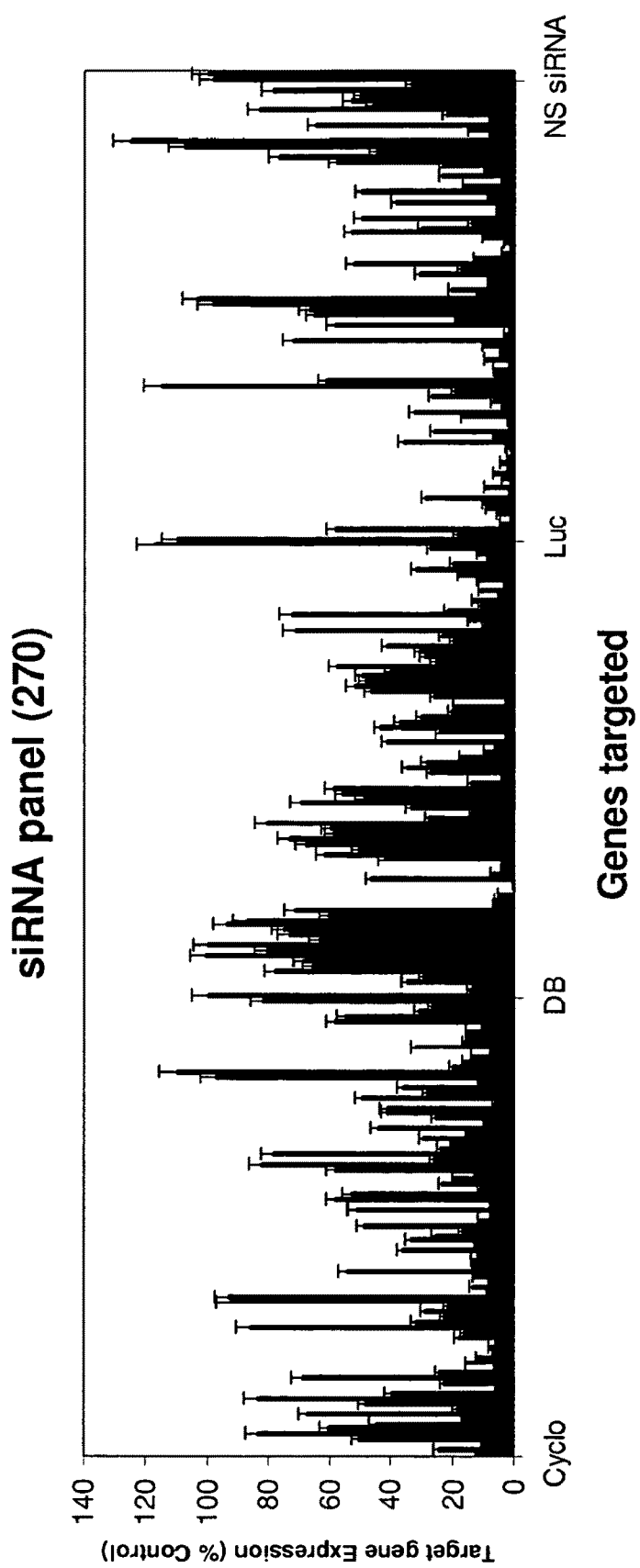
FIG. 2 is a representation of the functionality of two hundred and seventy siRNA duplexes that were generated to target human cyclophilin, human diazepam-binding inhibitor (DB), and firefly luciferase.
Figure 3A:
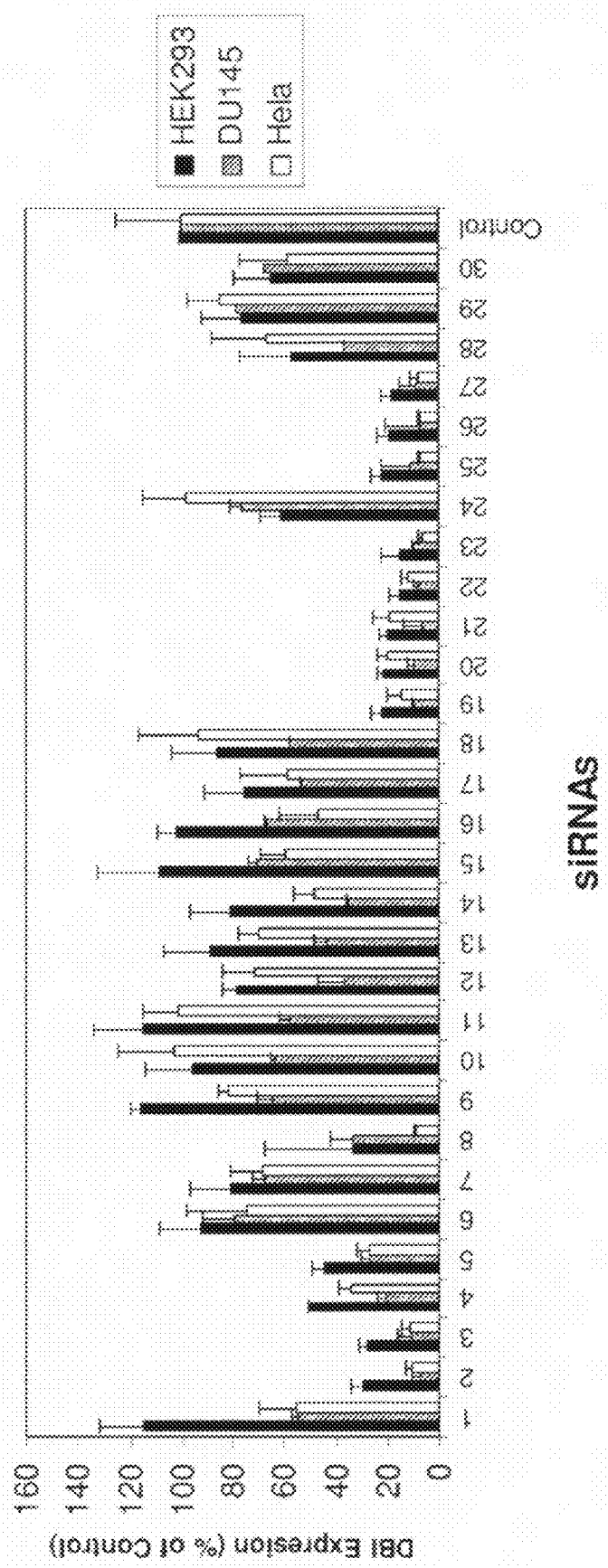
FIG. 3a is a representation of the silencing effect of 30 siRNAs in three different cells lines, HEK293, DU145, and Hela.

The original data set that was the source of the statistically derived criteria is shown in FIG. 2. Additionally, this figure shows that random selection yields siRNA duplexes with unpredictable and widely varying silencing potencies as measured in tissue culture using HEK293 cells. In the figure, duplexes are plotted such that each x-axis tick-mark represents an individual siRNA, with each subsequent siRNA differing in target position by two nucleotides for Human Cyclophilin B and Firefly Luciferase, and by one nucleotide for Human DBI. Furthermore, the y-axis denotes the level of target expression remaining after transfection of the duplex into cells and subsequent silencing of the target.

siRNA identified and optimized in this document work equally well in a wide range of cell types. FIG. 3a shows the evaluation of thirty siRNAs targeting the DBI gene in three cell lines derived from different tissues. Each DBI siRNA displays very similar functionality in HEK293 (ATCC, CRL-1573, human embryonic kidney), HeLa (ATCC, CCL-2, cervical epithelial adenocarcinoma) and DU145 (HTB-81, prostate) cells as deterimined by the B-DNA assay. Thus, siRNA functionality is determined by the primary sequence of the siRNA and not by the intracellular environment. Additionally, it should be noted that although the present invention provides for a determination of the functionality of siRNA for a given target, the same siRNA may silence more than one gene. For example, the complementary sequence of the silencing siRNA may be present in more than one gene. Accordingly, in these circumstances, it may be desirable not to use the siRNA with highest SMARTscore™. In such circumstances, it may be desirable to use the siRNA with the next highest SMARTscore™.

Figure 3B:
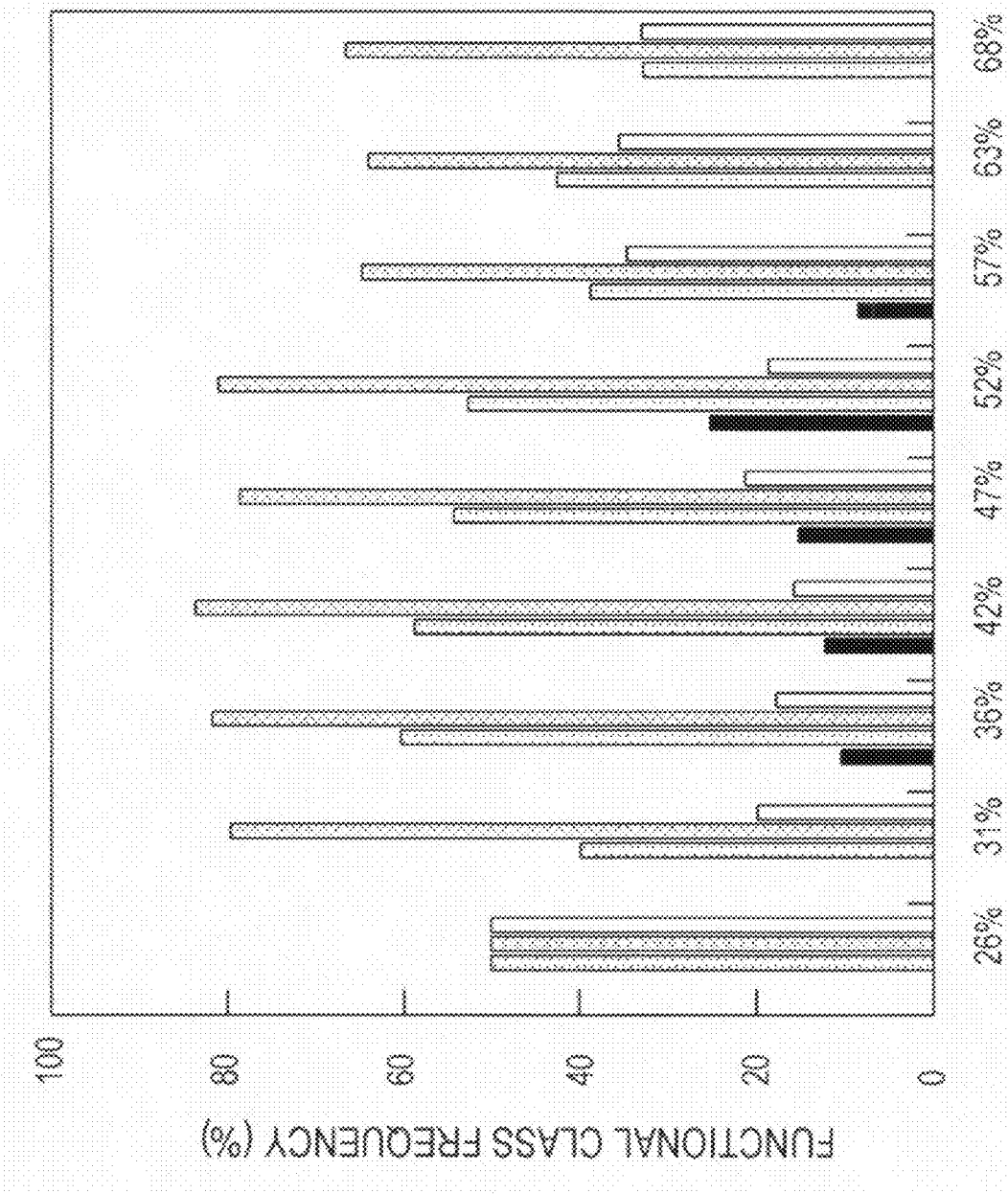
FIG. 3b shows the frequency of different functional groups (>95% silencing (black), >80% silencing (gray), >50% silencing (dark gray), and <50% silencing (white)) based on GC content. In cases where a given bar is absent from a particular GC percentage, no siRNA were identified for that particular group.

To determine the relevance of G/C content in siRNA function, the G/C content of each duplex in the panel was calculated and the functional classes of siRNAs (<F50, ≧F50, ≧F80, ≧F95 where F refers to the percent gene silencing) were sorted accordingly. The majority of the highly-functional siRNAs (≧F95) fell within the G/C content range of 36%-52% (FIG. 3B). Twice as many non-functional (<F50) duplexes fell within the high G/C content groups (>57% GC content) compared to the 36%-52% group. The group with extremely low GC content (26% or less) contained a higher proportion of non-functional siRNAs and no highly-functional siRNAs. The G/C content range of 30%-52% was therefore selected as Criterion I for siRNA functionality, consistent with the observation that a G/C range 30%-70% promotes efficient RNAi targeting. Application of this criterion alone provided only a marginal increase in the probability of selecting functional siRNAs from the panel: selection of F50 and F95 siRNAs was improved by 3.6% and 2.2%, respectively. The siRNA panel presented here permitted a more systematic analysis and quantification of the importance of this criterion than that used previously.

A relative measure of local internal stability is the A/U base pair (bp) content; therefore, the frequency of A/U by was determined for each of the five terminal positions of the duplex (5' sense (S)/5' antisense (AS)) of all siRNAs in the panel. Duplexes were then categorized by the number of A/U by in positions 1-5 and 15-19 of the sense strand. The thermodynamic flexibility of the duplex 5'-end (positions 1-5; S) did not appear to correlate appreciably with silencing potency, while that of the 3'-end (positions 15-19; S) correlated with efficient silencing. No duplexes lacking A/U by in positions 15-19 were functional. The presence of one A/U by in this region conferred some degree of functionality, but the presence of three or more A/Us was preferable and therefore defined as Criterion II. When applied to the test panel, only a marginal increase in the probability of functional siRNA selection was achieved: a 1.8% and 2.3% increase for F50 and F95 duplexes, respectively (Table IV).

Figure 3C:
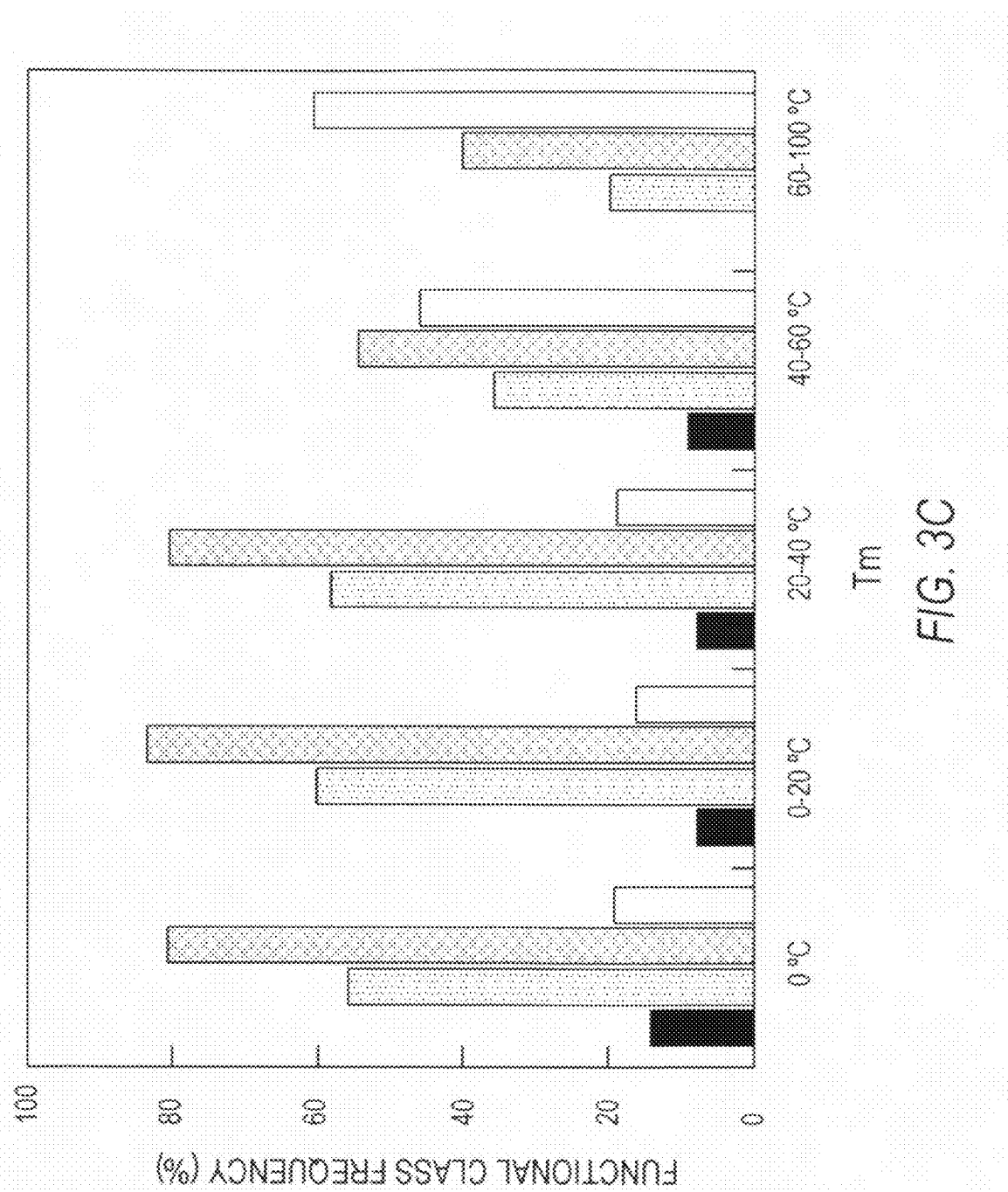
FIG. 3c shows the frequency of different functional groups based on melting temperature (Tm).

The complementary strands of siRNAs that contain internal repeats or palindromes may form internal fold-back structures. These hairpin-like structures exist in equilibrium with the duplexed form effectively reducing the concentration of functional duplexes. The propensity to form internal hairpins and their relative stability can be estimated by predicted melting temperatures. High Tm reflects a tendency to form hairpin structures. Lower Tm values indicate a lesser tendency to form hairpins. When the functional classes of siRNAs were sorted by $T_m$ (FIG. 3c), the following trends were identified: duplexes lacking stable internal repeats were the most potent silencers (no F95 duplex with predicted hairpin structure $T_m > 60°$ C.). In contrast, about 60% of the duplexes in the groups having internal hairpins with calculated $T_m$ values less than 20° C. were F80. Thus, the stability of internal repeats is inversely proportional to the silencing effect and defines Criterion III (predicted hairpin structure $T_m \leq 20°$ C.).

Sequence-Based Determinants of siRNA Functionality

Figure 4E:
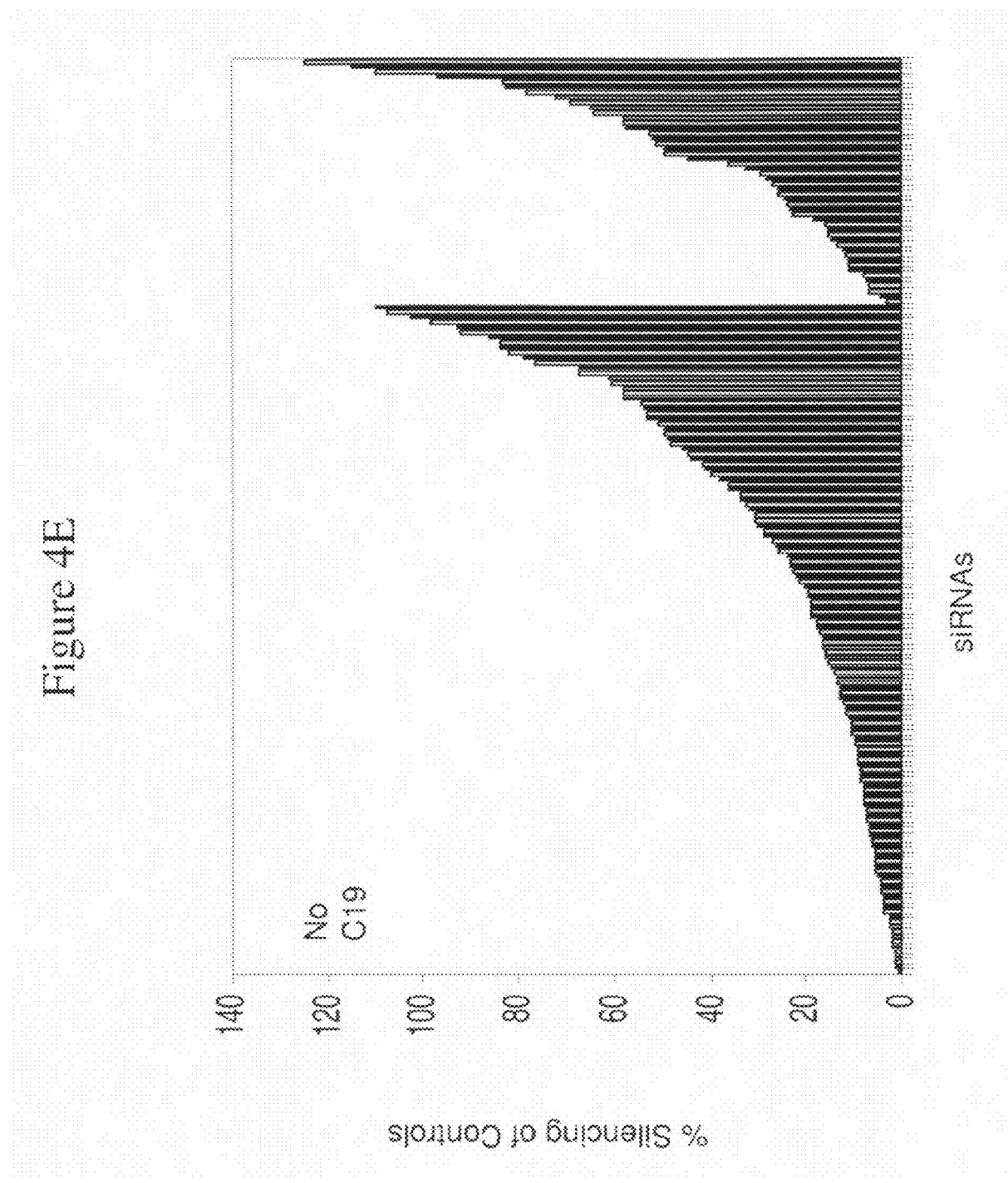
FIG. 4 is a representation of a statistical analysis that revealed correlations between silencing and five sequence-related properties of siRNA: (A) an A at position 19 of the sense strand, (B) an A at position 3 of the sense strand, (C) a U at position 10 of the sense strand, (D) a base other than G at position 13 of the sense strand, and (E) a base other than C at position 19 of the sense strand. All variables were correlated with siRNA silencing of firefly luciferase and human cyclophilin. siRNAs satisfying the criterion are grouped on the left (Selected) while those that do not, are grouped on the right (Eliminated). Y-axis is "% Silencing of Control." Each position on the X-axis represents a unique siRNA.

When the siRNA panel was sorted into functional and non-functional groups, the frequency of a specific nucleotide at each position in a functional siRNA duplex was compared with that of a nonfunctional duplex in order to assess the preference for or against a certain nucleotide. FIG. 4 shows the results of these queries and the subsequent resorting of the data set (from FIG. 2). The data is separated into two sets: those duplexes that meet the criteria, a specific nucleotide in a certain position—grouped on the left (Selected) and those that do not—grouped on the right (Eliminated). The duplexes are further sorted from most functional to least functional with the y-axis of FIG. 4a-e representing the % expression i.e., the amount of silencing that is elicited by the duplex (Note: each position on the X-axis represents a different duplex). Statistical analysis revealed correlations between silencing and several sequence-related properties of siRNAs. FIG. 4 and Table IV show quantitative analysis for the following five sequence-related properties of siRNA: (A) an A at position 19 of the sense strand; (B) an A at position 3 of the sense strand; (C) a U at position 10 of the sense strand; (D) a base other than G at position 13 of the sense strand; and (E) a base other than C at position 19 of the sense strand.

When the siRNAs in the panel were evaluated for the presence of an A at position 19 of the sense strand, the percentage of non-functional duplexes decreased. from 20% to 11.8%, and the percentage of F95 duplexes increased from 21.7% to 29.4% (Table IV). Thus, the presence of an A in this position defined Criterion IV.

Another sequence-related property correlated with silencing was the presence of an A in position 3 of the sense strand (FIG. 4b). Of the siRNAs with A3, 34.4% were F95, compared with 21.7% randomly selected siRNAs. The presence of a U base in position 10 of the sense strand exhibited an even greater impact (FIG. 4c). Of the duplexes in this group, 41.7% were F95. These properties became criteria V and VI, respectively.

Two negative sequence-related criteria that were identified also appear on FIG. 4. The absence of a G at position 13 of the sense strand, conferred a marginal increase in selecting functional duplexes (FIG. 4d). Similarly, lack of a C at position 19 of the sense strand also correlated with functionality (FIG. 4e). Thus, among functional duplexes, position 19 was most likely occupied by A, and rarely occupied by C. These rules were defined as criteria VII and VIII, respectively.

Application of each criterion individually provided marginal but statistically significant increases in the probability of selecting a potent siRNA. Although the results were informative, the inventors sought to maximize potency and therefore consider multiple criteria or parameters. Optimization is particularly important when developing therapeutics. Interestingly, the probability of selecting a functional siRNA based on each thermodynamic criteria was 2%-4% higher than random, but 4%-8% higher for the sequence-related determinates. Presumably, these sequence-related increases reflect the complexity of the RNAi mechanism and the multitude of protein-RNA interactions that are involved in RNAi-mediated silencing.

TABLE IV

| Criterion | | % Functional | Improvement over Random |
|---|---|---|---|
| I. 30%-52% G/C content | <F50 | 16.4% | −3.6% |
| | ≧F50 | 83.6% | 3.6% |
| | ≧F80 | 60.4% | 4.3% |
| | ≧F95 | 23.9% | 2.2% |
| II. At least 3 A/U bases at positions 15-19 of the sense strand | <F50 | 18.2% | −1.8% |
| | ≧F50 | 81.8% | 1.8% |
| | ≧F80 | 59.7% | 3.6% |
| | ≧F95 | 24.0% | 2.3% |
| III. Absence of internal repeats, as measured by $T_m$ of secondary structure ≦20° C. | <F50 | 16.7% | −3.3% |
| | ≧F50 | 83.3% | 3.3% |
| | ≧F80 | 61.1% | 5.0% |
| | ≧F95 | 24.6% | 2.9% |
| IV. An A base at position 19 of the sense strand | <F50 | 11.8% | −8.2% |
| | ≧F50 | 88.2% | 8.2% |
| | ≧F80 | 75.0% | 18.9% |
| | ≧F95 | 29.4% | 7.7% |
| V. An A base at position 3 of the sense strand | <F50 | 17.2% | −2.8% |
| | ≧F50 | 82.8% | 2.8% |
| | ≧F80 | 62.5% | 6.4% |
| | ≧F95 | 34.4% | 12.7% |
| VI. A U base at position 10 of the sense strand | <F50 | 13.9% | −6.1% |
| | ≧F50 | 86.1% | 6.1% |
| | ≧F80 | 69.4% | 13.3% |
| | ≧F95 | 41.7% | 20% |
| VII. A base other than C at position 19 of the sense strand | <F50 | 18.8% | −1.2% |
| | ≧F50 | 81.2% | 1.2% |
| | ≧F80 | 59.7% | 3.6% |
| | ≧F95 | 24.2% | 2.5% |
| VIII. A base other than G at position 13 of the sense strand | <F50 | 15.2% | −4.8% |
| | ≧F50 | 84.8% | 4.8% |
| | ≧F80 | 61.4% | 5.3% |
| | ≧F95 | 26.5% | 4.8% |

The siRNA Selection Algorithm

Figure 5B:
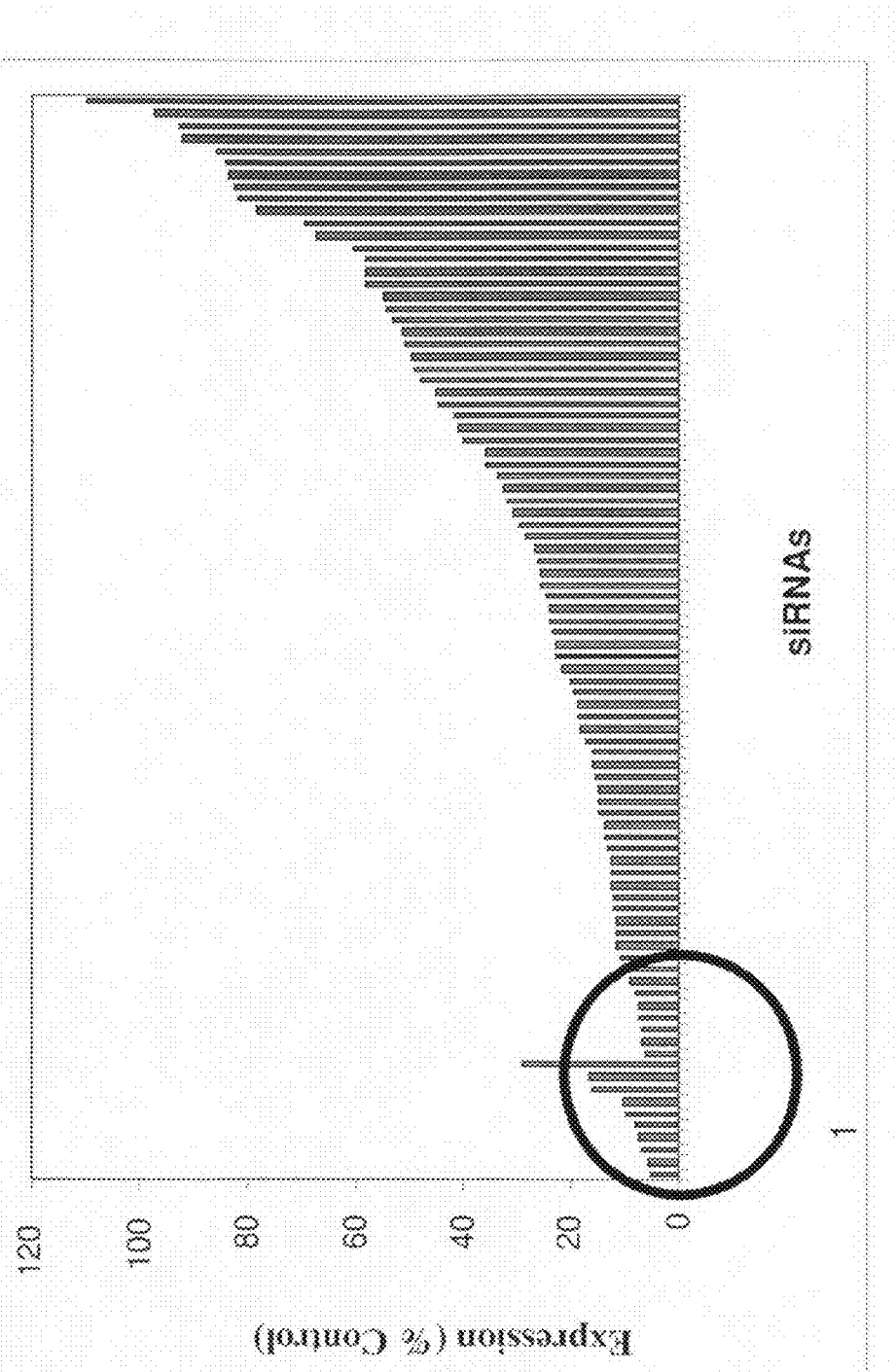

In an effort to improve selection further, all identified criteria, including but not limited to those listed in Table IV were combined into the algorithms embodied in Formula VIII, Formula IX, and Formula X. Each siRNA was then assigned a score (referred to as a SMARTscore™) according to the values derived from the formulas. Duplexes that scored higher than 0 or −20 (unadjusted), for Formulas VIII and IX, respectively, effectively selected a set of functional siRNAs and excluded all non-functional siRNAs. Conversely, all duplexes scoring lower than 0 and −20 (minus 20) according to formulas VIII and IX, respectively, contained some functional siRNAs but included all non-functional siRNAs. A graphical representation of this selection is shown in FIG. 5. It should be noted that the scores derived from the algorithm can also be provided as "adjusted" scores. To convert Formula VIII unadjusted scores into adjusted scores it is necessary to use the following equation:

$$(160+\text{unadjusted score})/2.25$$

When this takes place, an unadjusted score of "0" (zero) is converted to 75. Similarly, unadjusted scores for Formula X can be converted to adjusted scores. In this instance, the following equation is applied:

$$(228+\text{unadjusted score})/3.56$$

When these manipulations take place, an unadjusted score of 38 is converted to an adjusted score of 75.

The methods for obtaining the seven criteria embodied in Table IV are illustrative of the results of the process used to develop the information for Formulas VIII, IX, and X. Thus similar techniques were used to establish the other variables and their multipliers. As described above, basic statistical methods were use to determine the relative values for these multipliers.

To determine the value for "Improvement over Random" the difference in the frequency of a given attribute (e.g., GC content, base preference) at a particular position is determined between individual functional groups (e.g., <F50) and the total siRNA population studied (e.g., 270 siRNA molecules selected randomly). Thus, for instance, in Criterion I (30%-52% GC content) members of the <F50 group were observed to have GC contents between 30-52% in 16.4% of the cases. In contrast, the total group of 270 siRNAs had GC contents in this range, 20% of the time. Thus for this particular attribute, there is a small negative correlation between 30%-52% GC content and this functional group (i.e., 16.4%−20%=−3.6%). Similarly, for Criterion VI, (a "U" at position 10 of the sense strand), the >F95 group contained a "U" at this position 41.7% of the time. In contrast, the total group of 270 siRNAs had a "U" at this position 21.7% of the time, thus the improvement over random is calculated to be 20% (or 41.7%−21.7%).

Identifying the Average Internal Stability Profile of Strong siRNA

In order to identify an internal stability profile that is characteristic of strong siRNA, 270 different siRNAs derived from the cyclophilin B, the diazepam binding inhibitor (DBI), and the luciferase gene were individually transfected into HEK293 cells and tested for their ability to induce RNAi of the respective gene. Based on their performance in the in vivo assay, the sequences were then subdivided into three groups, (i) >95% silencing; (ii) 80-95% silencing; and (iii) less than 50% silencing. Sequences exhibiting 51-84% silencing were eliminated from further consideration to reduce the difficulties in identifying relevant thermodynamic patterns.

Following the division of siRNA into three groups, a statistical analysis was performed on each member of each group to determine the average internal stability profile (AISP) of the siRNA. To accomplish this the Oligo 5.0 Primer Analysis Software and other related statistical packages (e.g., Excel) were exploited to determine the internal stability of pentamers using the nearest neighbor method described by Freier et al., (1986) *Improved free-energy parameters for predictions of RNA duplex stability*, Proc Natl. Acad. Sci. U.S.A. 83(24): 9373-7. Values for each group at each position were then averaged, and the resulting data were graphed on a linear coordinate system with the Y-axis expressing the $\Delta G$ (free energy) values in kcal/mole and the X-axis identifying the position of the base relative to the 5' end.

Figure 6A:
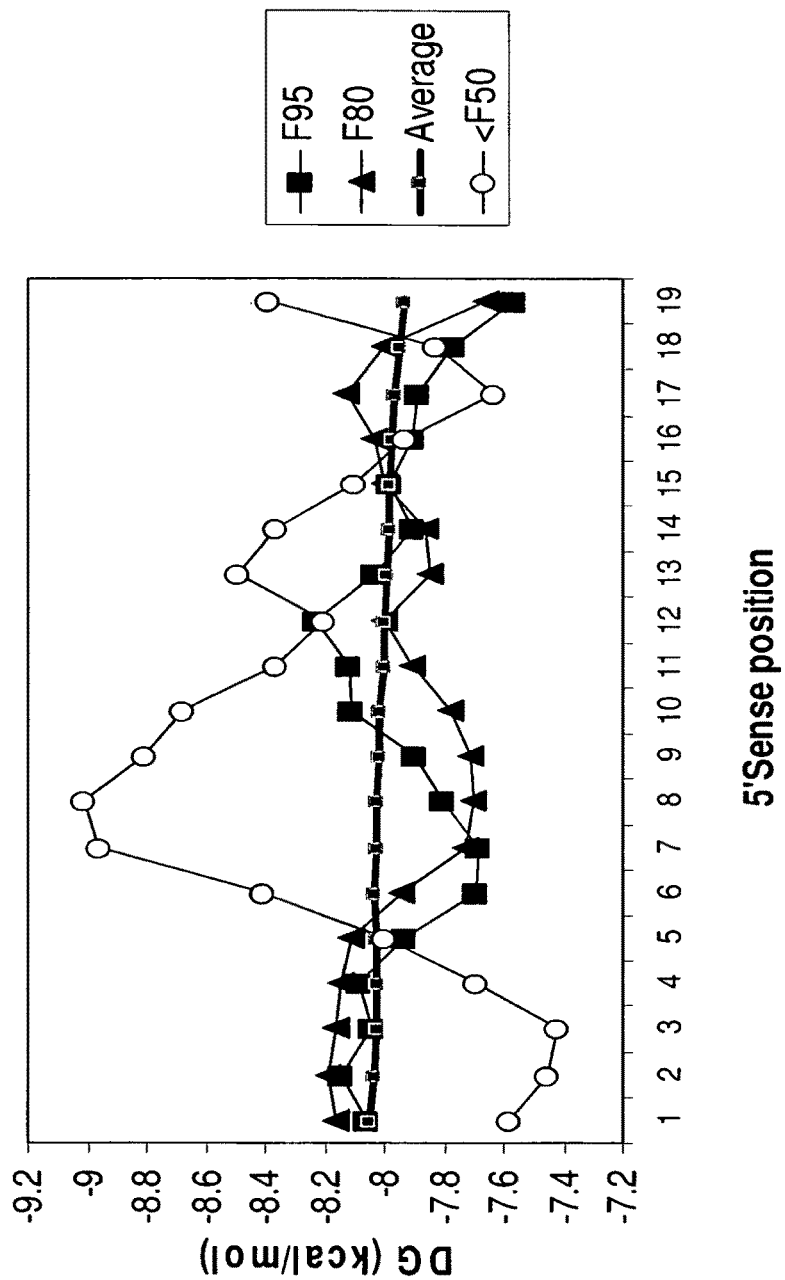
FIG. 6A is a representation of the average internal stability profile (AISP) derived from 270 siRNAs taken from three separate genes (cyclophilin B, DBI and firefly luciferase). Graphs represent AISP values of highly functional, functional, and non-functional siRNA.

The results of the analysis identified multiple key regions in siRNA molecules that were critical for successful gene silencing. At the 3'-most end of the sense strand (5' antisense), highly functional siRNA (>95% gene silencing, see FIG. 6a, >F95) have a low internal stability (AISP of position 19=~−7.6 kcal/mol). In contrast low-efficiency siRNA (i.e., those exhibiting less than 50% silencing, <F50) display a distinctly different profile, having high $\Delta G$ values (~−8.4 kcal/mol) for the same position. Moving in a 5' (sense strand) direction, the internal stability of highly efficient siRNA rises (position 12=~−8.3 kcal/mole) and then drops again (position 7=~−7.7 kcal/mol) before leveling off at a value of approximately −8.1 kcal/mol for the 5' terminus. siRNA with poor silencing capabilities show a distinctly different profile. While the AISP value at position 12 is nearly identical with that of strong siRNAs, the values at positions 7 and 8 rise considerably, peaking at a high of ~−9.0 kcal/mol. In addition, at the 5' end of the molecule the AISP profile of strong and weak siRNA differ dramatically. Unlike the relatively strong values exhibited by siRNA in the >95% silencing group, siRNAs that exhibit poor silencing activity have weak AISP values (−7.6, −7.5, and −7.5 kcal/mol for positions 1, 2 and 3 respectively).

Overall the profiles of both strong and weak siRNAs form distinct sinusoidal shapes that are roughly 180° out-of-phase with each other. While these thermodynamic descriptions define the archetypal profile of a strong siRNA, it will likely be the case that neither the $\Delta G$ values given for key positions in the profile or the absolute position of the profile along the Y-axis (i.e., the $\Delta G$-axis) are absolutes. Profiles that are shifted upward or downward (i.e., having on an average, higher or lower values at every position) but retain the relative shape and position of the profile along the X-axis can be foreseen as being equally effective as the model profile described here. Moreover, it is likely that siRNA that have strong or even stronger gene-specific silencing effects might have exaggerated $\Delta G$ values (either higher or lower) at key positions. Thus, for instance, it is possible that the 5'-most position of the sense strand (position 19) could have $\Delta G$ values of 7.4 kcal/mol or lower and still be a strong siRNA if, for instance, a G-C→G-T/U mismatch were substituted at position 19 and altered duplex stability. Similarly, position 12 and position 7 could have values above 8.3 kcal/mol and below 7.7 kcal/mole, respectively, without abating the silencing effectiveness of the molecule. Thus, for instance, at position 12, a stabilizing chemical modification (e.g., a chemical modification of the 2' position of the sugar backbone) could be added that increases the average internal stability at that position. Similarly, at position 7, mismatches similar to those described previously could be introduced that would lower the $\Delta G$ values at that position.

Lastly, it is important to note that while functional and non-functional siRNA were originally defined as those molecules having specific silencing properties, both broader or more limiting parameters can be used to define these molecules. As used herein, unless otherwise specified, "non-functional siRNA" are defined as those siRNA that induce less than 50% (<50%) target silencing, "semi-functional siRNA" induce 50-79% target silencing, "functional siRNA" are molecules that induce 80-95% gene silencing, and "highly-functional siRNA" are molecules that induce great than 95% gene silencing. These definitions are not intended to be rigid and can vary depending upon the design and needs of the application. For instance, it is possible that a researcher attempting to map a gene to a chromosome using a functional assay, may identify an siRNA that reduces gene activity by only 30%. While this level of gene silencing may be "non-functional" for, e.g., therapeutic needs, it is sufficient for gene mapping purposes and is, under these uses and conditions, "functional." For these reasons, functional siRNA can be defined as those molecules having greater than 10%, 20%, 30%, 40%, 50%, 60%, 70%, 80%, or 90% silencing capabilities at 100 nM transfection conditions. Similarly, depending upon the needs of the study and/or application, non-functional and semi-functional siRNA can be defined as having different parameters. For instance, semi-functional siRNA can be defined as being those molecules that induce 20%, 30%, 40%, 50%, 60%, or 70% silencing at 100 nM transfection conditions. Similarly, non-functional siRNA can be defined as being those molecules that silence gene expression by less than 70%, 60%, 50%, 40%, 30%, or less. Nonetheless, unless otherwise stated, the descriptions stated in the "Definitions" section of this text should be applied.

Functional attributes can be assigned to each of the key positions in the AISP of strong siRNA. The low 5' (sense strand) AISP values of strong siRNAs may be necessary for determining which end of the molecule enters the RISC complex. In contrast, the high and low AISP values observed in the central regions of the molecule may be critical for siRNA-target mRNA interactions and product release, respectively.

Figure 6B:
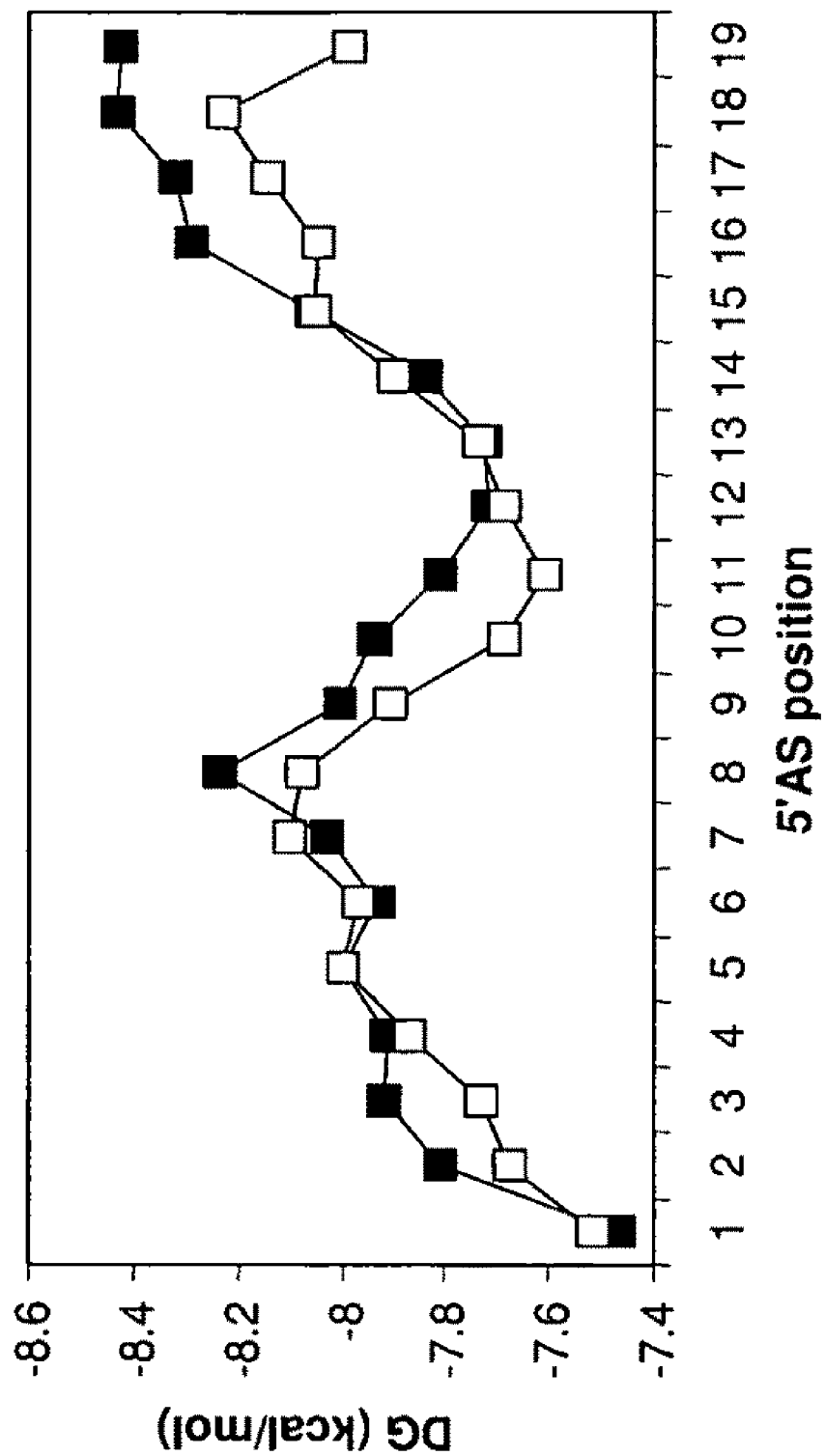
FIG. 6B is a comparison between the AISP of naturally derived GFP siRNA (filled squares) and the AISP of siRNA from cyclophilin B, DBI, and luciferase having >90% silencing properties (no fill) for the antisense strand. "DG" is the symbol for ΔG, free energy.

If the AISP values described above accurately define the thermodynamic parameters of strong siRNA, it would be expected that similar patterns would be observed in strong siRNA isolated from nature. Natural siRNAs exist in a harsh, RNase-rich environment and it can be hypothesized that only those siRNA that exhibit heightened affinity for RISC (i.e., siRNA that exhibit an average internal stability profile similar to those observed in strong siRNA) would survive in an intracellular environment. This hypothesis was tested using GFP-specific siRNA isolated from *N. benthamiana*. Llave et al. (2002) *Endogenous and Silencing-Associated Small RNAs in Plants*, The Plant Cell 14, 1605-1619, introduced long double-stranded GFP-encoding RNA into plants and subsequently re-isolated GFP-specific siRNA from the tissues. The AISP of fifty-nine of these GFP-siRNA were determined, averaged, and subsequently plotted alongside the AISP profile obtained from the cyclophilin B/DBI/luciferase siRNA having >90% silencing properties (FIG. 6*b*). Comparison of the two groups show that profiles are nearly identical. This finding validates the information provided by the internal stability profiles and demonstrates that: (1) the profile identified by analysis of the cyclophilin B/DBI/luciferase siRNAs are not gene specific; and (2) AISP values can be used to search for strong siRNAs in a variety of species.

Figure 7:
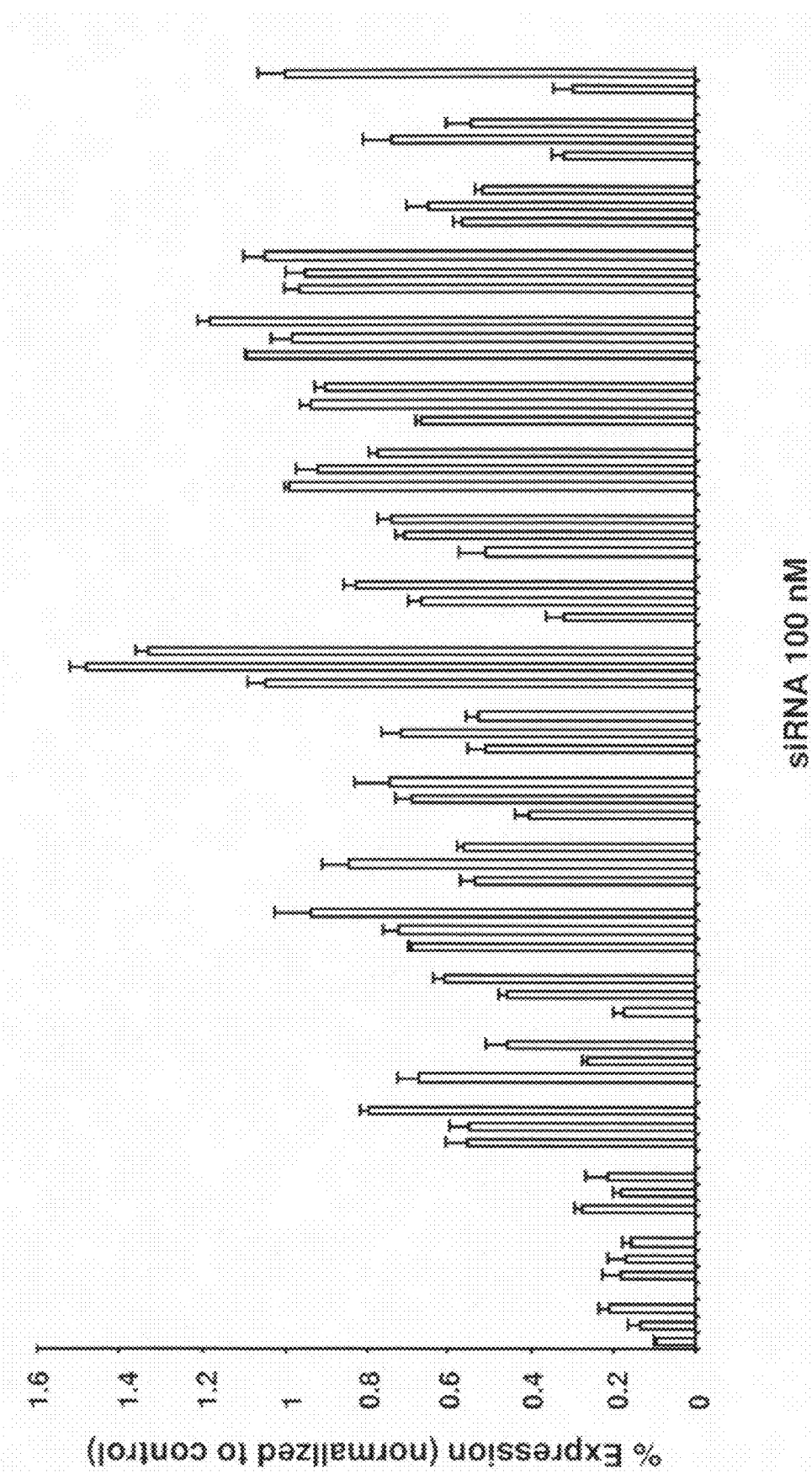
FIG. 7 is a histogram showing the differences in duplex functionality upon introduction of basepair mismatches. The X-axis shows the mismatch introduced in the siRNA and the position it is introduced (e.g., 8C>A reveals that position 8 (which normally has a C) has been changed to an A). The Y-axis is "% Silencing (Normalized to Control)."
Figure 8A:
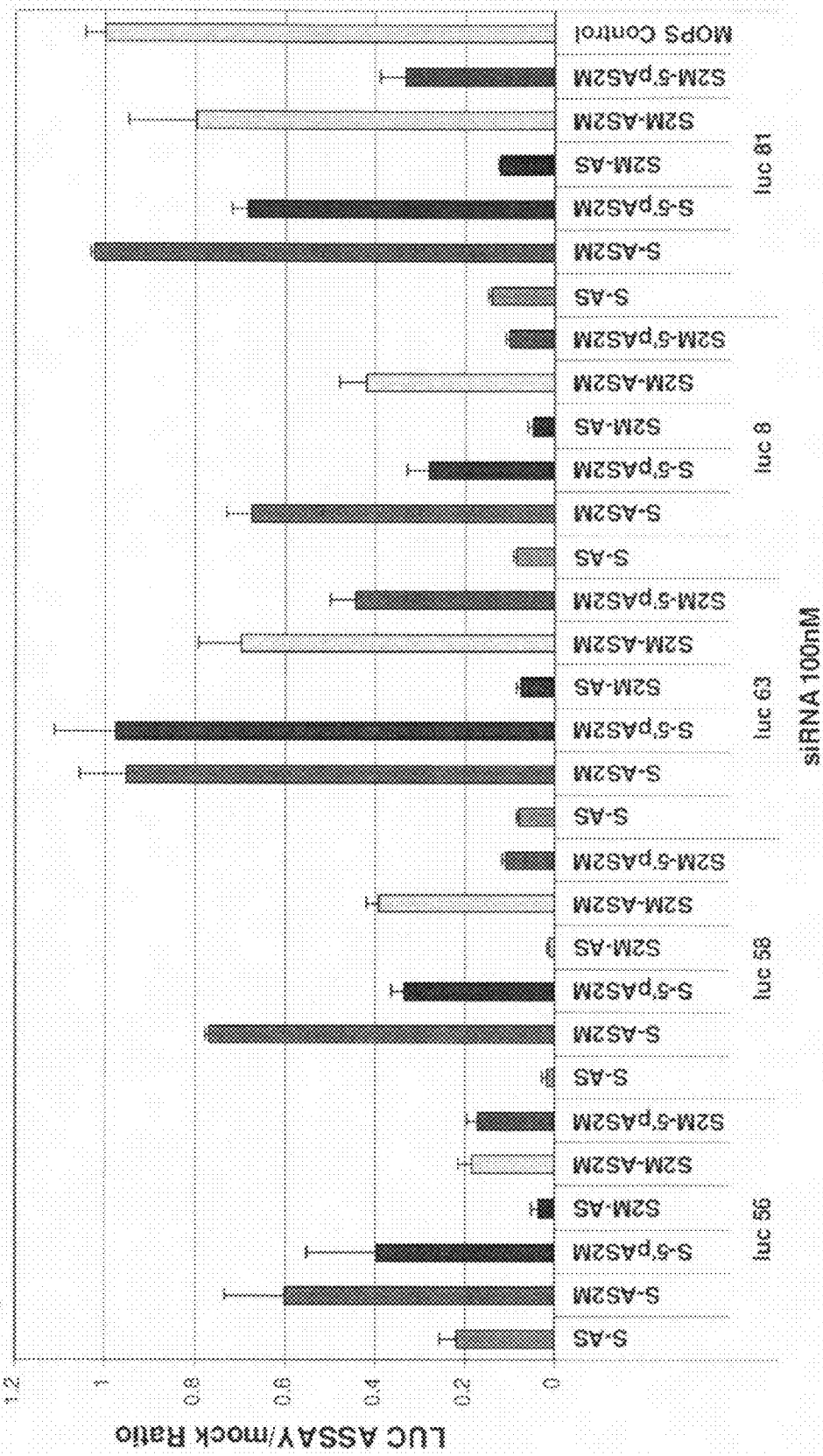
FIG. 8a is histogram that shows the effects of 5' sense and antisense strand modification with 2'-O-methylation on functionality.
Figure 8B:
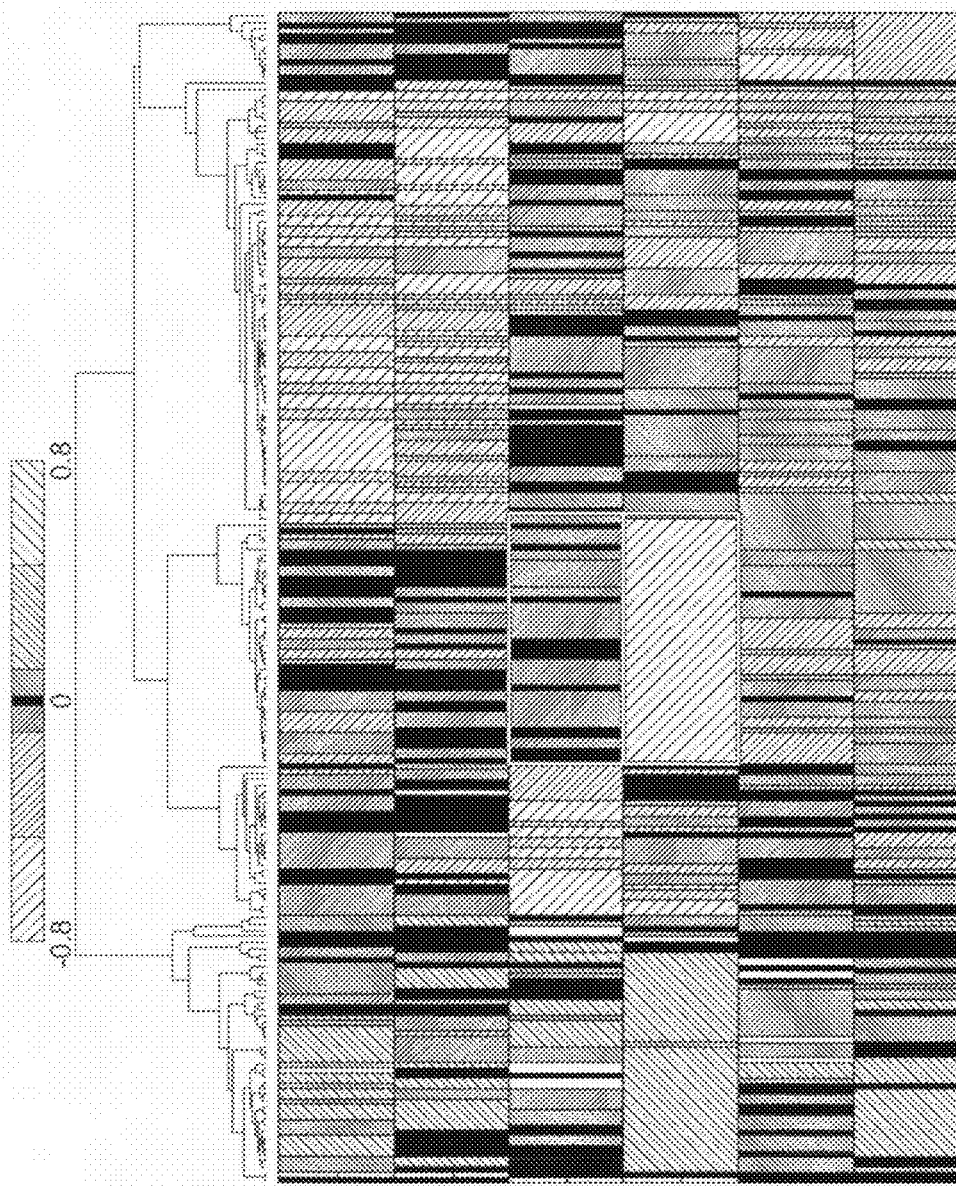
FIG. 8b is an expression profile showing a comparison of sense strand off-target effects for IGF1R-3 and 2'-O-methyl IGF1R-3. Sense strand off-targets (lower box) are not induced when the 5' end of the sense strand is modified with 2'-O-methyl groups (top box).

Both chemical modifications and base-pair mismatches can be incorporated into siRNA to alter the duplex's AISP and functionality. For instance, introduction of mismatches at positions 1 or 2 of the sense strand destabilized the 5' end of the sense strand and increases the functionality of the molecule (see Luc, FIG. 7). Similarly, addition of 2'-O-methyl groups to positions 1 and 2 of the sense strand can also alter the AISP and (as a result) increase both the functionality of the molecule and eliminate off-target effects that results from sense strand homology with the unrelated targets (FIGS. 8*a*, 8*b*).

Rationale for Criteria in a Biological Context

The fate of siRNA in the RNAi pathway may be described in 5 major steps: (1) duplex recognition and pre-RISC complex formation; (2) ATP-dependent duplex unwinding/strand selection and RISC activation; (3) mRNA target identification; (4) mRNA cleavage, and (5) product release (FIG. 1). Given the level of nucleic acid-protein interactions at each step, siRNA functionality is likely influenced by specific biophysical and molecular properties that promote efficient interactions within the context of the multi-component complexes. Indeed, the systematic analysis of the siRNA test set identified multiple factors that correlate well with functionality. When combined into a single algorithm, they proved to be very effective in selecting active siRNAs.

The factors described here may also be predictive of key functional associations important for each step in RNAi. For example, the potential formation of internal hairpin structures correlated negatively with siRNA functionality. Complementary strands with stable internal repeats are more likely to exist as stable hairpins thus decreasing the effective concentration of the functional duplex form. This suggests that the duplex is the preferred conformation for initial pre-RISC association. Indeed, although single complementary strands can induce gene silencing, the effective concentration required is at least two orders of magnitude higher than that of the duplex form.

siRNA-pre-RISC complex formation is followed by an ATP-dependent duplex unwinding step and "activation" of the RISC. The siRNA functionality was shown to correlate with overall low internal stability of the duplex and low internal stability of the 3' sense end (or differential internal stability of the 3' sense compare to the 5' sense strand), which may reflect strand selection and entry into the RISC. Overall duplex stability and low internal stability at the 3' end of the sense strand were also correlated with siRNA functionality. Interestingly, siRNAs with very high and very low overall stability profiles correlate strongly with non-functional duplexes. One interpretation is that high internal stability prevents efficient unwinding while very low stability reduces siRNA target affinity and subsequent mRNA cleavage by the RISC.

Several criteria describe base preferences at specific positions of the sense strand and are even more intriguing when considering their potential mechanistic roles in target recognition and mRNA cleavage. Base preferences for A at position 19 of the sense strand but not C, are particularly interesting because they reflect the same base preferences observed for naturally occurring miRNA precursors. That is, among the reported miRNA precursor sequences 75% contain a U at position 1 which corresponds to an A in position 19 of the sense strand of siRNAs, while G was under-represented in this same position for miRNA precursors. These observations support the hypothesis that both miRNA precursors and siRNA duplexes are processed by very similar if not identical protein machinery. The functional interpretation of the predominance of a U/A base pair is that it promotes flexibility at the 5' antisense ends of both siRNA duplexes and miRNA precursors and facilitates efficient unwinding and selective strand entrance into an activated RISC.

Among the criteria associated with base preferences that are likely to influence mRNA cleavage or possibly product release, the preference for U at position 10 of the sense strand exhibited the greatest impact, enhancing the probability of selecting an F80 sequence by 13.3%. Activated RISC preferentially cleaves target mRNA between nucleotides 10 and 11 relative to the 5' end of the complementary targeting strand. Therefore, it may be that U, the preferred base for most endoribonucleases, at this position supports more efficient cleavage. Alternatively, a U/A by between the targeting siRNA strand and its cognate target mRNA may create an optimal conformation for the RISC-associated "slicing" activity.

Post Algorithm Filters

According to another embodiment, the output of any one of the formulas previously listed can be filtered to remove or select for siRNAs containing undesirable or desirable motifs or properties, respectively. In one example, sequences identified by any of the formulas can be filtered to remove any and all sequences that induce toxicity or cellular stress. Introduction of an siRNA containing a toxic motif into a cell can induce cellular stress and/or cell death (apoptosis) which in turn can mislead researchers into associating a particular (e.g., nonessential) gene with, e.g., an essential function. Alternatively, sequences generated by any of the before mentioned formulas can be filtered to identify and retain duplexes that contain toxic motifs. Such duplexes may be valuable from a variety of perspectives including, for instance, uses as therapeutic molecules. A variety of toxic motifs exist and can exert their influence on the cell through RNAi and non-RNAi pathways. Examples of toxic motifs are explained more fully in commonly assigned U.S. Provisional Patent Application Ser. No. 60/538,874, entitled "Identification of Toxic Sequences," filed Jan. 23, 2004. Briefly, toxic motifs include A/G UUU A/G/U, G/C AAA G/C, and GCCA, or a complement of any of the foregoing.

In another instance, sequences identified by any of the before mentioned formulas can be filtered to identify duplexes that contain motifs (or general properties) that provide serum stability or induce serum instability. In one envisioned application of siRNA as therapeutic molecules, duplexes targeting disease-associated genes will be introduced into patients intravenously. As the half-life of single and double stranded RNA in serum is short, post-algorithm filters designed to select molecules that contain motifs that enhance duplex stability in the presence of serum and/or (conversely) eliminate duplexes that contain motifs that destabilize siRNA in the presence of serum, would be beneficial.

In another instance, sequences identified by any of the before mentioned formulas can be filtered to identify duplexes that are hyperfunctional. Hyperfunctional sequences are defined as those sequences that (1) induce greater than 95% silencing of a specific target when they are transfected at subnanomolar concentrations (i.e., less than one nanomolar); and/or (2) induce functional (or better) levels of silencing for greater than 96 hours. Filters that identify hyperfunctional molecules can vary widely. In one example, the top ten, twenty, thirty, or forty siRNA can be assessed for the ability to silence a given target at, e.g., concentrations of 1 nM and 0.5 nM to identify hyperfunctional molecules.

Pooling

According to another embodiment, the present invention provides a pool of at least two siRNAs, preferably in the form of a kit or therapeutic reagent, wherein one strand of each of the siRNAs, the sense strand comprises a sequence that is substantially similar to a sequence within a target mRNA. The opposite strand, the antisense strand, will preferably comprise a sequence that is substantially complementary to that of the target mRNA. More preferably, one strand of each siRNA will comprise a sequence that is identical to a sequence that is contained in the target mRNA. Most preferably, each siRNA will be 19 base pairs in length, and one strand of each of the siRNAs will be 100% complementary to a portion of the target mRNA.

By increasing the number of siRNAs directed to a particular target using a pool or kit, one is able both to increase the likelihood that at least one siRNA with satisfactory functionality will be included, as well as to benefit from additive or synergistic effects. Further, when two or more siRNAs directed against a single gene do not have satisfactory levels of functionality alone, if combined, they may satisfactorily promote degradation of the target messenger RNA and successfully inhibit translation. By including multiple siRNAs in the system, not only is the probability of silencing increased, but the economics of operation are also improved when compared to adding different siRNAs sequentially. This effect is contrary to the conventional wisdom that the concurrent use of multiple siRNA will negatively impact gene silencing (e.g., Holen, T. et al. (2003) "Similar behavior of single strand and double strand siRNAs suggests they act through a common RNAi pathway." NAR 31: 2401-21407).

In fact, when two siRNAs were pooled together, 54% of the pools of two siRNAs induced more than 95% gene silencing. Thus, a 2.5-fold increase in the percentage of functionality was achieved by randomly combining two siRNAs. Further, over 84% of pools containing two siRNAs induced more than 80% gene silencing.

More preferably, the kit is comprised of at least three siRNAs, wherein one strand of each siRNA comprises a sequence that is substantially similar to a sequence of the target mRNA and the other strand comprises a sequence that is substantially complementary to the region of the target mRNA. As with the kit that comprises at least two siRNAs, more preferably one strand will comprise a sequence that is identical to a sequence that is contained in the mRNA and another strand that is 100% complementary to a sequence that is contained in the mRNA. During experiments, when three siRNAs were combined together, 60% of the pools induced more than 95% gene silencing and 92% of the pools induced more than 80% gene silencing.

Further, even more preferably, the kit is comprised of at least four siRNAs, wherein one strand of each siRNA comprises a sequence that is substantially similar to a region of the sequence of the target mRNA, and the other strand comprises a sequence that is substantially complementary to the region of the target mRNA. As with the kit or pool that comprises at least two siRNAs, more preferably one strand of each of the siRNA duplexes will comprise a sequence that is identical to a sequence that is contained in the mRNA, and another strand that is 100% complementary to a sequence that is contained in the mRNA.

Additionally, kits and pools with at least five, at least six, and at least seven siRNAs may also be useful with the present invention. For example, pools of five siRNA induced 95% gene silencing with 77% probability and 80% silencing with 98.8% probability. Thus, pooling of siRNAs together can result in the creation of a target-specific silencing reagent with almost a 99% probability of being functional. The fact that such high levels of success are achievable using such pools of siRNA, enables one to dispense with costly and time-consuming target-specific validation procedures.

For this embodiment, as well as the other aforementioned embodiments, each of the siRNAs within a pool will preferably comprise 18-30 base pairs, more preferably 18-25 base pairs, and most preferably 19 base pairs. Within each siRNA, preferably at least 18 contiguous bases of the antisense strand will be 100% complementary to the target mRNA. More preferably, at least 19 contiguous bases of the antisense strand will be 100% complementary to the target mRNA. Additionally, there may be overhangs on either the sense strand or the antisense strand, and these overhangs may be at either the 5' end or the 3' end of either of the strands, for example there may be one or more overhangs of 1-6 bases. When overhangs are present, they are not included in the calculation of the number of base pairs. The two nucleotide 3' overhangs mimic natural siRNAs and are commonly used but are not essential. Preferably, the overhangs should consist of two nucleotides, most often dTdT or UU at the 3' end of the sense and antisense strand that are not complementary to the target sequence. The siRNAs may be produced by any method that is now known or that comes to be known for synthesizing double stranded RNA that one skilled in the art would appreciate would be useful in the present invention. Preferably, the siRNAs will be produced by Dharmacon's proprietary ACE® technology. However, other methods for synthesizing siRNAs are well known to persons skilled in the art and include, but are not limited to, any chemical synthesis of RNA oligonucleotides, ligation of shorter oligonucleotides, in vitro transcription of RNA oligonucleotides, the use of vectors for expression within cells, recombinant Dicer products and PCR products.

The siRNA duplexes within the aforementioned pools of siRNAs may correspond to overlapping sequences within a particular mRNA, or non-overlapping sequences of the mRNA. However, preferably they correspond to non-overlapping sequences. Further, each siRNA may be selected randomly, or one or more of the siRNA may be selected according to the criteria discussed above for maximizing the effectiveness of siRNA.

Included in the definition of siRNAs are siRNAs that contain substituted and/or labeled nucleotides that may, for example, be labeled by radioactivity, fluorescence or mass. The most common substitutions are at the 2' position of the ribose sugar, where moieties such as H (hydrogen) F, $NH_3$, $OCH_3$ and other O-alkyl, alkenyl, alkynyl, and orthoesters, may be substituted, or in the phosphorous backbone, where sulfur, amines or hydrocarbons may be substituted for the bridging of non-bridging atoms in the phosphodiester bond. Examples of modified siRNAs are explained more fully in commonly assigned U.S. patent application Ser. No. 10/613, 077, filed Jul. 1, 2003.

Additionally, as noted above, the cell type into which the siRNA is introduced may affect the ability of the siRNA to enter the cell; however, it does not appear to affect the ability of the siRNA to function once it enters the cell. Methods for introducing double-stranded RNA into various cell types are well known to persons skilled in the art.

As persons skilled in the art are aware, in certain species, the presence of proteins such as RdRP, the RNA-dependent RNA polymerase, may catalytically enhance the activity of the siRNA. For example, RdRP propagates the RNAi effect in *C. elegans* and other non-mammalian organisms. In fact, in organisms that contain these proteins, the siRNA may be inherited. Two other proteins that are well studied and known to be a part of the machinery are members of the Argonaute family and Dicer, as well as their homologues. There is also initial evidence that the RISC complex might be associated with the ribosome so the more efficiently translated mRNAs will be more susceptible to silencing than others.

Another very important factor in the efficacy of siRNA is mRNA localization. In general, only cytoplasmic mRNAs are considered to be accessible to RNAi to any appreciable degree. However, appropriately designed siRNAs, for example, siRNAs modified with internucleotide linkages or 2'-O-methyl groups, may be able to cause silencing by acting in the nucleus. Examples of these types of modifications are described in commonly assigned U.S. patent application Ser. Nos. 10/431,027 and 10/613,077.

As described above, even when one selects at least two siRNAs at random, the effectiveness of the two may be greater than one would predict based on the effectiveness of two individual siRNAs. This additive or synergistic effect is particularly noticeable as one increases to at least three siRNAs, and even more noticeable as one moves to at least four siRNAs. Surprisingly, the pooling of the non-functional and semi-functional siRNAs, particularly more than five siRNAs, can lead to a silencing mixture that is as effective if not more effective than any one particular functional siRNA.

Within the kits of the present invention, preferably each siRNA will be present in a concentration of between 0.001 and 200 µM, more preferably between 0.01 and 200 nM, and most preferably between 0.1 and 10 nM.

In addition to preferably comprising at least four or five siRNAs, the kits of the present invention will also preferably comprise a buffer to keep the siRNA duplex stable. Persons skilled in the art are aware of buffers suitable for keeping siRNA stable. For example, the buffer may be comprised of 100 mM KCl, 30 mM HEPES-pH 7.5, and 1 mM $MgCl_2$. Alternatively, kits might contain complementary strands that contain any one of a number of chemical modifications (e.g., a 2'-O-ACE) that protect the agents from degradation by nucleases. In this instance, the user may (or may not) remove the modifying protective group (e.g., deprotect) before annealing the two complementary strands together.

By way of example, the kits may be organized such that pools of siRNA duplexes are provided on an array or microarray of wells or drops for a particular gene set or for unrelated genes. The array may, for example, be in 96 wells, 384 wells or 1284 wells arrayed in a plastic plate or on a glass slide using techniques now known or that come to be known to persons skilled in the art. Within an array, preferably there will be controls such as functional anti-lamin A/C, cyclophilin and two siRNA duplexes that are not specific to the gene of interest.

In order to ensure stability of the siRNA pools prior to usage, they may be retained in lyophilized form at minus twenty degrees (−20° C.) until they are ready for use. Prior to usage, they should be resuspended; however, even once resuspended, for example, in the aforementioned buffer, they should be kept at minus twenty degrees, (−20° C.) until used. The aforementioned buffer, prior to use, may be stored at approximately 4° C. or room temperature. Effective temperatures at which to conduct transfections are well known to persons skilled in the art and include for example, room temperature.

The kits may be applied either in vivo or in vitro. Preferably, the siRNA of the pools or kits is applied to a cell through transfection, employing standard transfection protocols. These methods are well known to persons skilled in the art and include the use of lipid-based carriers, electroporation, cationic carriers, and microinjection. Further, one could apply the present invention by synthesizing equivalent DNA sequences (either as two separate, complementary strands, or as hairpin molecules) instead of siRNA sequences and introducing them into cells through vectors. Once in the cells, the cloned DNA could be transcribed, thereby forcing the cells to generate the siRNA. Examples of vectors suitable for use with the present application include but are not limited to the standard transient expression vectors, adenoviruses, retroviruses, lentivirus-based vectors, as well as other traditional expression vectors. Any vector that has an adequate siRNA expression and procession module may be used. Furthermore, certain chemical modifications to siRNAs, including but not limited to conjugations to other molecules, may be used to facilitate delivery. For certain applications it may be preferable to deliver molecules without transfection by simply formulating in a physiological acceptable solution.

This embodiment may be used in connection with any of the aforementioned embodiments. Accordingly, the sequences within any pool may be selected by rational design.

Multigene Silencing

In addition to developing kits that contain multiple siRNA directed against a single gene, another embodiment includes the use of multiple siRNA targeting multiple genes. Multiple genes may be targeted through the use of high- or hyper-functional siRNA. High- or hyper-functional siRNA that exhibit increased potency, require lower concentrations to induce desired phenotypic (and thus therapeutic) effects. This circumvents RISC saturation. It therefore reasons that if lower concentrations of a single siRNA are needed for knockout or knockdown expression of one gene, then the remaining (uncomplexed) RISC will be free and available to interact with siRNA directed against two, three, four, or more, genes. Thus in this embodiment, the authors describe the use of highly functional or hyper-functional siRNA to knock out three separate genes. More preferably, such reagents could be combined to knockout four distinct genes. Even more preferably, highly functional or hyperfunctional siRNA could be used to knock out five distinct genes. Most preferably, siRNA of this type could be used to knockout or knockdown the expression of six or more genes.

Hyperfunctional siRNA

The term hyperfunctional siRNA (hf-siRNA) describes a subset of the siRNA population that induces RNAi in cells at low- or sub-nanomolar concentrations for extended periods of time. These traits, heightened potency and extended longevity of the RNAi phenotype, are highly attractive from a therapeutic standpoint. Agents having higher potency require lesser amounts of the molecule to achieve the desired physiological response, thus reducing the probability of side effects due to "off-target" interference. In addition to the potential therapeutic benefits associated with hyperfunctional siRNA, hf-siRNA are also desirable from an economic perspective. Hyperfunctional siRNA may cost less on a per-treatment basis, thus reducing overall expenditures to both the manufacturer and the consumer.

Figure 9:
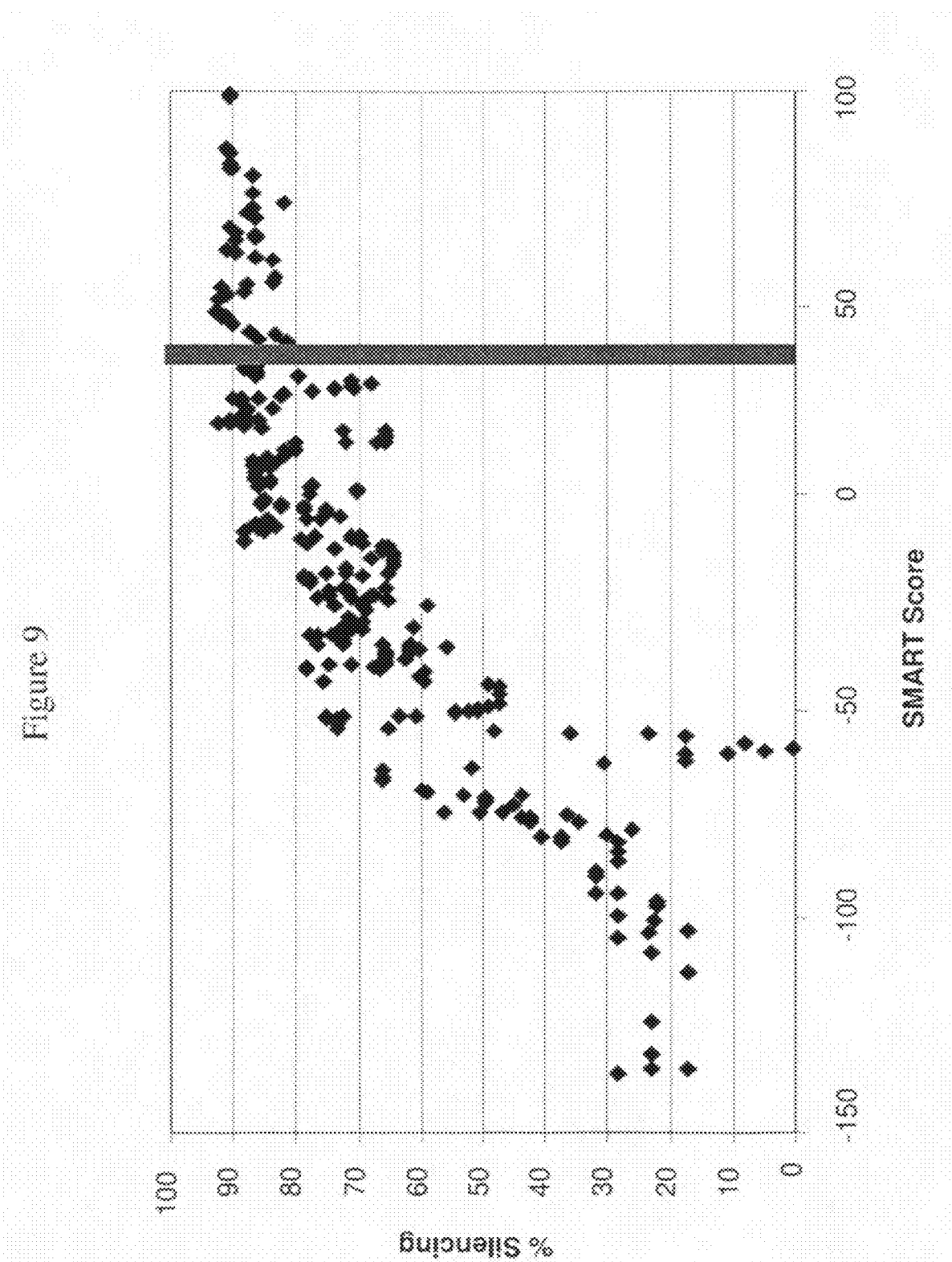
FIG. 9 shows a graph of SMARTscores™ versus RNAi silencing values for more than 360 siRNA directed against 30 different genes. siRNA to the right of the vertical bar represent those siRNA that have desirable SMARTscores™.

Identification of hyperfunctional siRNA involves multiple steps that are designed to examine an individual siRNA agent's concentration- and/or longevity-profiles. In one non-limiting example, a population of siRNA directed against a single gene are first analyzed using the previously described algorithm (Formula VIII). Individual siRNA are then introduced into a test cell line and assessed for the ability to degrade the target mRNA. It is important to note that when performing this step it is not necessary to test all of the siRNA. Instead, it is sufficient to test only those siRNA having the highest SMARTscores™ (i.e., SMARTscore™>−10). Subsequently, the gene silencing data is plotted against the SMARTscores™ (see FIG. 9). siRNA that (1) induce a high degree of gene silencing (i.e., they induce greater than 80% gene knockdown) and (2) have superior SMARTscores™ (i.e., a SMARTscore™ of >−10, suggesting a desirable average internal stability profile) are selected for further investigations designed to better understand the molecule's potency and longevity. In one, non-limiting study dedicated to understanding a molecule's potency, an siRNA is introduced into one (or more) cell types in increasingly diminishing concentrations (e.g., 3.0→0.3 nM). Subsequently, the level of gene silencing induced by each concentration is examined and siRNA that exhibit hyperfunctional potency (i.e., those that induce 80% silencing or greater at, e.g., picomolar concentrations) are identified. In a second study, the longevity profiles of siRNA having high (>−10) SMARTscores™ and greater than 80% silencing are examined. In one non-limiting example of how this is achieved, siRNA are introduced into a test cell line and the levels of RNAi are measured over an extended period of time (e.g., 24-168 hrs). siRNAs that exhibit strong RNA interference patterns (i.e., >80% interference) for periods of time greater than, e.g., 120 hours, are thus identified. Studies similar to those described above can be performed on any and all of the >$10^6$ siRNA included in this document to further define the most functional molecule for any given gene. Molecules possessing one or both properties (extended longevity and heightened potency) are labeled "hyperfunctional siRNA," and earmarked as candidates for future therapeutic studies.

While the example(s) given above describe one means by which hyperfunctional siRNA can be isolated, neither the assays themselves nor the selection parameters used are rigid and can vary with each family of siRNA. Families of siRNA include siRNAs directed against a single gene, or directed against a related family of genes.

The highest quality siRNA achievable for any given gene may vary considerably. Thus, for example, in the case of one gene (gene X), rigorous studies such as those described above may enable the identification of an siRNA that, at picomolar concentrations, induces 99$^{+}$% silencing for a period of 10 days. Yet identical studies of a second gene (gene Y) may yield an siRNA that at high nanomolar concentrations (e.g., 100 nM) induces only 75% silencing for a period of 2 days. Both molecules represent the very optimum siRNA for their respective gene targets and therefore are designated "hyperfunctional." Yet due to a variety of factors including but not limited to target concentration, siRNA stability, cell type, off-target interference, and others, equivalent levels of potency and longevity are not achievable. Thus, for these reasons, the parameters described in the before mentioned assays can vary. While the initial screen selected siRNA that had SMARTscores™ above −10 and a gene silencing capability of greater than 80%, selections that have stronger (or weaker) parameters can be implemented. Similarly, in the subsequent studies designed to identify molecules with high potency and longevity, the desired cutoff criteria (i.e., the lowest concentration that induces a desirable level of interference, or the longest period of time that interference can be observed) can vary. The experimentation subsequent to application of the rational criteria of this application is significantly reduced where one is trying to obtain a suitable hyperfunctional siRNA for, for example, therapeutic use. When, for example, the additional experimentation of the type described herein is applied by one skilled in the art with this disclosure in hand, a hyperfunctional siRNA is readily identified.

The siRNA may be introduced into a cell by any method that is now known or that comes to be known and that from reading this disclosure, persons skilled in the art would determine would be useful in connection with the present invention in enabling siRNA to cross the cellular membrane. These methods include, but are not limited to, any manner of transfection, such as, for example, transfection employing DEAE-Dextran, calcium phosphate, cationic lipids/liposomes, micelles, manipulation of pressure, microinjection, electroporation, immunoporation, use of vectors such as viruses, plasmids, cosmids, bacteriophages, cell fusions, and coupling of the polynucleotides to specific conjugates or ligands such as antibodies, antigens, or receptors, passive introduction, adding moieties to the siRNA that facilitate its uptake, and the like.

Having described the invention with a degree of particularity, examples will now be provided. These examples are not intended to and should not be construed to limit the scope of the claims in any way.

EXAMPLES

General Techniques and Nomenclatures siRNA nomenclature. All siRNA duplexes are referred to by sense strand. The first nucleotide of the 5'-end of the sense strand is position 1, which corresponds to position 19 of the antisense strand for a 19-mer. In most cases, to compare results from different experiments, silencing was determined by measuring specific transcript mRNA levels or enzymatic activity associated with specific transcript levels, 24 hours post-transfection, with siRNA concentrations held constant at 100 nM. For all experiments, unless otherwise specified, transfection efficiency was ensured to be over 95%, and no detectable cellular toxicity was observed. The following system of nomenclature was used to compare and report siRNA-silencing functionality: "F" followed by the degree of minimal knockdown. For example, F50 signifies at least 50% knockdown, F80 means at least 80%, and so forth. For this study, all sub-F50 siRNAs were considered non-functional.

Cell culture and transfection. 96-well plates are coated with 50 µl of 50 mg/ml poly-L-lysine (Sigma) for 1 hr, and then washed 3× with distilled water before being dried for 20 min. HEK293 cells or HEK293Lucs or any other cell type of interest are released from their solid support by trypsinization, diluted to 3.5×10⁵ cells/ml, followed by the addition of 100 µL of cells/well. Plates are then incubated overnight at 37° C., 5% $CO_2$. Transfection procedures can vary widely depending on the cell type and transfection reagents. In one non-limiting example, a transfection mixture consisting of 2 mL Opti-MEM I (Gibco-BRL), 80 µl Lipofectamine 2000 (Invitrogen), 15 µL SUPERNasin at 20 U/µl (Ambion), and 1.5 µl of reporter gene plasmid at 1 µg/µl is prepared in 5-ml polystyrene round bottom tubes. One hundred µl of transfection reagent is then combined with 100 µl of siRNAs in polystyrene deep-well titer plates (Beckman) and incubated for 20 to 30 min at room temperature. Five hundred and fifty microliters of Opti-MEM is then added to each well to bring the final siRNA concentration to 100 nM. Plates are then sealed with parafilm and mixed. Media is removed from HEK293 cells and replaced with 95 µl of transfection mixture. Cells are incubated overnight at 37° C., 5% $CO_2$.

Quantification of gene knockdown. A variety of quantification procedures can be used to measure the level of silencing induced by siRNA or siRNA pools. In one non-limiting example: to measure mRNA levels 24 hrs post-transfection, QuantiGene branched-DNA (bDNA) kits (Bayer) (Wang, et al, Regulation of insulin preRNA splicing by glucose. Proc. Natl. Acad. Sci. USA 1997, 94:4360.) are used according to manufacturer instructions. To measure luciferase activity, media is removed from HEK293 cells 24 hrs post-transfection, and 50 µl of Steady-GLO reagent (Promega) is added. After 5 minutes, plates are analyzed on a plate reader.

Example I

Sequences Used to Develop the Algorithm

Anti-Firefly and anti-Cyclophilin siRNAs panels (FIG. 5a, b) sorted according to using Formula VIII predicted values.

All siRNAs scoring more than 0 (formula VIII) and more then 20 (formula IX) are fully functional. All ninety sequences for each gene (and DBI) appear below in Table III.

TABLE III

| Cyclo | 1  | SEQ. ID 0032 | GUUCCAAAAACAGUGGAUA |
|-------|----|--------------|---------------------|
| Cyclo | 2  | SEQ. ID 0033 | UCCAAAAACAGUGGAUAAU |
| Cyclo | 3  | SEQ. ID 0034 | CAAAAACAGUGGAUAAUUU |
| Cyclo | 4  | SEQ. ID 0035 | AAAACAGUGGAUAAUUUUG |
| Cyclo | 5  | SEQ. ID 0036 | AACAGUGGAUAAUUUUGUG |
| Cyclo | 6  | SEQ. ID 0037 | CAGUGGAUAAUUUUGUGGC |
| Cyclo | 7  | SEQ. ID 0038 | GUGGAUAAUUUUGUGGCCU |
| Cyclo | 8  | SEQ. ID 0039 | GGAUAAUUUUGUGGCCUUA |
| Cyclo | 9  | SEQ. ID 0040 | AUAAUUUUGUGGCCUUAGC |
| Cyclo | 10 | SEQ. ID 0041 | AAUUUUGUGGCCUUAGCUA |
| Cyclo | 11 | SEQ. ID 0042 | UUUUGUGGCCUUAGCUACA |
| Cyclo | 12 | SEQ. ID 0043 | UUGUGGCCUUAGCUACAGG |
| Cyclo | 13 | SEQ. ID 0044 | GUGGCCUUAGCUACAGGAG |
| Cyclo | 14 | SEQ. ID 0045 | GGCCUUAGCUACAGGAGAG |
| Cyclo | 15 | SEQ. ID 0046 | CCUUAGCUACAGGAGAGAA |
| Cyclo | 16 | SEQ. ID 0047 | UUAGCUACAGGAGAGAAAG |
| Cyclo | 17 | SEQ. ID 0048 | AGCUACAGGAGAGAAAGGA |
| Cyclo | 18 | SEQ. ID 0049 | CUACAGGAGAGAAAGGAUU |
| Cyclo | 19 | SEQ. ID 0050 | ACAGGAGAGAAAGGAUUUG |
| Cyclo | 20 | SEQ. ID 0051 | AGGAGAGAAAGGAUUUGGC |
| Cyclo | 21 | SEQ. ID 0052 | GAGAGAAAGGAUUUGGCUA |
| Cyclo | 22 | SEQ. ID 0053 | GAGAAAGGAUUUGGCUACA |
| Cyclo | 23 | SEQ. ID 0054 | GAAAGGAUUUGGCUACAAA |
| Cyclo | 24 | SEQ. ID 0055 | AAGGAUUUGGCUACAAAAA |
| Cyclo | 25 | SEQ. ID 0056 | GGAUUUGGCUACAAAAACA |
| Cyclo | 26 | SEQ. ID 0057 | AUUUGGCUACAAAAACAGC |
| Cyclo | 27 | SEQ. ID 0058 | UUGGCUACAAAAACAGCAA |
| Cyclo | 28 | SEQ. ID 0059 | GGCUACAAAAACAGCAAAU |
| Cyclo | 29 | SEQ. ID 0060 | CUACAAAAACAGCAAAUUC |
| Cyclo | 30 | SEQ. ID 0061 | ACAAAAACAGCAAAUUCCA |
| Cyclo | 31 | SEQ. ID 0062 | AAAAACAGCAAAUUCCAUC |
| Cyclo | 32 | SEQ. ID 0063 | AAACAGCAAAUUCCAUCGU |
| Cyclo | 33 | SEQ. ID 0064 | ACAGCAAAUUCCAUCGUGU |
| Cyclo | 34 | SEQ. ID 0065 | AGCAAAUUCCAUCGUGUAA |
| Cyclo | 35 | SEQ. ID 0066 | CAAAUUCCAUCGUGUAAUC |
| Cyclo | 36 | SEQ. ID 0067 | AAUUCCAUCGUGUAAUCAA |
| Cyclo | 37 | SEQ. ID 0068 | UUCCAUCGUGUAAUCAAGG |
| Cyclo | 38 | SEQ. ID 0069 | CCAUCGUGUAAUCAAGGAC |

TABLE III-continued

| | | | |
|---|---|---|---|
| Cyclo | 39 | SEQ. ID 0070 | AUCGUGUAAUCAAGGACUU |
| Cyclo | 40 | SEQ. ID 0071 | CGUGUAAUCAAGGACUUCA |
| Cyclo | 41 | SEQ. ID 0072 | UGUAAUCAAGGACUUCAUG |
| Cyclo | 42 | SEQ. ID 0073 | UAAUCAAGGACUUCAUGAU |
| Cyclo | 43 | SEQ. ID 0074 | AUCAAGGACUUCAUGAUCC |
| Cyclo | 44 | SEQ. ID 0075 | CAAGGACUUCAUGAUCCAG |
| Cyclo | 45 | SEQ. ID 0076 | AGGACUUCAUGAUCCAGGG |
| Cyclo | 46 | SEQ. ID 0077 | GACUUCAUGAUCCAGGGCG |
| Cyclo | 47 | SEQ. ID 0078 | CUUCAUGAUCCAGGGCGGA |
| Cyclo | 48 | SEQ. ID 0079 | UCAUGAUCCAGGGCGGAGA |
| Cyclo | 49 | SEQ. ID 0080 | AUGAUCCAGGGCGGAGACU |
| Cyclo | 50 | SEQ. ID 0081 | GAUCCAGGGCGGAGACUUC |
| Cyclo | 51 | SEQ. ID 0082 | UCCAGGGCGGAGACUUCAC |
| Cyclo | 52 | SEQ. ID 0083 | CAGGGCGGAGACUUCACCA |
| Cyclo | 53 | SEQ. ID 0084 | GGGCGGAGACUUCACCAGG |
| Cyclo | 54 | SEQ. ID 0085 | GCGGAGACUUCACCAGGGG |
| Cyclo | 55 | SEQ. ID 0086 | GGAGACUUCACCAGGGGAG |
| Cyclo | 56 | SEQ. ID 0087 | AGACUUCACCAGGGGAGAU |
| Cyclo | 57 | SEQ. ID 0088 | ACUUCACCAGGGGAGAUGG |
| Cyclo | 58 | SEQ. ID 0089 | UUCACCAGGGGAGAUGGCA |
| Cyclo | 59 | SEQ. ID 0090 | CACCAGGGGAGAUGGCACA |
| Cyclo | 60 | SEQ. ID 0091 | CCAGGGGAGAUGGCACAGG |
| Cyclo | 61 | SEQ. ID 0092 | AGGGGAGAUGGCACAGGAG |
| Cyclo | 62 | SEQ. ID 0093 | GGGAGAUGGCACAGGAGGA |
| Cyclo | 63 | SEQ. ID 0094 | GAGAUGGCACAGGAGGAAA |
| Cyclo | 64 | SEQ. ID 0095 | GAUGGCACAGGAGGAAAGA |
| Cyclo | 65 | SEQ. ID 0096 | UGGCACAGGAGGAAAGAGC |
| Cyclo | 66 | SEQ. ID 0097 | GCACAGGAGGAAAGAGCAU |
| Cyclo | 67 | SEQ. ID 0098 | ACAGGAGGAAAGAGCAUCU |
| Cyclo | 68 | SEQ. ID 0099 | AGGAGGAAAGAGCAUCUAC |
| Cyclo | 69 | SEQ. ID 0100 | GAGGAAAGAGCAUCUACGG |
| Cyclo | 70 | SEQ. ID 0101 | GGAAAGAGCAUCUACGGUG |
| Cyclo | 71 | SEQ. ID 0102 | AAAGAGCAUCUACGGUGAG |
| Cyclo | 72 | SEQ. ID 0103 | AGAGCAUCUACGGUGAGCG |
| Cyclo | 73 | SEQ. ID 0104 | AGCAUCUACGGUGAGCGCU |
| Cyclo | 74 | SEQ. ID 0105 | CAUCUACGGUGAGCGCUUC |
| Cyclo | 75 | SEQ. ID 0106 | UCUACGGUGAGCGCUUCCC |
| Cyclo | 76 | SEQ. ID 0107 | UACGGUGAGCGCUUCCCCG |
| Cyclo | 77 | SEQ. ID 0108 | CGGUGAGCGCUUCCCCGAU |
| Cyclo | 78 | SEQ. ID 0109 | GUGAGCGCUUCCCCGAUGA |
| Cyclo | 79 | SEQ. ID 0110 | GAGCGCUUCCCCGAUGAGA |
| Cyclo | 80 | SEQ. ID 0111 | GCGCUUCCCCGAUGAGAAC |
| Cyclo | 81 | SEQ. ID 0112 | GCUUCCCCGAUGAGAACUU |
| Cyclo | 82 | SEQ. ID 0113 | UUCCCCGAUGAGAACUUCA |
| Cyclo | 83 | SEQ. ID 0114 | CCCCGAUGAGAACUUCAAA |
| Cyclo | 84 | SEQ. ID 0115 | CCGAUGAGAACUUCAAACU |
| Cyclo | 85 | SEQ. ID 0116 | GAUGAGAACUUCAAACUGA |
| Cyclo | 86 | SEQ. ID 0117 | UGAGAACUUCAAACUGAAG |
| Cyclo | 87 | SEQ. ID 0118 | AGAACUUCAAACUGAAGCA |
| Cyclo | 88 | SEQ. ID 0119 | AACUUCAAACUGAAGCACU |
| Cyclo | 89 | SEQ. ID 0120 | CUUCAAACUGAAGCACUAC |
| Cyclo | 90 | SEQ. ID 0121 | UCAAACUGAAGCACUACGG |
| DB | 1 | SEQ. ID 0122 | ACGGGCAAGGCCAAGUGGG |
| DB | 2 | SEQ. ID 0123 | CGGGCAAGGCCAAGUGGGA |
| DB | 3 | SEQ. ID 0124 | GGGCAAGGCCAAGUGGGAU |
| DB | 4 | SEQ. ID 0125 | GGCAAGGCCAAGUGGGAUG |
| DB | 5 | SEQ. ID 0126 | GCAAGGCCAAGUGGGAUGC |
| DB | 6 | SEQ. ID 0127 | CAAGGCCAAGUGGGAUGCC |
| DB | 7 | SEQ. ID 0128 | AAGGCCAAGUGGGAUGCCU |
| DB | 8 | SEQ. ID 0129 | AGGCCAAGUGGGAUGCCUG |
| DB | 9 | SEQ. ID 0130 | GGCCAAGUGGGAUGCCUGG |
| DB | 10 | SEQ. ID 0131 | GCCAAGUGGGAUGCCUGGA |
| DB | 11 | SEQ. ID 0132 | CCAAGUGGGAUGCCUGGAA |
| DB | 12 | SEQ. ID 0133 | CAAGUGGGAUGCCUGGAAU |
| DB | 13 | SEQ. ID 0134 | AAGUGGGAUGCCUGGAAUG |
| DB | 14 | SEQ. ID 0135 | AGUGGGAUGCCUGGAAUGA |
| DB | 15 | SEQ. ID 0136 | GUGGGAUGCCUGGAAUGAG |
| DB | 16 | SEQ. ID 0137 | UGGGAUGCCUGGAAUGAGC |
| DB | 17 | SEQ. ID 0138 | GGGAUGCCUGGAAUGAGCU |
| DB | 18 | SEQ. ID 0139 | GGAUGCCUGGAAUGAGCUG |
| DB | 19 | SEQ. ID 0140 | GAUGCCUGGAAUGAGCUGA |
| DB | 20 | SEQ. ID 0141 | AUGCCUGGAAUGAGCUGAA |
| DB | 21 | SEQ. ID 0142 | UGCCUGGAAUGAGCUGAAA |
| DB | 22 | SEQ. ID 0143 | GCCUGGAAUGAGCUGAAAG |
| DB | 23 | SEQ. ID 0144 | CCUGGAAUGAGCUGAAAGG |
| DB | 24 | SEQ. ID 0145 | CUGGAAUGAGCUGAAAGGG |
| DB | 25 | SEQ. ID 0146 | UGGAAUGAGCUGAAAGGGA |
| DB | 26 | SEQ. ID 0147 | GGAAUGAGCUGAAAGGGAC |
| DB | 27 | SEQ. ID 0148 | GAAUGAGCUGAAAGGGACU |
| DB | 28 | SEQ. ID 0149 | AAUGAGCUGAAAGGGACUU |

TABLE III-continued

| | | | |
|---|---|---|---|
| DB | 29 | SEQ. ID 0150 | AUGAGCUGAAAGGGACUUC |
| DB | 30 | SEQ. ID 0151 | UGAGCUGAAAGGGACUUCC |
| DB | 31 | SEQ. ID 0152 | GAGCUGAAAGGGACUUCCA |
| DB | 32 | SEQ. ID 0153 | AGCUGAAAGGGACUUCCAA |
| DB | 33 | SEQ. ID 0154 | GCUGAAAGGGACUUCCAAG |
| DB | 34 | SEQ. ID 0155 | CUGAAAGGGACUUCCAAGG |
| DB | 35 | SEQ. ID 0156 | UGAAAGGGACUUCCAAGGA |
| DB | 36 | SEQ. ID 0157 | GAAAGGGACUUCCAAGGAA |
| DB | 37 | SEQ. ID 0158 | AAAGGGACUUCCAAGGAAG |
| DB | 38 | SEQ. ID 0159 | AAGGGACUUCCAAGGAAGA |
| DB | 39 | SEQ. ID 0160 | AGGGACUUCCAAGGAAGAU |
| DB | 40 | SEQ. ID 0161 | GGGACUUCCAAGGAAGAUG |
| DB | 41 | SEQ. ID 0162 | GGACUUCCAAGGAAGAUGC |
| DB | 42 | SEQ. ID 0163 | GACUUCCAAGGAAGAUGCC |
| DB | 43 | SEQ. ID 0164 | ACUUCCAAGGAAGAUGCCA |
| DB | 44 | SEQ. ID 0165 | CUUCCAAGGAAGAUGCCAU |
| DB | 45 | SEQ. ID 0166 | UUCCAAGGAAGAUGCCAUG |
| DB | 46 | SEQ. ID 0167 | UCCAAGGAAGAUGCCAUGA |
| DB | 47 | SEQ. ID 0168 | CCAAGGAAGAUGCCAUGAA |
| DB | 48 | SEQ. ID 0169 | CAAGGAAGAUGCCAUGAAA |
| DB | 49 | SEQ. ID 0170 | AAGGAAGAUGCCAUGAAAG |
| DB | 50 | SEQ. ID 0171 | AGGAAGAUGCCAUGAAAGC |
| DB | 51 | SEQ. ID 0172 | GGAAGAUGCCAUGAAAGCU |
| DB | 52 | SEQ. ID 0173 | GAAGAUGCCAUGAAAGCUU |
| DB | 53 | SEQ. ID 0174 | AAGAUGCCAUGAAAGCUUA |
| DB | 54 | SEQ. ID 0175 | AGAUGCCAUGAAAGCUUAC |
| DB | 55 | SEQ. ID 0176 | GAUGCCAUGAAAGCUUACA |
| DB | 56 | SEQ. ID 0177 | AUGCCAUGAAAGCUUACAU |
| DB | 57 | SEQ. ID 0178 | UGCCAUGAAAGCUUACAUC |
| DB | 58 | SEQ. ID 0179 | GCCAUGAAAGCUUACAUCA |
| DB | 59 | SEQ. ID 0180 | CCAUGAAAGCUUACAUCAA |
| DB | 60 | SEQ. ID 0181 | CAUGAAAGCUUACAUCAAC |
| DB | 61 | SEQ. ID 0182 | AUGAAAGCUUACAUCAACA |
| DB | 62 | SEQ. ID 0183 | UGAAAGCUUACAUCAACAA |
| DB | 63 | SEQ. ID 0184 | GAAAGCUUACAUCAACAAA |
| DB | 64 | SEQ. ID 0185 | AAAGCUUACAUCAACAAAG |
| DB | 65 | SEQ. ID 0186 | AAGCUUACAUCAACAAAGU |
| DB | 66 | SEQ. ID 0187 | AGCUUACAUCAACAAAGUA |
| DB | 67 | SEQ. ID 0188 | GCUUACAUCAACAAAGUAG |
| DB | 68 | SEQ. ID 0189 | CUUACAUCAACAAAGUAGA |
| DB | 69 | SEQ. ID 0190 | UUACAUCAACAAAGUAGAA |
| DB | 70 | SEQ. ID 0191 | UACAUCAACAAAGUAGAAG |
| DB | 71 | SEQ. ID 0192 | ACAUCAACAAAGUAGAAGA |
| DB | 72 | SEQ. ID 0193 | CAUCAACAAAGUAGAAGAG |
| DB | 73 | SEQ. ID 0194 | AUCAACAAAGUAGAAGAGC |
| DB | 74 | SEQ. ID 0195 | UCAACAAAGUAGAAGAGCU |
| DB | 75 | SEQ. ID 0196 | CAACAAAGUAGAAGAGCUA |
| DB | 76 | SEQ. ID 0197 | AACAAAGUAGAAGAGCUAA |
| DB | 77 | SEQ. ID 0198 | ACAAAGUAGAAGAGCUAAA |
| DB | 78 | SEQ. ID 0199 | CAAAGUAGAAGAGCUAAAG |
| DB | 79 | SEQ. ID 0200 | AAAGUAGAAGAGCUAAAGA |
| DB | 80 | SEQ. ID 0201 | AAGUAGAAGAGCUAAAGAA |
| DB | 81 | SEQ. ID 0202 | AGUAGAAGAGCUAAAGAAA |
| DB | 82 | SEQ. ID 0203 | GUAGAAGAGCUAAAGAAAA |
| DB | 83 | SEQ. ID 0204 | UAGAAGAGCUAAAGAAAAA |
| DB | 84 | SEQ. ID 0205 | AGAAGAGCUAAAGAAAAAA |
| DB | 85 | SEQ. ID 0206 | GAAGAGCUAAAGAAAAAAU |
| DB | 86 | SEQ. ID 0207 | AAGAGCUAAAGAAAAAAUA |
| DB | 87 | SEQ. ID 0208 | AGAGCUAAAGAAAAAUAC |
| DB | 88 | SEQ. ID 0209 | GAGCUAAAGAAAAAUACG |
| DB | 89 | SEQ. ID 0210 | AGCUAAAGAAAAAUACGG |
| DB | 90 | SEQ. ID 0211 | GCUAAAGAAAAAUACGGG |
| Luc | 1 | SEQ. ID 0212 | AUCCUCAUAAAGGCCAAGA |
| Luc | 2 | SEQ. ID 0213 | AGAUCCUCAUAAAGGCCAA |
| Luc | 3 | SEQ. ID 0214 | AGAGAUCCUCAUAAAGGCC |
| Luc | 4 | SEQ. ID 0215 | AGAGAGAUCCUCAUAAAGG |
| Luc | 5 | SEQ. ID 0216 | UCAGAGAGAUCCUCAUAAA |
| Luc | 6 | SEQ. ID 0217 | AAUCAGAGAGAUCCUCAUA |
| Luc | 7 | SEQ. ID 0218 | AAAAUCAGAGAGAUCCUCA |
| Luc | 8 | SEQ. ID 0219 | GAAAAUCAGAGAGAUCCU |
| Luc | 9 | SEQ. ID 0220 | AAGAAAAUCAGAGAGAUC |
| Luc | 10 | SEQ. ID 0221 | GCAAGAAAAUCAGAGAGA |
| Luc | 11 | SEQ. ID 0222 | ACGCAAGAAAAUCAGAGA |
| Luc | 12 | SEQ. ID 0223 | CGACGCAAGAAAAUCAGA |
| Luc | 13 | SEQ. ID 0224 | CUCGACGCAAGAAAAUCA |
| Luc | 14 | SEQ. ID 0225 | AACUCGACGCAAGAAAAU |
| Luc | 15 | SEQ. ID 0226 | AAAACUCGACGCAAGAAA |
| Luc | 16 | SEQ. ID 0227 | GGAAAACUCGACGCAAGAA |
| Luc | 17 | SEQ. ID 0228 | CCGGAAAACUCGACGCAAG |
| Luc | 18 | SEQ. ID 0229 | UACCGGAAAACUCGACGCA |

TABLE III-continued

| | | | |
|---|---|---|---|
| Luc | 19 | SEQ. ID 0230 | CUUACCGGAAAACUCGACG |
| Luc | 20 | SEQ. ID 0231 | GUCUUACCGGAAAACUCGA |
| Luc | 21 | SEQ. ID 0232 | AGGUCUUACCGGAAAACUC |
| Luc | 22 | SEQ. ID 0233 | AAAGGUCUUACCGGAAAAC |
| Luc | 23 | SEQ. ID 0234 | CGAAAGGUCUUACCGGAAA |
| Luc | 24 | SEQ. ID 0235 | ACCGAAAGGUCUUACCGGA |
| Luc | 25 | SEQ. ID 0236 | GUACCGAAAGGUCUUACCG |
| Luc | 26 | SEQ. ID 0237 | AAGUACCGAAAGGUCUUAC |
| Luc | 27 | SEQ. ID 0238 | CGAAGUACCGAAAGGUCUU |
| Luc | 28 | SEQ. ID 0239 | GACGAAGUACCGAAAGGUC |
| Luc | 29 | SEQ. ID 0240 | UGGACGAAGUACCGAAAGG |
| Luc | 30 | SEQ. ID 0241 | UGUGGACGAAGUACCGAAA |
| Luc | 31 | SEQ. ID 0242 | UUUGUGGACGAAGUACCGA |
| Luc | 32 | SEQ. ID 0243 | UGUUUGUGGACGAAGUACC |
| Luc | 33 | SEQ. ID 0244 | UGUGUUUGUGGACGAAGUA |
| Luc | 34 | SEQ. ID 0245 | GUUGUGUUUGUGGACGAAG |
| Luc | 35 | SEQ. ID 0246 | GAGUUGUGUUUGUGGACGA |
| Luc | 36 | SEQ. ID 0247 | AGGAGUUGUGUUUGUGGAC |
| Luc | 37 | SEQ. ID 0248 | GGAGGAGUUGUGUUUGUGG |
| Luc | 38 | SEQ. ID 0249 | GCGGAGGAGUUGUGUUUGU |
| Luc | 39 | SEQ. ID 0250 | GCGCGGAGGAGUUGUGUUU |
| Luc | 40 | SEQ. ID 0251 | UUGCGCGGAGGAGUUGUGU |
| Luc | 41 | SEQ. ID 0252 | AGUUGCGCGGAGGAGUUGU |
| Luc | 42 | SEQ. ID 0253 | AAAGUUGCGCGGAGGAGUU |
| Luc | 43 | SEQ. ID 0254 | AAAAGUUGCGCGGAGGAG |
| Luc | 44 | SEQ. ID 0255 | CGAAAAGUUGCGCGGAGG |
| Luc | 45 | SEQ. ID 0256 | CGCGAAAAGUUGCGCGGA |
| Luc | 46 | SEQ. ID 0257 | ACCGCGAAAAGUUGCGCG |
| Luc | 47 | SEQ. ID 0258 | CAACCGCGAAAAGUUGCG |
| Luc | 48 | SEQ. ID 0259 | AACAACCGCGAAAAGUUG |
| Luc | 49 | SEQ. ID 0260 | GUAACAACCGCGAAAAGU |
| Luc | 50 | SEQ. ID 0261 | AAGUAACAACCGCGAAAAA |
| Luc | 51 | SEQ. ID 0262 | UCAAGUAACAACCGCGAAA |
| Luc | 52 | SEQ. ID 0263 | AGUCAAGUAACAACCGCGA |
| Luc | 53 | SEQ. ID 0264 | CCAGUCAAGUAACAACCGC |
| Luc | 54 | SEQ. ID 0265 | CGCCAGUCAAGUAACAACC |
| Luc | 55 | SEQ. ID 0266 | GUCGCCAGUCAAGUAACAA |
| Luc | 56 | SEQ. ID 0267 | ACGUCGCCAGUCAAGUAAC |
| Luc | 57 | SEQ. ID 0268 | UUACGUCGCCAGUCAAGUA |
| Luc | 58 | SEQ. ID 0269 | GAUUACGUCGCCAGUCAAG |
| Luc | 59 | SEQ. ID 0270 | UGGAUUACGUCGCCAGUCA |
| Luc | 60 | SEQ. ID 0271 | CGUGGAUUACGUCGCCAGU |
| Luc | 61 | SEQ. ID 0272 | AUCGUGGAUUACGUCGCCA |
| Luc | 62 | SEQ. ID 0273 | AGAUCGUGGAUUACGUCGC |
| Luc | 63 | SEQ. ID 0274 | AGAGAUCGUGGAUUACGUC |
| Luc | 64 | SEQ. ID 0275 | AAAGAGAUCGUGGAUUACG |
| Luc | 65 | SEQ. ID 0276 | AAAAAGAGAUCGUGGAUUA |
| Luc | 66 | SEQ. ID 0277 | GGAAAAAGAGAUCGUGGAU |
| Luc | 67 | SEQ. ID 0278 | ACGGAAAAAGAGAUCGUGG |
| Luc | 68 | SEQ. ID 0279 | UGACGGAAAAAGAGAUCGU |
| Luc | 69 | SEQ. ID 0280 | GAUGACGGAAAAAGAGAUC |
| Luc | 70 | SEQ. ID 0281 | ACGAUGACGGAAAAAGAGA |
| Luc | 71 | SEQ. ID 0282 | AGACGAUGACGGAAAAAGA |
| Luc | 72 | SEQ. ID 0283 | AAAGACGAUGACGGAAAAA |
| Luc | 73 | SEQ. ID 0284 | GGAAAGACGAUGACGGAAA |
| Luc | 74 | SEQ. ID 0285 | ACGGAAAGACGAUGACGGA |
| Luc | 75 | SEQ. ID 0286 | GCACGGAAAGACGAUGACG |
| Luc | 76 | SEQ. ID 0287 | GAGCACGGAAAGACGAUGA |
| Luc | 77 | SEQ. ID 0288 | UGGAGCACGGAAAGACGAU |
| Luc | 78 | SEQ. ID 0289 | UUUGGAGCACGGAAAGACG |
| Luc | 79 | SEQ. ID 0290 | GUUUUGGAGCACGGAAAGA |
| Luc | 80 | SEQ. ID 0291 | UUGUUUUGGAGCACGGAAA |
| Luc | 81 | SEQ. ID 0292 | UGUUGUUUUGGAGCACGGA |
| Luc | 82 | SEQ. ID 0293 | GUUGUUGUUUUGGAGCACG |
| Luc | 83 | SEQ. ID 0294 | CCGUUGUUGUUUUGGAGCA |
| Luc | 84 | SEQ. ID 0295 | CGCCGUUGUUGUUUUGGAG |
| Luc | 85 | SEQ. ID 0296 | GCCGCCGUUGUUGUUUUGG |
| Luc | 86 | SEQ. ID 0297 | CCGCCGCCGUUGUUGUUUU |
| Luc | 87 | SEQ. ID 0298 | UCCCGCCGCCGUUGUUGUU |
| Luc | 88 | SEQ. ID 0299 | CUUCCCGCCGCCGUUGUUG |
| Luc | 89 | SEQ. ID 0300 | AACUUCCCGCCGCCGUUGU |
| Luc | 90 | SEQ. ID 0301 | UGAACUUCCCGCCGCCGUU |

Example II

Validation of the Algorithm Using DBI, Luciferase, PLK, EGFR, and SEAP

Figure 10B:
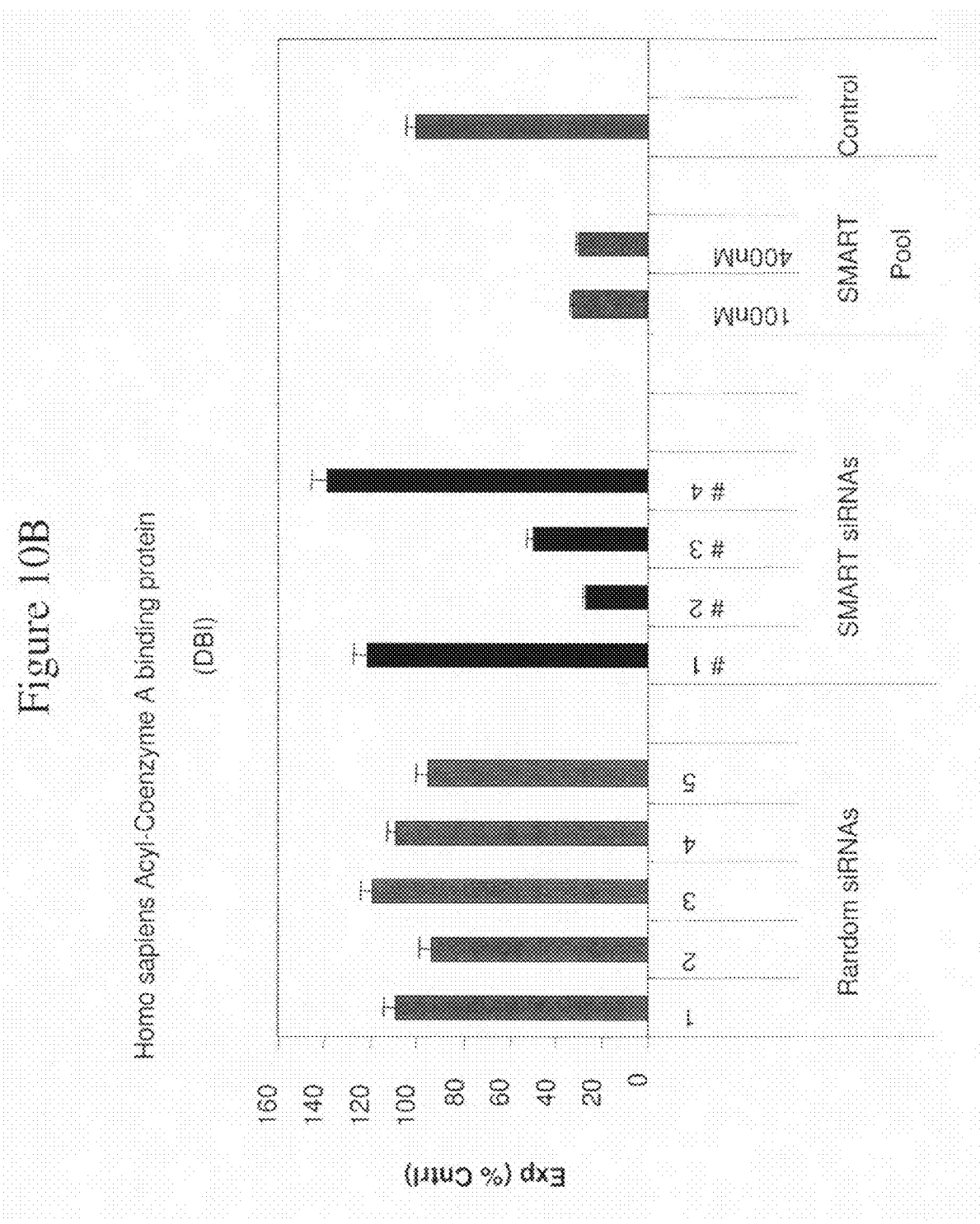
FIGS. 10A-E compare the RNAi of five different genes (SEAP, DBI, PLK, Firefly Luciferase, and Renila Luciferase) by varying numbers of randomly selected siRNA and four rationally designed (SMART-selected) siRNA chosen using the algorithm described in Formula VIII. In addition, RNAi induced by a pool of the four SMART-selected siRNA is reported at two different concentrations (100 and 400 nM). 10F is a comparison between a pool of randomly selected EGFR siRNA (Pool 1) and a pool of SMART selected EGFR siRNA (Pool 2). Pool 1, S1-S4 and Pool 2 S1-S4 represent the individual members that made up each respective pool. Note that numbers for random siRNAs represent the position of the 5' end of the sense strand of the duplex. The Y-axis represents the % expression of the control(s). The X-axis is the percent expression of the control.
Figure 10C:
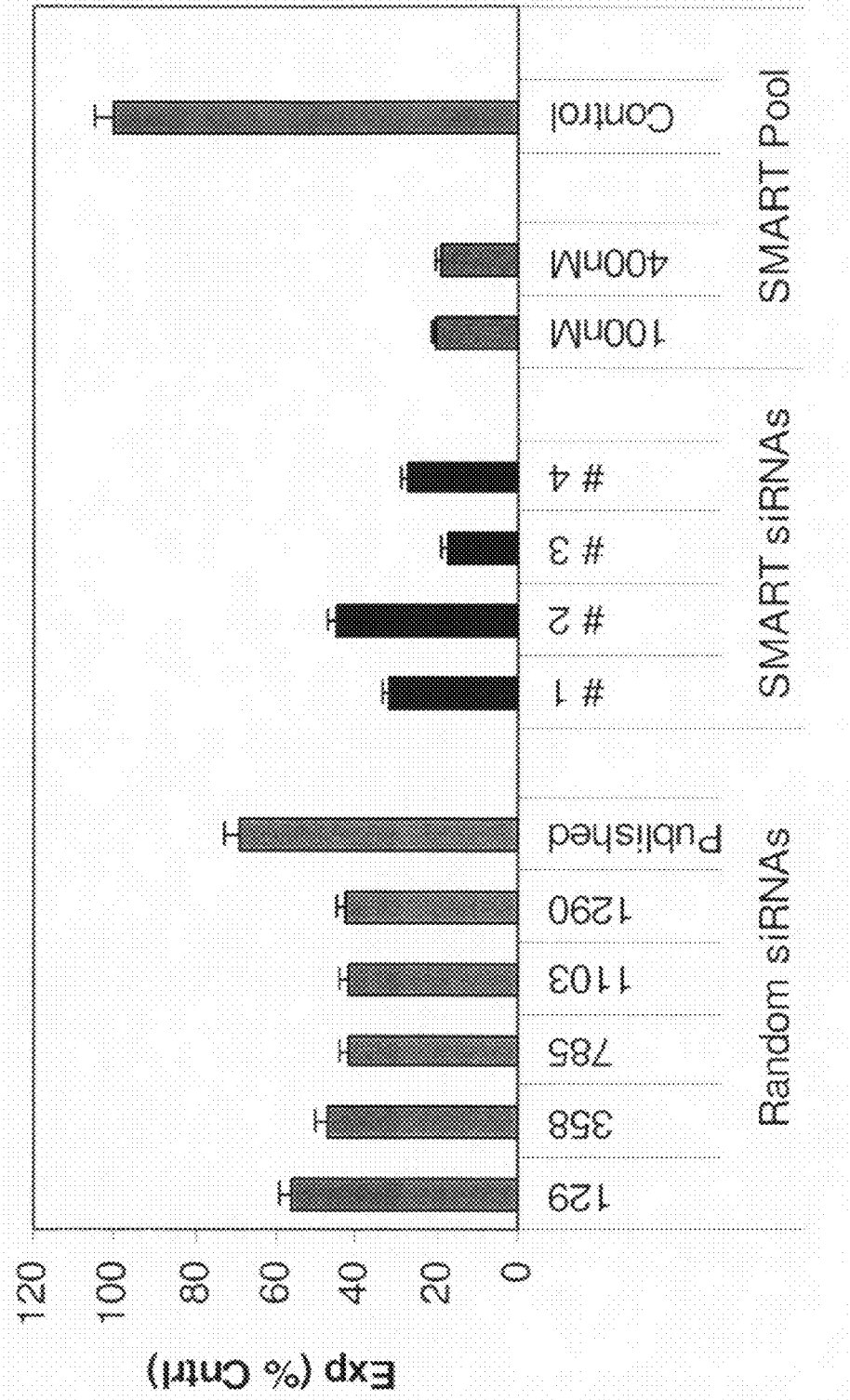
Figure 10F:
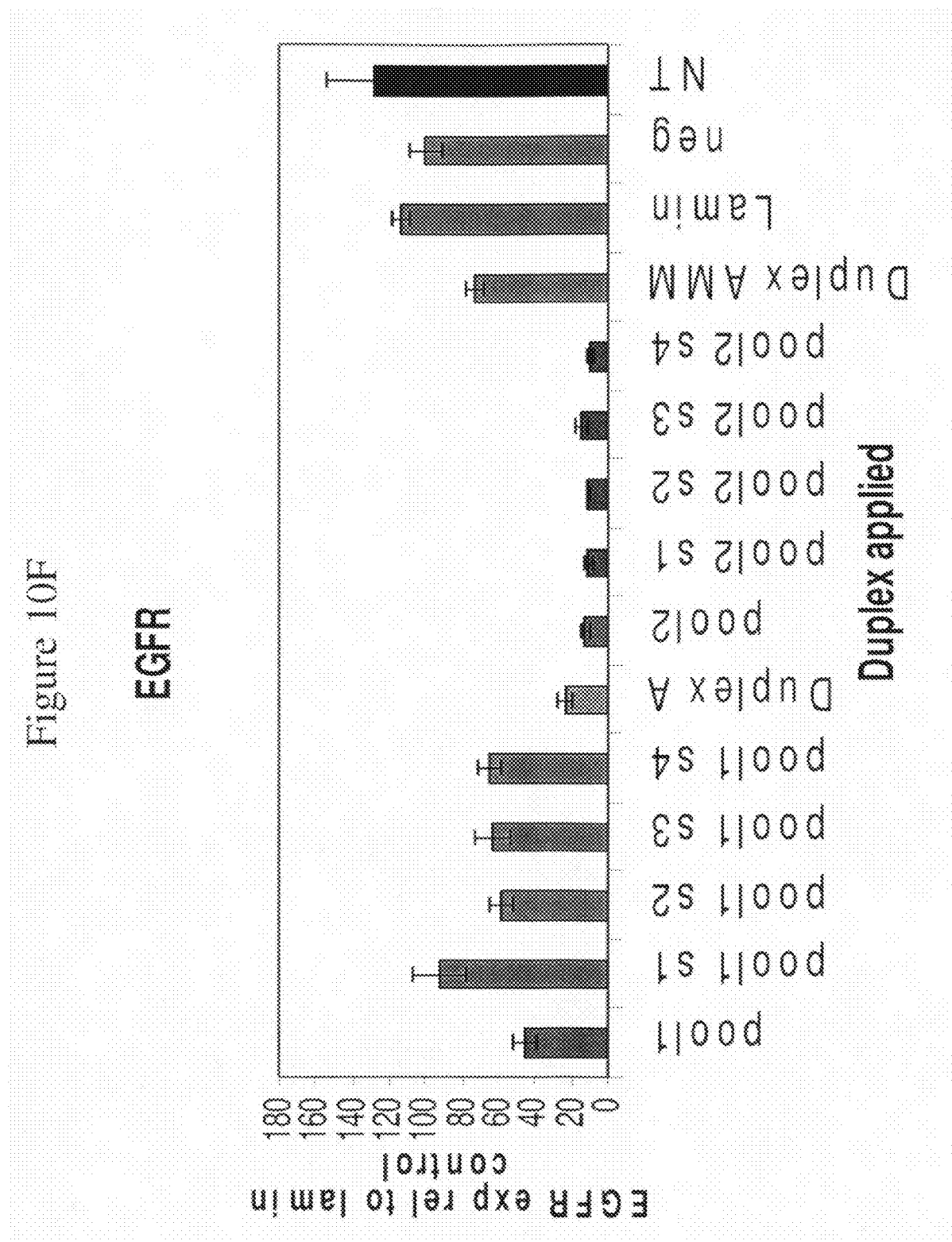

The algorithm (Formula VIII) identified siRNAs for five genes, human DBI, firefly luciferase (fLuc), *renilla luciferase* (rLuc), human PLK, and human secreted alkaline phosphatase (SEAP). Four individual siRNAs were selected on the basis of their SMARTscores™ derived by analysis of their sequence using Formula VIII (all of the siRNAs would be selected with Formula IX as well) and analyzed for their ability to silence their targets' expression. In addition to the scoring, a BLAST search was conducted for each siRNA. To minimize the potential for off-target silencing effects, only those target sequences with more than three mismatches against un-related sequences were selected. Semizarov, et al, *Specificity of short interfering RNA determined through gene expression signatures*. Proc. Natl. Acad. Sci. U.S.A. 2003, 100:6347. These duplexes were analyzed individually and in pools of 4 and compared with several siRNAs that were randomly selected. The functionality was measured as a percentage of targeted gene knockdown as compared to controls. All siRNAs were transfected as described by the methods above at 100 nM concentration into HEK293 using Lipofectamine 2000. The level of the targeted gene expression was evaluated by B-DNA as described above and normalized to the non-specific control. FIG. 10 shows that the siRNAs selected by the algorithm disclosed herein were significantly more potent than randomly selected siRNAs. The algorithm increased the chances of identifying an F50 siRNA from 48% to 91%, and an F80 siRNA from 13% to 57%. In addition, pools of SMART siRNA silence the selected target better than randomly selected pools (see FIG. 10F).

Example III

Validation of the Algorithm Using Genes Involved in Clathrin-Dependent Endocytosis Components of clathrin-mediated endocytosis pathway are key to modulating intracellular signaling and play important roles in disease. Chromosomal rearrangements that result in fusion transcripts between the Mixed-Lineage Leukemia gene (MLL) and CALM (clathrin assembly lymphoid myeloid leukemia gene) are believed to play a role in leukemogenesis. Similarly, disruptions in Rab7 and Rab9, as well as HIP1 (Huntingtin-interacting protein), genes that are believed to be involved in endocytosis, are potentially responsible for ailments resulting in lipid storage, and neuronal diseases, respectively. For these reasons, siRNA directed against clathrin and other genes involved in the clathrin-mediated endocytotic pathway are potentially important research and therapeutic tools.

siRNAs directed against genes involved in the clathrin-mediated endocytosis pathways were selected using Formula VIII. The targeted genes were clathrin heavy chain (CHC, accession # NM_004859), clathrin light chain A (CLCa, NM_001833), clathrin light chain B (CLCb, NM_001834), CALM (U45976), β2 subunit of AP-2 (β2, NM_001282), Eps15 (NM_001981), Eps15R (NM_021235), dynamin II (DYNII, NM_004945), Rab5a (BC001267), Rab5b (NM_002868), Rab5c (AF141304), and EEA.1 (XM_018197).

For each gene, four siRNAs duplexes with the highest scores were selected and a BLAST search was conducted for each of them using the Human EST database. In order to minimize the potential for off-target silencing effects, only those sequences with more than three mismatches against un-related sequences were used. All duplexes were synthesized at Dharmacon, Inc. as 21-mers with 3'-UU overhangs using a modified method of 2'-ACE chemistry, Scaringe, *Advanced 5'-silyl-2'-orthoester approach to RNA oligonucleotide synthesis*, Methods Enzymol 2000, 317:3, and the antisense strand was chemically phosphorylated to insure maximized activity.

HeLa cells were grown in Dulbecco's modified Eagle's medium (DMEM) containing 10% fetal bovine serum, antibiotics and glutamine. siRNA duplexes were resuspended in 1×siRNA Universal buffer (Dharmacon, Inc.) to 20 µM prior to transfection. HeLa cells in 12-well plates were transfected twice with 4 µl of 20 µM siRNA duplex in 3 µl Lipofectamine 2000 reagent (Invitrogen, Carlsbad, Calif., USA) at 24-hour intervals. For the transfections in which 2 or 3 siRNA duplexes were included, the amount of each duplex was decreased, so that the total amount was the same as in transfections with single siRNAs. Cells were plated into normal culture medium 12 hours prior to experiments, and protein levels were measured 2 or 4 days after the first transfection.

Equal amounts of lysates were resolved by electrophoresis, blotted, and stained with the antibody specific to targeted protein, as well as antibodies specific to unrelated proteins, PP1 phosphatase and Tsg101 (not shown). The cells were lysed in Triton X-100/glycerol solubilization buffer as described previously. Tebar, Bohlander, & Sorkin, *Clathrin Assembly Lymphoid Myeloid Leukemia (CALM) Protein: Localization in Endocytic-coated Pits, Interactions with Clathrin, and the Impact of Overexpression on Clathrin-mediated Traffic*, Mol. Biol. Cell August 1999, 10:2687. Cell lysates were electrophoresed, transferred to nitrocellulose membranes, and Western blotting was performed with several antibodies followed by detection using enhanced chemiluminescence system (Pierce, Inc). Several x-ray films were analyzed to determine the linear range of the chemiluminescence signals, and the quantifications were performed using densitometry and AlphaImager v5.5 software (Alpha Innotech Corporation). In experiments with Eps15R-targeted siRNAs, cell lysates were subjected to immunoprecipitation with Ab860, and Eps15R was detected in immunoprecipitates by Western blotting as described above.

The antibodies to assess the levels of each protein by Western blot were obtained from the following sources: monoclonal antibody to clathrin heavy chain (TD.1) was obtained from American Type Culture Collection (Rockville, Md., USA); polyclonal antibody to dynamin II was obtained from Affinity Bioreagents, Inc. (Golden, Colo., USA); monoclonal antibodies to EEA.1 and Rab5a were purchased from BD Transduction Laboratories (Los Angeles, Calif., USA); the monoclonal antibody to Tsg101 was purchased from Santa Cruz Biotechnology, Inc. (Santa Cruz, Calif., USA); the monoclonal antibody to GFP was from ZYMED Laboratories Inc. (South San Francisco, Calif., USA); the rabbit polyclonal antibodies Ab32 specific to α-adaptins and Ab20 to CALM were described previously Sorkin, et al, *Stoichiometric Interaction of the Epidermal Growth Factor Receptor with the Clathrin-associated Protein Complex AP-2*, J. Biol. Chem. January 1995, 270:619, the polyclonal antibodies to clathrin light chains A and B were kindly provided by Dr. F. Brodsky (UCSF); monoclonal antibodies to PP1 (BD Transduction Laboratories) and α-Actinin (Chemicon) were kindly provided by Dr. M. Dell'Acqua (University of Colorado); Eps15 Ab577 and Eps15R Ab860 were kindly provided by Dr. P.P. Di Fiore (European Cancer Institute).

Figure 11:
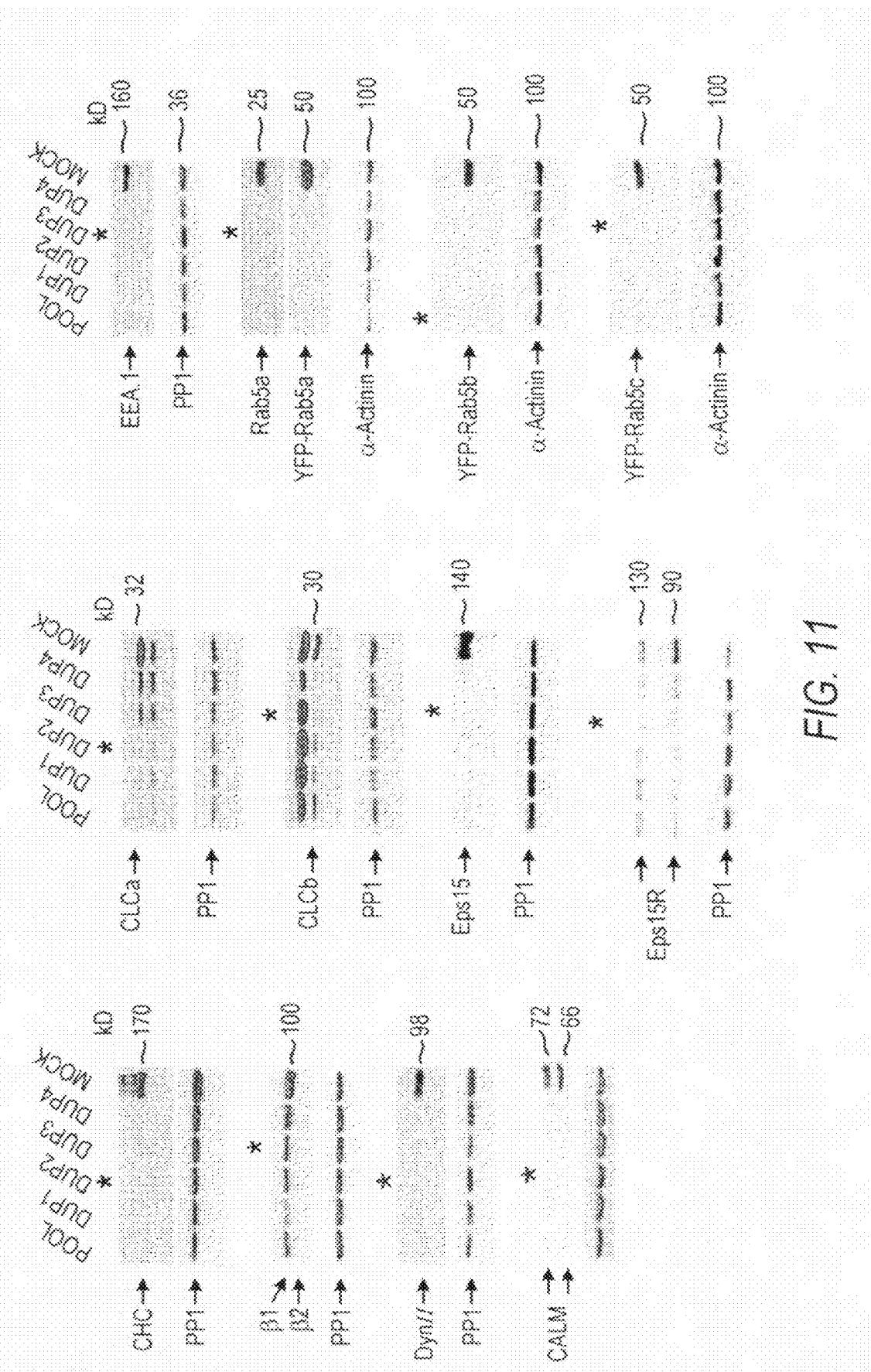
FIG. 11 shows the Western blot results from cells treated with siRNA directed against twelve different genes involved in the clathrin-dependent endocytosis pathway (CHC, DynII, CALM, CLCa, CLCb, Eps15, Eps15R, Rab5a, Rab5b, Rab5c, β2 subunit of AP-2 and EEA.1). siRNA were selected using Formula VIII. "Pool" represents a mixture of duplexes 1-4. Total concentration of each siRNA in the pool is 25 nM. Total concentration=4×25 =100 nM.

FIG. 11 demonstrates the in vivo functionality of 48 individual siRNAs, selected using Formula VIII (most of them will meet the criteria incorporated by Formula IX as well) targeting 12 genes. Various cell lines were transfected with siRNA duplexes (Dup1-4) or pools of siRNA duplexes (Pool), and the cells were lysed 3 days after transfection with the exception of CALM (2 days) and β2 (4 days).

Note a β1-adaptin band (part of AP-1 Golgi adaptor complex) that runs slightly slower than β2 adaptin. CALM has two splice variants, 66 and 72 kD. The full-length Eps15R (a doublet of ~130 kD) and several truncated spliced forms of ~100 kD and ~70 kD were detected in Eps15R immunoprecipitates (shown by arrows). The cells were lysed 3 days after transfection. Equal amounts of lysates were resolved by electrophoresis and blotted with the antibody specific to a targeted protein (GFP antibody for YFP fusion proteins) and the antibody specific to unrelated proteins PP1 phosphatase or α-actinin, and TSG101. The amount of protein in each specific band was normalized to the amount of non-specific proteins in each lane of the gel. Nearly all of them appear to be functional, which establishes that Formula VIII and IX can be used to predict siRNAs' functionality in general in a genome wide manner.

To generate the fusion of yellow fluorescent protein (YFP) with Rab5b or Rab5c (YFP-Rab5b or YFP-Rab5c), a DNA fragment encoding the full-length human Rab5b or Rab5c was obtained by PCR using Pfu polymerase (Stratagene) with a SacI restriction site introduced into the 5' end and a KpnI site into the 3' end and cloned into pEYFP-C1 vector (CLONTECH, Palo Alto, Calif., USA). GFP-CALM and YFP-Rab5a were described previously Tebar, Bohlander, & Sorkin, Clathrin Assembly Lymphoid Myeloid Leukemia (CALM) Protein: Localization in Endocytic-coated Pits, Interactions with Clathrin, and the Impact of Overexpression on Clathrin-mediated Traffic, Mol. Biol. Cell August 1999, 10:2687.

Example IV

Validation of the Algorithm Using Eg5, GADPH, ATE1, MEK2, MEK1, QB, LaminA/C, c-myc, Human Cyclophilin, and Mouse Cyclophilin A number of genes have been identified as playing potentially important-roles in disease etiology. Expression profiles of normal and diseased kidneys has implicated Edg5 in immunoglobulin A neuropathy, a common renal glomerular disease. Myc1, MEK1/2 and other related kinases have been associated with one or more cancers, while lamins have been implicated in muscular dystrophy and other diseases. For these reasons, siRNA directed against the genes encoding these classes of molecules would be important research and therapeutic tools.

Figure 12:
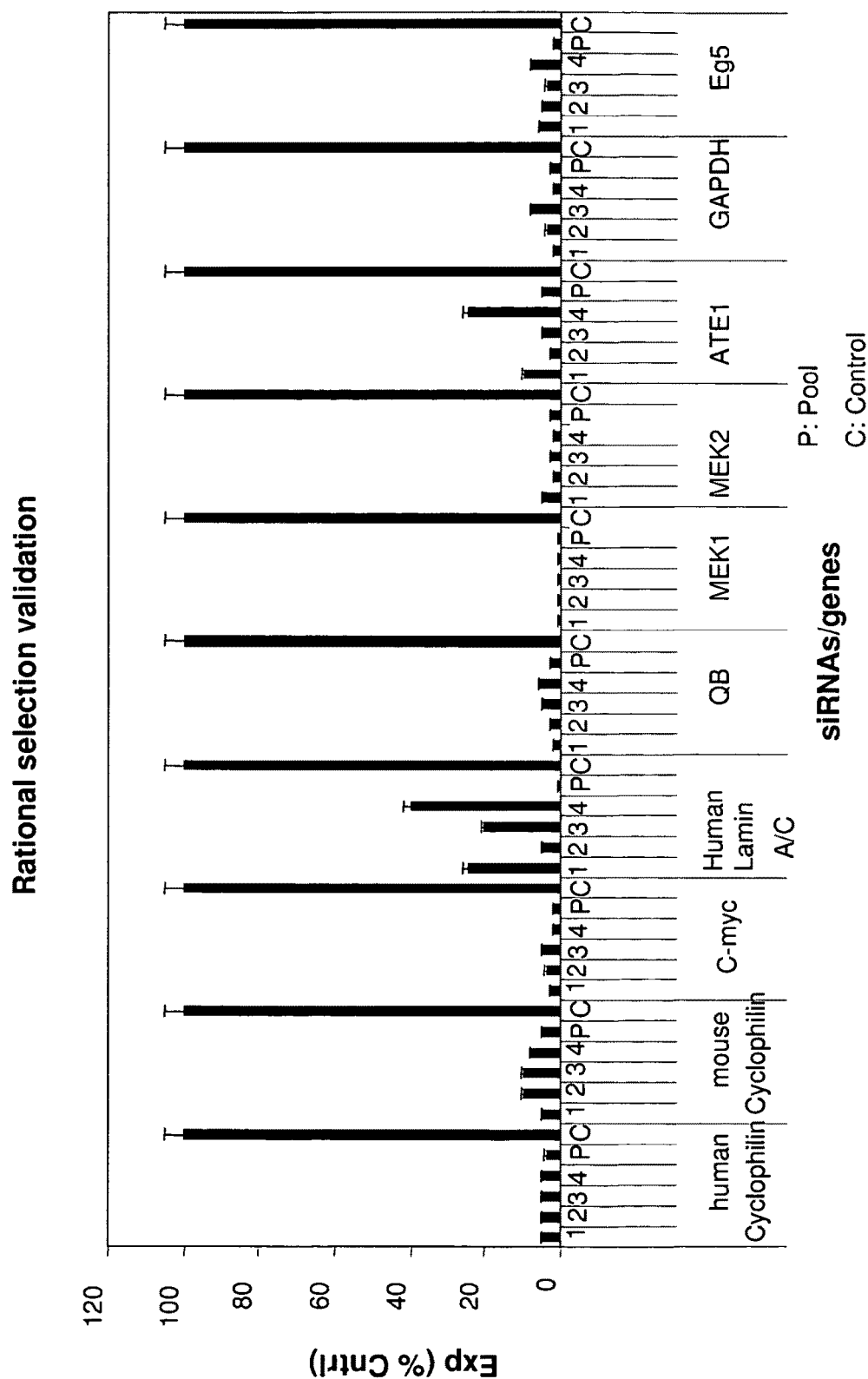
FIG. 12 is a representation of the gene silencing capabilities of rationally-selected siRNA directed against ten different genes (human and mouse cyclophilin, C-myc, human lamin A/C, QB (ubiquinol-cytochrome c reductase core protein I), MEK1 and MEK2, ATE1 (arginyl-tRNA protein transferase), GAPDH, and Eg5). The Y-axis is the percent expression of the control. Numbers 1, 2, 3 and 4 represent individual rationally selected siRNA. "Pool" represents a mixture of the four individual siRNA.

FIG. 12 illustrates four siRNAs targeting 10 different genes (Table V for sequence and accession number information) that were selected according to the Formula VIII and assayed as individuals and pools in HEK293 cells. The level of siRNA induced silencing was measured using the B-DNA assay. These studies demonstrated that thirty-six out of the forty individual SMART-selected siRNA tested are functional (90%) and all 10 pools are fully functional.

Example V

Validation of the Algorithm Using Bcl2

Bcl-2 is a ~0.25 kD, 205-239 amino acid, anti-apoptotic protein that contains considerable homology with other members of the BCL family including BCLX, MCL1, BAX, BAD, and BIK. The protein exists in at least two forms (Bcl2a, which has a hydrophobic tail for membrane anchorage, and Bcl2b, which lacks the hydrophobic tail) and is predominantly localized to the mitochondrial membrane. While Bcl2 expression is widely distributed, particular interest has focused on the expression of this molecule in B and T cells. Bcl2 expression is down-regulated in normal germinal center B cells yet in a high percentage of follicular lymphomas, Bcl2 expression has been observed to be elevated. Cytological studies have identified a common translocation ((14;18)(q32;q32)) amongst a high percentage (>70%) of these lymphomas. This genetic lesion places the Bcl2 gene in juxtaposition to immunoglobulin heavy chain gene (IgH) encoding sequences and is believed to enforce inappropriate levels of gene expression, and resistance to programmed cell death in the follicle center B cells. In other cases, hypomethylation of the Bcl2 promoter leads to enhanced expression and again, inhibition of apoptosis. In addition to cancer, dysregulated expression of Bcl-2 has been correlated with multiple sclerosis and various neurological diseases.

The correlation between Bcl-2 translocation and cancer makes this gene an attractive target for RNAi. Identification of siRNA directed against the bcl2 transcript (or Bcl2-IgH fusions) would further our understanding Bcl2 gene function and possibly provide a future therapeutic agent to battle diseases that result from altered expression or function of this gene.

In Silico Identification of Functional siRNA.

To identify functional and hyperfunctional siRNA against the Bcl2 gene, the sequence for Bcl-2 was downloaded from the NCBI Unigene database and analyzed using the Formula VIII algorithm. As a result of these procedures, both the sequence and SMARTscores™ of the Bcl2 siRNA were obtained and ranked according to their functionality. Subsequently, these sequences were BLAST'ed (database) to insure that the selected sequences were specific and contained minimal overlap with unrealated genes. The SMARTscores™ for the top 10 Bcl-2 siRNA are identified in FIG. 13.

In Vivo Testing of Bcl-2 SiRNA

Bcl-2 siRNAs having the top ten SMARTscores™ were selected and tested in a functional assay to determine silencing efficiency. To accomplish this, each of the ten duplexes were synthesized using 2'-O-ACE chemistry and transfected at 100 nM concentrations into cells. Twenty-four hours later assays were performed on cell extracts to assess the degree of target silencing. Controls used in these experiments included mock transfected cells, and cells that were transfected with a non-specific siRNA duplex.

Figure 14:
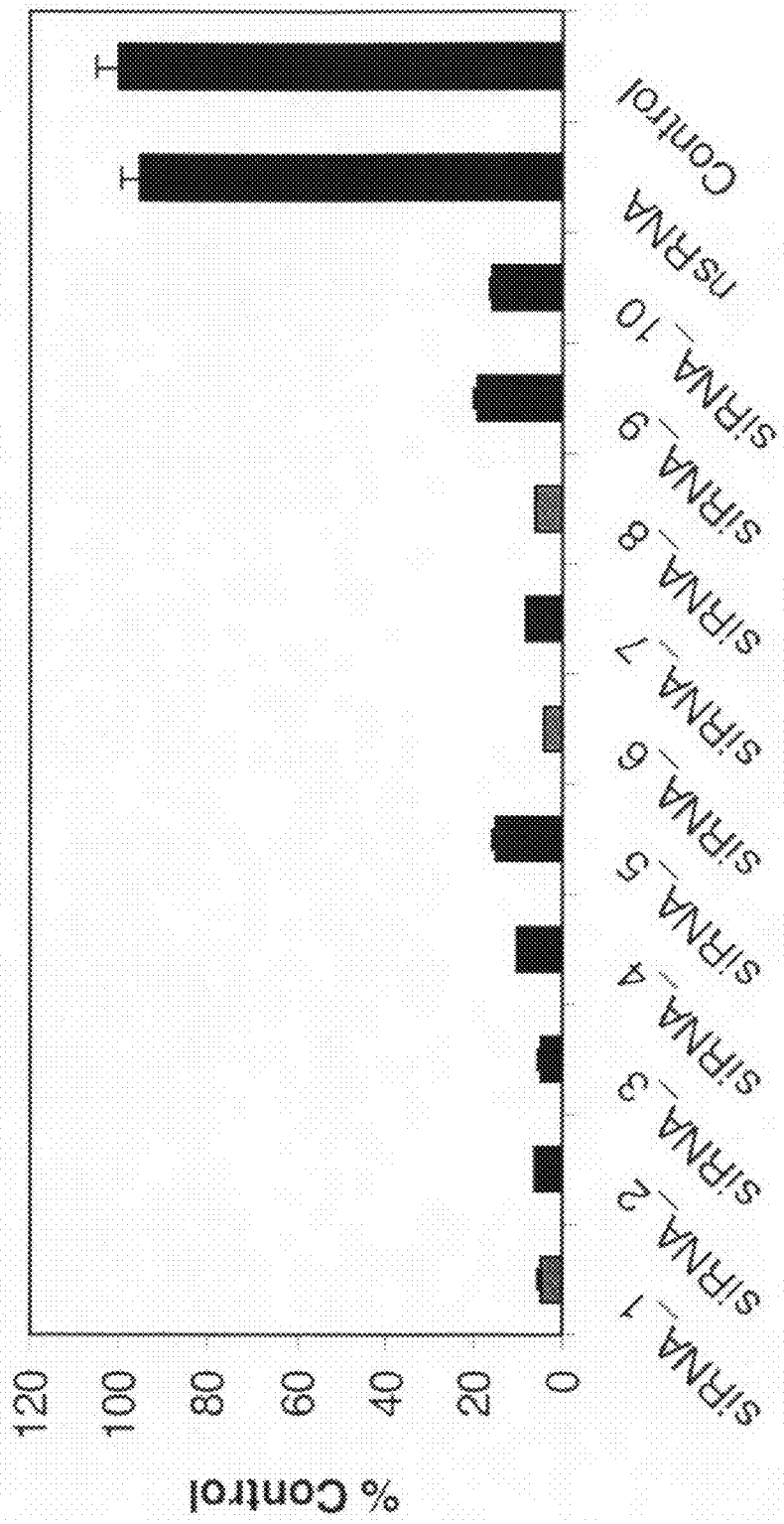
FIG. 14 is the knockdown by the top ten Bcl2 siRNAs at 100 nM concentrations. The Y-axis represents the amount of expression relative to the non-specific (ns) and transfection mixture control.

The results of these experiments are presented below (and in FIG. 14) and show that all ten of the selected siRNA induce 80% or better silencing of the Bcl2 message at 100 nM concentrations. These data verify that the algorithm successfully identified functional Bcl2 siRNA and provide a set of functional agents that can be used in experimental and therapeutic environments.

```
siRNA 1    GGGAGAUAGUGAUGAAGUA    SEQ. ID NO. 302
siRNA 2    GAAGUACAUCCAUUAUAAG    SEQ. ID NO. 303
siRNA 3    GUACGACAACCGGGAGAUA    SEQ. ID NO. 304
siRNA 4    AGAUAGUGAUGAAGUACAU    SEQ. ID NO. 305
siRNA 5    UGAAGACUCUGCUCAGUUU    SEQ. ID NO. 306
siRNA 6    GCAUGCGGCCUCUGUUUGA    SEQ. ID NO. 307
siRNA 7    UGCGGCCUCUGUUUGAUUU    SEQ. ID NO. 308
siRNA 8    GAGAUAGUGAUGAAGUACA    SEQ. ID NO. 309
siRNA 9    GGAGAUAGUGAUGAAGUAC    SEQ. ID NO. 310
siRNA 10   GAAGACUCUGCUCAGUUUG    SEQ. ID NO. 311
```

Bcl2 siRNA: Sense Strand, 5' → 3'

Example VI

Sequences Selected by the Algorithm

Sequences of the siRNAs selected using Formulas (Algorithms) VIII and IX with their corresponding ranking, which have been evaluated for the silencing activity in vivo in the present study (Formula VIII and IX, respectively) are shown in Table V. It should be noted that the "t" residues in Table V, and elsewhere, when referring to siRNA, should be replaced by "u" residues.

TABLE V

| Gene Name | Accession Number | SEQ. ID NO. | FT11SeqTence | Formula VIII | Formula IX |
|---|---|---|---|---|---|
| CLTC | NM_004859 | SEQ. ID NO. 0312 | GAAAGAATCTGTAGAGAAA | 76 | 94.2 |
| CLTC | NM_004859 | SEQ. ID NO. 0313 | GCAATGAGCTGTTTGAAGA | 65 | 39.9 |
| CLTC | NM_004859 | SEQ. ID NO. 0314 | TGACAAAGGTGGATAAATT | 57 | 38.2 |
| CLTC | NM_004859 | SEQ. ID NO. 0315 | GGAAATGGATCTCTTTGAA | 54 | 49.4 |
| CLTA | NM_001833 | SEQ. ID NO. 0316 | GGAAAGTAATGGTCCAACA | 22 | 55.5 |
| CLTA | NM_001833 | SEQ. ID NO. 0317 | AGACAGTTATGCAGCTATT | 4 | 22.9 |
| CLTA | NM_001833 | SEQ. ID NO. 0318 | CCAATTCTCGGAAGCAAGA | 1 | 17 |
| CLTA | NM_001833 | SEQ. ID NO. 0319 | GAAAGTAATGGTCCAACAG | -1 | -13 |
| CLTB | NM_001834 | SEQ. ID NO. 0320 | GCGCCAGAGTGAACAAGTA | 17 | 57.5 |
| CLTB | NM_001834 | SEQ. ID NO. 0321 | GAAGGTGGCCCAGCTATGT | 15 | -8.6 |
| CLTB | NM_001834 | SEQ. ID NO. 0322 | GGAACCAGCGCCAGAGTGA | 13 | 40.5 |
| CLTB | NM_001834 | SEQ. ID NO. 0323 | GAGCGAGATTGCAGGCATA | 20 | 61.7 |
| CALM | U45976 | SEQ. ID NO. 0324 | GTTAGTATCTGATGACTTG | 36 | -34.6 |
| CALM | U45976 | SEQ. ID NO. 0325 | GAAATGGAACCACTAAGAA | 33 | 46.1 |
| CALM | U45976 | SEQ. ID NO. 0326 | GGAAATGGAACCACTAAGA | 30 | 61.2 |
| CALM | U45976 | SEQ. ID NO. 0327 | CAACTACACTTTCCAATGC | 28 | 6.8 |
| EPS15 | NM_001981 | SEQ. ID NO. 0328 | CCACCAAGATTTCATGATA | 48 | 25.2 |
| EPS15 | NM_001981 | SEQ. ID NO. 0329 | GATCGGAACTCCAACAAGA | 43 | 49.3 |
| EPS15 | NM_001981 | SEQ. ID NO. 0330 | AAACGGAGCTACAGATTAT | 39 | 11.5 |
| EPS15 | NM_001981 | SEQ. ID NO. 0331 | CCACACAGCATTCTTGTAA | 33 | -23.6 |
| EPS15R | NM_021235 | SEQ. ID NO. 0332 | GAAGTTACCTTGAGCAATC | 48 | 33 |
| EPS15R | NM_021235 | SEQ. ID NO. 0333 | GGACTTGGCCGATCCAGAA | 27 | 33 |
| EPS15R | NM_021235 | SEQ. ID NO. 0334 | GCACTTGGATCGAGATGAG | 20 | 1.3 |
| EPS15R | NM_021235 | SEQ. ID NO. 0335 | CAAAGACCAATTCGCGTTA | 17 | 27.7 |
| DNM2 | NM_004945 | SEQ. ID NO. 0336 | CCGAATCAATCGCATCTTC | 6 | -29.6 |
| DNM2 | NM_004945 | SEQ. ID NO. 0337 | GACATGATCCTGCAGTTCA | 5 | -14 |
| DNM2 | NM_004945 | SEQ. ID NO. 0338 | GAGCGAATCGTCACCACTT | 5 | 24 |
| DNM2 | NM_004945 | SEQ. ID NO. 0339 | CCTCCGAGCTGGCGTCTAC | -4 | -63.6 |
| ARF6 | AF93885 | SEQ. ID NO. 0340 | TCACATGGTTAACCTCTAA | 27 | -21.1 |
| ARF6 | AF93885 | SEQ. ID NO. 0341 | GATGAGGGACGCCATAATC | 7 | -38.4 |
| ARF6 | AF93885 | SEQ. ID NO. 0342 | CCTCTAACTACAAATCTTA | 4 | 16.9 |
| ARF6 | AF93885 | SEQ. ID NO. 0343 | GGAAGGTGCTATCCAAAAT | 4 | 11.5 |
| RAB5A | BC001267 | SEQ. ID NO. 0344 | GCAAGCAAGTCCTAACATT | 40 | 25.1 |
| RAB5A | BC001267 | SEQ. ID NO. 0345 | GGAAGAGGAGTAGACCTTA | 17 | 50.1 |
| RAB5A | BC001267 | SEQ. ID NO. 0346 | AGGAATCAGTGTTGTAGTA | 16 | 11.5 |
| RAB5A | BC001267 | SEQ. ID NO. 0347 | GAAGAGGAGTAGACCTTAC | 12 | 7 |
| RAB5B | NM_002868 | SEQ. ID NO. 0348 | GAAAGTCAAGCCTGGTATT | 14 | 18.1 |
| RAB5B | NM_002868 | SEQ. ID NO. 0349 | AAAGTCAAGCCTGGTATTA | 6 | -17.8 |
| RAB5B | NM_002868 | SEQ. ID NO. 0350 | GCTATGAACGTGAATGATC | 3 | -21.1 |

TABLE V-continued

| Gene Name | Accession Number | SEQ. ID NO. | FT11SeqTence | Formula VIII | Formula IX |
|---|---|---|---|---|---|
| RAB5B | NM_002868 | SEQ. ID NO. 0351 | CAAGCCTGGTATTACGTTT | −7 | −37.5 |
| RAB5C | AF141304 | SEQ. ID NO. 0352 | GGAACAAGATCTGTCAATT | 38 | 51.9 |
| RAB5C | AF141304 | SEQ. ID NO. 0353 | GCAATGAACGTGAACGAAA | 29 | 43.7 |
| RAB5C | AF141304 | SEQ. ID NO. 0354 | CAATGAACGTGAACGAAAT | 18 | 43.3 |
| RAB5C | AF141304 | SEQ. ID NO. 0355 | GGACAGGAGCGGTATCACA | 6 | 18.2 |
| EEA1 | XM_018197 | SEQ. ID NO. 0356 | AGACAGAGCTTGAGAATAA | 67 | 64.1 |
| EEA1 | XM_018197 | SEQ. ID NO. 0357 | GAGAAGATCTTTATGCAAA | 60 | 48.7 |
| EEA1 | XM_018197 | SEQ. ID NO. 0358 | GAAGAGAAATCAGCAGATA | 58 | 45.7 |
| EEA1 | XM_018197 | SEQ. ID NO. 0359 | GCAAGTAACTCAACTAACA | 56 | 72.3 |
| AP2B1 | NM_001282 | SEQ. ID NO. 0360 | GAGCTAATCTGCCACATTG | 49 | −12.4 |
| AP2B1 | NM_001282 | SEQ. ID NO. 0361 | GCAGATGAGTTACTAGAAA | 44 | 48.9 |
| AP2B1 | NM_001282 | SEQ. ID NO. 0362 | CAACTTAATTGTCCAGAAA | 41 | 28.2 |
| AP2B1 | NM_001282 | SEQ. ID NO. 0363 | CAACACAGGATTCTGATAA | 33 | −5.8 |
| PLK | NM_005030 | SEQ. ID NO. 0364 | AGATTGTGCCTAAGTCTCT | −35 | −3.4 |
| PLK | NM_005030 | SEQ. ID NO. 0365 | ATGAAGATCTGGAGGTGAA | 0 | −4.3 |
| PLK | NM_005030 | SEQ. ID NO. 0366 | TTTGAGACTTCTTGCCTAA | −5 | −27.7 |
| PLK | NM_005030 | SEQ. ID NO. 0367 | AGATCACCCTCCTTAAATA | 15 | 72.3 |
| GAPDH | NM_002046 | SEQ. ID NO. 0368 | CAACGGATTTGGTCGTATT | 27 | −2.8 |
| GAPDH | NM_002046 | SEQ. ID NO. 0369 | GAAATCCCATCACCATCTT | 24 | 3.9 |
| GAPDH | NM_002046 | SEQ. ID NO. 0370 | GACCTCAACTACATGGTTT | 22 | −22.9 |
| GAPDH | NM_002046 | SEQ. ID NO. 0371 | TGGTTTACATGTTCCAATA | 9 | 9.8 |
| c-Myc |  | SEQ. ID NO. 0372 | GAAGAAATCGATGTTGTTT | 31 | −11.7 |
| c-Myc |  | SEQ. ID NO. 0373 | ACACAAACTTGAACAGCTA | 22 | 51.3 |
| c-Myc |  | SEQ. ID NO. 0374 | GGAAGAAATCGATGTTGTT | 18 | 26 |
| c-Myc |  | SEQ. ID NO. 0375 | GAAACGACGAGAACAGTTG | 18 | −8.9 |
| MAP2K1 | NM_002755 | SEQ. ID NO. 0376 | GCACATGGATGGAGGTTCT | 26 | 16 |
| MAP2K1 | NM_002755 | SEQ. ID NO. 0377 | GCAGAGAGAGCAGATTTGA | 16 | 0.4 |
| MAP2K1 | NM_002755 | SEQ. ID NO. 0378 | GAGGTTCTCTGGATCAAGT | 14 | 15.5 |
| MAP2K1 | NM_002755 | SEQ. ID NO. 0379 | GAGCAGATTTGAAGCAACT | 14 | 18.5 |
| MAP2K2 | NM_030662 | SEQ. ID NO. 0380 | CAAAGACGATGACTTCGAA | 37 | 26.4 |
| MAP2K2 | NM_030662 | SEQ. ID NO. 0381 | GATCAGCATTTGCATGGAA | 24 | −0.7 |
| MAP2K2 | NM_030662 | SEQ. ID NO. 0382 | TCCAGGAGTTTGTCAATAA | 17 | −4.5 |
| MAP2K2 | NM_030662 | SEQ. ID NO. 0383 | GGAAGCTGATCCACCTTGA | 16 | 59.2 |
| KNSL1(EG5) | NM_004523 | SEQ. ID NO. 0384 | GCAGAAATCTAAGGATATA | 53 | 35.8 |
| KNSL1(EG5) | NM_004523 | SEQ. ID NO. 0385 | CAACAAGGATGAAGTCTAT | 50 | 18.3 |
| KNSL1(EG5) | NM_004523 | SEQ. ID NO. 0386 | CAGCAGAAATCTAAGGATA | 41 | 32.7 |
| KNSL1(EG5) | NM_004523 | SEQ. ID NO. 0387 | CTAGATGGCTTTCTCAGTA | 39 | 3.9 |
| CyclophilinA | NM_021130 | SEQ. ID NO. 0388 | AGACAAGGTCCCAAAGACA | −16 | 58.1 |

TABLE V-continued

| Gene Name | Accession Number | SEQ. ID NO. | FT11SeqTence | Formula VIII | Formula IX |
|---|---|---|---|---|---|
| CyclophilinA | NM_021130 | SEQ. ID NO. 0389 | GGAATGGCAAGACCAGCAA | -6 | 36 |
| CyclophilinA | NM_021130 | SEQ. ID NO. 0390 | AGAATTATTCCAGGGTTTA | -3 | 16.1 |
| CyclophilinA | NM_021130 | SEQ. ID NO. 0391 | GCAGACAAGGTCCCAAAGA | 8 | 8.9 |
| LAMIN A/C | NM_170707 | SEQ. ID NO. 0392 | AGAAGCAGCTTCAGGATGA | 31 | 38.8 |
| LAMIN A/C | NM_170707 | SEQ. ID NO. 0393 | GAGCTTGACTTCCAGAAGA | 33 | 22.4 |
| LAMIN A/C | NM_170707 | SEQ. ID NO. 0394 | CCACCGAAGTTCACCCTAA | 21 | 27.5 |
| LAMIN A/C | NM_170707 | SEQ. ID NO. 0395 | GAGAAGAGCTCCTCCATCA | 55 | 30.1 |
| CyclophilinB | M60857 | SEQ. ID NO. 0396 | GAAAGAGCATCTACGGTGA | 41 | 83.9 |
| CyclophilinB | M60857 | SEQ. ID NO. 0397 | GAAAGGATTTGGCTACAAA | 53 | 59.1 |
| CyclophilinB | M60857 | SEQ. ID NO. 0398 | ACAGCAAATTCCATCGTGT | -20 | 28.8 |
| CyclophilinB | M60857 | SEQ. ID NO. 0399 | GGAAAGACTGTTCCAAAAA | 2 | 27 |
| DBI1 | NM_020548 | SEQ. ID NO. 0400 | CAACACGCCTCATCCTCTA | 27 | -7.6 |
| DBI2 | NM_020548 | SEQ. ID NO. 0401 | CATGAAAGCTTACATCAAC | 25 | -30.8 |
| DBI3 | NM_020548 | SEQ. ID NO. 0402 | AAGATGCCATGAAAGCTTA | 17 | 22 |
| DBI4 | NM_020548 | SEQ. ID NO. 0403 | GCACATACCGCCTGAGTCT | 15 | 3.9 |
| rLUC1 | | SEQ. ID NO. 0404 | GATCAAATCTGAAGAAGGA | 57 | 49.2 |
| rLUC2 | | SEQ. ID NO. 0405 | GCCAAGAAGTTTCCTAATA | 50 | 13.7 |
| rLUC3 | | SEQ. ID NO. 0406 | CAGCATATCTTGAACCATT | 41 | -2.2 |
| rLUC4 | | SEQ. ID NO. 0407 | GAACAAAGGAAACGGATGA | 39 | 29.2 |
| SeAP1 | NM_031313 | SEQ. ID NO. 0408 | CGGAAACGGTCCAGGCTAT | 6 | 26.9 |
| SeAP2 | NM_031313 | SEQ. ID NO. 0409 | GCTTCGAGCAGACATGATA | 4 | -11.2 |
| SeAP3 | NM_031313 | SEQ. ID NO. 0410 | CCTACACGGTCCTCCTATA | 4 | 4.9 |
| SeAP4 | NM_031313 | SEQ. ID NO. 0411 | GCCAAGAACCTCATCATCT | 1 | -9.9 |
| fLUC1 | | SEQ. ID NO. 0412 | GATATGGGCTGAATACAAA | 54 | 40.4 |
| fLUC2 | | SEQ. ID NO. 0413 | GCACTCTGATTGACAAATA | 47 | 54.7 |
| fLUC3 | | SEQ. ID NO. 0414 | TGAAGTCTCTGATTAAGTA | 46 | 34.5 |
| fLUC4 | | SEQ. ID NO. 0415 | TCAGAGAGATCCTCATAAA | 40 | 11.4 |
| mCyclo_1 | NM_008907 | SEQ. ID NO. 0416 | GCAAGAAGATCACCATTTC | 52 | 46.4 |
| mCyclo_2 | NM_008907 | SEQ. ID NO. 0417 | GAGAGAAATTTGAGGATGA | 36 | 70.7 |
| mCyclo_3 | NM_008907 | SEQ. ID NO. 0418 | GAAAGGATTTGGCTATAAG | 35 | -1.5 |
| mCyclo_4 | NM_008907 | SEQ. ID NO. 0419 | GAAAGAAGGCATGAACATT | 27 | 10.3 |
| BCL2_1 | NM_000633 | SEQ. ID NO. 0420 | GGGAGATAGTGATGAAGTA | 21 | 72 |
| BCL2_2 | NM_000633 | SEQ. ID NO. 0421 | GAAGTACATCCATTATAAG | 1 | 3.3 |
| BCL2_3 | NM_000633 | SEQ. ID NO. 0422 | GTACGACAACCGGGAGATA | 1 | 35.9 |
| BCL2_4 | NM_000633 | SEQ. ID NO. 0423 | AGATAGTGATGAAGTACAT | -12 | 22.1 |
| BCL2_5 | NM_000633 | SEQ. ID NO. 0424 | TGAAGACTCTGCTCAGTTT | 36 | 19.1 |
| BCL2_6 | NM_000633 | SEQ. ID NO. 0425 | GCATGCGGCCTCTGTTTGA | 5 | -9.7 |
| QB1 | NM_003365.1 | SEQ. ID NO. 0426 | GCACACAGCUUACUACAUC | 52 | -4.8 |
| QB2 | NM_003365.1 | SEQ. ID NO. 0427 | GAAAUGCCCUGGUAUCUCA | 49 | 22.1 |

TABLE V-continued

| Gene Name | Accession Number | SEQ. ID NO. | FT11SeqTence | Formula VIII | Formula IX |
|---|---|---|---|---|---|
| QB3 | NM_003365.1 | SEQ. ID NO. 0428 | GAAGGAACGUGAUGUGAUC | 34 | 22.9 |
| QB4 | NM_003365.1 | SEQ. ID NO. 0429 | GCACUACUCCUGUGUGUGA | 28 | 20.4 |
| ATE1-1 | NM_007041 | SEQ. ID NO. 0430 | GAACCCAGCUGGAGAACUU | 45 | 15.5 |
| ATE1-2 | NM_007041 | SEQ. ID NO. 0431 | GAUAUACAGUGUGAUCUUA | 40 | 12.2 |
| ATE1-3 | NM_007041 | SEQ. ID NO. 0432 | GUACUACGAUCCUGAUUAU | 37 | 32.9 |
| ATE1-4 | NM_007041 | SEQ. ID NO. 0433 | GUGCCGACCUUUACAAUUU | 35 | 18.2 |
| EGFR-1 | NM_005228 | SEQ. ID NO. 0434 | GAAGGAAACTGAATTCAAA | 68 | 79.4 |
| EGFR-1 | NM_005228 | SEQ. ID NO. 0435 | GGAAATATGTACTACGAAA | 49 | 49.5 |
| EGFR-1 | NM_005228 | SEQ. ID NO. 0436 | CCACAAAGCAGTGAATTTA | 41 | 7.6 |
| EGFR-1 | NM_005228 | SEQ. ID NO. 0437 | GTAACAAGCTCACGCAGTT | 40 | 25.9 |

Example VII

Genome-Wide Application of Formula VIII or Formula X

The examples described above demonstrate that the algorithm(s) can successfully identify functional siRNA and that these duplexes can be used to induce the desirable phenotype of transcriptional knockdown or knockout. Each gene or family of genes in each organism plays an important role in maintaining physiological homeostasis and the algorithm can be used to develop functional, highly functional, or hyperfunctional siRNA to each gene. In one example of how this is accomplished, the entire online ncbi refseq, locuslink, and/or unigene database for the human genome is first downloaded to local servers. Concomitantly, the most current version of the BLAST algorithm/program is also downloaded to enable analysis of all siRNA identified by the algorithm. Prior to applying the algorithm, sequences are filtered to eliminate all non-coding sequences (e.g., 3' and 5' UTRs) and sequences that contain single nucleotide polymorphisms (SNPs). In addition, in one version of the siRNA selection process, only those sequences that are associated with all isoforms (e.g., splice variants) of a given gene are reserved and considered for targeting. Subsequently, a list of all potential siRNAs (including a 19 basepair "core" sequence with two basepair 3' overhangs) is generated for each gene sequence. This group is then filtered to eliminate sequences that contain any one of a number of undesirable traits including, but not limited to: 1) sequences that contain more than two GC basepairs in the last 5 nucleotides of the 3' end of the sense strand, and 2) sequences that contained internal repeats that could potentially form hairpin structures. The output of these procedures are then submitted for scoring by the algorithm. In this example, the pre-filtered database was processed with Formula VIII or Formula X and the top 5-100 siRNAs having scores of 75 (adjusted) or greater were selected. If desired, the sequences of these siRNA can be BLAST'ed against the Unigene database containing all sequences in the genome of choice (e.g., the human genome) to eliminate any duplexes that show undesirable degrees of homology to sequences other than the intended target. The sequences of the (roughly) top 100 sequences for each gene are provided on the enclosed CDs in electronic form. In this example, the Formula X sequences were first generated using the procedures described above and subsequently compared to Formula VIII generated sequences. Formula VIII sequences that were also identified by Formula X were then removed (subtracted) from this database to eliminate duplications.

Many of the genes to which the described siRNA are directed play critical roles in disease etiology. For this reason, the siRNAs listed in the accompanying compact disk may potentially act as therapeutic agents. A number of prophetic examples follow and should be understood in view of the siRNA that are identified on the accompanying CD. To isolate these siRNAs, the appropriate message sequence for each gene is analyzed using one of the before mentioned formulas (preferably formula VIII) to identify potential siRNA targets. Subsequently these targets are BLAST'ed to eliminate homology with potential off-targets.

The list of potential disease targets is extensive. For instance, over-expression of Bc110 has been implicated in the development of MALT lymphoma (mucosa associated lymphoid tissue lymphoma) and thus, functional, highly functional, or hyperfunctional siRNA directed against that gene (e.g., SEQ. ID NO. 0427: GGAAACCUCUCAUUGCUAA; SEQ. ID NO. 0428: GAAAGAACCUUGCCGAUCA; SEQ. ID NO. 0429: GGAAAUACAUCAGAGCUUA, or SEQ. ID NO. 0430: GAAAGUAUGUGUCUUAAGU) may contribute to treatment of this disorder.

In another example, studies have shown that molecules that inhibit glutamine:fructose-6-phosphate aminotransferase (GFA) may act to limit the symptoms suffered by Type II diabetics. Thus, functional, highly functional, or hyperfunctional siRNA directed against GFA (also known as GFPT1: siRNA=SEQ. ID NO. 0433 UGAAACGGCUGCCUGA-UUU; SEQ. ID NO. 0434 GAAGUUACCUCUUACAUUU; SEQ. ID NO. 0435 GUACGAAACUGUAUGAUUA; SEQ. ID NO. 0436 GGACGAGGCUAUCAUUAUG) may contribute to treatment of this disorder.

In another example, the von Hippel-Lindau (VHL) tumor suppressor has been observed to be inactivated at a high frequency in sporadic clear cell renal cell carcinoma (RCC) and RCCs associated with VHL disease. The VHL tumor suppressor targets hypoxia-inducible factor-1 alpha (HIF-1 alpha), a transcription factor that can induce vascular endothelial growth factor (VEGF) expression, for ubiquitination and degradation. Inactivation of VHL can lead to increased levels of HIF-1 alpha, and subsequent VEGF over expression. Such over expression of VEGF has been used to explain the increased (and possibly necessary) vascularity observed in RCC. Thus, functional, highly functional, or hyperfunctional siRNAs directed against either HIF-1 alpha (SEQ. ID NO. 438 GAAGGAACCUGAUGCUUUA; SEQ. ID NO. 439 GCAUAUAUCUAGAAGGUAU; SEQ. ID NO. 440 GAACAAAUACAUGGGAUUA; SEQ. ID NO. 441 GGACACAGAUUUAGACUUG) or VEGF (SEQ. ID NO. 442 GAACGUACUUGCAGAUGUG; SEQ. ID NO. 443 GAGAAAGCAUUUGUUUGUA; SEQ. ID NO. 444 GGAGAAAGCAUUUGUUUGU; SEQ. ID NO. 445 CGAGGCAGCUUGAGUUAAA) may be useful in the treatment of renal cell carcinoma.

In another example, gene expression of platelet derived growth factor A and B (PDGF-A and PDGF-B) has been observed to be increased 22- and 6-fold, respectively, in renal tissues taken from patients with diabetic nephropathy as compared with controls. These findings suggest that over expression of PDGF A and B may play a role in the development of the progressive fibrosis that characterizes human diabetic kidney disease. Thus, functional, highly functional, or hyperfunctional siRNAs directed against either PDGF A
(SEQ. ID NO. 0446: GGUAAGAUAUUGUGCUUUA;
SEQ. ID NO. 0447: CCGCAAAUAUGCAGAAUUA;
SEQ. ID NO. 0448: GGAUGUACAUGGCGUGUUA;
SEQ. ID NO. 0449: GGUGAAGUUUGUAUGUUUA) or PDGF B
(SEQ. ID NO. 0450: CCGAGGAGCUUUAUGAGAU;
SEQ. ID NO. 0451: GCUCCGCGCUUUCCGAUUU;
SEQ. ID NO. 0452 GAGCAGGAAUGGUGAGAUG;
SEQ. ID NO. 0453: GAACUUGGGAUAAGAGUGU;
SEQ. ID NO. 0454 CCGAGGAGCUUUAUGAGAU;
SEQ. ID NO. 0455 UUUAUGAGAUGCUGAGUGA) may be useful in the treatment of this form of kidney disorder.

In another example, a strong correlation exists between the over-expression of glucose transporters (e.g., GLUT12) and cancer cells. It is predicted that cells undergoing uncontrolled cell growth up-regulate GLUT molecules so that they can cope with the heightened energy needs associated with increased rates of proliferation and metastasis. Thus, siRNA-based therapies that target the molecules such as
GLUT1 (also known as SLC2A1: siRNA=
SEQ. ID NO.: 0456 GCAAUGAUGUCCAGAAGAA;
SEQ. ID NO.: 0457 GAAGAAUAUUCAGGACUUA;
SEQ. ID NO.: 0458 GAAGAGAGUCGGCAGAUGA;
SEQ. ID NO.: 0459 CCAAGAGUGUGCUAAAGAA)
GLUT 12 (also known as SLCA12: siRNA=
SEQ. ID NO. 0460GAGACACUCUGAAAUGAUA;
SEQ. ID NO. 0461 GAAAUGAUGUGGAUAAGAG;
SEQ. ID NO. 0462 GAUCAAAUCCUCCCUGAAA;
SEQ. ID NO. 0463 UGAAUGAGCUGAUGAUUGU) and other related transporters, may be of value in treating a multitude of malignancies.

The siRNA sequences listed above are presented in a 5'→3' sense strand direction. In addition, siRNA directed against the targets listed above as well as those directed against other targets and listed in the accompanying compact disk may be useful as therapeutic agents.

Example VIII

Evidence for the Benefits of Pooling

Evidence for the benefits of pooling have been demonstrated using the reporter gene, luciferase. Ninety siRNA duplexes were synthesized using Dharmacon proprietary ACE® chemistry against one of the standard reporter genes: firefly luciferase. The duplexes were designed to start two base pairs apart and to cover approximately 180 base pairs of the luciferase gene (see sequences in Table III). Subsequently, the siRNA duplexes were co-transfected with a luciferase expression reporter plasmid into HEK293 cells using standard transfection protocols and luciferase activity was assayed at 24 and 48 hours.

Figure 15:
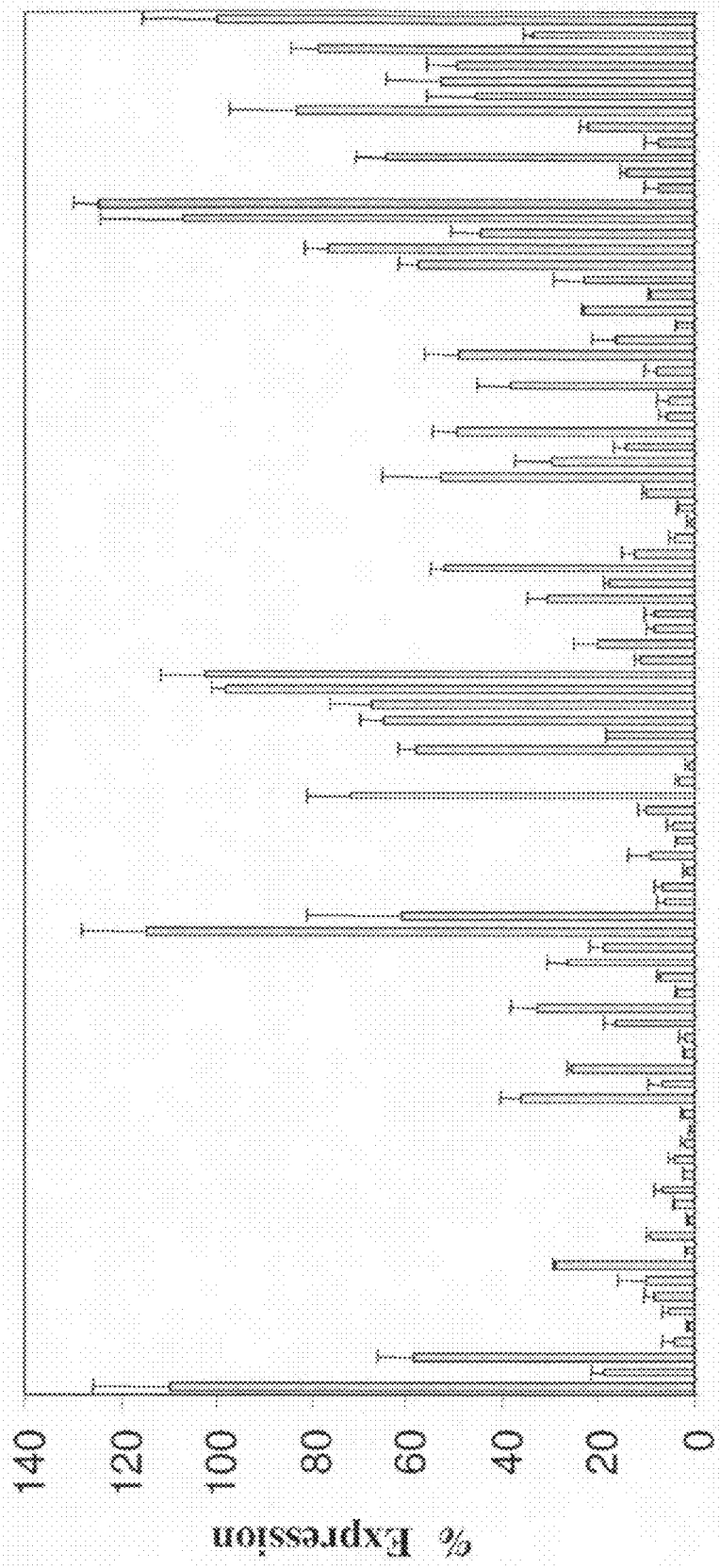
FIG. 15 represents a functional walk where siRNA beginning on every other base pair of a region of the luciferase gene are tested for the ability to silence the luciferase gene. The Y-axis represents the percent expression relative to a control. The X-axis represents the position of each individual siRNA.

Transfection of individual siRNAs showed standard distribution of inhibitory effect. Some duplexes were active, while others were not. FIG. 15 represents a typical screen of ninety siRNA duplexes (SEQ. ID NO. 0032-0120) positioned two base pairs apart. As the figure suggests, the functionality of the siRNA duplex is determined more by a particular sequence of the oligonucleotide than by the relative oligonucleotide position within a gene or excessively sensitive part of the mRNA, which is important for traditional anti-sense technology.

Figure 16:
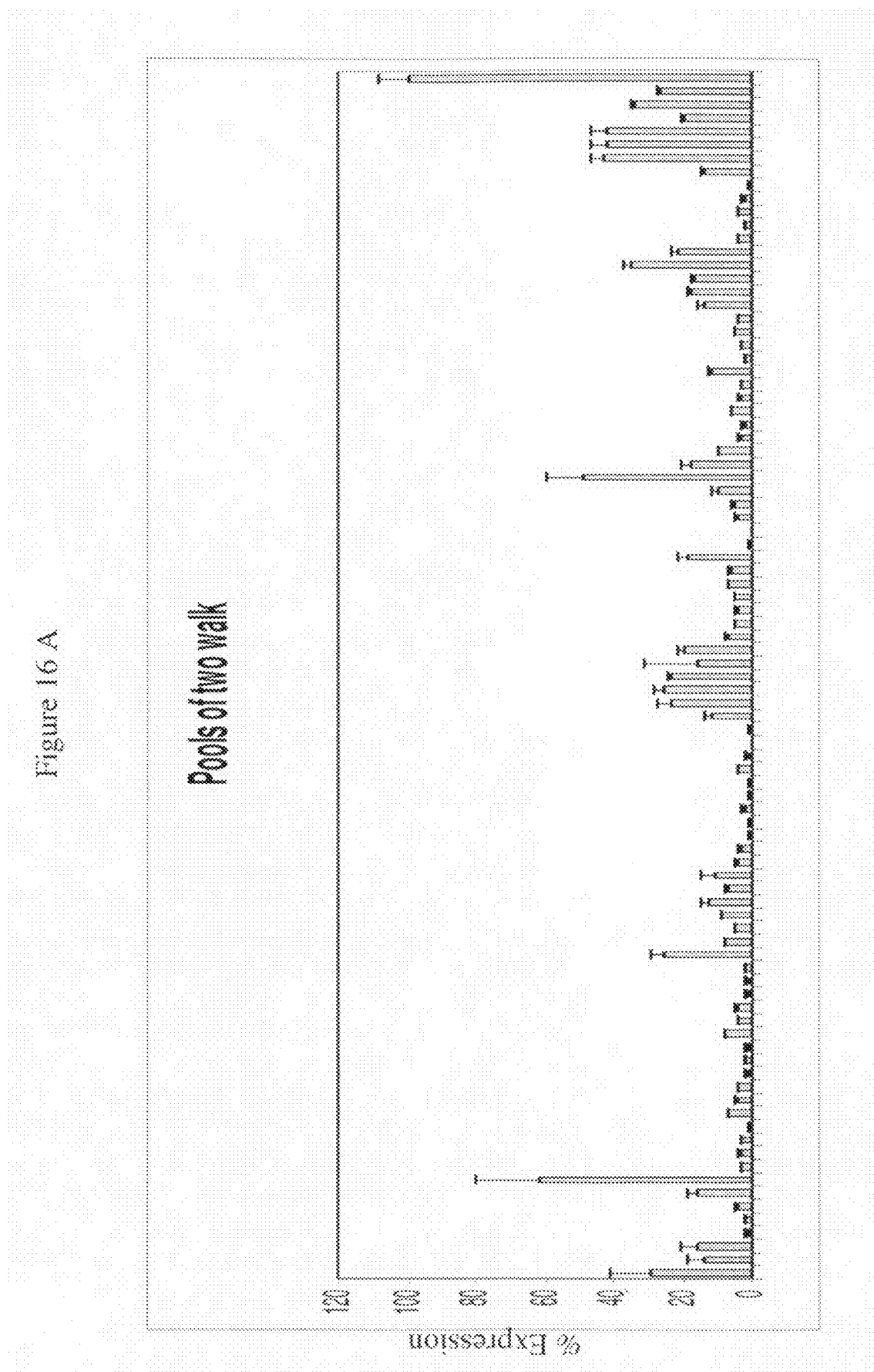
Figure 16:
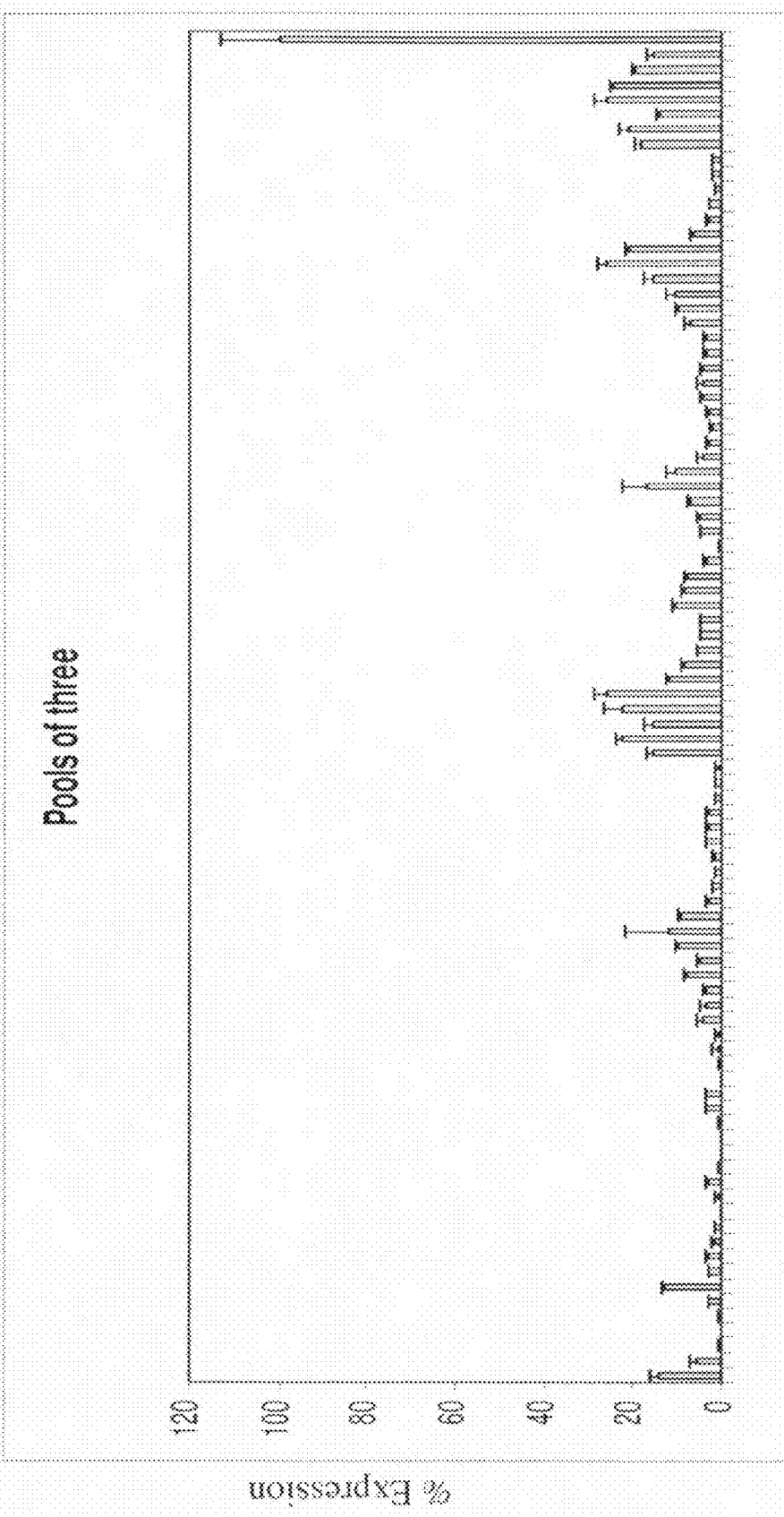
Figure 17A:
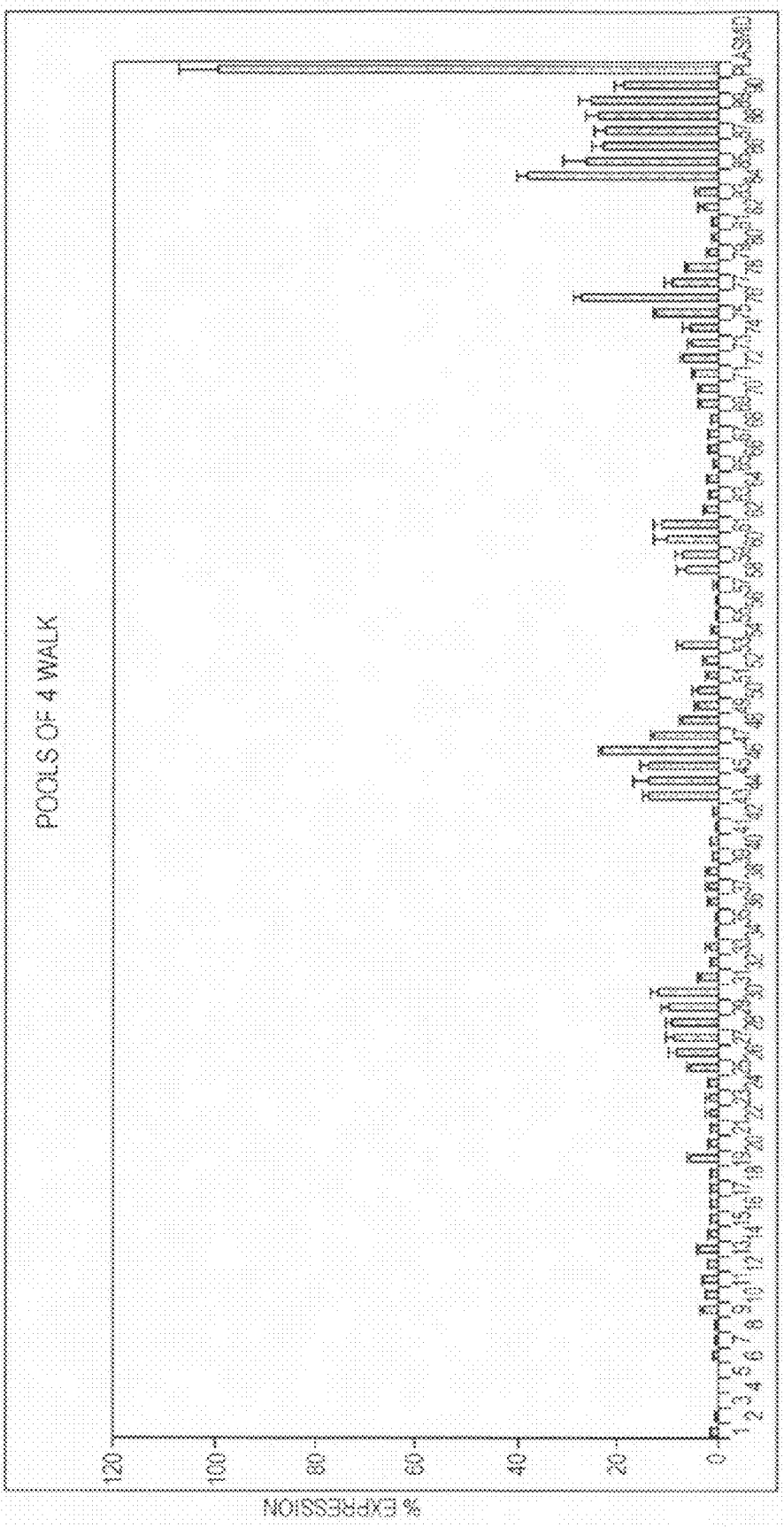
FIG. 17 is a histogram demonstrating the inhibition of target gene expression by pools of 4 and 5 siRNA duplexes. The Y-axis represents the percent expression relative to a control. The X-axis represents the position of the first siRNA in each pool.
Figure 17B:
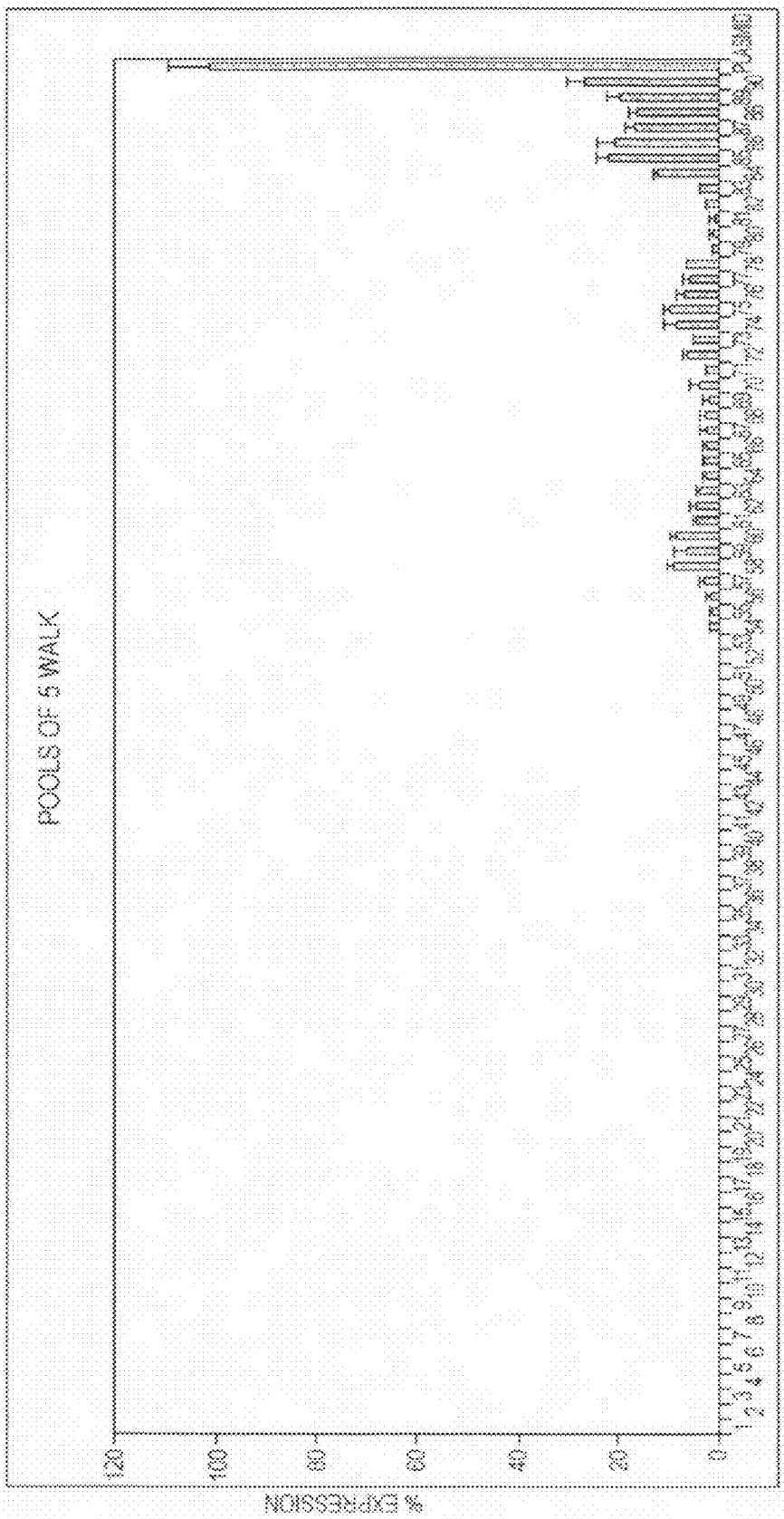
Figure 18:
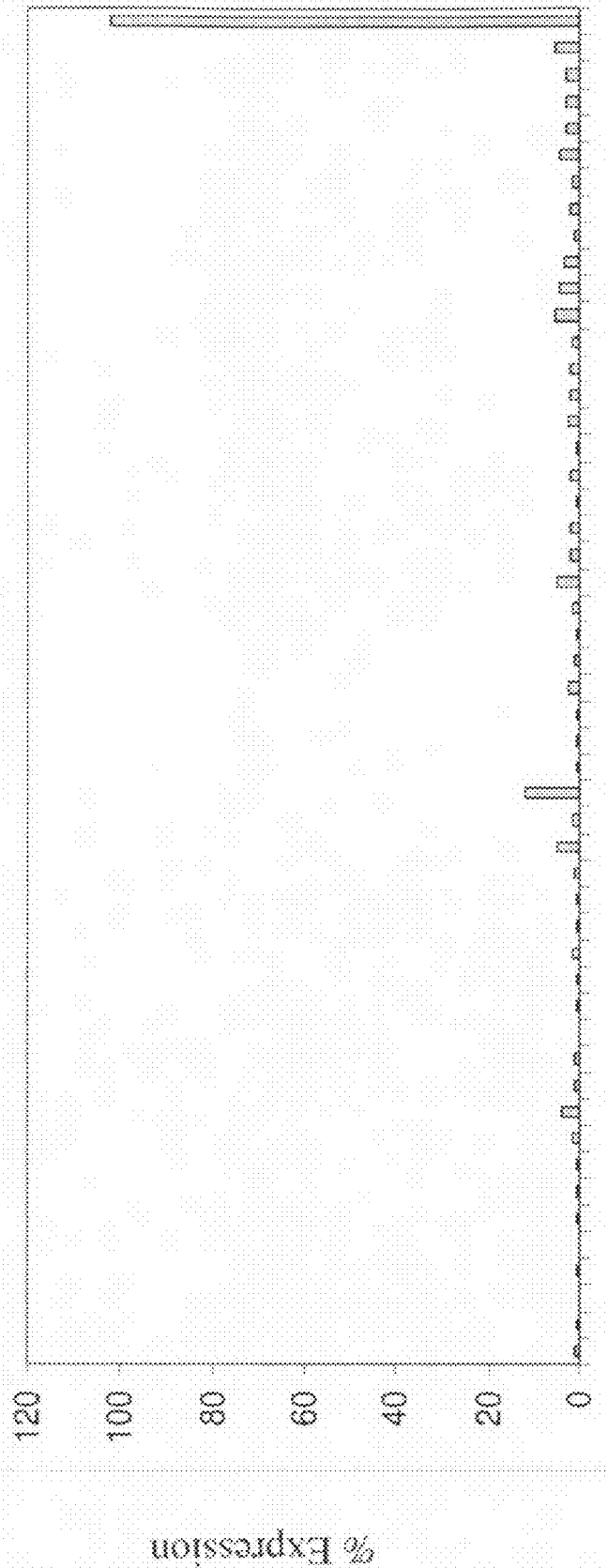
FIG. 18 is a histogram demonstrating the inhibition of target gene expression by siRNAs that are ten and twenty basepairs apart. The Y-axis represents the percent expression relative to a control. The X-axis represents the position of the first siRNA in each pool.

When two continuous oligonucleotides were pooled together, a significant increase in gene silencing activity was observed. (See FIG. 16) A gradual increase in efficacy and the frequency of pools functionality was observed when the number of siRNAs increased to 3 and 4. (FIGS. 16, 17). Further, the relative positioning of the oligonucleotides within a pool did not determine whether a particular pool was functional (see FIG. 18, in which 100% of pools of oligonucleotides distanced by 2, 10 and 20 base pairs were functional).

However, relative positioning may nonetheless have an impact. An increased functionality may exist when the siRNA are positioned continuously head to toe (5' end of one directly adjacent to the 3' end of the others).

Figure 19:
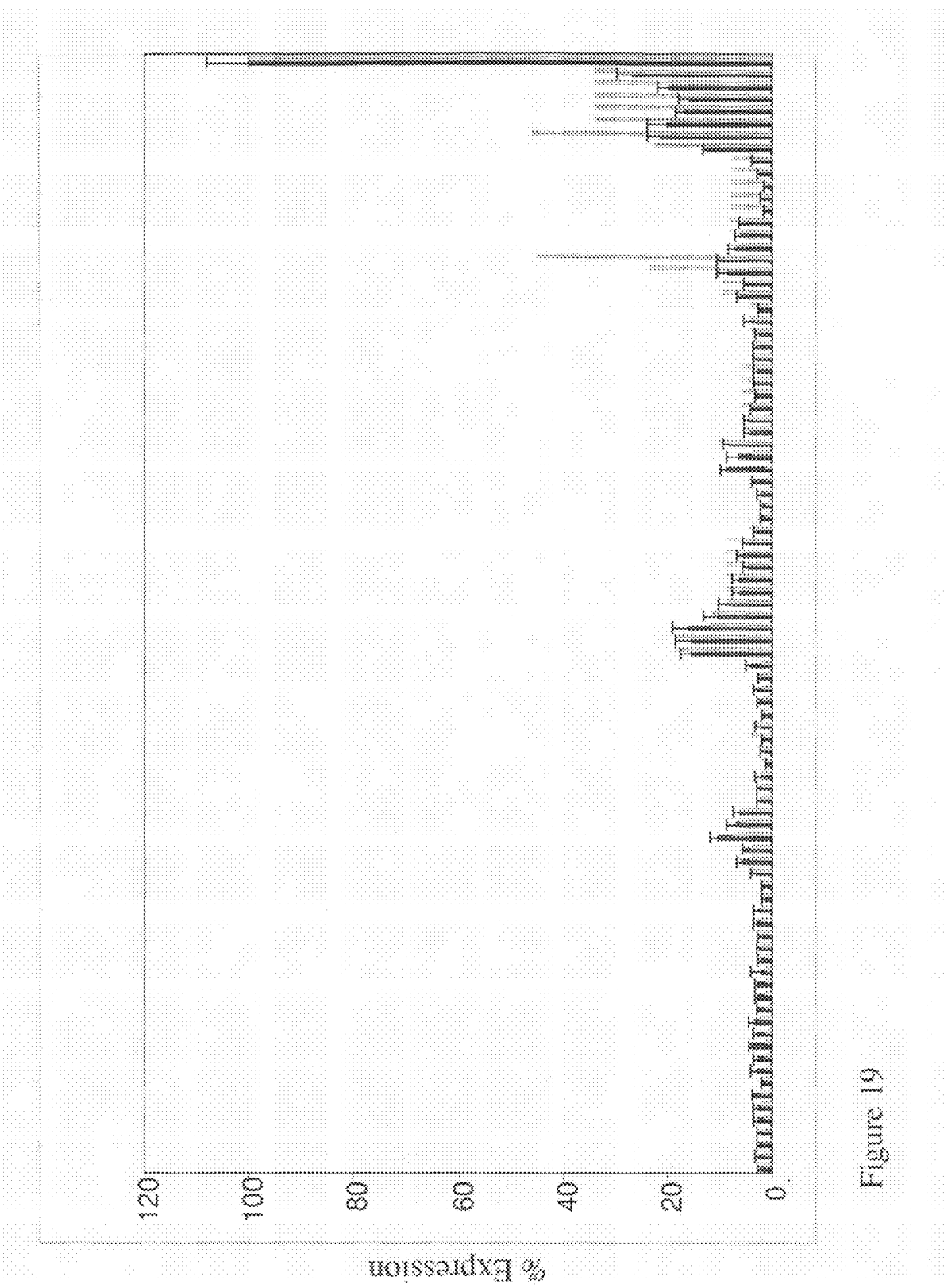
FIG. 19 shows that pools of siRNAs (dark gray bar) work as well (or better) than the best siRNA in the pool (light gray bar). The Y-axis represents the percent expression relative to a control. The X-axis represents the position of the first siRNA in each pool.
Figure 20:
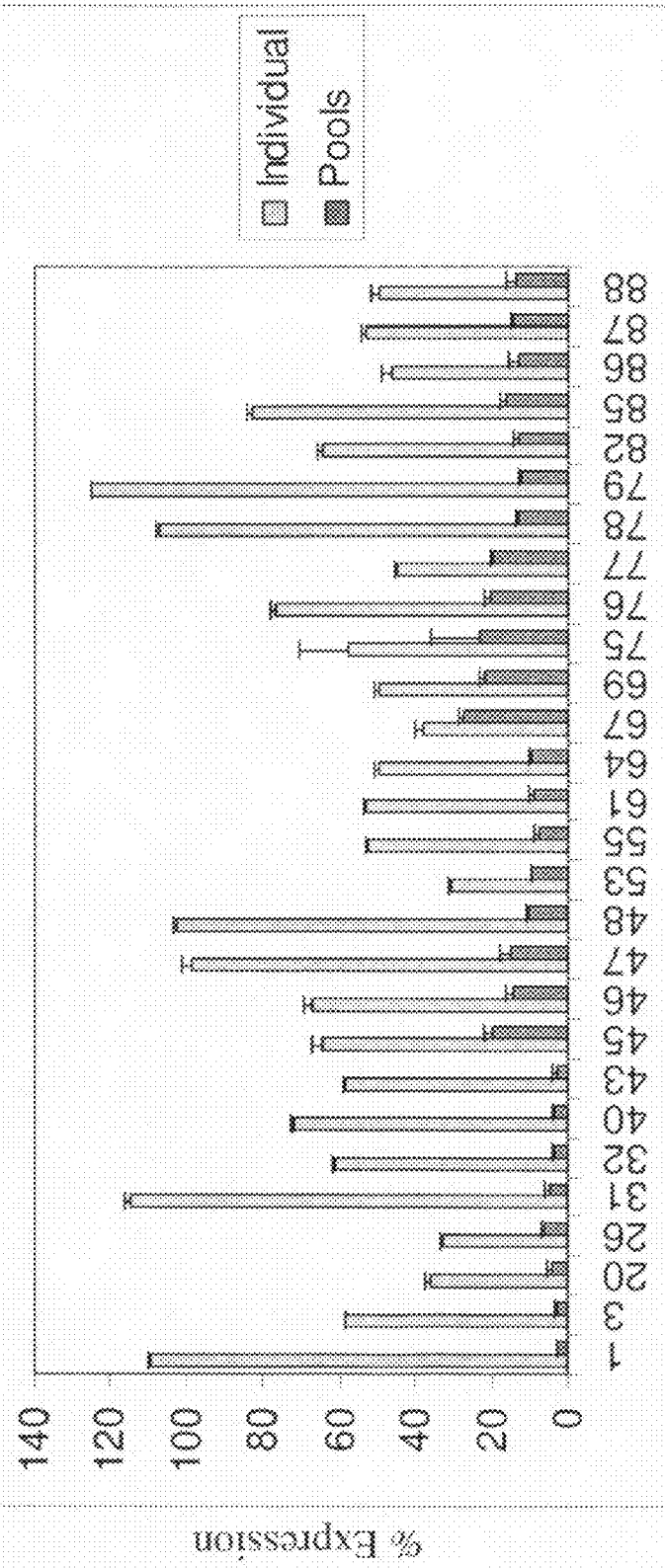
FIG. 20 shows that the combination of several semifunctional siRNAs (dark gray) result in a significant improvement of gene expression inhibition over individual (semi-functional; light gray) siRNA. The Y-axis represents the percent expression relative to a control.
Figure 21B:
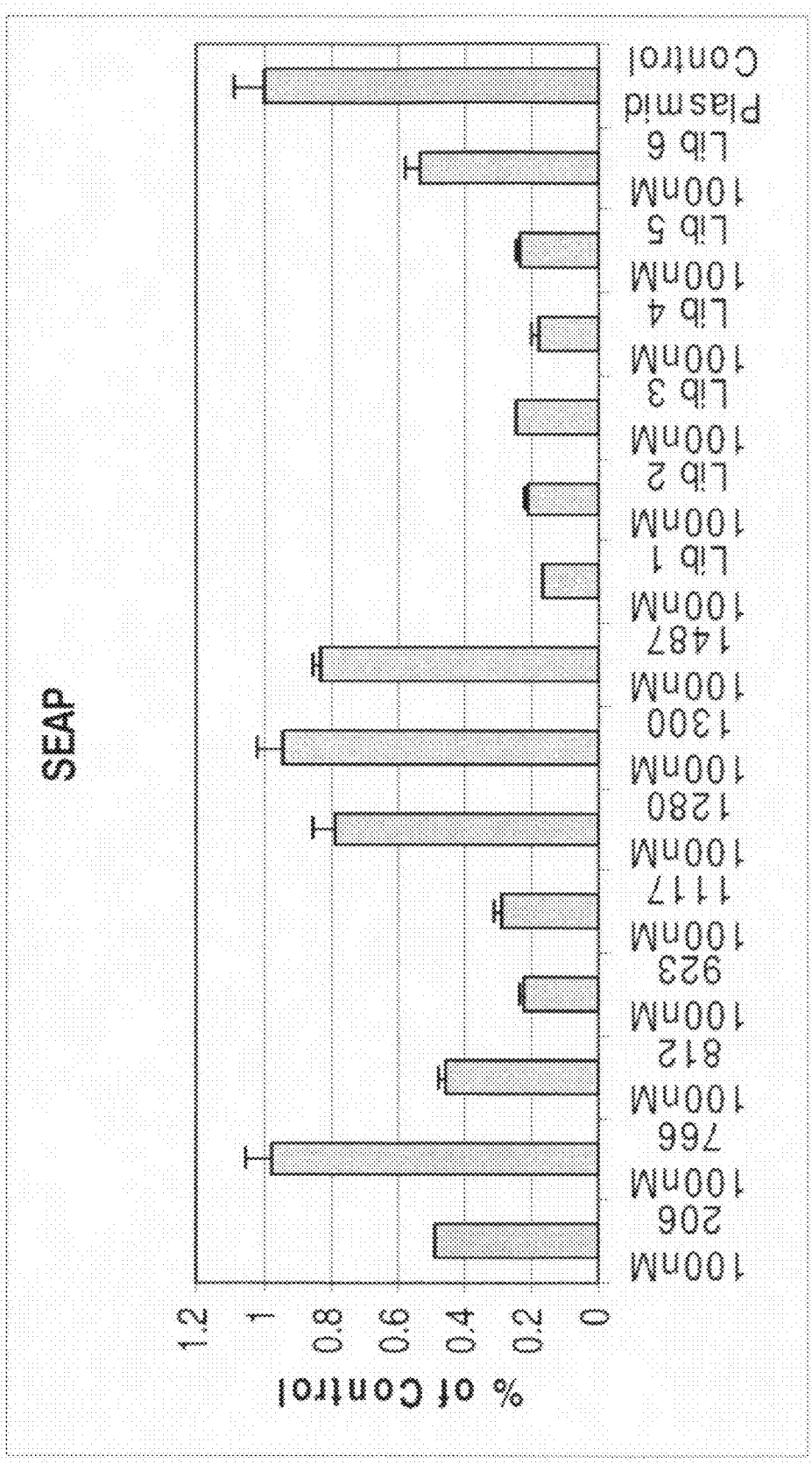
FIG. 21 shows both pools (Library, Lib) and individual siRNAs in inhibition of gene expression of Beta-Galactosidase, Renilla Luciferase and SEAP (alkaline phosphatase). Numbers on the X-axis indicate the position of the 5'-most nucleotide of the sense strand of the duplex. The Y-axis represents the percent expression of each gene relative to a control. Libraries contain 19 nucleotide long siRNAs (not including overhangs) that begin at the following nucleotides: SEAP: Lib 1: 206, 766, 812, 923, Lib 2: 1117, 1280, 1300, 1487, Lib 3: 206, 766, 812, 923, 1117, 1280, 1300, 1487, Lib 4: 206, 812, 1117, 1300, Lib 5: 766, 923, 1280, 1487, Lib 6: 206, 1487; Bgal: Lib 1: 979, 1339, 2029, 2590, Lib 2: 1087, 1783, 2399, 3257, Lib 3: 979, 1783, 2590, 3257, Lib 4: 979, 1087, 1339, 1783, 2029, 2399, 2590, 3257, Lib 5: 979, 1087, 1339, 1783, Lib 6: 2029, 2399, 2590, 3257; Renilla: Lib 1: 174, 300, 432, 568, Lib 2: 592, 633, 729, 867, Lib 3: 174, 300, 432, 568, 592, 633, 729, 867, Lib 4: 174, 432, 592, 729, Lib 5: 300, 568, 633, 867, Lib 6: 592, 568.
Figure 21C:
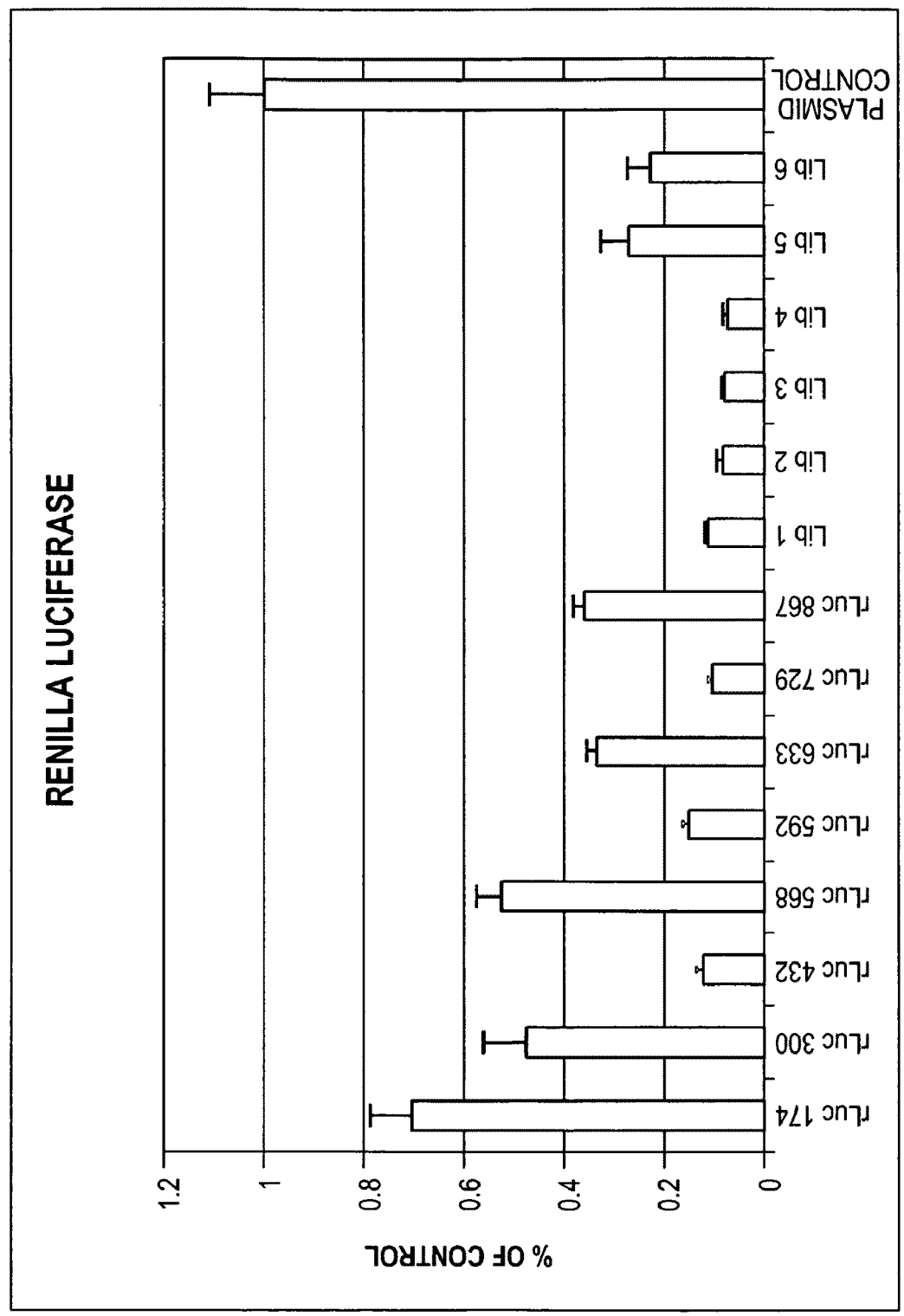

Additionally, siRNA pools that were tested performed at least as well as the best oligonucleotide in the pool, under the experimental conditions whose results are depicted in FIG. 19. Moreover, when previously identified non-functional and marginally (semi) functional siRNA duplexes were pooled together in groups of five at a time, a significant functional cooperative action was observed. (See FIG. 20) In fact, pools of semi-active oligonucleotides were 5 to 25 times more functional than the most potent oligonucleotide in the pool. Therefore, pooling several siRNA duplexes together does not interfere with the functionality of the most potent siRNAs within a pool, and pooling provides an unexpected significant increase in overall functionality Example IX Additional Evidence of the Benefits of Pooling Experiments were performed on the following genes: β-galactosidase, *Renilla* luciferase, and Secreted alkaline phosphatase, which demonstrates the benefits of pooling. (see FIG. 21). Individual and pools of siRNA (described in Figure legend 21) were transfected into cells and tested for silencing efficiency. Approximately 50% of individual siRNAs designed to silence the above-specified genes were functional, while 100% of the pools that contain the same siRNA duplexes were functional.

Example X

Highly Functional siRNA

Pools of five siRNAs in which each two siRNAs overlap to 10-90% resulted in 98% functional entities (>80% silencing). Pools of siRNAs distributed throughout the mRNA that were evenly spaced, covering an approximate 20-2000 base pair range, were also functional. When the pools of siRNA were positioned continuously head to tail relative to mRNA sequences and mimicked the natural products of Dicer cleaved long double stranded RNA, 98% of the pools evidenced highly functional activity (>95% silencing).

Example XI

Human Cyclophilin B

Table III above lists the siRNA sequences for the human cyclophilin B protein. A particularly functional siRNA may be selected by applying these sequences to any of Formula I to VII above.

Alternatively, one could pool 2, 3, 4, 5 or more of these sequences to create a kit for silencing a gene. Preferably, within the kit there would be at least one sequence that has a relatively high predicted functionality when any of Formulas I-VII is applied.

Example XII

Sample Pools of siRNAs and their Application to Human Disease

The genetic basis behind human disease is well documented and siRNA may be used as both research or diagnostic tools and therapeutic agents, either individually or in pools. Genes involved in signal transduction, the immune response, apoptosis, DNA repair, cell cycle control, and a variety of other physiological functions have clinical relevance and therapeutic agents that can modulate expression of these genes may alleviate some or all of the associated symptoms. In some instances, these genes can be described as a member of a family or class of genes and siRNA (randomly, conventionally, or rationally designed) can be directed against one or multiple members of the family to induce a desired result.

To identify rationally designed siRNA to each gene, the sequence was analyzed using Formula VIII or Formula X to identify rationally designed siRNA. To confirm the activity of these sequences, the siRNA are introduced into a cell type of choice (e.g., HeLa cells, HEK293 cells) and the levels of the appropriate message are analyzed using one of several art proven techniques. siRNA having heightened levels of potency can be identified by testing each of the before mentioned duplexes at increasingly limiting concentrations. Similarly, siRNA having increased levels of longevity can be identified by introducing each duplex into cells and testing functionality at 24, 48, 72, 96, 120, 144, 168, and 192 hours after transfection. Agents that induce >95% silencing at subnanomolar concentrations and/or induce functional levels of silencing for >96 hours are considered hyperfunctional.

Example XIII

The information presented in Tables XII and XIII provides the siRNA sequence (sense strand), the gene name, the NCBI accession number, the adjusted algorithm score, and the sequence ID number. All sequences have an adjusted score of 75 or above. For Table XIII, Formula X derived sequences were compared with Formula VIII sequences. Sequences that were in common with both were eliminated from Table XIII. Pool picks are typically identified as gene specific siRNA that have the hightest adjusted scores.

The following are non-limiting examples of families of proteins to which siRNA described in this document are targeted against:

Transporters, Pumps, and Channels

Transporters, pumps, and channels represent one class of genes that are attractive targets for siRNAs. One major class of transporter molecules are the ATP-binding cassette (ABC) transporters. To date, nearly 50 human ABC-transporter genes have been characterized and have been shown to be involved in a variety of physiological functions including transport of bile salts, nucleosides, chloride ions, cholesterol, toxins, and more. Predominant among this group are MDR1 (which encodes the P-glycoprotein, NP_000918), the MDR-related proteins (MRP1-7), and the breast cancer resistance protein (BCRP). In general, these transporters share a common structure, with each protein containing a pair of ATP-binding domains (also known as nucleotide binding folds, NBF) and two sets of transmembrane (TM) domains, each of which typically contains six membrane-spanning $\alpha$-helices. The genes encoding this class of transporter are organized as either full transporters (i.e., containing two TM and two NBF domains) or as half transporters that assemble as either homodimers or heterodimers to create functional transporters. As a whole, members of the family are widely dispersed throughout the genome and show a high degree of amino acid sequence identify among eukaryotes.

ABC-transporters have been implicated in several human diseases. For instance, molecular efflux pumps of this type play a major role in the development of drug resistance exhibited by a variety of cancers and pathogenic microorganisms. In the case of human cancers, increased expression of the MDR1 gene and related pumps have been observed to generate drug resistance to a broad collection of commonly used chemotherapeutics including doxorubicin, daunorubicin, vinblastine, vincristine, colchicines. In addition to the contribution these transporters make to the development of multi-drug resistance, there are currently 13 human genetic diseases associated with defects in 14 different transporters. The most common of these conditions include cystic fibrosis, Stargardt disease, age-related macular degeneration, adrenoleukodystrophy, Tangier disease, Dubin-Johnson syndrome and progressive familial intrahepatic cholestasis. For this reason, siRNAs directed against members of this, and related, families are potentially valuable research and therapeutic tools.

With respect to channels, analysis of *Drosophila* mutants has enabled the initial molecular isolation and characterization of several distinct channels including (but not limited to) potassium (K+) channels. This list includes shaker (Sh), which encodes a voltage activated $K^+$ channel, slowpoke (Slo), a $Ca^{2+}$ activated $K^+$ channel, and ether-a-go-go (Eag). The Eag family is further divided into three subfamilies: Eag, Elk (eag-like K channels), and Erg (Eag related genes).

The Erg subfamily contains three separate family members (Erg1-3) that are distantly related to the sh family of voltage activated $K^+$ channels. Like sh, erg polypetides contain the classic six membrane spanning architecture of $K^+$ channels (S1-S6) but differ in that each includes a segment associated with the C-terminal cytoplasmic region that is homologous to cyclic nucleotide binding domains (cNBD). Like many isolated ion channel mutants, erg mutants are temperature-sensitive paralytics, a phenotype caused by spontaneous repetitive firing (hyperactivity) in neurons and enhanced transmitter release at the neuromuscular junction.

Initial studies on the tissue distribution of all three members of the erg subfamily show two general patterns of expression. Erg1 and erg3 are broadly expressed throughout the nervous system and are observed in the heart, the superior mesenteric ganglia, the celiac ganglia, the retina, and the brain. In contrast, erg2 shows a much more restricted pattern of expression and is only observed in celiac ganglia and superior mesenteric ganglia. Similarly, the kinetic properties of the three erg potassium channels are not homogeneous. Erg1 and erg2 channels are relatively slow activating delayed rectifiers whereas the erg3 current activates rapidly and then exhibits a predominantly transient component that decays to a sustained plateau. The current properties of all three channels are sensitive to methanesulfonanilides, suggesting a high degree of conservation in the pore structure of all three proteins.

Recently, the erg family of $K^+$ channels has been implicated in human disease. Consistent with the observation that erg1 is expressed in the heart, single strand conformation polymorphism and DNA sequence analyses have identified HERG (human erg 1) mutations in six long-QT-syndrome (LQT) families, an inherited disorder that results in sudden death from a ventricular tachyarrythmia. Thus siRNA directed against this group of molecules (e.g., KCNH1-8) will be of extreme therapeutic value.

Another group of channels that are potential targets of siRNAs are the CLCA family that mediate a $Ca^{2+}$-activated $Cl^-$ conductance in a variety of tissues. To date, two bovine (bCLC1; bCLCA2 (Lu-ECAM-1)), three mouse (mCLCA1; mCLCA2; mCLCA3) and four human (hCLCA1; hCLCA2; hCLCA3; hCLCA4) CLCA family members have been isolated and patch-clamp studies with transfected human embryonic kidney (HEK-293) cells have shown that bCLCA1, mCLCA1, and hCLCA1 mediate a $Ca^{2+}$-activated $Cl^-$ conductance that can be inhibited by the anion channel blocker DIDS and the reducing agent dithiothreitol (DTT).

The protein size, structure, and processing seem to be similar among different CLCA family members and has been studied in greatest detail for Lu-ECAM-1. The Lu-ECAM-1 open reading frame encodes a precursor glycoprotein of 130 kDa that is processed to a 90-kDa amino-terminal cleavage product and a group of 30- to 40-kDa glycoproteins that are glycosylation variants of a single polypeptide derived from its carboxy terminus. Both subunits are associated with the outer cell surface, but only the 90-kDa subunit is thought to be anchored to the cell membrane via four transmembrane domains.

Although the protein processing and function appear to be conserved among CLCA homologs, significant differences exist in their tissue expression patterns. For example, bovine Lu-ECAM-1 is expressed primarily in vascular endothelia, bCLCA1 is exclusively detected in the trachea, and hCLCA1 is selectively expressed in a subset of human intestinal epithelial cells. Thus the emerging picture is that of a multigene family with members that are highly tissue specific, similar to the ClC family of voltage-gated $Cl^-$ channels. The human channel, hCLCA2, is particular interesting from a medical and pharmacological standpoint. CLCA2 is expressed on the luminal surface of lung vascular endothelia and serves as an adhesion molecule for lung metastatic cancer cells, thus mediating vascular arrest and lung colonization. Expression of this molecule in normal mammary epithelium is consistently lost in human breast cancer and in nearly all tumorigenic breast cancer cell lines. Moreover, re-expression of hCLCA2 in human breast cancer cells abrogates tumorigenicity in nude mice, implying that hCLCA2 acts as a tumour suppressor in breast cancer. For these reasons, siRNA directed against CLCA family members and related channels may prove to be valuable in research and therapeutic venues.

Transporters Involved in Synaptic Transmission

Synaptic transmission involves the release of a neurotransmitter into the synaptic cleft, interaction of that transmitter with a postsynaptic receptor, and subsequent removal of the transmitter from the cleft. In most synapses the signal is terminated by a rapid reaccumulation of the neurotransmitter into presynaptic terminals. This process is catalyzed by specific neurotransmitter transporters that are often energized by the electrochemical gradient of sodium across the plasma membrane of the presynaptic cells.

Aminobutyric acid (GABA) is the major inhibitory neurotransmitter in the central nervous system. The inhibitory action of GABA, mediated through $GABA_A$/$GABA_B$ receptors, and is regulated by GABA transporters (GATs), integral membrane proteins located perisynaptically on neurons and glia. So far four different carriers (GAT1-GAT4) have been cloned and their cellular distribution has been partly worked out. Comparative sequence analysis has revealed that GABA transporters are related to several other proteins involved in neurotransmitter uptake including gamma-aminobutyric acid transporters, monoamine transporters, amino acid transporters, certain "orphan" transporters, and the recently discovered bacterial transporters. Each of these proteins has a similar 12 transmembrane helices topology and relies upon the $Na^+$/$Cl^-$ gradient for transport function. Transport rates are dependent on substrate concentrations, with half-maximal effective concentrations for transport frequently occurring in the submicromolar to low micromolar range. In addition, transporter function is bidirectional, and non-vesicular efflux of transmitter may contribute to ambient extracellular transmitter levels.

Recent evidence suggests that GABA transporters, and neurotransmitter transporters in general, are not passive players in regulating neuronal signaling; rather, transporter function can be altered by a variety of initiating factors and signal transduction cascades. In general, this functional regulation occurs in two ways, either by changing the rate of transmitter flux through the transporter or by changing the number of functional transporters on the plasma membrane. A recurring theme in transporter regulation is the rapid redistribution of the transporter protein between intracellular locations and the cell surface. In general, this functional modulation occurs in part through activation of second messengers such as kinases, phosphatases, arachidonic acid, and pH. However, the mechanisms underlying transporter phosphorylation and transporter redistribution have yet to be fully elucidated.

GABA transporters play a pathophysiological role in a number of human diseases including temporal lobe epilepsy and are the targets of pharmacological interventions. Studies in seizure sensitive animals show some (but not all) of the GAT transporters have altered levels of expression at times prior to and post seizure, suggesting this class of transporter may affect epileptogenesis, and that alterations following seizure may be compensatory responses to modulate seizure activity. For these reasons, siRNAs directed against members of this family of genes (including but not limited to SLCG6A 1-12) may prove to be valuable research and therapeutic tools.

Organic Ion Transporters

The human body is continuously exposed to a great variety of xenobiotics, via food, drugs, occupation, and environment. Excretory organs such as kidney, liver, and intestine defend the body against the potentially harmful effects of these compounds by transforming them into less active metabolites that are subsequently secreted from the system.

Carrier-mediated transport of xenobiotics and their metabolites exist for the active secretion of organic anions and cations. Both systems are characterized by a high clearance capacity and tremendous diversity of substances accepted, properties that result from the existance of multiple transporters with overlapping substrate specificities. The class of organic anion transporters plays a critical role in the elimination of a large number of drugs (e.g., antibiotics, chemotherapeutics, diuretics, nonsteroidal anti-inflammatory drugs, radiocontrast agents, cytostatics); drug metabolites (especially conjugation products with glutathione, glucuronide, glycine, sulfate, acetate); and toxicants and their metabolites (e.g., mycotoxins, herbicides, plasticizers, glutathione S-conjugates of polyhaloalkenes, polyhaloalkenes, hydroquinones, aminophenols), many of which are specifically harmful to the kidney.

Over the past couple of years the number of identified anion transporting molecules has grown tremendously. Uptake of organic anions ($OA^-$) across the basolateral membrane is mediated by the classic sodium-dependent organic anion transport system, which includes α-ketoglutarate (α-$KG^{2-}$)/$OA^-$ exchange via the organic anion transporter (OAT1) and sodium-ketoglutarate cotransport via the $Na^+$/dicarboxylate cotransporter (SDCT2). The organic anion transporting polypeptide, Oatp1, and the kidney-specific OAT-K1 and OAT-K2 are seen as potential molecules that mediate facilitated $OA^-$ efflux but could also be involved in reabsorption via an exchange mechanism. Lastly the PEPT1 and PEPT2 mediate luminal uptake of peptide drugs, whereas CNT1 and CNT2 are involved in reabsorption of nucleosides.

The organic anion-transporting polypeptide 1 (Oatp1) is a $Na^+$- and ATP-independent transporter originally cloned from rat liver. The tissue distribution and transport properties of the Oatp1 gene product are complex. Oatp1 is localized to the basolateral membrane of hepatocytes, and is found on the apical membrane of S3 proximal tubules. Studies with transiently transfected cells (e.g., HeLa cells) have indicated that Oatp1 mediates transport of a variety of molecules including taurocholate, estrone-3-sulfate, aldosterone, cortisol, and others. The observed uptake of taurocholate by Oatp1 expressed in *X. laevis* oocytes is accompanied by efflux of GSH, suggesting that transport by this molecule may be glutathione dependent.

Computer modeling suggests that members of the Oatp family are highly conserved, hydrophobic, and have 12 transmembrane domains. Decreases in expression of Oatp family members have been associated with cholestatic liver diseases and human hepatoblastomas, making this family of proteins of key interest to researchers and the medical community. For these reasons, siRNAs directed against OAT family members (including but not limited to SLC21A2, 3, 6, 8, 9, 11, 12, 14, 15, and related transporters) are potentially useful as research and therapeutic tools.

Nucleoside Transporters

Nucleoside transporters play key roles in physiology and pharmacology. Uptake of exogenous nucleosides is a critical first step of nucleotide synthesis in tissues such as bone marrow and intestinal epithelium and certain parasitic organisms that lack de novo pathways for purine biosynthesis. Nucleoside transporters also control the extracellular concentration of adenosine in the vicinity of its cell surface receptors and regulate processes such as neurotransmission and cardiovascular activity. Adenosine itself is used clinically to treat cardiac arrhythmias, and nucleoside transport inhibitors such as dipyridamole, dilazep, and draflazine function as coronary vasodilators.

In mammals, plasma membrane transport of nucleosides is brought about by members of the concentrative, $Na^+$-dependent (CNT) and equilibrative, $Na^+$-independent (ENT) nucleoside transporter families. CNTs are expressed in a tissue-specific fashion; ENTs are present in most, possibly all, cell types and are responsible for the movement of hydrophilic nucleosides and nucleoside analogs down their concentration gradients. In addition, structure/function studies of ENT family members have predicted these molecules to contain eleven transmembrane helical segments with an amino terminus that is intracellular and a carboxyl terminus that is extracellular. The proteins have a large glycosylated loop between TMs 1 and 2 and a large cytoplasmic loop between TMs 6 and 7. Recent investigations have implicated the TM 3-6 region as playing a central role in solute recognition. The medical importance of the ENT family of proteins is broad. In humans adenosine exerts a range of cardioprotective effects and inhibitors of ENTs are seen as being valuable in alleviating a variety of cardio/cardiovascular ailments. In addition, responses to nucleoside analog drugs has been observed to vary considerably amongst, e.g., cancer patients. While some forms of drug resistance have been shown to be tied to the up-regulation of ABC-transporters (e.g., MDR1), resistance may also be the result of reduced drug uptake (i.e., reduced ENT expression). Thus, a clearer understanding of ENT transporters may aid in optimizing drug treatments for patients suffering a wide range of malignancies. For these reasons, siRNAs directed against this class of molecules (including SLC28A1-3, SLC29A1-4, and related molecules) may be useful as therapeutic and research tools.

Sulfate Transporters

All cells require inorganic sulfate for normal function. Sulfate is the fourth most abundant anion in human plasma and is the major source of sulfur in many organisms. Sulfation of extracellular matrix proteins is critical for maintaining normal cartilage metabolism and sulfate is an important constituent of myelin membranes found in the brain Because sulfate is a hydrophilic anion that cannot passively cross the lipid bilayer of cell membranes, all cells require a mechanism for sulfate influx and efflux to ensure an optimal supply. To date, a variety of sulfate transporters have been identified in tissues from many origins. These include the renal sulfate transporters (NaSi-1 and Sat-1), the ubiquitously expressed diastrophic dysplasia sulfate transporter (DTDST), the intestinal sulfate transporter (DRA), and the erythrocyte anion exchanger (AE1). Most, if not all, of these molecules contain the classic 12 transmembrane spanning domain architecture commonly found amongst members of the anion transporter superfamily.

Recently three different sulfate transporters have been associated with specific human genetic diseases. Family members SLC26A2, SLC26A3, and SLC26A4 have been recognized as the disease genes mutated in diastrophic dysplasia, congenital chloride diarrhea (CLD), and Pendred syndrome (PDS), respectively. DTDST is a particularly complex disorder. The gene encoding this molecule maps to chromosome 5q, and encodes two distinct transcripts due to alternative exon usage. In contrast to other sulfate transporters (e.g., Sat-1) anion movement by the DTDST protein is markedly inhibited by either extracellular chloride or bicarbonate. Impaired function of the DTDST gene product leads to undersulfation of proteoglycans and a complex family of recessively inherited osteochondrodysplasias (achondrogenesis type 1B, atelosteogenesis type II, and diastrophic dysplasia) with clinical features including but not limited to, dwarfism, spinal deformation, and specific joint abnormalities. Interestingly, while epidemiological studies have shown that the disease occurs in most populations, it is particularly prevalent in Finland owing to an apparent founder effect. For these reasons, siRNAs directed against this class of genes (including but not limited to SLC26A1-9, and related molecules) may be potentially helpful in both therapeutic and research venues.

Ion Exchangers

Intracellular pH regulatory mechanisms are critical for the maintenance of countless cellular processes. For instance, in muscle cells, contractile processes and metabolic reactions are influenced by pH. During periods of increased energy demands and ischemia, muscle cells produce large amounts of lactic acid that, without quick and efficient disposal, would lead to acidification of the sarcoplasm.

Several different transport mechanisms have evolved to maintain a relatively constant intracellular pH. The relative contribution of each of these processes varies with cell type, the metabolic requirements of the cell, and the local environmental conditions. Intracellular pH regulatory processes that have been characterized functionally include but are not limited to the $Na^+/H^+$ exchange, the $Na(HCO_3)_n$ cotransport, and the $Na^+$-dependent and -independent $Cl^-$/base exchangers. As bicarbonate and $CO_2$ comprise the major pH buffer of biological fluids, sodium biocarbonate cotransporters (NBCs) are critical. Studies have shown that these molecules exist in numerous tissues including the kidney, brain, liver, cornea, heart, and lung, suggesting that NBCs play an important role in mediating $HCO_3^-$ transport in both epithelial as well as nonepithelial cells.

Recent molecular cloning experiments have identified the existence of four NBC isoforms (NBC1, 2, 3 and 4) and two NBC-related proteins, AE4 and NCBE (Anion Exchanger 4 and Na-dependent Chloride-Bicarbonate Exchanger). The secondary structure analyses and hydropathy profile of this family predict them to be intrinsic membrane proteins with 12 putative transmembrane domains and several family members exhibit N-linked glycosylation sites, protein kinases A and C, casein kinase II, and ATP/GTP-binding consensus phosphorylation sites, as well as potential sites for myristylation and amidation. AE4 is a relatively recent addition to this family of proteins and shows between 30-48% homology with the other family members. When expressed in COS-7 cells and *Xenopus* oocytes AE4 exhibits sodium-independent and DIDS-insensitive anion exchanger activity. Exchangers have been shown to be responsible for a variety of human diseases. For instance, mutations in three genes of the anion transporter family (SLC) are believed to cause known hereditary diseases, including chondrodysplasia (SLC26A2, DTD), diarrhea (A3, down-regulated in adenoma/chloride-losing diarrhea protein: DRA/CLD), and goiter/deafness syndrome (A4, pendrin). Moreover, mutations in Na+/HCO3 co-transporters have also been associated with various human maladies. For these reasons, siRNAs directed against these sorts of genes (e.g., SLC4A4-10, and related genes) may be useful for therapeutic and research purposes.

Receptors Involved in Synaptic Transmission

In all vertebrates, fast inhibitory synaptic transmission is the result of the interaction between the neurotransmitters glycine (Gly) and γ-aminobutyric acid (GABA) and their respective receptors. The strychnine-sensitive glycine receptor is especially important in that it acts in the mammalian spinal cord and brain stem and has a well-established role in the regulation of locomotor behavior.

Glycine receptors display significant sequence homology to several other receptors including the nicotinic acetylcholine receptor, the aminobutyric acid receptor type A ($GABA_AR$), and the serotonin receptor type 3 ($5-HT_3R$) subunits. As members of the superfamily of ligand-gated ion channels, these polypeptides share common topological features. The glycine receptor is composed of two types of glycosylated integral membrane proteins (α1-α4 and β) arranged in a pentameric suprastructure. The alpha subunit encodes a large extracellular, N-terminal domain that carries the structural determinants essential for agonist and antagonist binding, followed by four transmembrane spanning regions (TM1-TM4), with TM2 playing the critical role of forming the inner wall of the chloride channel.

The density, location, and subunit composition of glycine neurotransmitter receptors changes over the course of development. It has been observed that the amount of GlyR gene translation (assessed by the injection of developing rat cerebral cortex mRNA into *Xenopus* oocytes) decreases with age, whereas that of GABARs increases. In addition, the type and location of mRNAs coding for GlyR changes over the course of development. For instance in a study of the expression of alpha 1 and alpha 2 subunits in the rat, it was observed that (in embryonic periods E11-18) the mantle zone was scarce in the alpha 1 mRNA, but the germinal zone (matrix layer) at E11-14 expressed higher levels of the message. At postnatal day 0 (P0), the alpha 1 signals became manifested throughout the gray matter of the spinal cord. By contrast, the spinal tissues at P0 exhibited the highest levels of alpha 2 mRNA, which decreased with the postnatal development.

In both, man and mouse mutant lines, mutations of GlyR subunit genes result in hereditary motor disorders characterized by exaggerated startle responses and increased muscle tone. Pathological alleles of the Glra1 gene are associated with the murine phenotypes oscillator ($spd^{ot}$) and spasmodic (spd). Similarly, a mutant allele of Glrb has been found to underly the molecular pathology of the spastic mouse (spa). Resembling the situation in the mouse, a variety of GLRA1 mutant alleles have been shown to be associated with the human neurological disorder hyperekplexia or startle disease. For these reasons, siRNA directed against glycine receptors (GLRA1-3, GLRB, and related molecules), glutamate receptors, GABA receptors, ATP receptors, and related neurotransmitter receptor molecules may be valuable therapeutic and research reagents.

Proteases

Kallikreins

One important class of proteases are the kallikreins, serine endopeptidases that split peptide substrates preferentially on the C-terminal side of internal arginyl and lysyl residues. Kallikreins are generally divided into two distinct groups, plasma kallikreins and tissue kallikreins. Tissue kallikreins represent a large group of enzymes that have substantial similarities at both the gene and protein level. The genes encoding this group are frequently found on a single chromosome, are organized in clusters, and are expressed in a broad range of tissues (e.g., pancreas, ovaries, breast). In contrast, the plasma form of the enzyme is encoded by a single gene (e.g., KLK3) that has been localized to chromosome 4q34-35 in humans. The gene encoding plasma kallikrein is expressed solely in the liver, contains 15 exons, and encodes a glycoprotein that is translated as a preprotein called prekallikrein.

Kallikreins are believed to play an important role in a host of physiological events. For instance, the immediate consequence of plasma prekallikrein activation is the cleavage of high molecular weight kininogen (HK) and the subsequent liberation of bradykinin, a nine amino acid vasoactive peptide that is an important mediator of inflammatory responses. Similarly, plasma kallikrein promotes single-chain urokinase activation and subsequent plasminogen activation, events that are critical to blood coaggulation and wound healing.

Disruptions in the function of kallikreins have been implicated in a variety of pathological processes including imbalances in renal function and inflammatory processes. For these reasons, siRNAs directed against this class of genes (e.g., KLK1-15) may prove valuable in both research-and-therapeutic settings.

ADAM Proteins

The process of fertilization takes place in a series of discrete steps whereby the sperm interacts with, i) the cumulus cells and the hyaluronic acid extracellular matrix (ECM) in which they are embedded, ii) the egg's own ECM, called the zona pellucida (ZP), and iii) the egg plasma membrane. During the course of these interactions, the "acrosome reaction," the exocytosis of the acrosome vesicle on the head of the sperm, is induced, allowing the sperm to penetrate the ZP and gain access to the perivitelline space. This process exposes new portions of the sperm membrane, including the inner acrosomal membrane and the equatorial segment, regions of the sperm head that can participate in initial gamete membrane binding.

The interactions of the gamete plasma membranes appear to involve multiple ligands and receptors and are frequently compared to leukocyte-endothelial interactions. These interactions lead to a series of signal transduction events in the egg, known as collectively as egg activation and include the initiation of oscillations in intracellular calcium concentration, the exit from meiosis, the entry into the first embryonic mitosis, and the formation of a block to polyspermy via the release of ZP-modifying enzymes from the egg's cortical granules. Ultimately, sperm and egg not only adhere to each other but also go on to undergo membrane fusion, making one cell (the zygote) from two.

Studies on the process of sperm-egg interactions have identified a number of proteins that are crucial for fertilization. One class of proteins, called the ADAM family (A Disintegrin And Metalloprotease), has been found to be important in spermatogenesis and fertilization, as well as various developmental systems including myogenesis and neurogenesis. Members of the family contain a disintegrin and metalloprotease domain (and therefore have (potentially) both cell adhesion and protease activities), as well as cysteine-rich regions, epidermal growth factor (EGF)-like domains, a transmembrane region, and a cytoplasmic tail. Currently, the ADAM gene family has 29 members and constituents are widely distributed in many tissues including the brain, testis, epididymis, ovary, breast, placenta, liver, heart, lung, bone, and muscle.

One of the best-studied members of the ADAM family is fertilin, a heterodimeric protein comprised of at least two subunits, fertilin alpha and fertilin beta. The fertilin beta gene (ADAM2) has been disrupted with a targeting gene construct corresponding to the exon encoding the fertilin beta disintegrin domain. Sperm from males homozygous for disruptions in this region exhibit defects in multiple facets of sperm function including reduced levels of sperm transit from the uterus to the oviduct, reduced sperm-ZP binding, and reduced sperm-egg binding, all of which contribute to male infertility.

Recently, four new ADAM family members (ADAM 24-27) have been isolated. The deduced amino acid sequences show that all four contain the complete domain organization common to ADAM family members and Northern Blot analysis has shown all four to be specific to the testes. siRNAs directed against this class of genes (e.g., ADAM2 and related proteins) may be useful as research tools and therapeutics directed toward fertility and birth control.

Aminopeptidases

Aminopeptidases are proteases that play critical roles in processes such as protein maturation, protein digestion in its terminal stage, regulation of hormone levels, selective or homeostatic protein turnover, and plasmid stabilization. These enzymes generally have broad substrate specificity, occur in several forms and play a major role in physiological homeostasis. For instance, the effects of bradykinin, angiotensin converting enzyme (ACE), and other vasoactive molecules are muted by one of several peptidases that cleave the molecule at an internal position and eliminate its ability to bind its cognate receptor (e.g., for bradykinin, the B2-receptor).

Among the enzymes that can cleave bradykinin is the membrane bound aminopeptidase P, also referred to as aminoacylproline aminopeptidase, proline aminopeptidase; X-Pro aminopeptidase (eukaryote) and XPNPEP2. Aminopeptidase P is an aminoacylproline aminopeptidase specific for $NH_2$-terminal Xaa-proline bonds. The enzyme i) is a mono-zinc-containing molecule that lacks any of the typical metal binding motifs found in other zinc metalloproteases, ii) has an active-site configuration similar to that of other members of the MG peptidase family, and iii) is present in a variety of tissues including but not limited to the lung, kidney, brain, and intestine.

Aminopeptidases play an important role in a diverse set of human diseases. Low plasma concentrations of aminopeptidase P are a potential predisposing factor for development of angio-oedema in patients treated with ACE inhibitors, and inhibitors of aminopeptidase P may act as cardioprotectors against other forms of illness including, but not limited to myocardial infarction. For these reasons, siRNAs directed against this family of proteins (including but not limited to XPNPEP1 and related proteins) may be useful as research and therapeutic tools.

Serine Proteases

One important class of proteases are the serine proteases. Serine proteases share a common catalytic triad of three amino acids in their active site (serine (nucleophile), aspartate (electrophile), and histidine (base)) and can hydrolyze either esters or peptide bonds utilizing mechanisms of covalent catalysis and preferential binding of the transition state. Based on the position of their introns serine proteases have been classified into a minimum of four groups including those in which 1) the gene has no introns interrupting the exon coding for the catalytic triad (e.g., the haptoglobin gene,); 2) each gene contains an intron just downstream from the codon for the histidine residue at the active site, a second intron downstream from the exon containing the aspartic acid residue of the active site and a third intron just upstream from the exon containing the serine of the active site (e.g., trypsinogen, chymotrypsinogen, kallikrein and proelastase); 3) the genes contain seven introns interrupting the exons coding the catalytic region (e.g., complement factor B gene); and 4) the genes contain two introns resulting in a large exon that contains both the active site aspartatic acid and serine residues (e.g., factor X, factor IX and protein C genes).

Cytotoxic lymphocytes (e.g., CD8(+) cytotoxic T cells and natural killer cells) form the major defense of higher organisms against virus-infected and transformed cells. A key function of these cells is to detect and eliminate potentially harmful cells by inducing them to undergo apoptosis. This is achieved through two principal pathways, both of which require direct but transient contact between the killer cell and its target. The first pathway involves ligation of TNF receptor-like molecules such as Fas/CD95 to their cognate ligands, and results in mobilization of conventional, programmed cell-death pathways centered on activation of pro-apoptotic caspases. The second mechanism consists of a pathway whereby the toxic contents of a specialized class of secretory vesicles are introduced into the target cell. Studies over the last two decades have identified the toxic components as Granzymes, a family of serine proteases that are expressed exclusively by cytotoxic T lymphocytes and natural killer (NK) cells. These agents are stored in specialized lytic granules and enter the target cell via endocytosis. Like caspases, cysteine proteases that play an important role in apoptosis, granzymes can cleave proteins after acidic residues, especially aspartic acid, and induce apoptosis in the recipient cell.

Granzymes have been grouped into three subfamilies according to substrate specificity. Members of the granzyme family that have enzymatic activity similar to the serine protease chymotrypsin are encoded by a gene cluster termed the 'chymase locus'. Similarly, granzymes with trypsin-like specificities are encoded by the 'tryptase locus', and a third subfamily cleaves after unbranched hydrophobic residues, especially methionine, and are encoded by the 'Met-ase locus'. All granzymes are synthesized as zymogens and, after clipping of the leader peptide, obtain maximal enzymatic activity subsequent to the removal of an amino-terminal dipeptide.

Granzymes have been found to be important in a number of important biological functions including defense against intracellular pathogens, graft versus host reactions, the susceptibility to transplantable and spontaneous malignancies, lymphoid homeostasis, and the tendency toward auto-immune diseases. For these reasons, siRNAs directed against granzymes (e.g., GZMA, GZMB, GZMH, GZHK, GZMM) and related serine proteases may be useful research and therapeutic reagents.

Kinases

Protein Kinases (PKs) have been implicated in a number of biological processes. Kinase molecules play a central role in modulating cellular physiology and developmental decisions, and have been implicated in a large list of human maladies including cancer, diabetes, and others.

During the course of the last three decades, over a hundred distinct protein kinases have been identified, all with presumed specific cellular functions. A few of these enzymes have been isolated to sufficient purity to perform in vitro studies, but most remain intractable due to the low abundance of these molecules in the cell. To counter this technical difficulty, a number of protein kinases have been isolated by molecular cloning strategies that utilize the conserved sequences of the catalytic domain to isolate closely related homologs. Alternatively, some kinases have been purified (and subsequently studied) based on their interactions with other molecules.

p58 is a member of the p34 cdc2-related supergene family and contains a large domain that is highly homologous to the cell division control kinase, cdc2. This new cell division control-related protein kinase was originally identified as a component of semipurified galactosyltransferase; thus, it has been denoted galactosyltransferase-associated protein kinase (GTA-kinase). GTA-kinase has been found to be expressed in both adult and embryonic tissues and is known to phosphorylate a number of substrates, including histone H1, and casein. Interestingly enough, over expression of this molecule in CHO cells has shown that elevated levels of p58 result in a prolonged late telophase and an early G1 phase, thus hinting of an important role for GTA-kinase in cell cycle regulation.

Cyclin Dependent Kinases

The cyclin-dependent kinases (Cdks) are a family of highly conserved serine/threonine kinases that mediate many of the cell cycle transitions that occur during duplication. Each of these Cdk catalytic subunits associates with a specific subset of regulatory subunits, termed cyclins, to produce a distinct Cdk.cyclin kinase complex that, in general, functions to execute a unique cell cycle event.

Activation of the Cdk.cyclin kinases during cellular transitions is controlled by a variety of regulatory mechanisms. For the Cdc2.cyclin B complex, inhibition of kinase activity during S phase and $G_2$ is accomplished by phosphorylation of two Cdc2 residues, $Thr^{14}$ and $Tyr^{15}$, which are positioned within the ATP-binding cleft. Phosphorylation of $Thr^{14}$ and/or $Tyr^{15}$ suppresses the catalytic activity of the molecule by disrupting the orientation of the ATP present within this cleft. In contrast, the abrupt dephosphorylation of these residues by the Cdc25 phosphatase results in the rapid activation of Cdc2.cyclin B kinase activity and subsequent downstream mitotic events. While the exact details of this pathway have yet to be elucidated, it has been proposed that $Thr^{14}/Tyr^{15}$ phosphorylation functions to permit a cell to attain a critical concentration of inactive Cdk.cyclin complexes, which, upon activation, induces a rapid and complete cell cycle transition. Furthermore, there is evidence in mammalian cells that $Thr^{14}/Tyr^{15}$ phosphorylation also functions to delay Cdk activation after DNA damage.

The *Schizosaccharomyces pombe* wee1 gene product was the first kinase identified that is capable of phosphorylating $Tyr^{15}$ in Cdc2. Homologs of the Wee1 kinase have been subsequently identified and biochemically characterized from a wide range of species including human, mouse, frog, *Saccharomyces cerevisiae*, and *Drosophila*. In vertebrate systems, where $Thr^{14}$ in Cdc2 is also phosphorylated, the Wee1 kinase was capable of phosphorylating Cdc2 on $Tyr^{15}$, but not $Thr^{14}$, indicating that another kinase was responsible for $Thr^{14}$ phosphorylation. This gene, Myt1 kinase, was recently isolated from the membrane fractions of *Xenopus* egg extracts and has been shown to be capable of phosphorylating $Thr^{14}$ and, to a lessor extent, $Tyr^{15}$ in Cdc2. A human Myt1 homolog displaying similar properties has been isolated, as well as a non-membrane-associated molecule with $Thr^{14}$ kinase activity.

In the past decade it has been shown that cancer can originate from overexpression of positive regulators, such as cyclins, or from underexpression of negative regulators (e.g., p16 (INK4a), p15 (INK4b), p21 (Cip1)). Inhibitors such as Myt1 are the focus of much cancer research because they are capable of controlling cell cycle proliferation, now considered the Holy Grail for cancer treatment. For these reasons, siRNA directed against kinases and kinase inhibitors including but not limited to ABL1, ABL2, ACK1, ALK, AXL, BLK, BMX, BTK, C20orf64, CSF1R, SCK, DDR1, DDR2, DKFZp761P1010, EGFR, EPHA1, EPHA2, EPHA3, EPHA4, EPHA7, EPHA8, EPHB1, EPHB2, EPHB3, EPHB4. EPHB6, ERBB2, ERBB3, ERBB4, FER, FES, FGFR1, FGFR2, FGFR3, FGFR4, FGR, FLT1, FLT3, FLT4, FRK, FYN, HCK, IGF1R, INSR, ITK, JAK1, JAK2, JAK3, KDR, KIAA1079, KIT, LCK, LTK, LYN, MATK, MERTK, MET, MST1R, MUSK, NTRK1, NTRK2, NTRK3, PDGFRA, PDGFRB, PTK2, PTK2B, PTK6, PTK7, PTK9, PTK9L, RET, ROR1, ROR2, ROS1, RYK, SRC, SYK, TEC, TEK, TIE, TNK1, TXK, TYK2, TYRO3, YES1, and related proteins, may be useful for research and therapeutic purposes.

G Protein Coupled Receptors

One important class of genes to which siRNAs can be directed are G-protein coupled receptors (GPCRs). GPCRs constitute a superfamily of seven transmembrane spanning proteins that respond to a diverse array of sensory and chemical stimuli, such as light, odor, taste, pheromones, hormones and neurotransmitters. GPCRs play a central role in cell proliferation, differentiation, and have been implicated in the etiology of disease.

The mechanism by which G protein-coupled receptors translate extracellular signals into cellular changes was initially envisioned as a simple linear model: activation of the receptor by agonist binding leads to dissociation of the heterotrimeric GTP-binding G protein (Gs, Gi, or Gq) into its alpha and beta/gamma subunits, both of which can activate or inhibit various downstream effector molecules. More specifically, activation of the GPCR induces a conformational change in the Gα subunit, causing GDP to be released and GTP to be bound in its place. The Gα and Gβγ subunits then dissociate from the receptor and interact with a variety of effector molecules. For instance in the case of the Gs family, the primary function is to stimulate the intracellular messenger adenylate cyclase (AC), which catalyzes the conversion of cytoplasmic ATP into the secondary messenger cyclic AMP (cAMP). In contrast, the Gi family inhibits this pathway and the Gq family activates phospholipases C(PLC), which cleaves phosphatidylinositol 4,5, bisphosphate (PIP2) to generate inositol-1,4,5-phosphate (IP3) and diacylglycerol (DAG).

More recently, studies have shown that the functions of GPCRs are not limited to their actions on G-proteins and that considerable cross-talk exists between this diverse group of receptor molecules and a second class of membrane bound proteins, the receptor tyrosine kinases (RTKs). A number of GPCRs such as endothelin-1, thrombin, bombesin, and dopamine receptors can activate MAPKs, a downstream effector of the RTK/Ras pathway. Interestingly, the interaction between these two families is not unidirectional and RTKs can also modulate the activity of signaling pathways traditionally thought to be controlled exclusively by ligands that couple to GPCRs. For instance, EGF, which normally activates the MAPK cascade via the EGF receptor can stimulate adenylate cyclase activity by activating Gαs.

There are dozens of members of the G Protein-Coupled Receptor family that have emerged as prominent drug targets in the last decade. One non-limiting list of potential GPCR-siRNA targets is as follows:
CMKLR1

CML1/CMKLR1 (Accession No. Q99788) is a member of the chemokine receptor family of GPCRs that may play a role in a number of diseases including those involved in inflammation and immunological responses (e.g., asthma, arthritis). For this reason, siRNA directed against this protein may prove to be important therapeutic reagents.

Studies of juvenile-onset neuronal ceroid lipofuscinosis (JNCL, Batten disease), the most common form of childhood encephalopathy that is characterized by progressive neural degeneration, show that it is brought on by mutations in a novel lysosomal membrane protein (CLN3). In addition to being implicated in JNCL, CLN3 (GPCR-like protein, Accession No. A57219) expression studies have shown that the CLN3 mRNA and protein are highly over-expressed in a number of cancers (e.g., glioblastomas, neuroblastomas, as well as cancers of the prostate, ovaries, breast, and colon) suggesting a possible contribution of this gene to tumor growth. For this reason, siRNA directed against this protein may prove to be important therapeutic reagents.
CLACR The calcitonin receptor (CTR/CALCR, Accession No. NM_001742) belongs to "family B" of GPCRs which typically recognized regulatory peptides such as parathyroid hormone, secretin, glucagons and vasoactive intestinal polypeptide. Although the CT receptor typically binds to calcitonin (CT), a 32 amino acid peptide hormone produced primarily by the thyroid, association of the receptor with RAMP (Receptor Activity Modulating Protein) enables it to readily bind other members of the calcitonin peptide family including amylin (AMY) and other CT gene-related peptides (e.g., αCGRP and βCGRP). While the primary function of the calcitonin receptor pertains to regulating osteoclast mediated bone resorption and enhanced $Ca^{+2}$ excretion by the kidney, recent studies have shown that CT and CTRs may play an important role in a variety of processes as wide ranging as embryonic/fetal development and sperm function/physiology. In addition, studies have shown that patients with particular CTR genotypes may be at higher risk to lose bone mass and that this GPCR may contribute to the formation of calcium oxalate urinary stones. For this reason, siRNA directed against CTR may be useful as therapeutic reagents.
OXTR The human oxytocin receptor (OTR, OXTR) is a 389 amino acid polypeptide that exhibits the seven transmembrane domain structure and belongs to the Class-I (rhodopsin-type) family of G-protein coupled receptors. OTR is expressed in a wide variety of tissues throughout development and mediates physiological changes through G(q) proteins and phospholipase C-beta. Studies on the functions of oxytocin and the oxytocin receptor have revealed a broad list of duties. OT and OTR play a role in a host of sexual, maternal and social behaviors that include egg-laying, birth, milk-letdown, feeding, grooming, memory and learning. In addition, it has been hypothesized that abnormalities in the functionality of oxytocin-OTR receptor-ligand system can lead to a host of irregularities including compulsive behavior, eating disorders (such as anorexia), depression, and various forms of neurodegenerative diseases. For these reasons, siRNA directed against this gene (NM_000916) may play an important role in combating OTR-associated illnesses.
EDG GPCRs Lysophosphatidic acid and other lipid-based hormones/growth factors induce their effects by activating signaling pathways through the G-protein coupled receptors (GPCRs) and have been observed to play important roles in a number of human diseases including cancer, asthma, and vascular pathologies. For instance, during studies of immunoglobulin A nephropathy (IgAN), researchers have observed an enhanced expression of EDG5 (NP_004221) suggesting a contribution of this gene product in the development of IgAN. For that reason, siRNA directed against Edg5 (NM_004230), Edg4 (NM_004720), Edg7 (Nm_012152) and related genes may play an important role in combating human disease.
Genes Involved in Cholesterol Signaling and Biosynthesis Studies on model genetic organisms such as *Drosophila* and *C. elegans* have led to the identification of a plethora of genes that are essential for early development. Mutational analysis and ectopic expression studies have allowed many of these genes to be grouped into discreet signal transduction pathways and have shown that these elements play critical roles in pattern formation and cell differentiation. Disruption of one or more of these genes during early stages of development frequently leads to birth defects whereas as alteration of gene function at later stages in life can result in tumorigenesis.

One critical set of interactions known to exist in both invertebrates and vertebrates is the Sonic Hedgehog-Patched-Gli pathway. Originally documented as a *Drosophila* segmentation mutant, several labs have recently identified human and mouse orthologs of many of the pathways members and have successfully related disruptions in these genes to known diseases. Pathway activation is initiated with the secretion of Sonic hedgehog. There are three closely related members of the Shh family (Sonic hedgehog, Desert, and Indian) with Shh being the most widely expressed form of the group. The Shh gene product is secreted as a small pro-signal molecule. To successfully initiate its developmental role, Shh is first cleaved, whereupon the N-terminal truncated fragment is covalently modified with cholesterol. The addition of the sterol moiety promotes the interaction between Shh and its cognate membrane bound receptor, Patched (Ptch). There are at least two isoforms of the Patched gene, Ptch1 and Ptch2. Both isoforms contain a sterol-sensing domain (SSD); a roughly 180 amino acid cluster that is found in at least seven different classes of molecules including those involved in cholesterol biosynthesis, vesicular traffic, signal transduction, cholesterol transport, and sterol homeostasis. In the absence of Shh, the Patched protein is a negative regulator of the pathway. In contrast, binding of Shh-cholesterol to the Patched receptor releases the negative inhibition which that molecule enforces on a G-protein coupled receptor known as Smoothened. Subsequent activation of Smoothened (directly or indirectly)-leads to the triggering of a trio of transcription factors that belong to the Gli family. All three factors are relatively large, contain a characteristic C2-H2 zinc-finger pentamer, and recognize one of two consensus sequences (SEQ. ID NO. 0464 GACCACCCA or SEQ. ID NO. 0465 GAACCACCCA). In the absence of Shh, Gli proteins are cleaved by the proteosome and the C-terminally truncated fragment translocates to the nucleus and acts as a dominant transcription repressor. In the presence of Shh-cholesterol, Gli repressor formation is inhibited and full-length Gli functions as a transcriptional activator.

Shh and other members of the Shh-PTCH-Gli pathway are expressed in a broad range of tissues (e.g., the notochord, the floorplate of the neural tube, the brain, and the gut) at early stages in development. Not surprisingly, mutations that lead to altered protein expression or function have been shown to induce developmental abnormalities. Defects in the human Shh gene have been shown to cause holoprosencephaly, a midline defect that manifests itself as cleft lip or palate, CNS septation, and a wide range of other phenotypes. Interestingly, defects in cholesterol biosynthesis generate similar Shh-like disorders (e.g., Smith-Lemli-Opitz syndrome) suggesting that cholesterol modification of the Shh gene product is crucial for pathway function. Both the Patched and Smoothened genes have also been shown to be clinically relevant with Smoothened now being recognized as an oncogene that, like PTCH-1 and PTCH-2, is believed to be the causative agent of several forms of adult tumors. For these reasons, siRNA directed against Smoothened (SMO, NM_005631), Patched (PTCH, nm_000264), and additional genes that participate in cholesterol signaling, biosynthesis, and degradation, have potentially useful research and therapeutic applications.

Targeted Pathways.

In addition to targeting siRNA against one or more members of a family of proteins, siRNA can be directed against members of a pathway. Thus, for instance, siRNA can be directed against members of a signal transduction pathway (e.g., the insulin pathway, including AKT1-3, CBL, CBLB, EIF4EBP1, FOXO1A, FOXO3A, FRAP1, GSK3A, GSK3B, IGF1, IGF1R, INPP5D, INSR, IRS1, MLLT7, PDPK1, PIK3CA, PIK3CB, PIK3R1, PIK3R2, PPP2R2B, PTEN, RPS6, RPS6KA1, RPX6KA3, SGK, TSC1, TSC2, AND XPO1), an apoptotic pathway (CASP3,6,7,8,9, DSH1/2, P110, P85, PDK1/2, CATENIN, HSP90, CDC37, P23, BAD, BCLXL, BCL2, SMAC, and others), pathways, involved in DNA damage, cell cycle, and other physiological (p53, MDM2, CHK1/2, BRCA1/2, ATM, ATR, P15INK4, P27, P21, SKP2, CDC25C/A, 14-3-3, PLK, RB, CDK4, GLUT4, Inos, Mtor, FKBP, PPAR, RXR, ER). Similarly, genes involved in immune system function including TNFR1, IL-IR, IRAK1/2, TRAF2, TRAF6, TRADD, FADD, IKKε, IKKγ, IKKβ, IKKα, IkBα, IkBβ, p50, p65, Rac, RhoA, Cdc42, ROCK, Pak1/2/3/4/5/6, cIAP, HDAC1/2, CBP, β-TrCP, Rip2/4, and others are also important targets for the siRNAs described in this document and may be useful in treating immune system disorders. Genes involved in apoptosis, such as Dsh1/2, PTEN, P110 (pan), P85, PDK1/2, Akt1, Akt2, Akt (pan), $p70^{S6K}$, GSK3β, PP2A (cat), β-catenin, HSP90, Cdc37/p50, P23, Bad, BclxL, Bcl2, Smac/Diablo, and Askl are potentially useful in the treatment of diseases that involve defects in programmed cell death (e.g., cancer), while siRNA agents directed against p53, MDM2, Chk1/2, BRCA1/2, ATM, ATR, $p15^{INK4}$, P27, P21, Skp2, Cdc25C/A, 14-3-3σ/ε, PLK, Rb, Cdk4, Glut4, iNOS, mTOR, FKBP, PPARγ, RXRα, ERα and related genes may play a critical role in combating diseases associated with disruptions in DNA repair, and cell cycle abnormalities.

Tables VI-Table X below provide examples of useful pools for inhibiting different genes in the human insulin pathway and tyrosine kinase pathways, proteins involved in the cell cycle, the production of nuclear receptors, and other genes. These particular pools are particularly useful in humans, but would be useful in any species that generates an appropriately homologous mRNA. Further, within each of the listed pools any one sequence maybe used independently but preferably at least two of the listed sequences, more preferably at least three, and most preferably all of the listed sequences for a given gene is present.

TABLE VI

| Gene Name | Acc# | GI | L.L. | Duplex # | Sequence | SEQ. ID NO. |
|---|---|---|---|---|---|---|
| AKT1 | NM_005163 | 4885060 | 207 | D-003000-05 | GACAAGGACGGGCACATTA | 464 |
| AKT1 | NM_005163 | 4885060 | 207 | D-003000-06 | GGACAAGGACGGGCACATT | 465 |
| AKT1 | NM_005163 | 4885060 | 207 | D-003000-07 | GCTACTTCCTCCTCAAGAA | 466 |
| AKT1 | NM_005163 | 4885060 | 207 | D-003000-08 | GACCGCCTCTGCTTTGTCA | 467 |
| AKT2 | | | | | | |
| AKT2 | NM_001626 | 6715585 | 208 | D-003001-05 | GTACTTCGATGATGAATTT | 468 |
| AKT2 | NM_001626 | 6715585 | 208 | D-003001-06 | GCAAAGAGGGCATCAGTGA | 469 |
| AKT2 | NM_001626 | 6715585 | 208 | D-003001-07 | GGGCTAAAGTGACCATGAA | 470 |
| AKT2 | NM_001626 | 6715585 | 208 | D-003001-08 | GCAGAATGCCAGCTGATGA | 471 |

TABLE VI-continued

| Gene Name | Acc# | GI | L.L. | Duplex # | Sequence | SEQ. ID NO. |
|---|---|---|---|---|---|---|
| AKT3 | | | | | | |
| AKT3 | NM_005465 | 32307164 | 10000 | D-003002-05 | GGAGTAAACTGGCAAGATG | 472 |
| AKT3 | NM_005465 | 32307164 | 10000 | D-003002-06 | GACATTAAATTTCCTCGAA | 473 |
| AKT3 | NM_005465 | 32307164 | 10000 | D-003002-07 | GACCAAAGCCAAACACATT | 474 |
| AKT3 | NM_005465 | 32307164 | 10000 | D-003002-08 | GAGGAGAGAATGAATTGTA | 475 |
| CBL | | | | | | |
| CBL | NM_005188 | 4885116 | 867 | D-003003-05 | GGAGACACATTTCGGATTA | 476 |
| CBL | NM_005188 | 4885116 | 867 | D-003003-06 | GATCTGACCTGCAATGATT | 477 |
| CBL | NM_005188 | 4885116 | 867 | D-003003-07 | GACAATCCCTCACAATAAA | 478 |
| CBL | NM_005188 | 4885116 | 867 | D-003003-08 | CCAGAAAGCTTTGGTCATT | 479 |
| CBLB | | | | | | |
| CBLB | NM_170662 | 29366807 | 868 | D-003004-05 | GACCATACCTCATAACAAG | 480 |
| CBLB | NM_170662 | 29366807 | 868 | D-003004-06 | TGAAAGACCTCCACCAATC | 481 |
| CBLB | NM_170662 | 29366807 | 868 | D-003004-07 | GATGAAGGCTCCAGGTGTT | 482 |
| CBLB | NM_170662 | 29366807 | 868 | D-003004-08 | TATCAGCATTTACGACTTA | 483 |
| EIF4EBP1 | | | | | | |
| EIF4EBP1 | NM_004095 | 20070179 | 1978 | D-003005-05 | GCAATAGCCCAGAAGATAA | 484 |
| EIF4EBP1 | NM_004095 | 20070179 | 1978 | D-003005-06 | CGCAATAGCCCAGAAGATA | 485 |
| EIF4EBP1 | NM_004095 | 20070179 | 1978 | D-003005-07 | GAGATGGACATTTAAAGCA | 486 |
| EIF4EBP1 | NM_004095 | 20070179 | 1978 | D-003005-08 | CAATAGCCCAGAAGATAAG | 487 |
| FOXO1A | | | | | | |
| FOXO1A | NM_002015 | 9257221 | 2308 | D-003006-05 | CCAGGCATCTCATAACAAA | 488 |
| FOXO1A | NM_002015 | 9257221 | 2308 | D-003006-06 | CCAGATGCCTATACAAACA | 489 |
| FOXO1A | NM_002015 | 9257221 | 2308 | D-003006-07 | GGAGGTATGAGTCAGTATA | 490 |
| FOXO1A | NM_002015 | 9257221 | 2308 | D-003006-08 | GAGGTATGAGTCAGTATAA | 491 |
| FOXO3A | | | | | | |
| FOXO3A | NM_001455 | 4503738 | 2309 | D-003007-01 | CAATAGCAACAAGTATACC | 492 |
| FOXO3A | NM_001455 | 4503738 | 2309 | D-003007-02 | TGAAGTCCAGGACGATGAT | 493 |
| FOXO3A | NM_001455 | 4503738 | 2309 | D-003007-03 | TGTCACACTATGGTAACCA | 494 |
| FOXO3A | NM_001455 | 4503738 | 2309 | D-003007-04 | TGTTCAATGGGAGCTTGGA | 495 |
| FRAP1 | | | | | | |
| FRAP1 | NM_004958 | 19924298 | 2475 | D-003008-05 | GAGAAGAAATGGAAGAAAT | 496 |
| FRAP1 | NM_004958 | 19924298 | 2475 | D-003008-06 | CCAAAGTGCTGCAGTACTA | 497 |
| FRAP1 | NM_004958 | 19924298 | 2475 | D-003008-07 | GAGCATGCCGTCAATAATA | 498 |
| FRAP1 | NM_004958 | 19924298 | 2475 | D-003008-08 | GGTCTGAACTGAATGAAGA | 499 |
| GSK3A | | | | | | |
| GSK3A | NM_019884 | 11995473 | 2931 | D-003009-05 | GGACAAAGGTGTTCAAATC | 500 |
| GSK3A | NM_019884 | 11995473 | 2931 | D-003009-06 | GAACCCAGCTGCCTAACAA | 501 |
| GSK3A | NM_019884 | 11995473 | 2931 | D-003009-07 | GCGCACAGCTTCTTTGATG | 502 |
| GSK3A | NM_019884 | 11995473 | 2931 | D-003009-08 | GCTCTAGCCTGCTGGAGTA | 503 |

TABLE VI-continued

| Gene Name | Acc# | GI | L.L. | Duplex # | Sequence | SEQ. ID NO. |
|---|---|---|---|---|---|---|
| GSK3B | | | | | | |
| GSK3B | NM_002093 | 21361339 | 2932 | D-003010-05 | GAAGAAAGATGAGGTCTAT | 504 |
| GSK3B | NM_002093 | 21361339 | 2932 | D-003010-06 | GGACCCAAATGTCAAACTA | 505 |
| GSK3B | NM_002093 | 21361339 | 2932 | D-003010-07 | GAAATGAACCCAAACTACA | 506 |
| GSK3B | NM_002093 | 21361339 | 2932 | D-003010-08 | GATGAGGTCTATCTTAATC | 507 |
| IGF1 | | | | | | |
| IGF1 | NM_000618 | | | D-003011-05 | GGAAGTACATTTGAAGAAC | 508 |
| IGF1 | NM_000618 | | | D-003011-06 | AGAAGGAAGTACATTTGAA | 509 |
| IGF1 | NM_000618 | | | D-003011-07 | CCTCAAGCCTGCCAAGTCA | 510 |
| IGF1 | NM_000618 | | | D-003011-08 | GGTGGATGCTCTTCAGTTC | 511 |
| IGF1R | | | | | | |
| IGF1R | NM_000875 | 11068002 | 3480 | D-003012-05 | CAACGAAGCTTCTGTGATG | 512 |
| IGF1R | NM_000875 | 11068002 | 3480 | D-003012-06 | GGCCAGAAATGGAGAATAA | 513 |
| IGF1R | NM_000875 | 11068002 | 3480 | D-003012-07 | GAAGCACCCTTTAAGAATG | 514 |
| IGF1R | NM_000875 | 11068002 | 3480 | D-003012-08 | GCAGACACCTACAACATCA | 515 |
| INPP5D | | | | | | |
| INPP5D | NM_005541 | 5031798 | 3635 | D-003013-05 | GGAATTGCGTTTACACTTA | 516 |
| INPP5D | NM_005541 | 5031798 | 3635 | D-003013-06 | GGAAACTGATCATTAAGAA | 517 |
| INPP5D | NM_005541 | 5031798 | 3635 | D-003013-07 | CGACAGGGATGAAGTACAA | 518 |
| INPP5D | NM_005541 | 5031798 | 3635 | D-003013-08 | AAACGCAGCTGCCCATCTA | 519 |
| INSR | | | | | | |
| INSR | NM_000208 | 4557883 | 3643 | D-003014-05 | GGAAGACGTTTGAGGATTA | 520 |
| INSR | NM_000208 | 4557883 | 3643 | D-003014-06 | GAACAAGGCTCCCGAGAGT | 521 |
| INSR | NM_000208 | 4557883 | 3643 | D-003014-07 | GGAGAGACCTTGGAAATTG | 522 |
| INSR | NM_000208 | 4557883 | 3643 | D-003014-08 | GGACGGAACCCACCTATTT | 523 |
| IRS1 | | | | | | |
| IRS1 | NM_005544 | 5031804 | 3667 | D-003015-05 | AAAGAGGTCTGGCAAGTGA | 524 |
| IRS1 | NM_005544 | 5031804 | 3667 | D-003015-06 | GAACCTGATTGGTATCTAC | 525 |
| IRS1 | NM_005544 | 5031804 | 3667 | D-003015-07 | CCACGGCGATCTAGTGCTT | 526 |
| IRS1 | NM_005544 | 5031804 | 3667 | D-003015-08 | GTCAGTCTGTCGTCCAGTA | 527 |
| MLLT7 | | | | | | |
| MLLT7 | NM_005938 | 5174578 | 4303 | D-003016-05 | GGACTGGACTTCAACTTTG | 528 |
| MLLT7 | NM_005938 | 5174578 | 4303 | D-003016-06 | CCACGAAGCAGTTCAAATG | 529 |
| MLLT7 | NM_005938 | 5174578 | 4303 | D-003016-07 | GAGAAGCGACTGACACTTG | 530 |
| MLLT7 | NM_005938 | 5174578 | 4303 | D-003016-08 | GACCAGAGATCGCTAACCA | 531 |
| PDPK1 | | | | | | |
| PDPK1 | NM_002613 | 4505694 | 5170 | D-003017-05 | CAAGAGACCTCGTGGAGAA | 532 |
| PDPK1 | NM_002613 | 4505694 | 5170 | D-003017-06 | GACCAGAGGCCAAGAATTT | 533 |

TABLE VI-continued

| Gene Name | Acc# | GI | L.L. | Duplex # | Sequence | SEQ. ID NO. |
|---|---|---|---|---|---|---|
| PDPK1 | NM_002613 | 4505694 | 5170 | D-003017-07 | GGAAACGAGTATCTTATAT | 534 |
| PDPK1 | NM_002613 | 4505694 | 5170 | D-003017-08 | GAGAAGCGACATATCATAA | 535 |
| PIK3CA | | | | | | |
| PIK3CA | NM_006218 | 5453891 | 5290 | D-003018-05 | GCTATCATCTGAACAATTA | 536 |
| PIK3CA | NM_006218 | 5453891 | 5290 | D-003018-06 | GGATAGAGGCCAAATAATA | 537 |
| PIK3CA | NM_006218 | 5453891 | 5290 | D-003018-07 | GGACAACTGTTTCATATAG | 538 |
| PIK3CA | NM_006218 | 5453891 | 5290 | D-003018-08 | GCCAGTACCTCATGGATTA | 539 |
| PIK3CB | | | | | | |
| PIK3CB | NM_006219 | 5453893 | 5291 | D-003019-05 | CGACAAGACTGCCGAGAGA | 540 |
| PIK3CB | NM_006219 | 5453893 | 5291 | D-003019-06 | TCAAGTGTCTCCTAATATG | 541 |
| PIK3CB | NM_006219 | 5453893 | 5291 | D-003019-07 | GGATTCAGTTGGAGTGATT | 542 |
| PIK3CB | NM_006219 | 5453893 | 5291 | D-003019-08 | TTTCAAGTGTCTCCTAATA | 543 |
| PIK3R1 | | | | | | |
| PIK3R1 | NM_181504 | 32455251 | 5295 | D-003020-05 | GGAAATATGGCTTCTCTGA | 544 |
| PIK3R1 | NM_181504 | 32455251 | 5295 | D-003020-06 | GAAAGACGAGAGACCAATA | 545 |
| PIK3R1 | NM_181504 | 32455251 | 5295 | D-003020-07 | GTAAAGCATTGTGTCATAA | 546 |
| PIK3R1 | NM_181504 | 32455251 | 5295 | D-003020-08 | GGATCAAGTTGTCAAAGAA | 547 |
| PIK3R2 | | | | | | |
| PIK3R2 | NM_005027 | 4826907 | 5296 | D-003021-05 | GGAAAGGCGGGAACAATAA | 548 |
| PIK3R2 | NM_005027 | 4826907 | 5296 | D-003021-06 | GATGAAGCGTACTGCAATT | 549 |
| PIK3R2 | NM_005027 | 4826907 | 5296 | D-003021-07 | GGACAGCGAATCTCACTAC | 550 |
| PIK3R2 | NM_005027 | 4826907 | 5296 | D-003021-08 | GCAAGATCCGAGACCAGTA | 551 |
| PPP2R2B | | | | | | |
| PPP2R2B | NM_004576 | 4758953 | 5521 | D-003022-05 | GAATGCAGCTTACTTTCTT | 552 |
| PPP2R2B | NM_004576 | 4758953 | 5521 | D-003022-06 | GACCGAAGCTGACATTATC | 553 |
| PPP2R2B | NM_004576 | 4758953 | 5521 | D-003022-07 | TCGATTACCTGAAGAGTTT | 554 |
| PPP2R2B | NM_004576 | 4758953 | 5521 | D-003022-08 | CCTGAAGAGTTTAGAAATA | 555 |
| PTEN | | | | | | |
| PTEN | NM_000314 | 4506248 | 5728 | D-003023-05 | GTGAAGATCTTGACCAATG | 556 |
| PTEN | NM_000314 | 4506248 | 5728 | D-003023-06 | GATCAGCATACACAAATTA | 557 |
| PTEN | NM_000314 | 4506248 | 5728 | D-003023-07 | GGCGCTATGTGTATTATTA | 558 |
| PTEN | NM_000314 | 4506248 | 5728 | D-003023-08 | GTATAGAGCGTGCAGATAA | 559 |
| RPS6 | | | | | | |
| RPS6 | NM_001010 | 17158043 | 6194 | D-003024-05 | GCCAGAAACTCATTGAAGT | 560 |
| RPS6 | NM_001010 | 17158043 | 6194 | D-003024-06 | GGATATTCCTGGACTGACT | 561 |
| RPS6 | NM_001010 | 17158043 | 6194 | D-003024-07 | CCAAGGAGAACTGGAGAAA | 562 |
| RPS6 | NM_001010 | 17158043 | 6194 | D-003024-08 | GCGTATGGCCACAGAAGTT | 563 |

TABLE VI-continued

| Gene Name | Acc# | GI | L.L. | Duplex # | Sequence | SEQ. ID NO. |
|---|---|---|---|---|---|---|
| RPS6KA1 | | | | | | |
| RPS6KA1 | NM_002953 | 20149546 | 6195 | D-003025-05 | GATGACACCTTCTACTTTG | 564 |
| RPS6KA1 | NM_002953 | 20149546 | 6195 | D-003025-06 | GAGAATGGGCTCCTCATGA | 565 |
| RPS6KA1 | NM_002953 | 20149546 | 6195 | D-003025-07 | CAAGCGGGATCCTTCAGAA | 566 |
| RPS6KA1 | NM_002953 | 20149546 | 6195 | D-003025-08 | CCACCGGCCTGATGGAAGA | 567 |
| RPS6KA3 | | | | | | |
| RPS6KA3 | NM_004586 | 4759049 | 6197 | D-003026-05 | GAAGGGAAGTTGTATCTTA | 568 |
| RPS6KA3 | NM_004586 | 4759049 | 6197 | D-003026-06 | GAAAGTATGTGTATGTAGT | 569 |
| RPS6KA3 | NM_004586 | 4759049 | 6197 | D-003026-07 | GGACAGCATCCAAACATTA | 570 |
| RPS6KA3 | NM_004586 | 4759049 | 6197 | D-003026-08 | GGAGGTGAATTGCTGGATA | 571 |
| SGK | | | | | | |
| SGK | NM_005627 | 5032090 | 6446 | D-003027-01 | TTAATGGTGGAGAGTTGTT | 572 |
| SGK | NM_005627 | 5032090 | 6446 | D-003027-04 | ATTAACTGGGATGATCTCA | 573 |
| SGK | NM_005627 | 25168262 | 6446 | D-003027-05 | GAAGAAAGCAATCCTGAAA | 574 |
| SGK | NM_005627 | 25168262 | 6446 | D-003027-06 | AAACACAGCTGAAATGTAC | 575 |
| TSC1 | | | | | | |
| TSC1 | NM_000368 | 24475626 | 7248 | D-003028-05 | GAAGATGGCTATTCTGTGT | 576 |
| TSC1 | NM_000368 | 24475626 | 7248 | D-003028-06 | TATGAAGGCTCGAGAGTTA | 577 |
| TSC1 | NM_000368 | 24475626 | 7248 | D-003028-07 | CGACACGGCTGATAACTGA | 578 |
| TSC1 | NM_000368 | 24475626 | 7248 | D-003028-08 | CGGCTGATGTTGTTAAATA | 579 |
| TSC2 | | | | | | |
| TSC2 | NM_000548 | 10938006 | 7249 | D-003029-05 | GCATTAATCTCTTACCATA | 580 |
| TSC2 | NM_000548 | 10938006 | 7249 | D-003029-06 | CCAATGTCCTCTTGTCTTT | 581 |
| TSC2 | NM_000548 | 10938006 | 7249 | D-003029-07 | GGAGACACATCACCTACTT | 582 |
| TSC2 | NM_000548 | 10938006 | 7249 | D-003029-08 | TCACCAGGCTCATCAAGAA | 583 |
| XPO1 | | | | | | |
| XPO1 | NM_003400 | 8051634 | 7514 | D-003030-05 | GAAAGTCTCTGTCAAAATA | 584 |
| XPO1 | NM_003400 | 8051634 | 7514 | D-003030-06 | GCAATAGGCTCCATTAGTG | 585 |
| XPO1 | NM_003400 | 8051634 | 7514 | D-003030-07 | GGAACATGATCAACTTATA | 586 |
| XPO1 | NM_003400 | 8051634 | 7514 | D-003030-08 | GGATACAGATTCCATAAAT | 587 |

TABLE VII

| Gene Name | Acc# | GI | L.L | Duplex # | Sequence | SEQ. ID NO. |
|---|---|---|---|---|---|---|
| ABL1 | | | | | | |
| ABL1 | NM_007313 | 6382057 | 25 | D-003100-05 | GGAAATCAGTGACATAGTG | 589 |
| ABL1 | NM_007313 | 6382057 | 25 | D-003100-06 | GGTCCACACTGCAATGTTT | 590 |
| ABL1 | NM_007313 | 6382057 | 25 | D-003100-07 | GAAGGAAATCAGTGACATA | 591 |
| ABL1 | NM_007313 | 6382057 | 25 | D-003100-08 | TCACTGAGTTCATGACCTA | 592 |

TABLE VII-continued

| Gene Name | Acc# | GI | L.L | Duplex # | Sequence | SEQ. ID NO. |
|---|---|---|---|---|---|---|
| ABL2 | | | | | | |
| ABL2 | NM_007314 | 6382061 | 27 | D-003101-05 | GAAATGGAGCGAACAGATA | 593 |
| ABL2 | NM_007314 | 6382061 | 27 | D-003101-06 | GAGCCAAATTTCCTATTAA | 594 |
| ABL2 | NM_007314 | 6382061 | 27 | D-003101-07 | GTAATAAGCCTACAGTCTA | 595 |
| ABL2 | NM_007314 | 6382061 | 27 | D-003101-08 | GGAGTGAAGTTCGCTCTAA | 596 |
| ACK1 | | | | | | |
| ACK1 | NM_005781 | 8922074 | 10188 | D-003102-05 | AAACGCAAGTCGTGGATGA | 597 |
| ACK1 | NM_005781 | 8922074 | 10188 | D-003102-06 | GCAAGTCGTGGATGAGTAA | 598 |
| ACK1 | NM_005781 | 8922074 | 10188 | D-003102-07 | GAGCACTACCTCAGAATGA | 599 |
| ACK1 | NM_005781 | 8922074 | 10188 | D-003102-08 | TCAGCAGCACCCACTATTA | 600 |
| ALK | | | | | | |
| ALK | NM_004304 | 29029631 | 238 | D-003103-05 | GACAAGATCCTGCAGAATA | 601 |
| ALK | NM_004304 | 29029631 | 238 | D-003103-06 | GGAAGAGTCTGGCAGTTGA | 602 |
| ALK | NM_004304 | 29029631 | 238 | D-003103-07 | GCACGTGGCTCGGGACATT | 603 |
| ALK | NM_004304 | 29029631 | 238 | D-003103-08 | GAACTGCAGTGAAGGAACA | 604 |
| AXL | | | | | | |
| AXL | NM_021913 | 21536465 | 558 | D-003104-05 | GGTCAGAGCTGGAGGATTT | 605 |
| AXL | NM_021913 | 21536465 | 558 | D-003104-06 | GAAAGAAGGAGACCCGTTA | 606 |
| AXL | NM_021913 | 21536465 | 558 | D-003104-07 | CCAAGAAGATCTACAATGG | 607 |
| AXL | NM_021913 | 21536465 | 558 | D-003104-08 | GGAACTGCATGCTGAATGA | 608 |
| BLK | | | | | | |
| BLK | NM_001715 | 4502412 | 640 | D-003105-05 | GAGGATGCCTGCTGGATTT | 609 |
| BLK | NM_001715 | 4502412 | 640 | D-003105-06 | ACATGAAGGTGGCCATTAA | 610 |
| BLK | NM_001715 | 4502412 | 640 | D-003105-07 | GGTCAGCGCCCAAGACAAG | 611 |
| BLK | NM_001715 | 4502412 | 640 | D-003105-08 | GAAACTCGGGTCTGGACAA | 612 |
| BMX | | | | | | |
| BMX | NM_001721 | 21359831 | 660 | D-003106-05 | AAACAAACCTTTCCTACTA | 613 |
| BMX | NM_001721 | 21359831 | 660 | D-003106-06 | GAAGGAGCATTTATGGTTA | 614 |
| BMX | NM_001721 | 21359831 | 660 | D-003106-07 | GAGAAGAGATTACCTTGTT | 615 |
| BMX | NM_001721 | 21359831 | 660 | D-003106-08 | GTAAGGCTGTGAATGATAA | 616 |
| BTK | | | | | | |
| BTK | NM_000061 | 4557376 | 695 | D-003107-05 | GAACAGGAATGGAAGCTTA | 617 |
| BTK | NM_000061 | 4557376 | 695 | D-003107-06 | GCTATGGGCTGCCAAATTT | 618 |
| BTK | NM_000061 | 4557376 | 695 | D-003107-07 | GAAAGCAACTTACCATGGT | 619 |
| BTK | NM_000061 | 4557376 | 695 | D-003107-08 | GGTAAACGATCAAGGAGTT | 620 |
| C20orf64 | | | | | | |
| C20orf64 | NM_033550 | 19923655 | 11285 | D-003108-05 | CAACTTAGCCAAGACAATT | 621 |
| C20orf64 | NM_033550 | 19923655 | 11285 | D-003108-06 | GAAATTGAAGGCTCAGTGA | 622 |

TABLE VII-continued

| Gene Name | Acc# | GI | L.L | Duplex # | Sequence | SEQ. ID NO. |
|---|---|---|---|---|---|---|
| C20orf64 | NM_033550 | 19923655 | 11285 | D-003108-07 | TGGAACAGCTGAACATTGT | 623 |
| C20orf64 | NM_033550 | 19923655 | 11285 | D-003108-08 | GCTTCCAACTGCTTATATA | 624 |
| CSF1R | | | | | | |
| CSF1R | NM_005211 | 27262658 | 1436 | D-003109-05 | GGAGAGCTCTGACGTTTGA | 625 |
| CSF1R | NM_005211 | 27262658 | 1436 | D-003109-06 | CAACAACGCTACCTTCCAA | 626 |
| CSF1R | NM_005211 | 27262658 | 1436 | D-003109-07 | CCACGCAGCTGCCTTACAA | 627 |
| CSF1R | NM_005211 | 27262658 | 1436 | D-003109-08 | GGAACAACCTGCAGTTTGG | 628 |
| CSK | | | | | | |
| CSK | NM_004383 | 4758077 | 1445 | D-003110-05 | CAGAATGTATTGCCAAGTA | 629 |
| CSK | NM_004383 | 4758077 | 1445 | D-003110-06 | GAACAAAGTCGCCGTCAAG | 630 |
| CSK | NM_004383 | 4758077 | 1445 | D-003110-07 | GCGAGTGCCTTATCCAAGA | 631 |
| CSK | NM_004383 | 4758077 | 1445 | D-003110-08 | GGAGAAGGGCTACAAGATG | 632 |
| DDR1 | | | | | | |
| DDR1 | NM_013994 | 7669484 | 780 | D-003111-05 | GGAGATGGAGTTTGAGTTT | 633 |
| DDR1 | NM_013994 | 7669484 | 780 | D-003111-06 | CAGAGGCCCTGTCATCTTT | 634 |
| DDR1 | NM_013994 | 7669484 | 780 | D-003111-07 | GCTGGTAGCTGTCAAGATC | 635 |
| DDR1 | NM_013994 | 7669484 | 780 | D-003111-08 | TGAAAGAGGTGAAGATCAT | 636 |
| DDR2 | | | | | | |
| DDR2 | NM_006182 | 5453813 | 4921 | D-003112-05 | GGTAAGAACTACACAATCA | 637 |
| DDR2 | NM_006182 | 5453813 | 4921 | D-003112-06 | GAACGAGAGTGCCACCAAT | 638 |
| DDR2 | NM_006182 | 5453813 | 4921 | D-003112-07 | ACACCAATCTGAAGTTTAT | 639 |
| DDR2 | NM_006182 | 5453813 | 4921 | D-003112-08 | CAACAAGAATGCCAGGAAT | 640 |
| DKFZp761P1010 | | | | | | |
| DKFZp761P1010 | NM_018423 | 8922178 | 55359 | D-003113-05 | CCTAGAAGCTGCCATTAAA | 641 |
| DKFZp761P1010 | NM_018423 | 8922178 | 55359 | D-003113-06 | GATTAGGCCTGGCTTATGA | 642 |
| DKFZp761P1010 | NM_018423 | 8922178 | 55359 | D-003113-07 | CCCAGTAGCTGCACACATA | 643 |
| DKFZp761P1010 | NM_018423 | 8922178 | 55359 | D-003113-08 | GGTGGTACCTGAACTGTAT | 644 |
| EGFR | | | | | | |
| EGFR | NM_005228 | 4885198 | 1956 | D-003114-05 | GAAGGAAACTGAATTCAAA | 645 |
| EGFR | NM_005228 | 4885198 | 1956 | D-003114-06 | GGAAATATGTACTACGAAA | 646 |
| EGFR | NM_005228 | 4885198 | 1956 | D-003114-07 | CCACAAAGCAGTGAATTTA | 647 |
| EGFR | NM_005228 | 4885198 | 1956 | D-003114-08 | GTAACAAGCTCACGCAGTT | 648 |
| EPHA1 | | | | | | |
| EPHA1 | NM_005232 | 4885208 | 2041 | D-003115-05 | GACCAGAGCTTCACCATTC | 649 |
| EPHA1 | NM_005232 | 4885208 | 2041 | D-003115-06 | GCAAGACTGTGGCCATTAA | 650 |
| EPHA1 | NM_005232 | 4885208 | 2041 | D-003115-07 | GGGCGAACCTGACCTATGA | 651 |
| EPHA1 | NM_005232 | 4885208 | 2041 | D-003115-08 | GATTGTAGCCGTCATCTTT | 652 |

TABLE VII-continued

| Gene Name | Acc# | GI | L.L | Duplex # | Sequence | SEQ. ID NO. |
|---|---|---|---|---|---|---|
| EPHA2 | | | | | | |
| EPHA2 | NM_004431 | 4758277 | 1969 | D-003116-05 | GGAGGGATCTGGCAACTTG | 653 |
| EPHA2 | NM_004431 | 4758277 | 1969 | D-003116-06 | GCAGCAAGGTGCACGAATT | 654 |
| EPHA2 | NM_004431 | 4758277 | 1969 | D-003116-07 | GGAGAAGGATGGCGAGTTC | 655 |
| EPHA2 | NM_004431 | 4758277 | 1969 | D-003116-08 | GAAGTTCACTACCGAGATC | 656 |
| EPHA3 | | | | | | |
| EPHA3 | NM_005233 | 21361240 | 2042 | D-003117-05 | GATCGGACCTCCAGAAATA | 657 |
| EPHA3 | NM_005233 | 21361240 | 2042 | D-003117-06 | GAACTCAGCTCAGAAGATT | 658 |
| EPHA3 | NM_005233 | 21361240 | 2042 | D-003117-07 | GCAAGAGGCACAAATGTTA | 659 |
| EPHA3 | NM_005233 | 21361240 | 2042 | D-003117-08 | GAGCATCAGTTTACAAAGA | 660 |
| EPHA4 | | | | | | |
| EPHA4 | NM_004438 | 4758279 | 2043 | D-003118-05 | GGTCTGGGATGAAGTATTT | 661 |
| EPHA4 | NM_004438 | 4758279 | 2043 | D-003118-06 | GAATGAAGTTACCTTATTG | 662 |
| EPHA4 | NM_004438 | 4758279 | 2043 | D-003118-07 | GAACTTGGGTGGATAGCAA | 663 |
| EPHA4 | NM_004438 | 4758279 | 2043 | D-003118-08 | GAGATTAAATTCACCTTGA | 664 |
| EPHA7 | | | | | | |
| EPHA7 | NM_004440 | 4758281 | 2045 | D-003119-05 | GAAAAGAGATGTTGCAGTA | 665 |
| EPHA7 | NM_004440 | 4758281 | 2045 | D-003119-06 | CTAGATGCCTCCTGTATTA | 666 |
| EPHA7 | NM_004440 | 4758281 | 2045 | D-003119-07 | AGAAGAAGGTTATCGTTTA | 667 |
| EPHA7 | NM_004440 | 4758281 | 2045 | D-003119-08 | TAGCAAAGCTGACCAAGAA | 668 |
| EPHA8 | | | | | | |
| EPHA8 | NM_020526 | 18201903 | 2046 | D-003120-05 | GAAGATGCACTATCAGAAT | 669 |
| EPHA8 | NM_020526 | 18201903 | 2046 | D-003120-06 | GAGAAGATGCACTATCAGA | 670 |
| EPHA8 | NM_020526 | 18201903 | 2046 | D-003120-07 | AACCTGATCTCCAGTGTGA | 671 |
| EPHA8 | NM_020526 | 18201903 | 2046 | D-003120-08 | TCTCAGACCTGGGCTATGT | 672 |
| EPHB1 | | | | | | |
| EPHB1 | NM_004441 | 21396502 | 2047 | D-003121-05 | GCGATAAGCTCCAGCATTA | 673 |
| EPHB1 | NM_004441 | 21396502 | 2047 | D-003121-06 | GAAACGGGCTTATAGCAAA | 674 |
| EPHB1 | NM_004441 | 21396502 | 2047 | D-003121-07 | GGATGAAGATCTACATTGA | 675 |
| EPHB1 | NM_004441 | 21396502 | 2047 | D-003121-08 | GCACGTCTCTGTCAACATC | 676 |
| EPHB2 | | | | | | |
| EPHB2 | NM_017449 | 17975764 | 2048 | D-003122-05 | ACTATGAGCTGCAGTACTA | 677 |
| EPHB2 | NM_017449 | 17975764 | 2048 | D-003122-06 | GTACAACGCCACAGCCATA | 678 |
| EPHB2 | NM_017449 | 17975764 | 2048 | D-003122-07 | GGAAAGCAATGACTGTTCT | 679 |
| EPHB2 | NM_017449 | 17975764 | 2048 | D-003122-08 | CGGACAAGCTGCAACACTA | 680 |

TABLE VII-continued

| Gene Name | Acc# | GI | L.L | Duplex # | Sequence | SEQ. ID NO. |
|---|---|---|---|---|---|---|
| EPHB3 | | | | | | |
| EPHB3 | NM_004443 | 17975767 | 2049 | D-003123-05 | GGTGTGATCTCCAATGTGA | 681 |
| EPHB3 | NM_004443 | 17975767 | 2049 | D-003123-06 | GGGATGACCTCCTGTACAA | 682 |
| EPHB3 | NM_004443 | 17975767 | 2049 | D-003123-07 | CAGAAGACCTGCTCCGTAT | 683 |
| EPHB3 | NM_004443 | 17975767 | 2049 | D-003123-08 | GAGATGAAGTACTTTGAGA | 684 |
| EPHB4 | | | | | | |
| EPHB4 | NM_004444 | 17975769 | 2050 | D-003124-05 | GGACAAACACGGACAGTAT | 685 |
| EPHB4 | NM_004444 | 17975769 | 2050 | D-003124-06 | GTACTAAGGTCTACATCGA | 686 |
| EPHB4 | NM_004444 | 17975769 | 2050 | D-003124-07 | GGAGAGAAGCAGAATATTC | 687 |
| EPHB4 | NM_004444 | 17975769 | 2050 | D-003124-08 | GCCAATAGCCACTCTAACA | 688 |
| EPHB6 | | | | | | |
| EPHB6 | NM_004445 | 4758291 | 2051 | D-003125-05 | GGAAGTCGATCCTGCTTAT | 689 |
| EPHB6 | NM_004445 | 4758291 | 2051 | D-003125-06 | GGACCAAGGTGGACACAAT | 690 |
| EPHB6 | NM_004445 | 4758291 | 2051 | D-003125-07 | TGTGGGAAGTGATGAGTTA | 691 |
| EPHB6 | NM_004445 | 4758291 | 2051 | D-003125-08 | CGGGAGACCTTCACCCTTT | 692 |
| ERBB2 | | | | | | |
| ERBB2 | NM_004448 | 4758297 | 2064 | D-003126-05 | GGACGAATTCTGCACAATG | 693 |
| ERBB2 | NM_004448 | 4758297 | 2064 | D-003126-06 | GACGAATTCTGCACAATGG | 694 |
| ERBB2 | NM_004448 | 4758297 | 2064 | D-003126-07 | CTACAACACAGACACGTTT | 695 |
| ERBB2 | NM_004448 | 4758297 | 2064 | D-003126-08 | AGACGAAGCATACGTGATG | 696 |
| ERBB3 | | | | | | |
| ERBB3 | NM_001982 | 4503596 | 2065 | D-003127-05 | AAGAGGATGTCAACGGTTA | 697 |
| ERBB3 | NM_001982 | 4503596 | 2065 | D-003127-06 | GAAGACTGCCAGACATTGA | 698 |
| ERBB3 | NM_001982 | 4503596 | 2065 | D-003127-07 | GACAAACACTGGTGCTGAT | 699 |
| ERBB3 | NM_001982 | 4503596 | 2065 | D-003127-08 | GCAGTGGATTCGAGAAGTG | 700 |
| ERBB4 | | | | | | |
| ERBB4 | NM_005235 | 4885214 | 2066 | D-003128-05 | GAGGAAAGATGCCAATTAA | 701 |
| ERBB4 | NM_005235 | 4885214 | 2066 | D-003128-06 | GCAGGAAACATCTATATTA | 702 |
| ERBB4 | NM_005235 | 4885214 | 2066 | D-003128-07 | GATCACAACTGCTGCTTAA | 703 |
| ERBB4 | NM_005235 | 4885214 | 2066 | D-003128-08 | CCTCAAAGATACCTAGTTA | 704 |
| FER | | | | | | |
| FER | NM_005246 | 4885230 | 2241 | D-003129-05 | GGAGTGACCTGAAGAATTC | 705 |
| FER | NM_005246 | 4885230 | 2241 | D-003129-06 | TAAAGCAGATTCCCATTAA | 706 |
| FER | NM_005246 | 4885230 | 2241 | D-003129-07 | GGAAAGTACTGTCCAAATG | 707 |
| FER | NM_005246 | 4885230 | 2241 | D-003129-08 | GAACAACGGCTGCTAAAGA | 708 |

TABLE VII-continued

| Gene Name | Acc# | GI | L.L | Duplex # | Sequence | SEQ. ID NO. |
|---|---|---|---|---|---|---|
| FES | | | | | | |
| FES | NM_002005 | 13376997 | 2242 | D-003130-05 | CGAGGATCCTGAAGCAGTA | 709 |
| FES | NM_002005 | 13376997 | 2242 | D-003130-06 | AGGAATACCTGGAGATTAG | 710 |
| FES | NM_002005 | 13376997 | 2242 | D-003130-07 | CAACAGGAGCTCCGGAATG | 711 |
| FES | NM_002005 | 13376997 | 2242 | D-003130-08 | GGTGTTGGGTGAGCAGATT | 712 |
| FGFR1 | | | | | | |
| FGFR1 | NM_000604 | 13186232 | 2260 | D-003131-05 | TAAGAAATGTCTCCTTTGA | 713 |
| FGFR1 | NM_000604 | 13186232 | 2260 | D-003131-06 | GAAGACTGCTGGAGTTAAT | 714 |
| FGFR1 | NM_000604 | 13186232 | 2260 | D-003131-07 | GATGGTCCCTTGTATGTCA | 715 |
| FGFR1 | NM_000604 | 13186232 | 2260 | D-003131-08 | CTTAAGAAATGTCTCCTTT | 716 |
| FGFR2 | | | | | | |
| FGFR2 | NM_000141 | 13186239 | 2263 | D-003132-05 | CCAAATCTCTCAACCAGAA | 717 |
| FGFR2 | NM_000141 | 13186239 | 2263 | D-003132-06 | GAACAGTATTCACCTAGTT | 718 |
| FGFR2 | NM_000141 | 13186239 | 2263 | D-003132-07 | GGCCAACACTGTCAAGTTT | 719 |
| FGFR2 | NM_000141 | 13186239 | 2263 | D-003132-08 | GTGAAGATGTTGAAAGATG | 720 |
| FGFR3 | | | | | | |
| FGFR3 | NM_000142 | 13112046 | 2261 | D-003133-05 | TGTCGGACCTGGTGTCTGA | 721 |
| FGFR3 | NM_000142 | 13112046 | 2261 | D-003133-06 | GCATCAAGCTGCGGCATCA | 722 |
| FGFR3 | NM_000142 | 13112046 | 2261 | D-003133-07 | GGACGGCACACCCTACGTT | 723 |
| FGFR3 | NM_000142 | 13112046 | 2261 | D-003133-08 | TGCACAACCTCGACTACTA | 724 |
| FGFR4 | | | | | | |
| FGFR4 | NM_002011 | 13112051 | 2264 | D-003134-05 | GCACTGGAGTCTCGTGATG | 725 |
| FGFR4 | NM_002011 | 13112051 | 2264 | D-003134-06 | CATAGGGACCTCTCGAATA | 726 |
| FGFR4 | NM_002011 | 13112051 | 2264 | D-003134-07 | ATACGGACATCATCCTGTA | 727 |
| FGFR4 | NM_002011 | 13112051 | 2264 | D-003134-08 | ATAGGGACCTCTCGAATAG | 728 |
| FGR | | | | | | |
| FGR | NM_005248 | 4885234 | 2268 | D-003135-05 | GCGATCATGTGAAGCATTA | 729 |
| FGR | NM_005248 | 4885234 | 2268 | D-003135-06 | TCACTGAGCTCATCACCAA | 730 |
| FGR | NM_005248 | 4885234 | 2268 | D-003135-07 | GAAGAGTGGTACTTTGGAA | 731 |
| FGR | NM_005248 | 4885234 | 2268 | D-003135-08 | CCCAGAAGCTGCCCTCTTT | 732 |
| FLT1 | | | | | | |
| FLT1 | NM_002019 | 4503748 | 2321 | D-003136-05 | GAGCAAACGTGACTTATTT | 733 |
| FLT1 | NM_002019 | 4503748 | 2321 | D-003136-06 | CCAAATGGGTTTCATGTTA | 734 |
| FLT1 | NM_002019 | 4503748 | 2321 | D-003136-07 | CAACAAGGATGCAGCACTA | 735 |
| FLT1 | NM_002019 | 4503748 | 2321 | D-003136-08 | GGACGTAACTGAAGAGGAT | 736 |

TABLE VII-continued

| Gene Name | Acc# | GI | L.L | Duplex # | Sequence | SEQ. ID NO. |
|---|---|---|---|---|---|---|
| FLT3 | | | | | | |
| FLT3 | NM_004119 | 4758395 | 2322 | D-003137-05 | GAAGGCATCTACACCATTA | 737 |
| FLT3 | NM_004119 | 4758395 | 2322 | D-003137-06 | GAAGGAGTCTGGAATAGAA | 738 |
| FLT3 | NM_004119 | 4758395 | 2322 | D-003137-07 | GAATTTAAGTCGTGTGTTC | 739 |
| FLT3 | NM_004119 | 4758395 | 2322 | D-003137-08 | GGAATTCATTTCACTCTGA | 740 |
| FLT4 | | | | | | |
| FLT4 | NM_002020 | 4503752 | 2324 | D-003138-05 | GCAAGAACGTGCATCTGTT | 741 |
| FLT4 | NM_002020 | 4503752 | 2324 | D-003138-06 | GCGAATACCTGTCCTACGA | 742 |
| FLT4 | NM_002020 | 4503752 | 2324 | D-003138-07 | GAAGACATTTGAGGAATTC | 743 |
| FLT4 | NM_002020 | 4503752 | 2324 | D-003138-08 | GAGCAGCCATTCATCAACA | 744 |
| FRK | | | | | | |
| FRK | NM_002031 | 4503786 | 2444 | D-003139-05 | GAAACAGACTCTTCATATT | 745 |
| FRK | NM_002031 | 4503786 | 2444 | D-003139-06 | GAACAATACCACTCCAGTA | 746 |
| FRK | NM_002031 | 4503786 | 2444 | D-003139-07 | CAAGACCGGTTCCTTTCTA | 747 |
| FRK | NM_002031 | 4503786 | 2444 | D-003139-08 | GCAAGAATATCTCCAAAAT | 748 |
| FYN | | | | | | |
| FYN | NM_002037 | 23510344 | 2534 | D-003140-05 | GGAATGGACTCATATGCAA | 749 |
| FYN | NM_002037 | 23510344 | 2534 | D-003140-06 | GCAGAAGAGTGGTACTTTG | 750 |
| FYN | NM_002037 | 23510344 | 2534 | D-003140-07 | CAAAGGAAGTTTACTGGAT | 751 |
| FYN | NM_002037 | 23510344 | 2534 | D-003140-08 | GAAGAGTGGTACTTTGGAA | 752 |
| HCK | | | | | | |
| HCK | NM_002110 | 4504356 | 3055 | D-003141-05 | GAGATACCGTGAAACATTA | 753 |
| HCK | NM_002110 | 4504356 | 3055 | D-003141-06 | GCAGGGAGATACCGTGAAA | 754 |
| HCK | NM_002110 | 4504356 | 3055 | D-003141-07 | CATCGTGGTTGCCCTGTAT | 755 |
| HCK | NM_002110 | 4504356 | 3055 | D-003141-08 | TGTGTAAGATTGCTGACTT | 756 |
| ITK | | | | | | |
| ITK | NM_005546 | 21614549 | 3702 | D-003144-05 | CAAATAATCTGGAAACCTA | 757 |
| ITK | NM_005546 | 21614549 | 3702 | D-003144-06 | GAAGAAACGAGGAATAATA | 758 |
| ITK | NM_005546 | 21614549 | 3702 | D-003144-07 | GAAACTCTCTCATCCCAAA | 759 |
| ITK | NM_005546 | 21614549 | 3702 | D-003144-08 | GGAATGGGCATGAAGGATA | 760 |
| JAK1 | | | | | | |
| JAK1 | NM_002227 | 4504802 | 3716 | D-003145-05 | CCACATAGCTGATCTGAAA | 761 |
| JAK1 | NM_002227 | 4504802 | 3716 | D-003145-06 | TGAAATCACTCACATTGTA | 762 |
| JAK1 | NM_002227 | 4504802 | 3716 | D-003145-07 | TAAGGAACCTCTATCATGA | 763 |
| JAK1 | NM_002227 | 4504802 | 3716 | D-003145-08 | GCAGGTGGCTGTTAAATCT | 764 |

TABLE VII-continued

| Gene Name | Acc# | GI | L.L | Duplex # | Sequence | SEQ. ID NO. |
|---|---|---|---|---|---|---|
| JAK2 | | | | | | |
| JAK2 | NM_004972 | 13325062 | 3717 | D-003146-05 | GCAAATAGATCCAGTTCTT | 765 |
| JAK2 | NM_004972 | 13325062 | 3717 | D-003146-06 | GAGCAAAGATCCAAGACTA | 766 |
| JAK2 | NM_004972 | 13325062 | 3717 | D-003146-07 | GCCAGAAACTTGAAACTTA | 767 |
| JAK2 | NM_004972 | 13325062 | 3717 | D-003146-08 | GTACAGATTTCGCAGATTT | 768 |
| JAK3 | | | | | | |
| JAK3 | NM_000215 | 4557680 | 3718 | D-003147-05 | GCGCCTATCTTTCTCCTTT | 769 |
| JAK3 | NM_000215 | 4557680 | 3718 | D-003147-06 | CCAGAAATCGTAGACATTA | 770 |
| JAK3 | NM_000215 | 4557680 | 3718 | D-003147-07 | CCTCATCTCTTCAGACTAT | 771 |
| JAK3 | NM_000215 | 4557680 | 3718 | D-003147-08 | TGTACGAGCTCTTCACCTA | 772 |
| KDR | | | | | | |
| KDR | NM_002253 | 11321596 | 3791 | D-003148-05 | GGAAATCTCTTGCAAGCTA | 773 |
| KDR | NM_002253 | 11321596 | 3791 | D-003148-06 | GATTACAGATCTCCATTTA | 774 |
| KDR | NM_002253 | 11321596 | 3791 | D-003148-07 | GCAGACAGATCTACGTTTG | 775 |
| KDR | NM_002253 | 11321596 | 3791 | D-003148-08 | GCGATGGCCTCTTCTGTAA | 776 |
| KIAA1079 | | | | | | |
| KIAA1079 | NM_014916 | 7662475 | 22853 | D-003149-05 | GAAATTCTCTCAACTGATG | 777 |
| KIAA1079 | NM_014916 | 7662475 | 22853 | D-003149-06 | GCAGAGGTCTTCACACTTT | 778 |
| KIAA1079 | NM_014916 | 7662475 | 22853 | D-003149-07 | TAAATGATCTTCAGACAGA | 779 |
| KIAA1079 | NM_014916 | 7662475 | 22853 | D-003149-08 | GAGCAGCCCTACTCTGATA | 780 |
| KIT | | | | | | |
| KIT | NM_000222 | 4557694 | 3815 | D-003150-05 | AAACACGGCTTAAGCAATT | 781 |
| KIT | NM_000222 | 4557694 | 3815 | D-003150-06 | GAACAGAACCTTCACTGAT | 782 |
| KIT | NM_000222 | 4557694 | 3815 | D-003150-07 | GGGAAGCCCTCATGTCTGA | 783 |
| KIT | NM_000222 | 4557694 | 3815 | D-003150-08 | GCAATTCCATTTATGTGTT | 784 |
| LCK | | | | | | |
| LCK | NM_005356 | 20428651 | 3932 | D-003151-05 | GAACTGCCATTATCCCATA | 785 |
| LCK | NM_005356 | 20428651 | 3932 | D-003151-06 | GAGAGGTGGTGAAACATTA | 786 |
| LCK | NM_005356 | 20428651 | 3932 | D-003151-07 | GGGCCAAGTTTCCCATTAA | 787 |
| LCK | NM_005356 | 20428651 | 3932 | D-003151-08 | GCACGCTGCTCATCCGAAA | 788 |
| LTK | | | | | | |
| LTK | NM_002344 | 4505044 | 4058 | D-003152-05 | TGAATTCACTCCTGCCAAT | 789 |
| LTK | NM_002344 | 4505044 | 4058 | D-003152-06 | GTGGCAACCTCAACACTGA | 790 |
| LTK | NM_002344 | 4505044 | 4058 | D-003152-07 | GGAGCTAGCTGTGGATAAC | 791 |
| LTK | NM_002344 | 4505044 | 4058 | D-003152-08 | GCAAGTTTCGCCATCAGAA | 792 |

TABLE VII-continued

| Gene Name | Acc# | GI | L.L | Duplex # | Sequence | SEQ. ID NO. |
|---|---|---|---|---|---|---|
| LYN | | | | | | |
| LYN | NM_002350 | 4505054 | 4067 | D-003153-05 | GCAGATGGCTTGTGCAGAA | 793 |
| LYN | NM_002350 | 4505054 | 4067 | D-003153-06 | GGAGAAGGCTTGTATTAGT | 794 |
| LYN | NM_002350 | 4505054 | 4067 | D-003153-07 | GATGAGCTCTATGACATTA | 795 |
| LYN | NM_002350 | 4505054 | 4067 | D-003153-08 | GGTGCTAAGTTCCCTATTA | 796 |
| MATK | | | | | | |
| MATK | NM_002378 | 21450841 | 4145 | D-003154-05 | TGAAGAATATCAAGTGTGA | 797 |
| MATK | NM_002378 | 21450841 | 4145 | D-003154-06 | CCGCTCAGCTCCTGCAGTT | 798 |
| MATK | NM_002378 | 21450841 | 4145 | D-003154-07 | TACTGAACCTGCAGCATTT | 799 |
| MATK | NM_002378 | 21450841 | 4145 | D-003154-08 | TGGGAGGTCTTCTCATATG | 800 |
| MERTK | | | | | | |
| MERTK | NM_006343 | 5453737 | 10461 | D-003155-05 | GAACTTACCTTACATAGCT | 801 |
| MERTK | NM_006343 | 5453737 | 10461 | D-003155-06 | GGACCTGCATACTTACTTA | 802 |
| MERTK | NM_006343 | 5453737 | 10461 | D-003155-07 | TGACAGGAATCTTCTAATT | 803 |
| MERTK | NM_006343 | 5453737 | 10461 | D-003155-08 | GGTAATGGCTCAGTCATGA | 804 |
| MET | | | | | | |
| MET | NM_000245 | 4557746 | 4233 | D-003156-05 | GAAAGAACCTCTCAACATT | 805 |
| MET | NM_000245 | 4557746 | 4233 | D-003156-06 | GGACAAGGCTGACCATATG | 806 |
| MET | NM_000245 | 4557746 | 4233 | D-003156-07 | CCAATGACCTGCTGAAATT | 807 |
| MET | NM_000245 | 4557746 | 4233 | D-003156-08 | GAGCATACATTAAACCAAA | 808 |
| MST1R | | | | | | |
| MST1R | NM_002447 | 4505264 | 4486 | D-003157-05 | GGATGGAGCTGCTGGCTTT | 809 |
| MST1R | NM_002447 | 4505264 | 4486 | D-003157-06 | CTGCAGACCTATAGATTTA | 810 |
| MST1R | NM_002447 | 4505264 | 4486 | D-003157-07 | GCACCTGTCTCACTCTTGA | 811 |
| MST1R | NM_002447 | 4505264 | 4486 | D-003157-08 | GAAAGAGTCCATCCAGCTA | 812 |
| MUSK | | | | | | |
| MUSK | NM_005592 | 5031926 | 4593 | D-003158-05 | GAAGAAGCCTCGGCAGATA | 813 |
| MUSK | NM_005592 | 5031926 | 4593 | D-003158-06 | GTAATAATCTCCATCATGT | 814 |
| MUSK | NM_005592 | 5031926 | 4593 | D-003158-07 | GGAATGAACTGAAAGTAGT | 815 |
| MUSK | NM_005592 | 5031926 | 4593 | D-003158-08 | GAGATTTCCTGGACTAGAA | 816 |
| NTRK1 | | | | | | |
| NTRK1 | NM_002529 | 4585711 | 4914 | D-003159-05 | GGACAACCCTTTCGAGTTC | 817 |
| NTRK1 | NM_002529 | 4585711 | 4914 | D-003159-06 | CCAGTGACCTCAACAGGAA | 818 |
| NTRK1 | NM_002529 | 4585711 | 4914 | D-003159-07 | CCACAATACTTCAGTGATG | 819 |
| NTRK1 | NM_002529 | 4585711 | 4914 | D-003159-08 | GAAGAGTGGTCTCCGTTTC | 820 |

TABLE VII-continued

| Gene Name | Acc# | GI | L.L | Duplex # | Sequence | SEQ. ID NO. |
|---|---|---|---|---|---|---|
| NTRK2 | | | | | | |
| NTRK2 | NM_006180 | 21361305 | 4915 | D-003160-05 | GAACAGAAGTAATGAAATC | 821 |
| NTRK2 | NM_006180 | 21361305 | 4915 | D-003160-06 | GTAATGCTGTTTCTGCTTA | 822 |
| NTRK2 | NM_006180 | 21361305 | 4915 | D-003160-07 | GCAAGACACTCCAAGTTTG | 823 |
| NTRK2 | NM_006180 | 21361305 | 4915 | D-003160-08 | GAAAGTCTATCACATTATC | 824 |
| NTRK3 | | | | | | |
| NTRK3 | NM_002530 | 4505474 | 4916 | D-003161-05 | GAGCGAATCTGCTAGTGAA | 825 |
| NTRK3 | NM_002530 | 4505474 | 4916 | D-003161-06 | GAAGTTCACTACAGAGAGT | 826 |
| NTRK3 | NM_002530 | 4505474 | 4916 | D-003161-07 | GGTCGACGGTCCAAATTTG | 827 |
| NTRK3 | NM_002530 | 4505474 | 4916 | D-003161-08 | GAATATCACTTCCATACAC | 828 |
| PDGFRA | | | | | | |
| PDGFRA | NM_006206 | 15451787 | 5156 | D-003162-05 | GAAACTTCCTGGACTATTT | 829 |
| PDGFRA | NM_006206 | 15451787 | 5156 | D-003162-06 | GAGATTTGGTCAACTATTT | 830 |
| PDGFRA | NM_006206 | 15451787 | 5156 | D-003162-07 | GCACGCCGCTTCCTGATAT | 831 |
| PDGFRA | NM_006206 | 15451787 | 5156 | D-003162-08 | CATCAGAGCTGGATCTAGA | 832 |
| PDGFRB | | | | | | |
| PDGFRB | NM_002609 | 15451788 | 5159 | D-003163-05 | GAAAGGAGACGTCAAATAT | 833 |
| PDGFRB | NM_002609 | 15451788 | 5159 | D-003163-06 | GGAATGAGGTGGTCAACTT | 834 |
| PDGFRB | NM_002609 | 15451788 | 5159 | D-003163-07 | CAACGAGTCTCCAGTGCTA | 835 |
| PDGFRB | NM_002609 | 15451788 | 5159 | D-003163-08 | GAGAGGACCTGCCGAGCAA | 836 |
| PTK2 | | | | | | |
| PTK2 | NM_005607 | 27886592 | 5747 | D-003164-05 | GAAGTTGGGTTGTCTAGAA | 837 |
| PTK2 | NM_005607 | 27886592 | 5747 | D-003164-06 | GAAGAACAATGATGTAATC | 838 |
| PTK2 | NM_005607 | 27886592 | 5747 | D-003164-07 | GGAAATTGCTTTGAAGTTG | 839 |
| PTK2 | NM_005607 | 27886592 | 5747 | D-003164-08 | GGTTCAAGCTGGATTATTT | 840 |
| PTK2B | | | | | | |
| PTK2B | NM_004103 | 27886583 | 2185 | D-003165-05 | GAACATGGCTGACCTCATA | 841 |
| PTK2B | NM_004103 | 27886583 | 2185 | D-003165-06 | GGACCACGCTGCTCTATTT | 842 |
| PTK2B | NM_004103 | 27886583 | 2185 | D-003165-07 | GGACGAGGACTATTACAAA | 843 |
| PTK2B | NM_004103 | 27886583 | 2185 | D-003165-08 | TGGCAGAGCTCATCAACAA | 844 |
| PTK6 | | | | | | |
| PTK6 | NM_005975 | 27886594 | 5753 | D-003166-05 | GAGAAAGTCCTGCCCGTTT | 845 |
| PTK6 | NM_005975 | 27886594 | 5753 | D-003166-06 | TGAAGAAGCTGCGGCACAA | 846 |
| PTK6 | NM_005975 | 27886594 | 5753 | D-003166-07 | CCGCGACTCTGATGAGAAA | 847 |
| PTK6 | NM_005975 | 27886594 | 5753 | D-003166-08 | TGCCCGAGCTTGTGAACTA | 848 |

TABLE VII-continued

| Gene Name | Acc# | GI | L.L | Duplex # | Sequence | SEQ. ID NO. |
|---|---|---|---|---|---|---|
| PTK7 | | | | | | |
| PTK7 | NM_002821 | 27886610 | 5754 | D-003167-05 | GAGAGAAGCCCACTATTAA | 849 |
| PTK7 | NM_002821 | 27886610 | 5754 | D-003167-06 | CGAGAGAAGCCCACTATTA | 850 |
| PTK7 | NM_002821 | 27886610 | 5754 | D-003167-07 | GGAGGGAGTTGGAGATGTT | 851 |
| PTK7 | NM_002821 | 27886610 | 5754 | D-003167-08 | GAAGACATGCCGCTATTTG | 852 |
| PTK9 | | | | | | |
| PTK9 | NM_002822 | 4506274 | 5756 | D-003168-05 | GAAGAACTACGACAGATTA | 853 |
| PTK9 | NM_002822 | 4506274 | 5756 | D-003168-09 | GAAGGAGACTATTTAGAGT | 854 |
| PTK9 | NM_002822 | 4506274 | 5756 | D-003168-10 | GAGCGGATGCTGTATTCTA | 855 |
| PTK9 | NM_002822 | 4506274 | 5756 | D-003168-11 | CTGCAGACTTCCTTTATGA | 856 |
| PTK9L | | | | | | |
| PTK9L | NM_007284 | 31543446 | 11344 | D-003169-05 | AGAGAGAGCTCCAGCAGAT | 857 |
| PTK9L | NM_007284 | 31543446 | 11344 | D-003169-06 | TTAACGAGGTGAAGACAGA | 858 |
| PTK9L | NM_007284 | 31543446 | 11344 | D-003169-07 | ACACAGAGCCCACGGATGT | 859 |
| PTK9L | NM_007284 | 31543446 | 11344 | D-003169-08 | GCTGGGATCAGGACTATGA | 860 |
| RET | | | | | | |
| RET | NM_000323 | 21536316 | 5979 | D-003170-05 | GCAAAGACCTGGAGAAGAT | 861 |
| RET | NM_000323 | 21536316 | 5979 | D-003170-06 | GCACACGGCTGCATGAGAA | 862 |
| RET | NM_000323 | 21536316 | 5979 | D-003170-07 | GAACTGGCCTGGAGAGAGT | 863 |
| RET | NM_000323 | 21536316 | 5979 | D-003170-08 | TTAAATGGATGGCAATTGA | 864 |
| ROR1 | | | | | | |
| ROR1 | NM_005012 | 4826867 | 4919 | D-003171-05 | GCAAGCATCTTTACTAGGA | 865 |
| ROR1 | NM_005012 | 4826867 | 4919 | D-003171-06 | GAGCAAGGCTAAAGAGCTA | 866 |
| ROR1 | NM_005012 | 4826867 | 4919 | D-003171-07 | GAGAGCAACTTCATGTAAA | 867 |
| ROR1 | NM_005012 | 4826867 | 4919 | D-003171-08 | GAGAATGTCCTGTGTCAAA | 868 |
| ROR2 | | | | | | |
| ROR2 | NM_004560 | 19743897 | 4920 | D-003172-05 | GGAACTCGCTGCTGCCTAT | 869 |
| ROR2 | NM_004560 | 19743897 | 4920 | D-003172-06 | GCAGGTGCCTCCTCAGATG | 870 |
| ROR2 | NM_004560 | 19743897 | 4920 | D-003172-07 | GCAATGTGCTAGTGTACGA | 871 |
| ROR2 | NM_004560 | 19743897 | 4920 | D-003172-08 | GAAGACAGAATATGGTTCA | 872 |
| ROS1 | | | | | | |
| ROS1 | NM_002944 | 19924164 | 6098 | D-003173-05 | GAGGAGACCTTCTTACTTA | 873 |
| ROS1 | NM_002944 | 19924164 | 6098 | D-003173-06 | TTACAGAGGTTCAGGATTA | 874 |
| ROS1 | NM_002944 | 19924164 | 6098 | D-003173-07 | GAACAAACCTAAGCATGAA | 875 |
| ROS1 | NM_002944 | 19924164 | 6098 | D-003173-08 | GAAAGAGCACTTCAAATAA | 876 |
| RYK | | | | | | |
| RYK | NM_002958 | 11863158 | 6259 | D-003174-05 | GAAAGATGGTTACCGAATA | 877 |
| RYK | NM_002958 | 11863158 | 6259 | D-003174-06 | CAAAGTAGATTCTGAAGTT | 878 |

TABLE VII-continued

| Gene Name | Acc# | GI | L.L | Duplex # | Sequence | SEQ. ID NO. |
|---|---|---|---|---|---|---|
| RYK | NM_002958 | 11863158 | 6259 | D-003174-07 | TCACTACGCTCTATCCTTT | 879 |
| RYK | NM_002958 | 11863158 | 6259 | D-003174-08 | GGTGAAGGATATAGCAATA | 880 |
| SRC | | | | | | |
| SRC | NM_005417 | 21361210 | 6714 | D-003175-05 | GAGAACCTGGTGTGCAAAG | 881 |
| SRC | NM_005417 | 21361210 | 6714 | D-003175-09 | GAGAGAACCTGGTGTGCAA | 882 |
| SRC | NM_005417 | 21361210 | 6714 | D-003175-10 | GGAGTTTGCTGGACTTTCT | 883 |
| SRC | NM_005417 | 21361210 | 6714 | D-003175-11 | GAAAGTGAGACCACGAAAG | 884 |
| SYK | | | | | | |
| SYK | NM_003177 | 21361552 | 6850 | D-003176-05 | GGAATAATCTCAAGAATCA | 885 |
| SYK | NM_003177 | 21361552 | 6850 | D-003176-06 | GAACTGGGCTCTGGTAATT | 886 |
| SYK | NM_003177 | 21361552 | 6850 | D-003176-07 | GGAAGAATCTGAGCAAATT | 887 |
| SYK | NM_003177 | 21361552 | 6850 | D-003176-08 | GAACAGACATGTCAAGGAT | 888 |
| TEC | | | | | | |
| TEC | NM_003215 | 4507428 | 7006 | D-003177-05 | GAAATTGTCTAGTAAGTGA | 889 |
| TEC | NM_003215 | 4507428 | 7006 | D-003177-06 | CACCTGAAGTGTTTAATTA | 890 |
| TEC | NM_003215 | 4507428 | 7006 | D-003177-07 | GTACAAAGTCGCAATCAAA | 891 |
| TEC | NM_003215 | 4507428 | 7006 | D-003177-08 | TGGAGGAGATTCTTATTAA | 892 |
| TEK | | | | | | |
| TEK | NM_000459 | 4557868 | 7010 | D-003178-05 | GAAAGAATATGCCTCCAAA | 893 |
| TEK | NM_000459 | 4557868 | 7010 | D-003178-06 | GGAATGACATCAAATTTCA | 894 |
| TEK | NM_000459 | 4557868 | 7010 | D-003178-07 | TGAAGTACCTGATATTCTA | 895 |
| TEK | NM_000459 | 4557868 | 7010 | D-003178-08 | CGAAAGACCTACGTGAATA | 896 |
| TIE | | | | | | |
| TIE | NM_005424 | 4885630 | 7075 | D-003179-05 | GAGAGGAGGTTTATGTGAA | 897 |
| TIE | NM_005424 | 4885630 | 7075 | D-003179-06 | GGGACAGCCTCTACCCTTA | 898 |
| TIE | NM_005424 | 4885630 | 7075 | D-003179-07 | GAAGTTCTGTGCAAATTGG | 899 |
| TIE | NM_005424 | 4885630 | 7075 | D-003179-08 | CAACATGGCCTCAGAACTG | 900 |
| TNK1 | | | | | | |
| TNK1 | NM_003985 | 4507610 | 8711 | D-003180-05 | GTTCTGGGCCTAAGTCTAA | 901 |
| TNK1 | NM_003985 | 4507610 | 8711 | D-003180-06 | GAACTGGGTCTACAAGATC | 902 |
| TNK1 | NM_003985 | 4507610 | 8711 | D-003180-07 | CGAGAGGTATCGGTCATGA | 903 |
| TNK1 | NM_003985 | 4507610 | 8711 | D-003180-08 | GGCGCATCCTGGAGCATTA | 904 |
| TXK | | | | | | |
| TXK | NM_003328 | 4507742 | 7294 | D-003181-05 | GAACATCTATTGAGACAAG | 905 |
| TXK | NM_003328 | 4507742 | 7294 | D-003181-06 | TCAAGGCACTTTATGATTT | 906 |
| TXK | NM_003328 | 4507742 | 7294 | D-003181-07 | GGAGAGGAATGGCTATATT | 907 |
| TXK | NM_003328 | 4507742 | 7294 | D-003181-08 | GGATATATGTGAAGGAATG | 908 |

TABLE VII-continued

| Gene Name | Acc# | GI | L.L | Duplex # | Sequence | SEQ. ID NO. |
|---|---|---|---|---|---|---|
| TYK2 | | | | | | |
| TYK2 | NM_003331 | 4507748 | 7297 | D-003182-05 | GAGGAGATCCACCACTTTA | 909 |
| TYK2 | NM_003331 | 4507748 | 7297 | D-003182-06 | GCATCCACATTGCACATAA | 910 |
| TYK2 | NM_003331 | 4507748 | 7297 | D-003182-07 | TCAAATACCTAGCCACACT | 911 |
| TYK2 | NM_003331 | 4507748 | 7297 | D-003182-08 | CAATCTTGCTGACGTCTTG | 912 |
| TYRO3 | | | | | | |
| TYRO3 | NM_006293 | 27597077 | 7301 | D-003183-05 | GGTAGAAGGTGTGCCATTT | 913 |
| TYRO3 | NM_006293 | 27597077 | 7301 | D-003183-06 | ACGCTGAGATTTACAACTA | 914 |
| TYRO3 | NM_006293 | 27597077 | 7301 | D-003183-07 | GGATGGCTCCTTTGTGAAA | 915 |
| TYRO3 | NM_006293 | 27597077 | 7301 | D-003183-08 | GAGAGGAACTACGAAGATC | 916 |
| YES1 | | | | | | |
| YES1 | NM_005433 | 21071041 | 7525 | D-003184-05 | GAAGGACCCTGATGAAAGA | 917 |
| YES1 | NM_005433 | 21071041 | 7525 | D-003184-06 | TAAGAAGGGTGAAAGATTT | 918 |
| YES1 | NM_005433 | 21071041 | 7525 | D-003184-07 | TCAAGAAGCTCAGATAATG | 919 |
| YES1 | NM_005433 | 21071041 | 7525 | D-003184-08 | CAGAATCCCTCCATGAATT | 920 |

TABLE VIII

| Gene Name | Acc# | GI | Locus Link | Duplex # | Full Sequence | SEQ. ID NO. |
|---|---|---|---|---|---|---|
| APC2 | | | | | | |
| APC2 | NM_013366 | 7549800 | 29882 | D-003200-05 | GCAAGGACCTCTTCATCAA | 921 |
| APC2 | NM_013366 | 7549800 | 29882 | D-003200-06 | GAGAAGAAGTCCACACTAT | 922 |
| APC2 | NM_013366 | 7549800 | 29882 | D-003200-07 | GGAATGCCATCTCCCAATG | 923 |
| APC2 | NM_013366 | 7549800 | 29882 | D-003200-09 | CAACACGTGTGACATCATC | 924 |
| ATM | | | | | | |
| ATM | NM_000051 | 20336202 | 472 | D-003201-05 | GCAAGCAGCTGAAACAAAT | 925 |
| ATM | NM_000051 | 20336202 | 472 | D-003201-06 | GAATGTTGCTTTCTGAATT | 926 |
| ATM | NM_000051 | 20336202 | 472 | D-003201-07 | GACCTGAAGTCTTATTTAA | 927 |
| ATM | NM_000051 | 20336202 | 472 | D-003201-08 | AGACAGAATTCCCAAATAA | 928 |
| ATR | | | | | | |
| ATR | NM_001184 | 20143978 | 545 | D-003202-05 | GAACAACACTGCTGGTTTG | 929 |
| ATR | NM_001184 | 20143978 | 545 | D-003202-06 | GAAGTCATCTGTTCATTAT | 930 |
| ATR | NM_001184 | 20143978 | 545 | D-003202-07 | GAAATAAGGTAGACTCAAT | 931 |
| ATR | NM_001184 | 20143978 | 545 | D-003202-08 | CAACATAAATCCAAGAAGA | 932 |
| BTAK | | | | | | |
| BTAK | NM_003600 | 3213196 | 6790 | D-003545-04 | CAAAGAATCAGCTAGCAAA | 933 |
| BTAK | NM_003600 | 3213196 | 6790 | D-003203-05 | GAAGAGAGTTATTCATAGA | 934 |
| BTAK | NM_003600 | 3213196 | 6790 | D-003203-07 | CAAATGCCCTGTCTTACTG | 935 |
| STK6 | NM_003600 | 3213196 | 6790 | D-003203-09 | TCTCGTGACTCAGCAAATT | 936 |

TABLE VIII-continued

| Gene Name | Acc# | GI | Locus Link | Duplex # | Full Sequence | SEQ. ID NO. |
|---|---|---|---|---|---|---|
| CCNA1 | | | | | | |
| CCNA1 | NM_003914 | 16306528 | 8900 | D-003204-05 | GAACCTGGCTAAGTACGTA | 937 |
| CCNA1 | NM_003914 | 16306528 | 8900 | D-003204-06 | GCAGATCCATTCTTGAAAT | 938 |
| CCNA1 | NM_003914 | 16306528 | 8900 | D-003204-07 | TCACAAGAATCAGGTGTTA | 939 |
| CCNA1 | NM_003914 | 16306528 | 8900 | D-003204-08 | CATAAAGCGTACCTTGATA | 940 |
| CCNA2 | | | | | | |
| CCNA2 | NM_001237 | 16950653 | 890 | D-003205-05 | GCTGTGAACTACATTGATA | 941 |
| CCNA2 | NM_001237 | 16950653 | 890 | D-003205-06 | GATGATACCTACACCAAGA | 942 |
| CCNA2 | NM_001237 | 16950653 | 890 | D-003205-07 | GCTGTTAGCCTCAAAGTTT | 943 |
| CCNA2 | NM_001237 | 16950653 | 890 | D-003205-08 | AAGCTGGCCTGAATCATTA | 944 |
| CCNB1 | | | | | | |
| CCNB1 | NM_031966 | 14327895 | 891 | D-003206-05 | CAACATTACCTGTCATATA | 945 |
| CCNB1 | NM_031966 | 14327895 | 891 | D-003206-06 | CCAAATACCTGATGGAACT | 946 |
| CCNB1 | NM_031966 | 14327895 | 891 | D-003206-07 | GAAATGTACCCTCCAGAAA | 947 |
| CCNB1 | NM_031966 | 14327895 | 891 | D-003206-08 | GCACCTGGCTAAGAATGTA | 948 |
| CCNB2 | | | | | | |
| CCNB2 | NM_004701 | 10938017 | 9133 | D-003207-05 | CAACAAATGTCAACAAACA | 949 |
| CCNB2 | NM_004701 | 10938017 | 9133 | D-003207-06 | GCAGCAAACTCCTGAAGAT | 950 |
| CCNB2 | NM_004701 | 10938017 | 9133 | D-003207-07 | CCAGTGATTTGGAGAATAT | 951 |
| CCNB2 | NM_004701 | 10938017 | 9133 | D-003207-08 | GTGACTACGTTAAGGATAT | 952 |
| CCNB3 | | | | | | |
| CCNB3 | NM_033031 | 14719419 | 85417 | D-003208-05 | TGAACAAACTGCTGACTTT | 953 |
| CCNB3 | NM_033031 | 14719419 | 85417 | D-003208-06 | GCTAGCTGCTGCCTCCTTA | 954 |
| CCNB3 | NM_033031 | 14719419 | 85417 | D-003208-07 | CAACTCACCTCGTGTGGAT | 955 |
| CCNB3 | NM_033031 | 14719419 | 85417 | D-003208-08 | GTGGATCTCTACCTAATGA | 956 |
| CCNC | | | | | | |
| CCNC | NM_005190 | 7382485 | 892 | D-003209-05 | GCAGAGCTCCCACTATTTG | 957 |
| CCNC | NM_005190 | 7382485 | 892 | D-003209-06 | GGAGTAGTTTCAAATACAA | 958 |
| CCNC | NM_005190 | 7382485 | 892 | D-003209-07 | GACCTTTGCTCCAGTATGT | 959 |
| CCNC | NM_005190 | 7382485 | 892 | D-003209-08 | GAGATTCTATGCCAGGTAT | 960 |
| CCND1 | | | | | | |
| CCND1 | NM_053056 | 16950654 | 595 | D-003210-05 | TGAACAAGCTCAAGTGGAA | 961 |
| CCND1 | NM_053056 | 16950654 | 595 | D-003210-06 | CCAGAGTGATCAAGTGTGA | 962 |
| CCND1 | NM_053056 | 16950654 | 595 | D-003210-07 | GTTCGTGGCCTCTAAGATG | 963 |
| CCND1 | NM_053056 | 16950654 | 595 | D-003210-08 | CCAGAAGCTGTGCATCTA | 964 |
| CCND2 | | | | | | |
| CCND2 | NM_001759 | 16950656 | 894 | D-003211-06 | TGAATTACCTGGACCGTTT | 965 |
| CCND2 | NM_001759 | 16950656 | 894 | D-003211-07 | CGGAGAAGCTGTGCATTTA | 966 |

TABLE VIII-continued

| Gene Name | Acc# | GI | Locus Link | Duplex # | Full Sequence | SEQ. ID NO. |
|---|---|---|---|---|---|---|
| CCND2 | NM_001759 | 16950656 | 894 | D-003211-08 | CTACAGACGTGCGGGATAT | 967 |
| CCND2 | NM_001759 | 16950656 | 894 | D-003211-09 | CAACACAGACGTGGATTGT | 968 |
| CCND3 | | | | | | |
| CCND3 | NM_001760 | 16950657 | 896 | D-003212-05 | GGACCTGGCTGCTGTGATT | 969 |
| CCND3 | NM_001760 | 16950657 | 896 | D-003212-06 | GATTATACCTTTGCCATGT | 970 |
| CCND3 | NM_001760 | 16950657 | 896 | D-003212-07 | GACCAGCACTCCTACAGAT | 971 |
| CCND3 | NM_001760 | 16950657 | 896 | D-003212-08 | TGCGGAAGATGCTGGCTTA | 972 |
| CCNE1 | | | | | | |
| CCNE1 | NM_001238 | 17318558 | 898 | D-003213-05 | GTACTGAGCTGGGCAAATA | 973 |
| CCNE1 | NM_001238 | 17318558 | 898 | D-003213-06 | GGAAATCTATCCTCCAAAG | 974 |
| CCNE1 | NM_001238 | 17318558 | 898 | D-003213-07 | GGAGGTGTGTGAAGTCTAT | 975 |
| CCNE1 | NM_001238 | 17318558 | 898 | D-003213-08 | CTAAATGACTTACATGAAG | 976 |
| CCNE2 | | | | | | |
| CCNE2 | NM_057749 | 17318564 | 9134 | D-003214-05 | GGATGGAACTCATTATATT | 977 |
| CCNE2 | NM_057749 | 17318564 | 9134 | D-003214-06 | GCAGATATGTTCATGACAA | 978 |
| CCNE2 | NM_057749 | 17318564 | 9134 | D-003214-07 | CATAATATCCAGACACATA | 979 |
| CCNE2 | NM_057749 | 17318564 | 9134 | D-003214-08 | TAAGAAAGCCTCAGGTTTG | 980 |
| CCNF | | | | | | |
| CCNF | NM_001761 | 4502620 | 899 | D-003215-05 | TCACAAAGCATCCATATTG | 981 |
| CCNF | NM_001761 | 4502620 | 899 | D-003215-06 | GAAGTCATGTTTACAGTGT | 982 |
| CCNF | NM_001761 | 4502620 | 899 | D-003215-07 | TAGCCTACCTCTACAATGA | 983 |
| CCNF | NM_001761 | 4502620 | 899 | D-003215-08 | GCACCCGGTTTATCAGTAA | 984 |
| CCNG1 | | | | | | |
| CCNG1 | NM_004060 | 8670528 | 900 | D-003216-05 | GATAATGGCCTCAGAATGA | 985 |
| CCNG1 | NM_004060 | 8670528 | 900 | D-003216-06 | GCACGGCAATTGAAGCATA | 986 |
| CCNG1 | NM_004060 | 8670528 | 900 | D-003216-07 | GGAATAGAATGTCTTCAGA | 987 |
| CCNG1 | NM_004060 | 8670528 | 900 | D-003216-08 | TAACTCACCTTCCAACAAT | 988 |
| CCNG2 | | | | | | |
| CCNG2 | NM_004354 | 4757935 | 901 | D-003217-05 | GGAGAGAGTTGGTTTCTAA | 989 |
| CCNG2 | NM_004354 | 4757935 | 901 | D-003217-06 | GGTGAAACCTAAACATTTG | 990 |
| CCNG2 | NM_004354 | 4757935 | 901 | D-003217-07 | GAAATACTGAGCCTTGATA | 991 |
| CCNG2 | NM_004354 | 4757935 | 901 | D-003217-08 | TGCCAAAGTTGAAGATTTA | 992 |
| CCNH | | | | | | |
| CCNH | NM_001239 | 17738313 | 902 | D-003218-05 | GCTGATGACTTTCTTAATA | 993 |
| CCNH | NM_001239 | 17738313 | 902 | D-003218-06 | CAACTTAATTTCCACCTTA | 994 |
| CCNH | NM_001239 | 17738313 | 902 | D-003218-07 | ATACACACCTTCCCAAATT | 995 |
| CCNH | NM_001239 | 17738313 | 902 | D-003218-08 | GCTATGAAGATGATGATTA | 996 |

TABLE VIII-continued

| Gene Name | Acc# | GI | Locus Link | Duplex # | Full Sequence | SEQ. ID NO. |
|---|---|---|---|---|---|---|
| CCNI | | | | | | |
| CCNI | NM_006835 | 17738314 | 10983 | D-003219-05 | GCAAGCAGACCTCTACTAA | 997 |
| CCNI | NM_006835 | 17738314 | 10983 | D-003219-07 | TGAGAGAATTCCAGTACTA | 998 |
| CCNI | NM_006835 | 17738314 | 10983 | D-003219-08 | GGAATCAAACGGCTCTATA | 999 |
| CCNI | NM_006835 | 17738314 | 10983 | D-003219-09 | GAATTGGGATCTTCACACA | 1000 |
| CCNT1 | | | | | | |
| CCNT1 | NM_001240 | 17978465 | 904 | D-003220-05 | TATCAACACTGCTATAGTA | 1001 |
| CCNT1 | NM_001240 | 17978465 | 904 | D-003220-06 | GAACAAACGTCCTGGTGAT | 1002 |
| CCNT1 | NM_001240 | 17978465 | 904 | D-003220-07 | GCACAAGACTCACCCATCT | 1003 |
| CCNT1 | NM_001240 | 17978465 | 904 | D-003220-08 | GCACAGACTTCTTACTTCA | 1004 |
| CCNT2A | | | | | | |
| CCNT2A | NM_001241 | 17978467 | 905 | D-003221-05 | GCACAGACATCCTATTTCA | 1005 |
| CCNT2A | NM_001241 | 17978467 | 905 | D-003221-06 | GCAGGGACCTTCTATATCA | 1006 |
| CCNT2A | NM_001241 | 17978467 | 905 | D-003221-07 | GAACAGCTATATTCACAGA | 1007 |
| CCNT2A | NM_001241 | 17978467 | 905 | D-003221-09 | TTATATAGCTGCCCAGGTA | 1008 |
| CCNT2B | | | | | | |
| CCNT2B | NM_058241 | 17978468 | 905 | D-003222-05 | GCACAGACATCCTATTTCA | 1009 |
| CCNT2B | NM_058241 | 17978468 | 905 | D-003222-06 | GCAGGGACCTTCTATATCA | 1010 |
| CCNT2B | NM_058241 | 17978468 | 905 | D-003222-07 | GAACAGCTATATTCACAGA | 1011 |
| CCNT2B | NM_058241 | 17978468 | 905 | D-003222-08 | GGTGAAATGTACCCAGTTA | 1012 |
| CDC16 | | | | | | |
| CDC16 | NM_003903 | 14110370 | 8881 | D-003223-05 | GTAGATGGCTTGCAAGAGA | 1013 |
| CDC16 | NM_003903 | 14110370 | 8881 | D-003223-06 | TAAAGTAGCTTCACTCTCT | 1014 |
| CDC16 | NM_003903 | 14110370 | 8881 | D-003223-07 | GCTACAAGCTTACTTCTGT | 1015 |
| CDC16 | NM_003903 | 14110370 | 8881 | D-003223-08 | TGGAAGAGCCCATCAATAA | 1016 |
| CDC2 | | | | | | |
| CDC2 | NM_033379 | 27886643 | 983 | D-003552-01 | GTACAGATCTCCAGAAGTA | 1017 |
| CDC2 | NM_033379 | 27886643 | 983 | D-003552-02 | GATCAACTCTTCAGGATTT | 1018 |
| CDC2 | NM_033379 | 27886643 | 983 | D-003552-03 | GGTTATATCTCATCTTTGA | 1019 |
| CDC2 | NM_033379 | 27886643 | 983 | D-003552-04 | GAACTTCGTCATCCAAATA | 1020 |
| CDC20 | | | | | | |
| CDC20 | NM_001255 | 4557436 | 991 | D-003225-05 | GGGAATATATATCCTCTGT | 1021 |
| CDC20 | NM_001255 | 4557436 | 991 | D-003225-06 | GAAACGGCTTCGAAATATG | 1022 |
| CDC20 | NM_001255 | 4557436 | 991 | D-003225-07 | GAAGACCTGCCGTTACATT | 1023 |
| CDC20 | NM_001255 | 4557436 | 991 | D-003225-08 | CACCAGTGATCGACACATT | 1024 |
| CDC25A | | | | | | |
| CDC25A | NM_001789 | 4502704 | 993 | D-003226-05 | GAAATTATGGCATCTGTTT | 1025 |
| CDC25A | NM_001789 | 4502704 | 993 | D-003226-06 | TACAAGGAGTTCTTTATGA | 1026 |

TABLE VIII-continued

| Gene Name | Acc# | GI | Locus Link | Duplex # | Full Sequence | SEQ. ID NO. |
|---|---|---|---|---|---|---|
| CDC25A | NM_001789 | 4502704 | | 993 D-003226-07 | CCACGAGGACTTTAAAGAA | 1027 |
| CDC25A | NM_001789 | 4502704 | | 993 D-003226-08 | TGGGAAACATCAGGATTTA | 1028 |
| CDC25B | | | | | | |
| CDC25B | NM_004358 | 11641416 | | 994 D-003227-05 | GCAGATACCCCTATGAATA | 1029 |
| CDC25B | NM_004358 | 11641416 | | 994 D-003227-06 | CTAGGTCGCTTCTCTCTGA | 1030 |
| CDC25B | NM_004358 | 11641416 | | 994 D-003227-07 | GAGAGCTGATTGGAGATTA | 1031 |
| CDC25B | NM_004358 | 11641416 | | 994 D-003227-08 | AAAAGGACCTCGTCATGTA | 1032 |
| CDC25C | | | | | | |
| CDC25C | NM_001790 | 12408659 | | 995 D-003228-05 | GAGCAGAAGTGGCCTATAT | 1033 |
| CDC25C | NM_001790 | 12408659 | | 995 D-003228-06 | CAGAAGAGATTTCAGATGA | 1034 |
| CDC25C | NM_001790 | 12408659 | | 995 D-003228-07 | CCAGGGAGCCTTAAACTTA | 1035 |
| CDC25C | NM_001790 | 12408659 | | 995 D-003228-08 | GAAACTTGGTGGACAGTGA | 1036 |
| CDC27 | | | | | | |
| CDC27 | NM_001256 | 16554576 | | 996 D-003229-06 | CATGCAAGCTGAAAGAATA | 1037 |
| CDC27 | NM_001256 | 16554576 | | 996 D-003229-07 | CAACACAAGTACCTAATCA | 1038 |
| CDC27 | NM_001256 | 16554576 | | 996 D-003229-08 | GGAGATGGATCCTATTTAC | 1039 |
| CDC27 | NM_001256 | 16554576 | | 996 D-003229-09 | GAAAAGCCATGATGATATT | 1040 |
| CDC34 | | | | | | |
| CDC34 | NM_004359 | 16357476 | | 997 D-003230-05 | GCTCAGACCTCTTCTACGA | 1041 |
| CDC34 | NM_004359 | 16357476 | | 997 D-003230-06 | GGACGAGGGCGATCTATAC | 1042 |
| CDC34 | NM_004359 | 16357476 | | 997 D-003230-07 | GATCGGGAGTACACAGACA | 1043 |
| CDC34 | NM_004359 | 16357476 | | 997 D-003230-08 | TGAACGAGCCCAACACCTT | 1044 |
| CDC37 | | | | | | |
| CDC37 | NM_007065 | 16357478 | 11140 | D-003231-05 | GCGAGGAGACAGCCAATTA | 1045 |
| CDC37 | NM_007065 | 16357478 | 11140 | D-003231-06 | CACAAGACCTTCGTGGAAA | 1046 |
| CDC37 | NM_007065 | 16357478 | 11140 | D-003231-07 | ACAATCGTCATGCAATTTA | 1047 |
| CDC37 | NM_007065 | 16357478 | 11140 | D-003231-08 | GAGGAGAAATGTGCACTCA | 1048 |
| CDC45L | | | | | | |
| CDC45L | NM_003504 | 34335230 | | 8318 D-003232-05 | GCACACGGATCTCCTTTGA | 1049 |
| CDC45L | NM_003504 | 34335230 | | 8318 D-003232-06 | GCAAACACCTGCTCAAGTC | 1050 |
| CDC45L | NM_003504 | 34335230 | | 8318 D-003232-07 | TGAAGAGTCTGCAAATAAA | 1051 |
| CDC45L | NM_003504 | 34335230 | | 8318 D-003232-08 | GGACGTGGATGCTCTGTGT | 1052 |
| CDC6 | | | | | | |
| CDC6 | NM_001254 | 16357469 | | 990 D-003233-05 | GAACACAGCTGTCCCAGAT | 1053 |
| CDC6 | NM_001254 | 16357469 | | 990 D-003233-06 | GAGCAGAGATGTCCACTGA | 1054 |
| CDC6 | NM_001254 | 16357469 | | 990 D-003233-07 | GGAAATATCTTAGCTACTG | 1055 |
| CDC6 | NM_001254 | 16357469 | | 990 D-003233-08 | GGACGAAGATTGGTATTTG | 1056 |

TABLE VIII-continued

| Gene Name | Acc# | GI | Locus Link | Duplex # | Full Sequence | SEQ. ID NO. |
|---|---|---|---|---|---|---|
| CDC7 | | | | | | |
| CDC7 | NM_003503 | 11038647 | 8317 | D-003234-05 | GGAATGAGGTACCTGATGA | 1057 |
| CDC7 | NM_003503 | 11038647 | 8317 | D-003234-06 | CAGGAAAGGTGTTCACAAA | 1058 |
| CDC7 | NM_003503 | 11038647 | 8317 | D-003234-07 | CTACACAAATGCACAAATT | 1059 |
| CDC7 | NM_003503 | 11038647 | 8317 | D-003234-08 | GTACGGGAATATATGCTTA | 1060 |
| CDK10 | | | | | | |
| CDK10 | NM_003674 | 32528262 | 8558 | D-003235-05 | GAACTGCTGTTGGGAACCA | 1061 |
| CDK10 | NM_003674 | 32528262 | 8558 | D-003235-06 | GGAAGCAGCCCTACAACAA | 1062 |
| CDK10 | NM_003674 | 32528262 | 8558 | D-003235-07 | GCACGCCCAGTGAGAACAT | 1063 |
| CDK10 | NM_003674 | 32528262 | 8558 | D-003235-08 | GGAAGCAGCCCTACAACAA | 1064 |
| CDK2 | | | | | | |
| CDK2 | NM_001798 | 16936527 | 1017 | D-003236-05 | GAGCTTAACCATCCTAATA | 1065 |
| CDK2 | NM_001798 | 16936527 | 1017 | D-003236-06 | GAGCTTAACCATCCTAATA | 1066 |
| CDK2 | NM_001798 | 16936527 | 1017 | D-003236-07 | GTACCGAGCTCCTGAAATC | 1067 |
| CDK2 | NM_001798 | 16936527 | 1017 | D-003236-08 | GAGAGGTGGTGGCGCTTAA | 1068 |
| CDK3 | | | | | | |
| CDK3 | NM_001258 | 4557438 | 1018 | D-003237-05 | GAGCATTGGTTGCATCTTT | 1069 |
| CDK3 | NM_001258 | 4557438 | 1018 | D-003237-06 | GATCGGAGAGGGCACCTAT | 1070 |
| CDK3 | NM_001258 | 4557438 | 1018 | D-003237-07 | GAAGCTCTATCTGGTGTTT | 1071 |
| CDK3 | NM_001258 | 4557438 | 1018 | D-003237-08 | GCAGAGATGGTGACTCGAA | 1072 |
| CDK4 | | | | | | |
| CDK4 | NM_000075 | 456426 | 1019 | D-003238-05 | GCAGCACTCTTATCTACAT | 1073 |
| CDK4 | NM_000075 | 456426 | 1019 | D-003238-06 | GGAGGAGGCCTTCCCATCA | 1074 |
| CDK4 | NM_000075 | 456426 | 1019 | D-003238-07 | TCGAAAGCCTCTCTTCTGT | 1075 |
| CDK4 | NM_000075 | 456426 | 1019 | D-003238-08 | GTACCGAGCTCCCGAAGTT | 1076 |
| CDK5 | | | | | | |
| CDK5 | NM_004935 | 4826674 | 1020 | D-003239-05 | TGACCAAGCTGCCAGACTA | 1077 |
| CDK5 | NM_004935 | 4826674 | 1020 | D-003239-06 | GAGCTGAAATTGGCTGATT | 1078 |
| CDK5 | NM_004935 | 4826674 | 1020 | D-003239-07 | CAACATCCCTGGTGAACGT | 1079 |
| CDK5 | NM_004935 | 4826674 | 1020 | D-003239-08 | GGATTCCCGTCCGCTGTTA | 1080 |
| CDK6 | | | | | | |
| CDK6 | NM_001259 | 16950658 | 1021 | D-003240-05 | GCAAAGACCTACTTCTGAA | 1081 |
| CDK6 | NM_001259 | 16950658 | 1021 | D-003240-06 | GAAGAAGACTGGCCTAGAG | 1082 |
| CDK6 | NM_001259 | 16950658 | 1021 | D-003240-07 | GGTCTGGACTTTCTTCATT | 1083 |
| CDK6 | NM_001259 | 16950658 | 1021 | D-003240-08 | TAACAGATATCGATGAACT | 1084 |
| CDK7 | | | | | | |
| CDK7 | NM_001799 | 16950659 | 1022 | D-003241-05 | GGACATAGATCAGAAGCTA | 1085 |
| CDK7 | NM_001799 | 16950659 | 1022 | D-003241-06 | CAATAGAGCTTATACACAT | 1086 |

TABLE VIII-continued

| Gene Name | Acc# | GI | Locus Link | Duplex # | Full Sequence | SEQ. ID NO. |
|---|---|---|---|---|---|---|
| CDK7 | NM_001799 | 16950659 | 1022 | D-003241-07 | CATACAAGGCTTATTCTTA | 1087 |
| CDK7 | NM_001799 | 16950659 | 1022 | D-003241-08 | GGAGACGACTTACTAGATC | 1088 |
| CDK8 | | | | | | |
| CDK8 | NM_001260 | 4502744 | 1024 | D-003242-05 | CCACAGTACTCACATCAGA | 1089 |
| CDK8 | NM_001260 | 4502744 | 1024 | D-003242-06 | GCAATAACCACACTAATGG | 1090 |
| CDK8 | NM_001260 | 4502744 | 1024 | D-003242-07 | GAAGAAAGTGAGAGTTGTT | 1091 |
| CDK8 | NM_001260 | 4502744 | 1024 | D-003242-08 | GAACATGACCTCTGGCATA | 1092 |
| CDK9 | | | | | | |
| CDK9 | NM_001261 | 17017983 | 1025 | D-003243-05 | GGCCAAACGTGGACAACTA | 1093 |
| CDK9 | NM_001261 | 17017983 | 1025 | D-003243-06 | TGACGTCCATGTTCGAGTA | 1094 |
| CDK9 | NM_001261 | 17017983 | 1025 | D-003243-07 | CCAACCAGACGGAGTTTGA | 1095 |
| CDK9 | NM_001261 | 17017983 | 1025 | D-003243-08 | GAAGGTGGCTCTGAAGAAG | 1096 |
| CDKN1C | | | | | | |
| CDKN1C | NM_000076 | 4557440 | 1028 | D-003244-05 | GACCAGAACCGCTGGGATT | 1097 |
| CDKN1C | NM_000076 | 4557440 | 1028 | D-003244-06 | GGACCGAAGTGGACAGCGA | 1098 |
| CDKN1C | NM_000076 | 4557440 | 1028 | D-003244-08 | GCAAGAGATCAGCGCCTGA | 1099 |
| CDKN1C | NM_000076 | 4557440 | 1028 | D-003244-09 | CCGCTGGGATTACGACTTC | 1100 |
| CDKN2B | | | | | | |
| CDKN2B | NM_004936 | 17981693 | 1030 | D-003245-05 | GCGAGGAGAACAAGGGCAT | 1101 |
| CDKN2B | NM_004936 | 17981693 | 1030 | D-003245-06 | CCAACGGAGTCAACCGTTT | 1102 |
| CDKN2B | NM_004936 | 17981693 | 1030 | D-003245-07 | CGATCCAGGTCATGATGAT | 1103 |
| CDKN2B | NM_004936 | 17981693 | 1030 | D-003245-08 | CCTGGAAGCCGGCGCGGAT | 1104 |
| CDKN2C | | | | | | |
| CDKN2C | NM_001262 | 17981697 | 1031 | D-003246-05 | GGACACCGCCTGTGATTTG | 1105 |
| CDKN2C | NM_001262 | 17981697 | 1031 | D-003246-06 | GCCAGGAGACTGCTACTTA | 1106 |
| CDKN2C | NM_001262 | 17981697 | 1031 | D-003246-07 | TGAAAGACCGAACTGGTTT | 1107 |
| CDKN2C | NM_001262 | 17981697 | 1031 | D-003246-08 | GAACCTGCCCTTGCACTTG | 1108 |
| CDKN2D | | | | | | |
| CDKN2D | NM_001800 | 17981700 | 1032 | D-003247-05 | TGGCAGTTCAAGAGGGTCA | 1109 |
| CDKN2D | NM_001800 | 17981700 | 1032 | D-003247-06 | CTCAGGACCTCGTGGACAT | 1110 |
| CDKN2D | NM_001800 | 17981700 | 1032 | D-003247-07 | TGAAGGTCCTAGTGGAGCA | 1111 |
| CDKN2D | NM_001800 | 17981700 | 1032 | D-003247-08 | AGACGGCGCTGCAGGTCAT | 1112 |
| CDT1 | | | | | | |
| CDT1 | NM_030928 | 19923847 | 81620 | D-003248-05 | CCAAGGAGGCACAGAAGCA | 1113 |
| CDT1 | NM_030928 | 19923847 | 81620 | D-003248-06 | GCTTCAACGTGGATGAAGT | 1114 |
| CDT1 | NM_030928 | 19923847 | 81620 | D-003248-07 | TCTCCGGGCCAGAAGATAA | 1115 |
| CDT1 | NM_030928 | 19923847 | 81620 | D-003248-08 | GCGCAATGTTGGCCAGATC | 1116 |

TABLE VIII-continued

| Gene Name | Acc# | GI | Locus Link | Duplex # | Full Sequence | SEQ. ID NO. |
|---|---|---|---|---|---|---|
| CENPA | | | | | | |
| CENPA | NM_001809 | 4585861 | 1058 | D-003249-05 | GCACACACCTCTTGATAAG | 1117 |
| CENPA | NM_001809 | 4585861 | 1058 | D-003249-06 | GCAAGAGAAATATGTGTTA | 1118 |
| CENPA | NM_001809 | 4585861 | 1058 | D-003249-07 | TTACATGCAGGCCGAGTTA | 1119 |
| CENPA | NM_001809 | 4585861 | 1058 | D-003249-08 | GAGACAAGGTTGGCTAAAG | 1120 |
| CENPB | | | | | | |
| CENPB | NM_001810 | 26105977 | 1059 | D-003250-05 | GGACATAGCCGCCTGCTTT | 1121 |
| CENPB | NM_001810 | 26105977 | 1059 | D-003250-06 | GCACGATCCTGAAGAACAA | 1122 |
| CENPB | NM_001810 | 26105977 | 1059 | D-003250-07 | GGAGGAGGGTGATGTTGAT | 1123 |
| CENPB | NM_001810 | 26105977 | 1059 | D-003250-08 | CCGAATGGCTGCAGAGTCT | 1124 |
| CENPC1 | | | | | | |
| CENPC1 | NM_001812 | 4502778 | 1060 | D-003251-05 | GCGAATAGATTATCAAGGA | 1125 |
| CENPC1 | NM_001812 | 4502778 | 1060 | D-003251-06 | GAACAGAATCCATCACAAA | 1126 |
| CENPC1 | NM_001812 | 4502778 | 1060 | D-003251-07 | CCATAAACCTCACCCAGTA | 1127 |
| CENPC1 | NM_001812 | 4502778 | 1060 | D-003251-08 | CAAGAGAACACGTTTGAAA | 1128 |
| CENPE | | | | | | |
| CENPE | NM_001813 | 4502780 | 1062 | D-003252-05 | GAAGACAGCTCAAATAATA | 1129 |
| CENPE | NM_001813 | 4502780 | 1062 | D-003252-06 | CAACAAAGCTACTAAATCA | 1130 |
| CENPE | NM_001813 | 4502780 | 1062 | D-003252-07 | GGAAAGAAGTGCTACCATA | 1131 |
| CENPE | NM_001813 | 4502780 | 1062 | D-003252-08 | GGAAAGAAATGACACAGTT | 1132 |
| CENPF | | | | | | |
| CENPF | NM_016343 | 14670380 | 1063 | D-003253-05 | GCGAATATCTGAATTAGAA | 1133 |
| CENPF | NM_016343 | 14670380 | 1063 | D-003253-06 | GGAAATTAATGCATCCTTA | 1134 |
| CENPF | NM_016343 | 14670380 | 1063 | D-003253-07 | GAGCGAGGCTGGTGGTTTA | 1135 |
| CENPF | NM_016343 | 14670380 | 1063 | D-003253-08 | CAAGTCATCTTTCATCTAA | 1136 |
| CENPH | | | | | | |
| CENPH | NM_022909 | 21264590 | 64946 | D-003254-05 | GAAAGAAGAGATTGCAATT | 1137 |
| CENPH | NM_022909 | 21264590 | 64946 | D-003254-06 | CAGAACAAATTATGCAAGA | 1138 |
| CENPH | NM_022909 | 21264590 | 64946 | D-003254-07 | CTAGTGTGCTCATGGATAA | 1139 |
| CENPH | NM_022909 | 21264590 | 64946 | D-003254-08 | GAAACACCTATTAGAGCTA | 1140 |
| CHEK1 | | | | | | |
| CHEK1 | NM_001274 | 20127419 | 1111 | D-003255-05 | CAAATTGGATGCAGACAAA | 1141 |
| CHEK1 | NM_001274 | 20127419 | 1111 | D-003255-06 | GCAACAGTATTTCGGTATA | 1142 |
| CHEK1 | NM_001274 | 20127419 | 1111 | D-003255-07 | GGACTTCTCTCCAGTAAAC | 1143 |
| CHEK1 | NM_001274 | 20127419 | 1111 | D-003255-08 | AAAGATAGATGGTACAACA | 1144 |
| CHEK2 | | | | | | |
| CHEK2 | NM_007194 | 22209010 | 11200 | D-003256-02 | CTCTTACATTGCATACATA | 1145 |
| CHEK2 | NM_007194 | 22209010 | 11200 | D-003256-03 | TAAACGCCTGAAAGAAGCT | 1146 |

TABLE VIII-continued

| Gene Name | Acc# | GI | Locus Link | Duplex # | Full Sequence | SEQ. ID NO. |
|---|---|---|---|---|---|---|
| CHEK2 | NM_007194 | 22209010 | 11200 | D-003256-04 | GCATAGGACTCAAGTGTCA | 1147 |
| CHEK2 | NM_007194 | 22209010 | 11200 | D-003256-05 | GAAATTGCACTGTCACTAA | 1148 |
| CNK | | | | | | |
| CNK | NM_004073 | 4758015 | 1263 | D-003257-05 | GCGAGAAGATCCTAAATGA | 1149 |
| CNK | NM_004073 | 4758015 | 1263 | D-003257-07 | GCAAGTGGGTTGACTACTC | 1150 |
| CNK | NM_004073 | 4758015 | 1263 | D-003257-08 | GCACATCCGTTGGCCATCA | 1151 |
| CNK | NM_004073 | 4758015 | 1263 | D-003257-09 | GACCTCAAGTTGGGAAATT | 1152 |
| CRI1 | | | | | | |
| CRI1 | NM_014335 | 7656937 | 23741 | D-003258-05 | GTGATGAGATTATTGATAG | 1153 |
| CRI1 | NM_014335 | 7656937 | 23741 | D-003258-06 | GGACGAGGGCGAGGAATTT | 1154 |
| CRI1 | NM_014335 | 7656937 | 23741 | D-003258-07 | GGAAACGGAGCCTTGCTAA | 1155 |
| CRI1 | NM_014335 | 7656937 | 23741 | D-003258-08 | TCAATCGTCTGACCGAAGA | 1156 |
| E2F1 | | | | | | |
| E2F1 | NM_005225 | 12669910 | 1869 | D-003259-05 | GAACAGGGCCACTGACTCT | 1157 |
| E2F1 | NM_005225 | 12669910 | 1869 | D-003259-06 | TGGACCACCTGATGAATAT | 1158 |
| E2F1 | NM_005225 | 12669910 | 1869 | D-003259-07 | CCCAGGAGGTCACTTCTGA | 1159 |
| E2F1 | NM_005225 | 12669910 | 1869 | D-003259-08 | GGCTGGACCTGGAAACTGA | 1160 |
| E2F2 | | | | | | |
| E2F2 | NM_004091 | 34485718 | 1870 | D-003260-05 | GGGAGAAGACTCGGTATGA | 1161 |
| E2F2 | NM_004091 | 34485718 | 1870 | D-003260-06 | GAGGACAACCTGCAGATAT | 1162 |
| E2F2 | NM_004091 | 34485718 | 1870 | D-003260-07 | TGAAGGAGCTGATGAACAC | 1163 |
| E2F2 | NM_004091 | 34485718 | 1870 | D-003260-08 | CCAAGAAGTTCATTTACCT | 1164 |
| E2F3 | | | | | | |
| E2F3 | NM_001949 | 12669913 | 1871 | D-003261-05 | GAAATTAGATGAACTGATC | 1165 |
| E2F3 | NM_001949 | 12669913 | 1871 | D-003261-06 | TGAAGTGCCTGACTCAATA | 1166 |
| E2F3 | NM_001949 | 12669913 | 1871 | D-003261-07 | GAACAAGGCAGCAGAAGTG | 1167 |
| E2F3 | NM_001949 | 12669913 | 1871 | D-003261-08 | GAAACACACAGTCCAATGA | 1168 |
| E2F4 | | | | | | |
| E2F4 | NM_001950 | 12669914 | 1874 | D-003262-05 | GGAGATTGCTGACAAACTG | 1169 |
| E2F4 | NM_001950 | 12669914 | 1874 | D-003262-06 | GAAGGTATCGGGCTAATCG | 1170 |
| E2F4 | NM_001950 | 12669914 | 1874 | D-003262-07 | GTGCAGAAGTCCAGGGAAT | 1171 |
| E2F4 | NM_001950 | 12669914 | 1874 | D-003262-08 | GGACAGTGGTGAGCTCAGT | 1172 |
| E2F5 | | | | | | |
| E2F5 | NM_001951 | 12669916 | 1875 | D-003263-05 | GCAGATGACTACAACTTTA | 1173 |
| E2F5 | NM_001951 | 12669916 | 1875 | D-003263-06 | GACATCAGCTACAGATATA | 1174 |
| E2F5 | NM_001951 | 12669916 | 1875 | D-003263-07 | CAACATGTCTCTGAAAGAA | 1175 |
| E2F5 | NM_001951 | 12669916 | 1875 | D-003263-08 | GAAGACATCTGTAATTGCT | 1176 |

TABLE VIII-continued

| Gene Name | Acc# | GI | Locus Link | Duplex # | Full Sequence | SEQ. ID NO. |
|---|---|---|---|---|---|---|
| E2F6 | | | | | | |
| E2F6 | NM_001952 | 12669917 | 1876 | D-003264-05 | TAAACAAGGTTGCAACGAA | 1177 |
| E2F6 | NM_001952 | 12669917 | 1876 | D-003264-06 | TAGCATATGTGACCTATCA | 1178 |
| E2F6 | NM_001952 | 12669917 | 1876 | D-003264-07 | GAAACCAGATTGGATGTTC | 1179 |
| E2F6 | NM_001952 | 12669917 | 1876 | D-003264-09 | GGAACTTTCTGACTTATCA | 1180 |
| FOS | | | | | | |
| FOS | NM_005252 | 6552332 | 2353 | D-003265-05 | GGGATAGCCTCTCTTACTA | 1181 |
| FOS | NM_005252 | 6552332 | 2353 | D-003265-06 | GAACAGTTATCTCCAGAAG | 1182 |
| FOS | NM_005252 | 6552332 | 2353 | D-003265-07 | GGAGACAGACCAACTAGAA | 1183 |
| FOS | NM_005252 | 6552332 | 2353 | D-003265-08 | AGACCGAGCCCTTTGATGA | 1184 |
| HIPK2 | | | | | | |
| HIPK2 | NM_022740 | 13430859 | 28996 | D-003266-06 | GAGAATCACTCCAATCGAA | 1185 |
| HIPK2 | NM_022740 | 13430859 | 28996 | D-003266-07 | AGACAGGGATTAAGTCAAA | 1186 |
| HIPK2 | NM_022740 | 13430859 | 28996 | D-003266-08 | GGACAAAGACAACTAGGTT | 1187 |
| HIPK2 | NM_022740 | 13430859 | 28996 | D-003266-09 | GCACACACGTCAAATCATG | 1188 |
| HUS1 | | | | | | |
| HUS1 | NM_004507 | 31077213 | 3364 | D-003267-05 | ACAAAGGCCTTATGCAATA | 1189 |
| HUS1 | NM_004507 | 31077213 | 3364 | D-003267-06 | GAAGTGCACATAGATATTA | 1190 |
| HUS1 | NM_004507 | 31077213 | 3364 | D-003267-07 | AAGCTTAACTTCATCCTTT | 1191 |
| HUS1 | NM_004507 | 31077213 | 3364 | D-003267-08 | GAACTTCTTCAACGAATTT | 1192 |
| JUN | | | | | | |
| JUN | NM_002228 | 7710122 | 3725 | D-003268-05 | TGGAAACGACCTTCTATGA | 1193 |
| JUN | NM_002228 | 7710122 | 3725 | D-003268-06 | GAACTGCACAGCCAGAACA | 1194 |
| JUN | NM_002228 | 7710122 | 3725 | D-003268-07 | GAGCTGGAGCGCCTGATAA | 1195 |
| JUN | NM_002228 | 7710122 | 3725 | D-003268-08 | TAACGCAGCAGTTGCAAAC | 1196 |
| JUNB | | | | | | |
| JUNB | NM_002229 | 4504808 | 3726 | D-003269-05 | GCATCAAAGTGGAGCGCAA | 1197 |
| JUNB | NM_002229 | 4504808 | 3726 | D-003269-06 | TGGAAGACCAAGAGCGCAT | 1198 |
| JUNB | NM_002229 | 4504808 | 3726 | D-003269-07 | CATACACAGCTACGGGATA | 1199 |
| JUNB | NM_002229 | 4504808 | 3726 | D-003269-08 | CCATCAACATGGAAGACCA | 1200 |
| LOC51053 | | | | | | |
| LOC51053 | NM_015895 | 20127542 | 51053 | D-003270-05 | GGAGAAAGGCGCTGTATGA | 1201 |
| LOC51053 | NM_015895 | 20127542 | 51053 | D-003270-06 | GAATAGTTCTGTCCCAAGA | 1202 |
| LOC51053 | NM_015895 | 20127542 | 51053 | D-003270-07 | GAACATGTACAGTATATGG | 1203 |
| LOC51053 | NM_015895 | 20127542 | 51053 | D-003270-08 | GCAGAAACAAGAAGAAATC | 1204 |
| MAD2L1 | | | | | | |
| MAD2L1 | NM_002358 | 6466452 | 4085 | D-003271-05 | GAAAGATGGCAGTTTGATA | 1205 |
| MAD2L1 | NM_002358 | 6466452 | 4085 | D-003271-06 | TAAATAATGTGGTGGAACA | 1206 |

TABLE VIII-continued

| Gene Name | Acc# | GI | Locus Link | Duplex # | Full Sequence | SEQ. ID NO. |
|---|---|---|---|---|---|---|
| MAD2L1 | NM_002358 | 6466452 | 4085 | D-003271-07 | GAAATCCGTTCAGTGATCA | 1207 |
| MAD2L1 | NM_002358 | 6466452 | 4085 | D-003271-08 | TTACTCGAGTGCAGAAATA | 1208 |
| MAD2L2 | | | | | | |
| MAD2L2 | NM_006341 | 6006019 | 10459 | D-003272-05 | GGAAGAGCGCGCTCATAAA | 1209 |
| MAD2L2 | NM_006341 | 6006019 | 10459 | D-003272-06 | TGGAAGAGCGCGCTCATAA | 1210 |
| MAD2L2 | NM_006341 | 6006019 | 10459 | D-003272-07 | AGCCACTCCTGGAGAAGAA | 1211 |
| MAD2L2 | NM_006341 | 6006019 | 10459 | D-003272-08 | TGGAGAAATTCGTCTTTGA | 1212 |
| MCM2 | | | | | | |
| MCM2 | NM_004526 | 33356546 | 4171 | D-003273-05 | GAAGATCTTTGCCAGCATT | 1213 |
| MCM2 | NM_004526 | 33356546 | 4171 | D-003273-06 | GGATAAGGCTCGTCAGATC | 1214 |
| MCM2 | NM_004526 | 33356546 | 4171 | D-003273-07 | CAGAGCAGGTGACATATCA | 1215 |
| MCM2 | NM_004526 | 33356546 | 4171 | D-003273-08 | GCCGTGGGCTCCTGTATGA | 1216 |
| MCM3 | | | | | | |
| MCM3 | NM_002388 | 33356548 | 4172 | D-003274-05 | GGACATCAATATTCTTCTA | 1217 |
| MCM3 | NM_002388 | 33356548 | 4172 | D-003274-06 | GCCAGGACATCTCCAGTTA | 1218 |
| MCM3 | NM_002388 | 33356548 | 4172 | D-003274-07 | GCAGGTATGACCAGTATAA | 1219 |
| MCM3 | NM_002388 | 33356548 | 4172 | D-003274-08 | GGAAATGCCTCAAGTACAC | 1220 |
| MCM4 | | | | | | |
| MCM4 | XM_030274 | 22047061 | 4173 | D-003275-05 | GGACATATCTATTCTTACT | 1221 |
| MCM4 | XM_030274 | 22047061 | 4173 | D-003275-06 | GATGTTAGTTCACCACTGA | 1222 |
| MCM4 | XM_030274 | 22047061 | 4173 | D-003275-07 | CCAGCTGCCTCATACTTTA | 1223 |
| MCM4 | XM_030274 | 22047061 | 4173 | D-003275-08 | GAAAGTACAAGATCGGTAT | 1224 |
| MCM5 | | | | | | |
| MCM5 | NM_006739 | 23510447 | 4174 | D-003276-05 | GAAGATCCCTGGCATCATC | 1225 |
| MCM5 | NM_006739 | 23510447 | 4174 | D-003276-06 | GAACAGGGTTACCATCATG | 1226 |
| MCM5 | NM_006739 | 23510447 | 4174 | D-003276-07 | GGACAACATTGACTTCATG | 1227 |
| MCM5 | NM_006739 | 23510447 | 4174 | D-003276-08 | CCAAGGAGGTAGCTGATGA | 1228 |
| MCM6 | | | | | | |
| MCM6 | NM_005915 | 33469920 | 4175 | D-003277-05 | GGAAAGAGCTCAGAGATGA | 1229 |
| MCM6 | NM_005915 | 33469920 | 4175 | D-003277-06 | GAGCAGCGATGGAGAAATT | 1230 |
| MCM6 | NM_005915 | 33469920 | 4175 | D-003277-07 | GGAAACACCTGATGTCAAT | 1231 |
| MCM6 | NM_005915 | 33469920 | 4175 | D-003277-08 | CCAAACATCTGCCGAAATC | 1232 |
| MCM7 | | | | | | |
| MCM7 | NM_005916 | 33469967 | 4176 | D-003278-05 | GGAAATATCCCTCGTAGTA | 1233 |
| MCM7 | NM_005916 | 33469967 | 4176 | D-003278-06 | GGAAGAAGCAGTTCAAGTA | 1234 |
| MCM7 | NM_005916 | 33469967 | 4176 | D-003278-07 | CAACAAGCCTCGTGTGATC | 1235 |
| MCM7 | NM_005916 | 33469967 | 4176 | D-003278-08 | GGAGAGAACACAAGGATTG | 1236 |

TABLE VIII-continued

| Gene Name | Acc# | GI | Locus Link | Duplex # | Full Sequence | SEQ. ID NO. |
|---|---|---|---|---|---|---|
| MDM2 | | | | | | |
| MDM2 | NM_002392 | 4505136 | 4193 | D-003279-05 | GGAGATATGTTGTGAAAGA | 1237 |
| MDM2 | NM_002392 | 4505136 | 4193 | D-003279-06 | CCACAAATCTGATAGTATT | 1238 |
| MDM2 | NM_002392 | 4505136 | 4193 | D-003279-07 | GATGAGGTATATCAAGTTA | 1239 |
| MDM2 | NM_002392 | 4505136 | 4193 | D-003279-08 | GGAAGAAACCCAAGACAAA | 1240 |
| MKI67 | | | | | | |
| MKI67 | NM_002417 | 19923216 | 4288 | D-003280-05 | GCACAAAGCTTGGTTATAA | 1241 |
| MKI67 | NM_002417 | 19923216 | 4288 | D-003280-06 | CCTAAGACCTGAACTATTT | 1242 |
| MKI67 | NM_002417 | 19923216 | 4288 | D-003280-07 | CAAAGAGGAACACAAATTA | 1243 |
| MKI67 | NM_002417 | 19923216 | 4288 | D-003280-08 | GTAAATGGGTCTGTTATTG | 1244 |
| MNAT1 | | | | | | |
| MNAT1 | NM_002431 | 4505224 | 4331 | D-003281-05 | GGAAGAAGCTTTAGAAGTG | 1245 |
| MNAT1 | NM_002431 | 4505224 | 4331 | D-003281-06 | TAGATGAGCTGGAGAGTTC | 1246 |
| MNAT1 | NM_002431 | 4505224 | 4331 | D-003281-07 | GGACCTTGCTGGAGGCTAT | 1247 |
| MNAT1 | NM_002431 | 4505224 | 4331 | D-003281-08 | GCAGATAGAGACATATGGA | 1248 |
| MYC | | | | | | |
| MYC | NM_,00246 | 73154321 | 54609 | D-003282-05 | CAGAGAAGCTGGCCTCCTA | 1249 |
| MYC | NM_002467 | 31543215 | 4609 | D-003282-06 | GAAACGACGAGAACAGTTG | 1250 |
| MYC | NM_002467 | 31543215 | 4609 | D-003282-07 | CGACGAGACCTTCATCAAA | 1251 |
| MYC | NM_002467 | 31543215 | 4609 | D-003282-08 | CCACACATCAGCACAACTA | 1252 |
| ORC1L | | | | | | |
| ORC1L | NM_004153 | 31795543 | 4998 | D-003283-05 | GAACAGGAATTCCAAGACA | 1253 |
| ORC1L | NM_004153 | 31795543 | 4998 | D-003283-06 | TAAGAAACGTGCTCGAGTA | 1254 |
| ORC1L | NM_004153 | 31795543 | 4998 | D-003283-07 | GAGATCACCTCACCTTCTA | 1255 |
| ORC1L | NM_004153 | 31795543 | 4998 | D-003283-08 | GCAGAGAGCCCTTCTTGGA | 1256 |
| ORC2L | | | | | | |
| ORC2L | NM_006190 | 32454751 | 4999 | D-003284-05 | GAAGAAACCTCCTATGAGA | 1257 |
| ORC2L | NM_006190 | 32454751 | 4999 | D-003284-06 | GAAGGGAACTGATGGAGTA | 1258 |
| ORC2L | NM_006190 | 32454751 | 4999 | D-003284-07 | GAAGAATGATCCTGAGATT | 1259 |
| ORC2L | NM_006190 | 32454751 | 4999 | D-003284-08 | GAAGAGATGTTCAAGAATC | 1260 |
| ORC3L | | | | | | |
| ORC3L | NM_012381 | 32483366 | 23595 | D-003285-05 | GGACTGCTGTGTAGATATA | 1261 |
| ORC3L | NM_012381 | 32483366 | 23595 | D-003285-06 | GAACTGATGACCATACTTG | 1262 |
| ORC3L | NM_012381 | 32483366 | 23595 | D-003285-07 | AAAGATCTCTCTGCCAATA | 1263 |
| ORC3L | NM_012381 | 32483366 | 23595 | D-003285-08 | CAGCACAGCTAAGAGAATA | 1264 |
| ORC4L | | | | | | |
| ORC4L | NM_002552 | 32454749 | 5000 | D-003286-06 | GAAAGCACATTCCGTTTAT | 1265 |
| ORC4L | NM_002552 | 32454749 | 5000 | D-003286-07 | TGAAAGAACTCATGGAAAT | 1266 |

TABLE VIII-continued

| Gene Name | Acc# | GI | Locus Link | Duplex # | Full Sequence | SEQ. ID NO. |
|---|---|---|---|---|---|---|
| ORC4L | NM_002552 | 32454749 | 5000 | D-003286-08 | GCTGAGAAGTGGAATGAAA | 1267 |
| ORC4L | NM_002552 | 32454749 | 5000 | D-003286-09 | CCAGTGATCTTCATATTAG | 1268 |
| ORC5L | | | | | | |
| ORC5L | NM_002553 | 32454752 | 5001 | D-003287-05 | GAAATAACCTGTGAAACAT | 1269 |
| ORC5L | NM_002553 | 32454752 | 5001 | D-003287-06 | CAGATTACCTCTCTAGTGA | 1270 |
| ORC5L | NM_002553 | 32454752 | 5001 | D-003287-07 | GAACTTCCATATTACTCTA | 1271 |
| ORC5L | NM_002553 | 32454752 | 5001 | D-003287-08 | GTATTCAGCTGATTTCTAT | 1272 |
| ORC6L | | | | | | |
| ORC6L | NM_014321 | 32454755 | 23594 | D-003288-05 | GAACATGGCTTCAAAGATA | 1273 |
| ORC6L | NM_014321 | 32454755 | 23594 | D-003288-06 | GGACAGGGCTTATTTAATT | 1274 |
| ORC6L | NM_014321 | 32454755 | 23594 | D-003288-07 | GAAAGAAGATAGTGGTTGA | 1275 |
| ORC6L | NM_014321 | 32454755 | 23594 | D-003288-08 | TATCAGAGCTGTCTTAAAT | 1276 |
| PCNA | | | | | | |
| PCNA | NM_002592 | 33239449 | 5111 | D-003289-05 | GATCGAGGATGAAGAAGGA | 1277 |
| PCNA | NM_002592 | 33239449 | 5111 | D-003289-07 | GCCGAGATCTCAGCCATAT | 1278 |
| PCNA | NM_002592 | 33239449 | 5111 | D-003289-09 | GAGGCCTGCTGGGATATTA | 1279 |
| PCNA | NM_002592 | 33239449 | 5111 | D-003289-10 | GTGGAGAACTTGGAAATGG | 1280 |
| PLK | | | | | | |
| PLK | NM_005030 | 21359872 | 5347 | D-003290-05 | CAACCAAAGTCGAATATGA | 1281 |
| PLK | NM_005030 | 21359872 | 5347 | D-003290-06 | CAAGAAGAATGAATACAGT | 1282 |
| PLK | NM_005030 | 21359872 | 5347 | D-003290-07 | GAAGATGTCCATGGAAATA | 1283 |
| PLK | NM_005030 | 21359872 | 5347 | D-003290-08 | CAACACGCCTCATCCTCTA | 1284 |
| PIN1 | | | | | | |
| PIN1 | NM_006221 | 5453897 | 5300 | D-003291-05 | GGACCAAGGAGGAGGCCCT | 1285 |
| PIN1 | NM_006221 | 5453897 | 5300 | D-003291-06 | CGTCCTGGCGGCAGGAGAA | 1286 |
| PIN1 | NM_006221 | 5453897 | 5300 | D-003291-07 | CGGGAGAGGAGGACTTTGA | 1287 |
| PIN1 | NM_006221 | 5453897 | 5300 | D-003291-08 | AGTCGGGAGAGGAGGACTT | 1288 |
| PIN1L | | | | | | |
| PIN1L | NM_006222 | 5453899 | 5301 | D-003292-06 | CGACCTGGCGGCAGGAAAT | 1289 |
| PIN1L | NM_006222 | 5453899 | 5301 | D-003292-07 | AGGCAGGAGAGAAGGACTT | 1290 |
| PIN1L | NM_006222 | 5453899 | 5301 | D-003292-08 | GCTACATCCAGAAGATCAA | 1291 |
| PIN1L | NM_006222 | 5453899 | 5301 | D-003292-09 | GGACAGTGTTCACGGATTC | 1292 |
| RAD1 | | | | | | |
| RAD1 | NM_002853 | 19718797 | 5810 | D-003293-05 | GAAGATGGACAAATATGTT | 1293 |
| RAD1 | NM_002853 | 19718797 | 5810 | D-003293-06 | GGAAGAGTCTGTTACTTTT | 1294 |
| RAD1 | NM_002853 | 19718797 | 5810 | D-003293-07 | GATAACAGAGGCTTCCTTT | 1295 |
| RAD1 | NM_002853 | 19718797 | 5810 | D-003293-08 | GCATTAGTCCTATCTTGTA | 1296 |

TABLE VIII-continued

| Gene Name | Acc# | GI | Locus Link | Duplex # | Full Sequence | SEQ. ID NO. |
|---|---|---|---|---|---|---|
| RAD17 | | | | | | |
| RAD17 | NM_133338 | 19718783 | 5884 | D-003294-05 | GAATCAAGCTTCCATATGT | 1297 |
| RAD17 | NM_133338 | 19718783 | 5884 | D-003294-06 | CAACAAAGCCCGAGGATAT | 1298 |
| RAD17 | NM_133338 | 19718783 | 5884 | D-003294-07 | ACACATGCCTGGAGACTTA | 1299 |
| RAD17 | NM_133338 | 19718783 | 5884 | D-003294-08 | CTACATAGATTTCTTCATG | 1300 |
| RAD9A | | | | | | |
| RAD9A | NM_004584 | 19924112 | 5883 | D-003295-05 | TCAGCAAACTTGAATCTTA | 1301 |
| RAD9A | NM_004584 | 19924112 | 5883 | D-003295-06 | GACATTGACTCTTACATGA | 1302 |
| RAD9A | NM_004584 | 19924112 | 5883 | D-003295-08 | GGAAACCACTATAGGCAAT | 1303 |
| RAD9A | NM_004584 | 19924112 | 5883 | D-003295-09 | CGGACGACTTTGCCAATGA | 1304 |
| RB1 | | | | | | |
| RB1 | NM_000321 | 19924112 | 5925 | D-003296-05 | GAAAGGACATGTGAACTTA | 1305 |
| RB1 | NM_000321 | 19924112 | 5925 | D-003296-06 | GAAGAAGTATGATGTATTG | 1306 |
| RB1 | NM_000321 | 4506434 | 5925 | D-003296-07 | GAAATGACTTCTACTCGAA | 1307 |
| RB1 | NM_000321 | 4506434 | 5925 | D-003296-08 | GGAGGGAACATCTATATTT | 1308 |
| RBBP2 | | | | | | |
| RBBP2 | NM_005056 | 4826967 | 5927 | D-003297-05 | CAAAGAAGCTGAATAAACT | 1309 |
| RBBP2 | NM_005056 | 4826967 | 5927 | D-003297-06 | CAACACATATGGCGGATTT | 1310 |
| RBBP2 | NM_005056 | 4826967 | 5927 | D-003297-07 | GGACAAACCTAGAAAGAAG | 1311 |
| RBBP2 | NM_005056 | 4826967 | 5927 | D-003297-08 | GAAAGGCACTCTCTCTGTT | 1312 |
| RBL1 | | | | | | |
| RBL1 | NM_002895 | 34577078 | 5933 | D-003298-05 | CAAGAGAAGTTGTGGCATA | 1313 |
| RBL1 | NM_002895 | 34577078 | 5933 | D-003298-06 | CAGCAGCACTCCATTTATA | 1314 |
| RBL1 | NM_002895 | 34577078 | 5933 | D-003298-07 | ACAGAAAGGTCTATCATTT | 1315 |
| RBL1 | NM_002895 | 34577078 | 5933 | D-003298-08 | GGACATAAAGTTACAATTC | 1316 |
| RBL2 | | | | | | |
| RBL2 | NM_005611 | 21361291 | 5934 | D-003299-05 | GAGCAGAGCTTAATCGAAT | 1317 |
| RBL2 | NM_005611 | 21361291 | 5934 | D-003299-06 | GAGAATAGCCCTTGTGTGA | 1318 |
| RBL2 | NM_005611 | 21361291 | 5934 | D-003299-07 | GGACTTAGTTTATGGAAAT | 1319 |
| RBL2 | NM_005611 | 21361291 | 5934 | D-003299-08 | GAATTTAGATGAGCGGATA | 1320 |
| RBP1 | | | | | | |
| RBP1 | NM_002899 | 8400726 | 5947 | D-003300-05 | GAGACAAGCTCCAGTGTGT | 1321 |
| RBP1 | NM_002899 | 8400726 | 5947 | D-003300-06 | GCAAGCAAGTATTCAAGAA | 1322 |
| RBP1 | NM_002899 | 8400726 | 5947 | D-003300-07 | GCAGGACGGTGACCATATG | 1323 |
| RBP1 | NM_002899 | 8400726 | 5947 | D-003300-08 | GCAAGTGCATGACAACAGT | 1324 |
| RPA3 | | | | | | |
| RPA3 | NM_002947 | 19923751 | 6119 | D-003322-05 | GGAAGTGGTTGGAAGAGTA | 1325 |
| RPA3 | NM_002947 | 19923751 | 6119 | D-003322-06 | GAAGATAGCCATCCTTTTG | 1326 |
| RPA3 | NM_002947 | 19923751 | 6119 | D-003322-07 | CATGCTAGCTCAATTCATC | 1327 |
| RPA3 | NM_002947 | 19923751 | 6119 | D-003322-08 | GATCTTGGACTTTACAATG | 1328 |

TABLE VIII-continued

| Gene Name | Acc# | GI | Locus Link | Duplex # | Full Sequence | SEQ. ID NO. |
|---|---|---|---|---|---|---|
| SKP1A | | | | | | |
| SKP1A | NM_006930 | 25777710 | 6500 | D-003323-05 | GGAGAGATATTTGAAGTTG | 1329 |
| SKP1A | NM_006930 | 25777710 | 6500 | D-003323-06 | GGGAATGGATGATGAAGGA | 1330 |
| SKP1A | NM_006930 | 25777710 | 6500 | D-003323-07 | CAAACAATCTGTGACTATT | 1331 |
| SKP1A | NM_006930 | 25777710 | 6500 | D-003323-08 | TCAATTAAGTTGCAGAGTT | 1332 |
| SKP2 | | | | | | |
| SKP2 | NM_005983 | 16306594 | 6502 | D-003324-05 | CATCTAGACTTAAGTGATA | 1333 |
| SKP2 | NM_005983 | 16306594 | 6502 | D-003324-06 | GAAATCAGATCTCTCTACT | 1334 |
| SKP2 | NM_005983 | 16306594 | 6502 | D-003324-07 | CTAAAGGTCTCTGGTGTTT | 1335 |
| SKP2 | NM_005983 | 16306594 | 6502 | D-003324-08 | GATGGTACCCTTCAACTGT | 1336 |
| SNK | | | | | | |
| SNK | NM_006622 | 5730054 | 10769 | D-003325-05 | GAAGACATCTACAAGCTTA | 1337 |
| SNK | NM_006622 | 5730054 | 10769 | D-003325-06 | GAAATACCTTCATGAACAA | 1338 |
| SNK | NM_006622 | 5730054 | 10769 | D-003325-07 | GAAGGTCAATGGCTCATAT | 1339 |
| SNK | NM_006622 | 5730054 | 10769 | D-003325-08 | CCGGAGATCTCGCGGATTA | 1340 |
| STK12 | | | | | | |
| STK12 | NM_004217 | 4759177 | 9212 | D-003326-07 | CAGAAGAGCTGCACATTTG | 1341 |
| STK12 | NM_004217 | 4759177 | 9212 | D-003326-08 | CCAAACTGCTCAGGCATAA | 1342 |
| STK12 | NM_004217 | 4759177 | 9212 | D-003326-09 | ACGCGGCACTTCACAATTG | 1343 |
| STK12 | NM_004217 | 4759177 | 9212 | D-003326-10 | TGGGACACCCGACATCTTA | 1344 |
| TFDP1 | | | | | | |
| TFDP1 | NM_007111 | 34147667 | 7027 | D-003327-05 | GGAAGCAGCTCTTGCCAAA | 1345 |
| TFDP1 | NM_007111 | 34147667 | 7027 | D-003327-06 | GAGGAGACTTGAAAGAATA | 1346 |
| TFDP1 | NM_007111 | 34147667 | 7027 | D-003327-07 | GAACTTAGAGGTGGAAAGA | 1347 |
| TFDP1 | NM_007111 | 34147667 | 7027 | D-003327-08 | GCGAGAAGGTGCAGAGGAA | 1348 |
| TFDP2 | | | | | | |
| TFDP2 | NM_006286 | 5454111 | 7029 | D-003328-05 | GAAAGTGTGTGAGAAAGTT | 1349 |
| TFDP2 | NM_006286 | 5454111 | 7029 | D-003328-06 | CACAGGACCTTCTTGGTTA | 1350 |
| TFDP2 | NM_006286 | 5454111 | 7029 | D-003328-07 | CGAAATCCCTGGTGCCAAA | 1351 |
| TFDP2 | NM_006286 | 5454111 | 7029 | D-003328-08 | TGAGATCCATGATGACATA | 1352 |
| TP53 | | | | | | |
| TP53 | NM_000546 | 8400737 | 7157 | D-003329-05 | GAGGTTGGCTCTGACTGTA | 1353 |
| TP53 | NM_000546 | 8400737 | 7157 | D-003329-06 | CAGTCTACCTCCCGCCATA | 1354 |
| TP53 | NM_000546 | 8400737 | 7157 | D-003329-07 | GCACAGAGGAAGAGAATCT | 1355 |
| TP53 | NM_000546 | 8400737 | 7157 | D-003329-08 | GAAGAAACCACTGGATGGA | 1356 |
| TP63 | | | | | | |
| TP63 | NM_003722 | 31543817 | 8626 | D-003330-05 | CATCATGTCTGGACTATTT | 1357 |
| TP63 | NM_003722 | 31543817 | 8626 | D-003330-06 | CAAACAAGATTGAGATTAG | 1358 |

TABLE VIII-continued

| Gene Name | Acc# | GI | Locus Link | Duplex # | Full Sequence | SEQ. ID NO. |
|---|---|---|---|---|---|---|
| TP63 | NM_003722 | 31543817 | 8626 | D-003330-07 | GCACACAGACAAATGAATT | 1359 |
| TP63 | NM_003722 | 31543817 | 8626 | D-003330-08 | CGACAGTCTTGTACAATTT | 1360 |
| TP73 | | | | | | |
| TP73 | NM_005427 | 4885644 | 7161 | D-003331-05 | GCAAGCAGCCCATCAAGGA | 1361 |
| TP73 | NM_005427 | 4885644 | 7161 | D-003331-06 | GAGACGAGGACACGTACTA | 1362 |
| TP73 | NM_005427 | 4885644 | 7161 | D-003331-07 | CTGCAGAACCTGACCATTG | 1363 |
| TP73 | NM_005427 | 4885644 | 7161 | D-003331-08 | GGCCATGCCTGTTTACAAG | 1364 |
| YWHAZ | | | | | | |
| YWHAZ | NM_003406 | 21735623 | 7534 | D-003332-05 | GCAAGGAGCTGAATTATCC | 1365 |
| YWHAZ | NM_003406 | 21735623 | 7534 | D-003332-06 | TAAGAGATATCTGCAATGA | 1366 |
| YWHAZ | NM_003406 | 21735623 | 7534 | D-003332-07 | GACGGAAGGTGCTGAGAAA | 1367 |
| YWHAZ | NM_003406 | 21735623 | 7534 | D-003332-08 | AGAGCAAAGTCTTCTATTT | 1368 |

TABLE IX

| Gene Name | Accession # | GI# | Duplex # | Sequence | SEQ. ID NO. |
|---|---|---|---|---|---|
| AR | NM_000044 | 21322251 | D-003400-01 | GGAACTCGATCGTATCATT | 1369 |
| AR | NM_000044 | 21322251 | D-003400-02 | CAAGGGAGGTTACACCAAA | 1370 |
| AR | NM_000044 | 21322251 | D-003400-03 | TCAAGGAACTCGATCGTAT | 1371 |
| AR | NM_000044 | 21322251 | D-003400-04 | GAAATGATTGCACTATTGA | 1372 |
| ESR1 | NM_000125 | 4503602 | D-003401-01 | GAATGTGCCTGGCTAGAGA | 1373 |
| ESR1 | NM_000125 | 4503602 | D-003401-02 | CATGAGAGCTGCCAACCTT | 1374 |
| ESR1 | NM_000125 | 4503602 | D-003401-03 | AGAGAAAGATTGGCCAGTA | 1375 |
| ESR1 | NM_000125 | 4503602 | D-003401-04 | CAAGGAGACTCGCTACTGT | 1376 |
| ESR2 | NM_001437 | 10835012 | D-003402-01 | GAACATCTGCTCAACATGA | 1377 |
| ESR2 | NM_001437 | 10835012 | D-003402-02 | GCACGGCTCCATATACATA | 1378 |
| ESR2 | NM_001437 | 10835012 | D-003402-03 | CAAGAAGATTCCCGGCTTT | 1379 |
| ESR2 | NM_001437 | 10835012 | D-003402-04 | GGAAATGCGTAGAAGGAAT | 1380 |
| ESRRA | NM_004451 | 18860919 | D-003403-01 | GGCCTTCGCTGAGGACTTA | 1381 |
| ESRRA | NM_004451 | 18860919 | D-003403-02 | TGAATGCACTGGTGTCTCA | 1382 |
| ESRRA | NM_004451 | 18860919 | D-003403-03 | GCATTGAGCCTCTCTACAT | 1383 |
| ESRRA | NM_004451 | 18860919 | D-003403-04 | CCAGACAGCGGGCAAAGTG | 1384 |
| ESRRB | NM_004452 | 22035686 | D-003404-01 | TACCTGAGCTTACAAATTT | 1385 |
| ESRRB | NM_004452 | 22035686 | D-003404-02 | GCACTTCTATAGCGTCAAA | 1386 |
| ESRRB | NM_004452 | 22035686 | D-003404-03 | CAACTCCGATTCCATGTAC | 1387 |
| ESRRB | NM_004452 | 22035686 | D-003404-04 | GGACTCGCCACCCATGTTT | 1388 |
| ESRRG | NM_001438 | 4503604 | D-003405-01 | AAACAAAGATCGACACATT | 1389 |
| ESRRG | NM_001438 | 4503604 | D-003405-02 | TCAGGAAACTGTATGATGA | 1390 |
| ESRRG | NM_001438 | 4503604 | D-003405-03 | GAAGACCAGTCCAAATTAG | 1391 |
| ESRRG | NM_001438 | 4503604 | D-003405-04 | ATGAAGCGCTGCAGGATTA | 1392 |
| HNF4A | NM_000457 | 21361184 | D-003406-01 | CGACATCACTGGAGCATAT | 1393 |
| HNF4A | NM_000457 | 21361184 | D-003406-02 | GAAGGAAGCCGTCCAGAAT | 1394 |
| HNF4A | NM_000457 | 21361184 | D-003406-03 | CCAAGTACATCCCAGCTTT | 1395 |
| HNF4A | NM_000457 | 21361184 | D-003406-04 | GGACATGGCCGACTACAGT | 1396 |
| HNF4G | NM_004133 | 6631087 | D-003407-01 | GCACTGACATAAACGTTAA | 1397 |
| HNF4G | NM_004133 | 6631087 | D-003407-02 | ACAAAGAGATCCATGATGT | 1398 |
| HNF4G | NM_004133 | 6631087 | D-003407-03 | AGAGATCCATGATGTATAA | 1399 |
| HNF4G | NM_004133 | 6631087 | D-003407-04 | AAATGAACGTGACAGAATA | 1400 |
| HSAJ2425 | NM_017532 | 8923776 | D-003408-01 | GAATGAATCTACACCTTTG | 1401 |
| HSAJ2425 | NM_017532 | 8923776 | D-003408-02 | GGAAATACGTGGAGACACT | 1402 |
| HSAJ2425 | NM_017532 | 8923776 | D-003408-03 | CCAGATAACTACGGCGATA | 1403 |
| HSAJ2425 | NM_017532 | 8923776 | D-003408-04 | TGGCGTACCTTCTCATTGA | 1404 |

TABLE IX-continued

| Gene Name | Accession # | GI# | Duplex # | Sequence | SEQ. ID NO. |
|---|---|---|---|---|---|
| NR0B1 | NM_000475 | 5016089 | D-003409-01 | CAGCATGGATGATATGATG | 1405 |
| NR0B1 | NM_000475 | 5016089 | D-003409-02 | CTGCTGAGATTCATCAATG | 1406 |
| NR0B1 | NM_000475 | 5016089 | D-003409-03 | ACAGATTCATCGAACTTAA | 1407 |
| NR0B1 | NM_000475 | 5016089 | D-003409-04 | GAACGTGGCGCTCCTGTAC | 1408 |
| NR0B2 | NM_021969 | 13259502 | D-003410-01 | GAATATGCCTGCCTGAAAG | 1409 |
| NR0B2 | NM_021969 | 13259502 | D-003410-02 | GGAATATGCCTGCCTGAAA | 1410 |
| NR0B2 | NM_021969 | 13259502 | D-003410-03 | CGTAGCCGCTGCCTATGTA | 1411 |
| NR0B2 | NM_021969 | 13259502 | D-003410-04 | GCCATTCTCTACGCACTTC | 1412 |
| NR1D1 | NM_021724 | 13430847 | D-003411-01 | CAACACAGGTGGCGTCATC | 1413 |
| NR1D1 | NM_021724 | 13430847 | D-003411-02 | GGCATGGTGTTACTGTGTA | 1414 |
| NR1D1 | NM_021724 | 13430847 | D-003411-03 | CAACATGCATTCCGAGAAG | 1415 |
| NR1D1 | NM_021724 | 13430847 | D-003411-04 | GCGCTTTGCTTCGTTGTTC | 1416 |
| NR1H2 | NM_007121 | 11321629 | D-003412-01 | GAACAGATCCGGAAGAAGA | 1417 |
| NR1H2 | NM_007121 | 11321629 | D-003412-02 | GAAGAACAGATCCGGAAGA | 1418 |
| NR1H2 | NM_007121 | 11321629 | D-003412-03 | CTAAGCAAGTGCCTGGTTT | 1419 |
| NR1H2 | NM_007121 | 11321629 | D-003412-04 | GCTAACAGCGGCTCAAGAA | 1420 |
| NR1H3 | NM_005693 | 5031892 | D-003413-01 | GAACAGATCCGCCTGAAGA | 1421 |
| NR1H3 | NM_005693 | 5031892 | D-003413-02 | GGAGATAGTTGACTTTGCT | 1422 |
| NR1H3 | NM_005693 | 5031892 | D-003413-03 | GAGTTTGCCTTGCTCATTG | 1423 |
| NR1H3 | NM_005693 | 5031892 | D-003413-04 | TGACTTTGCTAAACAGCTA | 1424 |
| NR1H4 | NM_005123 | 4826979 | D-003414-01 | CAAGTGACCTCGACAACAA | 1425 |
| NR1H4 | NM_005123 | 4826979 | D-003414-02 | GAAAGAATTCGAAATAGTG | 1426 |
| NR1H4 | NM_005123 | 4826979 | D-003414-03 | CAACAGACTCTTCTACATT | 1427 |
| NR1H4 | NM_005123 | 4826979 | D-003414-04 | GAACCATACTCGCAATACA | 1428 |
| NR1I2 | NM_003889 | 11863133 | D-003415-01 | GAACCATGCTGACTTTGTA | 1429 |
| NR1I2 | NM_003889 | 11863133 | D-003415-02 | GATGGACGCTCAGATGAAA | 1430 |
| NR1I2 | NM_003889 | 11863133 | D-003415-03 | CAACCTACATGTTCAAAGG | 1431 |
| NR1I2 | NM_003889 | 11863133 | D-003415-04 | CAGGAGCAATTCGCCATTA | 1432 |
| NR1I3 | NM_005122 | 4826660 | D-003416-01 | GGAAATCTGTCACATCGTA | 1433 |
| NR1I3 | NM_005122 | 4826660 | D-003416-02 | TCGCAGACATCAACACTTT | 1434 |
| NR1I3 | NM_005122 | 4826660 | D-003416-03 | CCTCTTCGCTACACAATTG | 1435 |
| NR1I3 | NM_005122 | 4826660 | D-003416-04 | GAACAGTTTGTGCAGTTTA | 1436 |
| NR2C1 | NM_003297 | 4507672 | D-003417-01 | TGACAGCACTTGATCATAA | 1437 |
| NR2C1 | NM_003297 | 4507672 | D-003417-02 | GGAAGGAAGTGTACACCTA | 1438 |
| NR2C1 | NM_003297 | 4507672 | D-003417-03 | GAGCACATCTTCAAACTAC | 1439 |
| NR2C1 | NM_003297 | 4507672 | D-003417-04 | GAAGAAATTGCACATCAAA | 1440 |
| NR2C2 | NM_003298 | 4507674 | D-003418-01 | GAACAACGGTGACACTTCA | 1441 |
| NR2C2 | NM_003298 | 4507674 | D-003418-02 | CTGATGAGCTCCAACATAA | 1442 |
| NR2C2 | NM_003298 | 4507674 | D-003418-03 | CAACCTAAGTGAATCTTTG | 1443 |
| NR2C2 | NM_003298 | 4507674 | D-003418-04 | GAAGACACCTACCGATTGG | 1444 |
| NR2E1 | NM_003269 | 21361108 | D-003419-01 | GATCATATCTGAAATACAG | 1445 |
| NR2E1 | NM_003269 | 21361108 | D-003419-02 | CAAGACTGCTTTCAGATAT | 1446 |
| NR2E1 | NM_003269 | 21361108 | D-003419-03 | GTTAGATGCTACTGAATTT | 1447 |
| NR2E1 | NM_003269 | 21361108 | D-003419-04 | CAATGTATCTCTATGAAGT | 1448 |
| NR2E3 | NM_014249 | 7657394 | D-003420-01 | GAGAAGCTCCTTTGTGATA | 1449 |
| NR2E3 | NM_014249 | 7657394 | D-003420-02 | GAAGCACTATGGCATCTAT | 1450 |
| NR2E3 | NM_014249 | 7657394 | D-003420-03 | GAAGGATCCTGAGCACGTA | 1451 |
| NR2E3 | NM_014249 | 7657394 | D-003420-04 | GAAGCTCCTTTGTGATATG | 1452 |
| NR2F1 | NM_005654 | 20127484 | D-003421-01 | GAAACTCTCATCCGCGATA | 1453 |
| NR2F1 | NM_005654 | 20127484 | D-003421-02 | TCTCATCCGCGATATGTTA | 1454 |
| NR2F1 | NM_005654 | 20127484 | D-003421-03 | CAAGAAGTGCCTCAAAGTG | 1455 |
| NR2F1 | NM_005654 | 20127484 | D-003421-04 | GGAACTTAACTTACACATG | 1456 |
| NR2F2 | NM_021005 | 14149745 | D-003422-01 | GTACCTGTCCGGATATATT | 1457 |
| NR2F2 | NM_021005 | 14149745 | D-003422-02 | CCAACCAGCCGACGAGATT | 1458 |
| NR2F2 | NM_021005 | 14149745 | D-003422-03 | ACTCGTACCTGTCCGGATA | 1459 |
| NR2F2 | NM_021005 | 14149745 | D-003422-04 | GGCCGTATATGGCAATTCA | 1460 |
| NR2F6 | NM_005234 | 20070198 | D-003423-01 | CGACGCCTGTGGCCTCTCA | 1461 |
| NR2F6 | NM_005234 | 20070198 | D-003423-02 | CAGCCGGTGTCCGAACTGA | 1462 |
| NR2F6 | NM_005234 | 20070198 | D-003423-03 | CAACCGTGACTGCCAGATC | 1463 |
| NR2F6 | NM_005234 | 20070198 | D-003423-04 | GTACTGCCGTCTCAAGAAG | 1464 |
| NR3C1 | NM_000176 | 4504132 | D-003424-01 | GAGGACAGATGTACCACTA | 1465 |
| NR3C1 | NM_000176 | 4504132 | D-003424-02 | GATAAGACCATGAGTATTG | 1466 |

TABLE IX-continued

| Gene Name | Accession # | GI# | Duplex # | Sequence | SEQ. ID NO. |
|---|---|---|---|---|---|
| NR3C1 | NM_000176 | 4504132 | D-003424-03 | GAAGACGATTCATTCCTTT | 1467 |
| NR3C1 | NM_000176 | 4504132 | D-003424-04 | GGACAGATGTACCACTATG | 1468 |
| NR3C2 | NM_000901 | 4505198 | D-003425-01 | GCAAACAGATGATCCAAGT | 1469 |
| NR3C2 | NM_000901 | 4505198 | D-003425-02 | CAGCTAAGATTTATCAGAA | 1470 |
| NR3C2 | NM_000901 | 4505198 | D-003425-03 | GCACGAAAGTCAAAGAAGT | 1471 |
| NR3C2 | NM_000901 | 4505198 | D-003425-04 | GGTATCCGGTCTTAGAATA | 1472 |
| NR4A1 | NM_002135 | 21361341 | D-003426-01 | GAAGGAAGTTGTCCGAACA | 1473 |
| NR4A1 | NM_002135 | 21361341 | D-003426-02 | CAGGAGAGTTTGACACCTT | 1474 |
| NR4A1 | NM_002135 | 21361341 | D-003426-03 | CAGTGGCTCTGACTACTAT | 1475 |
| NR4A1 | NM_002135 | 21361341 | D-003426-04 | GAAGGCCGCTGTGCTGTGT | 1476 |
| NR4A2 | NM_006186 | 5453821 | D-003427-01 | GCAATGCGTTCGTGGCTTT | 1477 |
| NR4A2 | NM_006186 | 5453821 | D-003427-02 | CGGCTACACAGGAGAGTTT | 1478 |
| NR4A2 | NM_006186 | 5453821 | D-003427-03 | CCACGTGACTTTCAACAAT | 1479 |
| NR4A2 | NM_006186 | 5453821 | D-003427-04 | GAATACAGCTCCGATTTCT | 1480 |
| NR4A3 | NM_006981 | 11276070 | D-003428-01 | CAAAGAAGATCAGACATTA | 1481 |
| NR4A3 | NM_006981 | 11276070 | D-003428-02 | GATCAGACATTACTTATTG | 1482 |
| NR4A3 | NM_006981 | 11276070 | D-003428-03 | CCAGAGATCTTGATTATTC | 1483 |
| NR4A3 | NM_006981 | 11276070 | D-003428-04 | GAAGTTGTCCGTACAGATA | 1484 |
| NR5A1 | NM_004959 | 20070192 | D-003429-01 | GATTTGAAGTTCCTGAATA | 1485 |
| NR5A1 | NM_004959 | 20070192 | D-003429-02 | GGAGCGAGCTGCTGGTGTT | 1486 |
| NR5A1 | NM_004959 | 20070192 | D-003429-03 | GGAGGTGGCCGACCAGATG | 1487 |
| NR5A1 | NM_004959 | 20070192 | D-003429-04 | CAACGTGCCTGAGCTCATC | 1488 |
| NR5A2 | NM_003822 | 20070161 | D-003430-01 | CCAAACATATGGCCACTTT | 1489 |
| NR5A2 | NM_003822 | 20070161 | D-003430-02 | TCAGAGAACTTAAGGTTGA | 1490 |
| NR5A2 | NM_003822 | 20070161 | D-003430-03 | GGATCCATCTTCCTGGTTA | 1491 |
| NR5A2 | NM_003822 | 20070161 | D-003430-04 | AAGAATACCTCTACTACAA | 1492 |
| NR6A1 | NM_033334 | 15451847 | D-003431-01 | CAACGAACCTGTCTCATTT | 1493 |
| NR6A1 | NM_033334 | 15451847 | D-003431-02 | GAAGAACTACACAGATTTA | 1494 |
| NR6A1 | NM_033334 | 15451847 | D-003431-03 | GAAGATGGATACGCTGTGA | 1495 |
| NR6A1 | NM_033334 | 15451847 | D-003431-04 | AAACGATACTGGTACATTT | 1496 |
| null | D16815 | 2116671 | D-003432-01 | GAAGAATGATCGAATAGAT | 1497 |
| null | D16815 | 2116671 | D-003432-02 | GAACATGGAGCAATATAAT | 1498 |
| null | D16815 | 2116671 | D-003432-03 | GAGGAGCTCTTGGCCTTTA | 1499 |
| null | D16815 | 2116671 | D-003432-04 | TAAACAACATGCACTCTGA | 1500 |
| PGR | NM_000926 | 4505766 | D-003433-01 | GAGATGAGGTCAAGCTACA | 1501 |
| PGR | NM_000926 | 4505766 | D-003433-02 | CAGCGTTTCTATCAACTTA | 1502 |
| PGR | NM_000926 | 4505766 | D-003433-03 | AGATAACTCTCATTCAGTA | 1503 |
| PGR | NM_000926 | 4505766 | D-003433-04 | GTAGTCAAGTGGTCTAAAT | 1504 |
| PPARA | NM_005036 | 7549810 | D-003434-01 | TCACGGAGCTCACGGAATT | 1505 |
| PPARA | NM_005036 | 7549810 | D-003434-02 | GAACATGACATAGAAGATT | 1506 |
| PPARA | NM_005036 | 7549810 | D-003434-03 | GGATAGTTCTGGAAGCTTT | 1507 |
| PPARA | NM_005036 | 7549810 | D-003434-04 | GACTCAAGCTGGTGTATGA | 1508 |
| PPARD | NM_006238 | 5453939 | D-003435-01 | GAGCGCAGCTGCAAGATTC | 1509 |
| PPARD | NM_006238 | 5453939 | D-003435-02 | GCATGAAGCTGGAGTACGA | 1510 |
| PPARD | NM_006238 | 5453939 | D-003435-03 | GGAAGCAGTTGGTGAATGG | 1511 |
| PPARD | NM_006238 | 5453939 | D-003435-04 | GCTGCAAGATTCAGAAGAA | 1512 |
| PPARG | NM_138712 | 20336234 | D-003436-01 | AGACTCAGCTCTACAATAA | 1513 |
| PPARG | NM_138712 | 20336234 | D-003436-02 | GATTGAAGCTTATCTATGA | 1514 |
| PPARG | NM_138712 | 20336234 | D-003436-03 | AAGTAACTCTCCTCAAATA | 1515 |
| PPARG | NM_138712 | 20336234 | D-003436-04 | GCATTTCTACTCCACATTA | 1516 |
| RARA | NM_000964 | 4506418 | D-003437-01 | GACAAGAACTGCATCATCA | 1517 |
| RARA | NM_000964 | 4506418 | D-003437-02 | GCAAATACACTACGAACAA | 1518 |
| RARA | NM_000964 | 4506418 | D-003437-03 | GAACAACAGCTCAGAACAA | 1519 |
| RARA | NM_000964 | 4506418 | D-003437-04 | GAGCAGCAGTTCTGAAGAG | 1520 |
| RARB | NM_000965 | 14916493 | D-003438-01 | GCACACTGCTCAATCAATT | 1521 |
| RARB | NM_000965 | 14916493 | D-003438-02 | GCAGAAGTATTCAGAAGAA | 1522 |
| RARB | NM_000965 | 14916493 | D-003438-03 | GGAATGACAGGAACAAGAA | 1523 |
| RARB | NM_000965 | 14916493 | D-003438-04 | GCACAGTCCTAGCATCTCA | 1524 |
| RARG | NM_000966 | 21359851 | D-003439-01 | GAAATGACCGGAACAAGAA | 1525 |
| RARG | NM_000966 | 21359851 | D-003439-02 | TAGAAGAGCTCATCACCAA | 1526 |
| RARG | NM_000966 | 21359851 | D-003439-03 | CAAGGAAGCTGTGCGAAAT | 1527 |
| RARG | NM_000966 | 21359851 | D-003439-04 | TCAGTGAGCTGGCTACCAA | 1528 |

TABLE IX-continued

| Gene Name | Accession # | GI# | Duplex # | Sequence | SEQ. ID NO. |
|---|---|---|---|---|---|
| RORA | NM_134261 | 19743902 | D-003440-01 | GGAAAGAGTTTATGTTCTA | 1529 |
| RORA | NM_134261 | 19743902 | D-003440-02 | CAAGATCTGTGGAGACAAA | 1530 |
| RORA | NM_134261 | 19743902 | D-003440-03 | GCACCTGACTGAAGATGAA | 1531 |
| RORA | NM_134261 | 19743902 | D-003440-04 | CCGAGAAGATGGAATACTA | 1532 |
| RORB | NM_006914 | 19743906 | D-003441-01 | GCACAGAACATCATTAAGT | 1533 |
| RORB | NM_006914 | 19743906 | D-003441-02 | CCACACCTATGAAGAAATT | 1534 |
| RORB | NM_006914 | 19743906 | D-003441-03 | GATCAAATTCTACTTCTGA | 1535 |
| RORB | NM_006914 | 19743906 | D-003441-04 | TCAAACAGATAAAGCAAGA | 1536 |
| RORC | NM_005060 | 19743908 | D-003442-01 | TAGAACAGCTGCAGTACAA | 1537 |
| RORC | NM_005060 | 19743908 | D-003442-02 | TCACCGAGGCCATTCAGTA | 1538 |
| RORC | NM_005060 | 19743908 | D-003442-03 | GAACAGCTGCAGTACAATC | 1539 |
| RORC | NM_005060 | 19743908 | D-003442-04 | CCTCATGCCACCTTGAATA | 1540 |
| RXRA | NM_002957 | 21536318 | D-003443-01 | TGACGGAGCTTGTGTCCAA | 1541 |
| RXRA | NM_002957 | 21536318 | D-003443-02 | CAACAAGGACTGCCTGATT | 1542 |
| RXRA | NM_002957 | 21536318 | D-003443-03 | GCAAGGACCTGACCTACAC | 1543 |
| RXRA | NM_002957 | 21536318 | D-003443-04 | GCAAGGACCGGAACGAGAA | 1544 |
| RXRB | NM_021976 | 21687229 | D-003444-01 | GCAAAGACCTTACATACTC | 1545 |
| RXRB | NM_021976 | 21687229 | D-003444-02 | GCAATCATTCTGTTTAATC | 1546 |
| RXRB | NM_021976 | 21687229 | D-003444-03 | TCACACCGATCCATTGATG | 1547 |
| RXRB | NM_021976 | 21687229 | D-003444-04 | GCAAACGGCTATGTGCAAT | 1548 |
| RXRG | NM_006917 | 21361386 | D-003445-01 | GGAAGGACCTCATCTACAC | 1549 |
| RXRG | NM_006917 | 21361386 | D-003445-02 | CCGGATCTCTGGTTAAACA | 1550 |
| RXRG | NM_006917 | 21361386 | D-003445-03 | GCGAGCCATTGTACTCTTT | 1551 |
| RXRG | NM_006917 | 21361386 | D-003445-04 | GAGCCATTGTACTCTTTAA | 1552 |
| THRA | NM_003250 | 20127451 | D-003446-01 | GGACAAAGACGAGCAGTGT | 1553 |
| THRA | NM_003250 | 20127451 | D-003446-02 | GGAAACAGAGGCGGAAATT | 1554 |
| THRA | NM_003250 | 20127451 | D-003446-03 | GTAAGCTGATTGAGCAGAA | 1555 |
| THRA | NM_003250 | 20127451 | D-003446-04 | GAACCTCCATCCCACCTAT | 1556 |
| THRB | NM_000461 | 10835122 | D-003447-01 | GAATGTCGCTTTAAGAAAT | 1557 |
| THRB | NM_000461 | 10835122 | D-003447-02 | GAACAGTCGTCGCCACATC | 1558 |
| THRB | NM_000461 | 10835122 | D-003447-03 | GGACAAGCACCAATAGTCA | 1559 |
| THRB | NM_000461 | 10835122 | D-003447-04 | GTGGAAAGGTTGACTTGGA | 1560 |
| VDR | NM_000376 | 4507882 | D-003448-01 | TGAAGAAGCTGAACTTGCA | 1561 |
| VDR | NM_000376 | 4507882 | D-003448-02 | GCAACCAAGACTACAAGTA | 1562 |
| VDR | NM_000376 | 4507882 | D-003448-03 | TCAATGCTATGACCTGTGA | 1563 |
| VDR | NM_000376 | 4507882 | D-003448-04 | CCATTGAGGTCATCATGTT | 1564 |

TABLE X

| Gene Symbol | Sense | SEQ ID NO. |
|---|---|---|
| ABCB1 | GACCAUAAAUGUAAGGUUU | 1565 |
|  | UAGAAGAUCUGAUGUCAAA | 1566 |
|  | GAAAUGUUCACUUCAGUUA | 1567 |
|  | GAAGAUCGCUACUGAAGCA | 1568 |
| ABCC1 | GGAAGCAACUGCAGAGACA | 1569 |
|  | GAUGCACCUCUCAACAAA | 1570 |
|  | UAAAGUUGCUCAUCAAGUU | 1571 |
|  | CAACGAGUCUGCCGAAGGA | 1572 |
| ABCG2 | GCAGAUGCCUUCUUCGUUA | 1573 |
|  | AGGCAAAUCUUCGUUAUUA | 1574 |
|  | GGGAAGAAAUCUGGUCUAA | 1575 |
|  | UGACUCAUCCCAACAUUUA | 1576 |
| KCNH2 | CCGACGUGCUGCCUGAGUA | 1577 |
|  | GAGAAGAGCAGCGACACUU | 1578 |
|  | GAUCAUAGCACCUAAGAUA | 1579 |
|  | GCUAUUUACUGCUCUUAUU | 1580 |
|  | UCACUGGGCUCCUUUAAUU | 1581 |
|  | GUGCGAGCCUUCUGAAUAU | 1582 |
|  | GCUAAGCUAUACUACUGUA | 1583 |
|  | UGACGGCGCUCUACUUCAC | 1584 |
| KCNH1 | GAGAUGAAUUCCUUUGAAA | 1585 |
|  | GAAGAACGCAUGAAACGAA | 1586 |
|  | GAUAAAGACACGAUUGAAA | 1587 |
|  | GCUGAGAGGUCUAUUUAAA | 1588 |
| CLCA1 | GAACAACAAUGGCUAUGAA | 1589 |
|  | GUACAUACCUGGCUGGAUU | 1590 |
|  | GAACAGCUCACAAGUAUAU | 1591 |
|  | GGAAACGUGUGUCUAUAUU | 1592 |
| SLC6A1 | GGAGGUGGGAGGACAGUUA | 1593 |
|  | UCACAGCCCUGGUGGAUGA | 1594 |
|  | GAAGCUGGCUCCUAUGUUC | 1595 |
|  | GGUCAACACUACCAACAUG | 1596 |
| SLC6A2 | GAACACAAGGUCAACAUUG | 1597 |
|  | AGAAGGAGCUGGCCUAGUG | 1598 |
|  | CGGAAACUCUUCACAUUUG | 1599 |
|  | CAACAAAUUUGCAACAAC | 1600 |
| SLC21A2 | GUACAUCUCCAUCUUAUUU | 1601 |
|  | GGAAGUGCUGAGUUAUUA | 1602 |
|  | GAAGGGAGGCUCAAUGUAA | 1603 |
|  | GAAGGAAGUGGCUGAGUUA | 1604 |

TABLE X-continued

| Gene Symbol | Sense | SEQ ID NO. |
|---|---|---|
| SLC21A3 | GUAGAAACAGGAGCUAUUA | 1605 |
| | CAAGAUUACUGUCAAACAA | 1606 |
| | GCACAAGAGUAUUUGGUAA | 1607 |
| | GCAAAUGUCCCUUCUGUAU | 1608 |
| | GCAUGACUCCUAUAUAAUA | 1609 |
| | AAACAGCAAUUUCCCUUAA | 1610 |
| | GAAAAUGCCUCUUCAGGAA | 1611 |
| SLC28A1 | GUUCAUCGCUCUCCUCUUU | 1612 |
| | GGAUCAAGCUGUUUCUGAA | 1613 |
| | GGACUGCAGUUUGUACUUG | 1614 |
| | GAGUGAAACUGACCUAUGG | 1615 |
| SLC29A1 | GAACGCUGCUCCCGUGGAA | 1616 |
| | GAAAGCCACUCUAUCAAAG | 1617 |
| | GAAACCAGGUGCCUUCAGA | 1618 |
| | CCUCACAGCUGUAUUCAUG | 1619 |
| SLC26A1 | CCACGGAGCUGCUGGUCAU | 1620 |
| | GGGUUGACAUCUUUAUUGA | 1621 |
| | GCACGAGGGUCUCUGUGUU | 1622 |
| | GGCCAUCGCCUACUCAUUG | 1623 |
| | CAACACCCAUGGCAAUUAA | 1624 |
| | GAGGAAAGAUCUUGCUGAU | 1625 |
| | GAGCAAGCGUCCUCCAAAU | 1626 |
| | GCAACACCCAUGGCAAUUA | 1627 |
| SLC26A2 | CCAAAGAACUCAAUGAACA | 1628 |
| | ACAAGAACCUUCAGACUAA | 1629 |
| | GAAGGUAGAUAGAAGAAUG | 1630 |
| | GUAUUGAACGUACUGUAA | 1631 |
| SLC4A4 | GCAAUUCUCUUCAUUUAUC | 1632 |
| | GGAAAGAUGUCCACUGAAA | 1633 |
| | GGACAAAGCCUUCUCUCAAU | 1634 |
| | GGAAUGGGAUCCAGCAAUU | 1635 |
| GLRA1 | UGAAAGCCAUUGACAUUUG | 1636 |
| | CAGACACGCUGGAGUUUAA | 1637 |
| | CAAUAGCGCUUUCUGGUUU | 1638 |
| | GCAGGUAGCAGAUGGACUA | 1639 |
| KLK1 | UCAGAGUGCUGUCUUAUGU | 1640 |
| | CAACUUGUUUGACGACGAA | 1641 |
| | UGACAGAGCCUGCUGAUAC | 1642 |
| | AGGCGGCUCUGUACCAUUU | 1643 |
| ADAM2 | GAAACAUGCUGUGAUAUUG | 1644 |
| | GCAGAUGUUUCCUUAUAUA | 1645 |
| | CAACAGAGAUGCCAUGAUA | 1646 |
| | GAAAGGCGCUACAUUGAGA | 1647 |
| XPNPEP1 | GACCUGAGCUUCCCAACAA | 1648 |
| | GCGACUGGCUCAACAAUUA | 1649 |
| | GAGAUUGCGUGGCUAUUUA | 1650 |
| | GACAGCAACUGGACACUUA | 1651 |
| GZMA | GGAAGAGACUCGUGCAAUG | 1652 |
| | GGAACCAUGUGCCAAGUUG | 1653 |
| | GAAGUAACUCCUCAUUCAA | 1654 |
| | GAACUCCAUAGAUUUCUG | 1655 |
| CMKLR1 | CAUAGAAGCUUUACCAAGA | 1656 |
| | GAAUGGAGGAUGAAGAUUA | 1657 |
| | GGUCAAUGCUCUAAGUGAA | 1658 |
| | GAGAGGACUUCUAUGAAUG | 1659 |
| CLN3 | CAUCAUGCCUUCUGAAUAA | 1660 |
| | CAACAGCUCAUCACGAUUU | 1661 |
| | GCAACAACUUCUCUUAUGU | 1662 |
| | GGUCUUCGCUAGCAUUCA | 1663 |
| CALCR | GGACCUAGCUGUUGUAAAG | 1664 |
| | GAAAGACCAUGCAUUUAAA | 1665 |
| | GCAGGAAGAUGUAUGCUUU | 1666 |
| | GAAUAAACCAGUAUCGUUA | 1667 |
| OXTR | GGACCCAGAUAUCCAAAUA | 1668 |
| | GCAAUACUAUCCUAACUGA | 1669 |
| | GAAUAUAGAUUAGCGUUUG | 1670 |
| | GAUGAGGCAUGACUACUAA | 1671 |
| EDG4 | GCGAGUCUGUCCACAUAUC | 1672 |
| | GAGAACGGCCACCCACUGA | 1673 |
| | GAACGGCCACCCACUGAUG | 1674 |
| | GGUCAAUGCUGCUGUGUAC | 1675 |
| EDG5 | UCCAGGAACACUAUAAUUA | 1676 |
| | GUGACCAUCUUCUCCAUCA | 1677 |
| | CAUCCUCUGUUGCGCCAUU | 1678 |
| | CCAACAAGGUCCAGGAACA | 1679 |
| EDG7 | ACACUGAUACUGUCGAUGA | 1680 |
| | AAUAGGAGCAACACUGAUA | 1681 |
| | CAGCAGGAGUUACCUUGUU | 1682 |
| | GGACACCCAUGAAGCUAAU | 1683 |
| PTCH | GCACAGAACUCCACUCAAA | 1684 |
| | GGACAGCAGUUCAUUGUUA | 1685 |
| | GAGAAGAGGCUAUGUUUAA | 1686 |
| | GGACAAACUUCGACCCUUU | 1687 |
| SMO | UCGCUACCCUGCUGUUAUU | 1688 |
| | GCUACAAGAACUACCGAUA | 1689 |
| | CAAGAAAGCUUCCUUCAAC | 1690 |
| | GAGAAGAAAUACAGUCAAU | 1691 |
| CASP3 | CAAUAUAUCUGAAGAGCUA | 1692 |
| | GAACUGGACUGUGGCAUUG | 1693 |
| | GUGAGAAGAUGGUAUAUUU | 1694 |
| | GAGGGUACUUUAAGACAUA | 1695 |
| CASP6 | CAUGAGGUGUCAACUGUUA | 1696 |
| | GAAGUGAAAUGCUUUAAUG | 1697 |
| | AAAUAUGGCUCCUCCUUAG | 1698 |
| | GCAAUCACAUUUAUGCAUA | 1699 |
| | CAACAUAACUGAGGUGGAU | 1700 |
| | CAUGGUACAUUCAAGAUUU | 1701 |
| CASP7 | GAACUCUACUUCAGUCAAU | 1704 |
| | GGGCAAAUGCAUCAUAUA | 1703 |
| | CAACAGAGGGAGUUAAUA | 1704 |
| | GAACAAAGCCACUGACUGA | 1705 |
| CASP8 | GAAGUGAACUAUGAAGUAA | 1706 |
| | CAACAAGGAUGACAAGAAA | 1707 |
| | GGACAAAGUUUACCAAAUG | 1708 |
| | GAGGGUCGAUCAUCUAUUA | 1709 |
| | GAAUAUAGAGGGCUUUGA | 1710 |
| | CAACGACUAUGAAGAAUUC | 1711 |
| | GAAGUGAGCAGAUCAGAAU | 1712 |
| | GAGGAAAUCUCCAAAUGCA | 1713 |
| CASP9 | CCAGGCAGCUGAUCAUAGA | 1714 |
| | UCUCAGGUGUUGCCAAAUA | 1715 |
| | GAACAGCUGUAAUCUAUGA | 1716 |
| | CCACUGGUCUGUAGGGAUU | 1717 |
| DVL1 | UCGUAAAGCUGUUGAUAUC | 1718 |
| | GAGGAGAUCUUUGAUGACA | 1719 |
| | GUAAAGCUGUUGAUAUCGA | 1720 |
| | GAUCGUAAAGCUGUUGAUA | 1721 |
| DVL2 | AGACGAAGGUGAUUUACCA | 1722 |
| | UGUGAGAGCUACCUAGUCA | 1723 |
| | GAAGAAAUUUCAGAUGACA | 1724 |
| | UAAUAGGCAUUUCCUCUUU | 1725 |
| PTEN | GUGAAGAUCUUGACCAAUG | 1726 |
| | GAUCAGCAUACACAAAUUA | 1727 |
| | GAAUGAACCUUCUGCAACA | 1728 |
| | GGCGCUAUGUGUAUUAUUA | 1729 |

TABLE X-continued

| Gene Symbol | Sense | SEQ ID NO. |
|---|---|---|
| PDK1 | GUACAAAGCUGGUAUAUCC | 1730 |
|  | GAAAGACUCCCAGUGUAUA | 1731 |
|  | GGAAGUCCAUCUCAUCGAA | 1732 |
|  | CCAAAGACAUGACGACGUU | 1733 |
| PDK2 | GUAAAGAGGAGACUGAAUG | 1734 |
|  | GGUCUGUGAUGGUCCCUAA | 1735 |
|  | CAAAGAUGCCUACGACAUG | 1736 |
|  | GGGCGAUGCCUGAGGGUUA | 1737 |
| PPP2CA | UCACACAAGUUUAUGGUUU | 1738 |
|  | CAACAGCCGUGACCACUUU | 1739 |
|  | UAACCAAGCUGCAAUCAUG | 1740 |
|  | GAACUUGACGAUACUCUAA | 1741 |
| CTNNA1 | GAAGAGAGGUCGUUCUAAG | 1742 |
|  | AAGCAGAUGUGCAUGAUUA | 1743 |
|  | UCUAAUAACUGCAGUGUUU | 1744 |
|  | GUAAAGGGCCCUCUAAUAA | 1745 |
| CTNNA2 | GAAAGAAUAUGCCCAAGUU | 1746 |
|  | GAAGAAGAAUGCCACAAUG | 1747 |
|  | GCAGGAAGAUUAUGAUGUG | 1748 |
|  | AAAGAAAGCCCAUGUACUA | 1749 |
| HSPCA | GGGAAAGAGCUGCAUAUUA | 1750 |
|  | GCUUAGAACUCUUUACUGA | 1751 |
|  | UAUAAGAGCUUGACCAAUG | 1752 |
|  | GCAGAUAUCUCUAUGAUUG | 1753 |
| DCTN2 | CAACUCAUGUCCAAUACUG | 1754 |
|  | GGAAUGAGCCAGAUGUUUA | 1755 |
|  | GGAGACAGCUGUACGUUGU | 1756 |
|  | UCCAAGAGCUGACAACUGA | 1757 |
| CD2 | GUAAGGAGAAGCAAUAUAA | 1758 |
|  | AAGAUGAGCUUUCCAUGUA | 1759 |
|  | GGACAUCUAUCUCAUCAUU | 1760 |
|  | GACAAGAGCCCACAGAGUA | 1761 |
| BAD | GUACUUCCCUCAGGCCUAU | 1762 |
|  | GCUGUGCCUUGACUACGUA | 1763 |
|  | GUACUUCCCUCAGGCCUAU | 1764 |
|  | GGUCAGGUGCCUCGAGAUC | 1765 |
| SMAC | CAGCGUAACUUCAUUCUUC | 1766 |
|  | UAACUUCAUUCUUCAGGUA | 1767 |
|  | CAGCUGCUCUUACCCAUUU | 1768 |
|  | GAUUGAAGCUAUUACUGAA | 1769 |
|  | UAGAAGAGCUCCGUCAGAA | 1770 |
|  | CCACAUAUGCGUUGAUUGA | 1771 |
|  | GCGCAGGGCUCUCUACCUA | 1772 |
| MAP3K5 | GAACAGCCUUCAAAUCAAA | 1773 |
|  | GAUGUUCUCUACUAUGUUA | 1774 |
|  | GCAAAUACUGGAAGGAUUA | 1775 |
|  | CAGGAAAGCUCGUAAUUUA | 1776 |
| PVR | CCACACGGCUGACCUCAUA | 1777 |
|  | CAGCAGAAUUCCUCUUAUA | 1778 |
|  | GCAGAAUUCUCUAUAAAA | 1779 |
|  | GAUCGGGAUUUAUUUCUAU | 1780 |
| ERBB2 | UGUGGGAGCUGAUGACUUU | 1781 |
|  | UCACAGAGAUCUUGAAAGG | 1782 |
|  | UGGAAGACACAGGUUA | 1783 |
|  | GCUCAUCGCUCACAACCAA | 1784 |
| SOS1 | GAGCACCACUUCUAUGAUU | 1785 |
|  | CAAAGAAGCUGUUCAAUAU | 1786 |
|  | UGAAAGCCCUCCCUUAUUA | 1787 |
|  | GAAAUAGCAUGGAGAAGGA | 1788 |
| BRCA1 | CCAUCAGCUUCAUAAAUA | 1789 |
|  | GAAGAGAACUUAUCUAGUG | 1790 |
|  | GAAGUGGGCUCCAGUAUUA | 1791 |
|  | GCAAGAUGCUGAUUCAUUA | 1792 |
|  | GAAGUGGGCUCCAGUAUUA | 1793 |
|  | GAACGGACACUGAAAUAUU | 1794 |
|  | GCAGAUAGUUCUACCAGUA | 1795 |
| CDKN1A | GAACAAGGAGUCAGACAUU | 1796 |
|  | AAACUAGGCGGUUGAAUGA | 1797 |
|  | GAUGGAACUUCGACUUUGU | 1798 |
|  | GUAAACAGAUGGCACUUUG | 1799 |
| CDKN1B | GGAAUGGACAUCCUGUAUA | 1800 |
|  | GGAGAAAGAUGUCAAACGU | 1801 |
|  | GAAUGGACAUCCUGUAUAA | 1802 |
|  | GUAAACAGCUCGAAUUAAG | 1803 |
| SLC2A4 | CAGAUAGGCUCCGAAGAUG | 1804 |
|  | AGACUCAGCUCCAGAAUAC | 1805 |
|  | GAUCGGUUCUUUCAUCUUC | 1806 |
|  | CAGGAUCGGUUCUUUCAUC | 1807 |
| NOS2A | CCAGAUAAGUGACAUAAGU | 1808 |
|  | UAAGUGACCUGCUUUGUAA | 1809 |
|  | GAAGAGAGAUUCCAUUGAA | 1810 |
|  | UGAAAGAGCUCAACAACAA | 1811 |
| FRAP1 | GAGCAUGCCGUCAAUAAUA | 1812 |
|  | CAAGAGAACUCAUCAUAAG | 1813 |
|  | CCAAAGUGCUGCAGUACUA | 1814 |
|  | UAAGAAAGCUAUCCAGAUU | 1815 |
| FKBP1A | GAAACAAGCCCUUUAAGUU | 1816 |
|  | GAAUUACUCUCCAAGUUGA | 1817 |
|  | CAGCACAAGUGGUAGGUUA | 1818 |
|  | GUUGAGGACUGAAUUACUC | 1819 |
|  | GAUGGCAGCUGUUUAAAUG | 1820 |
|  | GAGUAUCCUUUCAGUGUUA | 1821 |
| TNFRSF1A | CAAAGGAACCUACUUGUAC | 1822 |
|  | GGAACCUACUUGUACAAUG | 1823 |
|  | GAACCUACUUGUACAAUGA | 1824 |
|  | GAGUGUGUCUCCUGUAGUA | 1825 |
| IL1R1 | GGACAAGAAUCAAUGGAUA | 1826 |
|  | GAACAAGCCUCCAGGAUUC | 1827 |
|  | GGACUUGUGUGCCCUUAUA | 1828 |
|  | GAACACAAAGGCACUAUAA | 1829 |
| IRAK1 | CGAAGAAAGUGAUGAAUUU | 1830 |
|  | GCUCUUUGCCCAUCUCUUU | 1831 |
|  | UGAAAGACCUGGUGGAAGA | 1832 |
|  | GCAAUUCAGUUUCUACAUC | 1833 |
| TRAF2 | GAAGACAGAGUUAUUAAAC | 1834 |
|  | UCACGAAGACAGAGUUAUU | 1835 |
|  | AGACAGAGUUAUUAAACCA | 1836 |
|  | CACGAAGACAGAGUUAUUA | 1837 |
|  | GCUGAAGCCUGUCUGAUGU | 1838 |
| TRAF6 | CAAAUGAUCUGAGGCAGUU | 1839 |
|  | GUUCAUAGUUUGAGCGUUA | 1840 |
|  | GGAGAAACCUGUUGUGAUU | 1841 |
|  | GGACAAAGUUGCUGAAAUC | 1842 |
|  | CAAAUGAUCUGAGGCAGUU | 1843 |
|  | GGAGAAACCUGUUGUGAUU | 1844 |
|  | GGACAAAGUUGCUGAAAUC | 1845 |
|  | GUUCAUAGUUUGAGCGUUA | 1846 |
| TRADD | UGAAGCACCUUGAUCUUUG | 1847 |
|  | GGGCAGCGCAUACCUGUUU | 1848 |
|  | GAGGAGCUGUGGUUGAGUU | 1849 |
|  | GGACGAGGAGCGCUGUUUG | 1850 |
|  | GAGGAGCGCUGUUUGAGUU | 1851 |
|  | GGAUGUCUCUCUCCUCUUU | 1852 |
|  | GCUCACUCCUUUCUACUAA | 1853 |
|  | UGAAGCACCUUGAUCUUUG | 1854 |

TABLE X-continued

| Gene Symbol | Sense | SEQ ID NO. |
|---|---|---|
| FADD | GCACAGAUAUUUCCAUUUC | 1855 |
| | GCAGUCCUCUUAUUCCUAA | 1856 |
| | GAACUCAAGCUGCGUUUAU | 1857 |
| | GGACGAAUUGAGAUAAUAU | 1858 |
| IKBKE | UAAGAACACUGCUCAUGAA | 1859 |
| | GAGGCAUCCUGAAGCAUUA | 1860 |
| | GAAGGCGGCUGCAGAACUG | 1861 |
| | GGAACAAGGAGAUCAUGUA | 1862 |
| IKBKG | CUAUCGAGGUCGUUAAAUU | 1863 |
| | GAAUGCAGCUGGAAGAUCU | 1864 |
| | GCGGCGAGCUGGACUGUUU | 1865 |
| | CCAGACCGAUGUGUAUUUA | 1866 |
| TNFRSF5 | GGUCUCACCUCGCUAUGGU | 1867 |
| | GAAAGCGAAUUCCUAGACA | 1868 |
| | GCACAAACAAGACUGAUGU | 1869 |
| | GAAGGGCACCUCAGAAACA | 1870 |
| | UCUCCCAACUUGUAUUAAA | 1871 |
| RELA | UCAAGUGUCUUCCAUCAUG | 1872 |
| | UCAAGUGCCUUAAUAGUAG | 1873 |
| | GGAGUACCCUGAGGCUAUA | 1874 |
| | GAUGAGAUCUUCCUACUGU | 1875 |
| ARHA | GAGCUGGGCUAAGUAAAUA | 1876 |
| | GACCAAAGAUGGAGUGAGA | 1877 |
| | GGAAGAAACUGGUGAUUGU | 1878 |
| | GGCUGUAACUACUUUAUAA | 1879 |
| CDC42 | GGACAUUUGUUUGCCAUUU | 1880 |
| | GGAGAACCAUAUACUCUUG | 1881 |
| | GAACCAAUGCUUUCUCAUG | 1882 |
| | GAAGACCUGUUAUGUAGAG | 1883 |
| | GAUCAAGAAUUGCAAUAUC | 1884 |
| | GAAAAGGGGUGACCUAGUA | 1885 |
| | UGACAAACCUUAUGGAAAA | 1886 |
| ROCK1 | GGAAUGAGCUUCAGAUGCA | 1887 |
| | GGACACAGCUGUAAGAUUG | 1888 |
| | GACAAGAGAUUACAGAUAA | 1889 |
| | GAAGAAACAUUCCCUAUUC | 1890 |
| PAK1 | GAGGGUGGUUUAUGAUUAA | 1891 |
| | CAACAAAGAACAAUCACUA | 1892 |
| | GAAGAAAUAUACACGGUUU | 1893 |
| | UACAUGAGCUUUACAGAUA | 1894 |
| PAK2 | GGUAGGAGAUGAAUUGUUU | 1895 |
| | AGAAGGAACUGAUCAUUAA | 1896 |
| | CUACAGACCUCCAUAUCA | 1897 |
| | GAAACUGGCCAAACCGUUA | 1898 |
| PAK3 | GAUUAUCGCUGCAAAGGAA | 1899 |
| | GAGAGUGCCUGCAAGCUUU | 1900 |
| | GACAAGAGGUGGCCAUAAA | 1901 |
| | UUAAAUCGCUGUCUUGAGA | 1902 |
| PAK4 | ACUAAGAGGUGAACAUGUA | 1903 |
| | GAUCAUGAAUGUCCGAAGA | 1904 |
| | GAUGAGACCCUACUACUGA | 1905 |
| | CAGCAAAGGUGCCAAAGAU | 1906 |
| PAK6 | UAAAGGCAGUUGUCCACUA | 1907 |
| | GAAGGGACCUGCUUUCUUG | 1908 |
| | GCAAAGACGUCCCUAAGAG | 1909 |
| | CCAAUGGGCUGGCUGCAAA | 1910 |
| PAK7 | GAGCACGGCUUUAAUAAGU | 1911 |
| | CAAACUCCGUUAUGAUAUA | 1912 |
| | GGAUAAAGUUGUCUGAUUU | 1913 |
| | GGAAAUGCCUCCAUAAAUA | 1914 |
| HDAC1 | GGACAUCGCUGUGAAUUGG | 1915 |
| | AGAAGAAGUCACCGAAGA | 1916 |
| | GGACAAGGCCACCCAAUGA | 1917 |
| | CCACAGCGAUGACUACAUU | 1918 |
| HDAC2 | GCUGUUAAAUUAUGGCUUA | 1919 |
| | GCAAAGAAAGCUAGAAUUG | 1920 |
| | CAUCAGAGAGUCUUAUAUA | 1921 |
| | CCAAUGAGUUGCCAUAUAA | 1922 |
| CREBBP | GGCCAUAGCUUAAUUAAUC | 1923 |
| | GCACAGCCGUUUACCAUGA | 1924 |
| | GGACAGCCCUUUAGUCAAG | 1925 |
| | GAACUGAUUCCUGAAAUAA | 1926 |
| BTRC | CACAUAAACUCGUAUCUUA | 1927 |
| | GAGAAGGCACUCAAGUUUA | 1928 |
| | AGACAUAGUUUACAGAGAA | 1929 |
| | GCAGAGAGAUUUCAUAACU | 1930 |
| RIPK2 | GAACAUACCUGUAAAUCAU | 1931 |
| | GGACAUCGACCUGUUAUUA | 1932 |
| | UAAAUGAACUCCUACACAG | 1933 |
| | GGAAUUAUCUCUGAACAUA | 1934 |
| VAV1 | GCAGAAAUACAUCUACUAA | 1935 |
| | GCUAUGAGCUGUUCUUCAA | 1936 |
| | CGACAAAGCUCUACUCAUC | 1937 |
| | GCUCAACCCUGGAGACAUU | 1938 |
| VAV2 | GGACAAGACUCGCAGAUUU | 1939 |
| | GCUGAGCGCUUUGCAAUAA | 1940 |
| | CAAGAAGUCUCACGGGAAA | 1941 |
| | UCACAGAGGCCAAGAAAUU | 1942 |
| GRB2 | UGGAAGCCAUCGCCAAAUA | 1943 |
| | CAUCAGUGCAUGACGUUUA | 1944 |
| | UGAAUGAGCUGGUGGAUUA | 1945 |
| | UGCCAAAACUUACCUAUAA | 1946 |
| PLCG1 | GAGCUGCACUCCAAUGAGA | 1947 |
| | GAAACCAAGCCAUUAAUGA | 1948 |
| | CCAAGGAGCUACUGACAUU | 1949 |
| | AGAGAAACAUGGCCCAAUA | 1950 |
| ITGB1 | CCACAGACAUUUACAUUAA | 1951 |
| | GAAGGGAGUUUGCUAAAUU | 1952 |
| | GAACGAUCGUGAGAUGA | 1953 |
| | CAAGAGAGCUGAAGACUAU | 1954 |
| ITGA4 | GCAUAUAUAUUCAGCAUUG | 1955 |
| | CAACUUGACUGCAGUAUUG | 1956 |
| | GAACUUAACUUUCCAUGUU | 1957 |
| | GACAAGACCUGUAGUAAUU | 1958 |
| STAT1 | AGAAAGAGCUUGACAGUAA | 1959 |
| | GGAAGUAGUUCACAAAAUA | 1960 |
| | UGAAGUAUCUGUAUCCAAA | 1961 |
| | GAGCUUCACUCCCUUAGUU | 1962 |
| KRAS2 | UAAGGACUCUGAAGAUGUA | 1963 |
| | GACAAAGUGUGUAAUUAUG | 1964 |
| | GCUCAGGACUUAGCAAGAA | 1965 |
| | GAAACUGAAUACCUAAGAU | 1966 |
| | GAAACUGAUAUACCUAAGAU | 1967 |
| | UAAGGACUCUGAAGAUGUA | 1968 |
| | GACAAAGUGUGUAAUUAUG | 1969 |
| | GCUCAGGACUUAGCAAGAA | 1970 |
| HRAS | CCAUCCAGCUGAUCCAGAA | 1971 |
| | GAACCCUCCUGAUGAGAGU | 1972 |
| | GAGGACAUCCACCAGUACA | 1973 |
| BRAF | GAUUAGAGACCAAGGAUUU | 1974 |
| | CCACUGAUGUGUGUUAAUU | 1975 |
| | CAAUAGAACCUGUCAAUAU | 1976 |
| | GAAGCAGGAAUCGAAUGA | 1977 |
| ELK1 | GAUGUGAGUAGAAGAGUUA | 1978 |
| | GGAAGAAUUUGUACCAUUU | 1979 |
| | GAACGACCUUUCUUUCUUU | 1980 |
| | GGAGUCAUCUCUUCCUAUA | 1981 |

TABLE X-continued

| Gene Symbol | Sense | SEQ ID NO. |
|---|---|---|
| RALGDS | GGAGAAGCCUCACCUCUUG | 1982 |
| | GCAGAAAGGACUCAAGAUU | 1983 |
| | GAGAACAACUACUCAUUGA | 1984 |
| | GAACUUCUCGUCACUGUAU | 1985 |
| PRKCA | GGAUUGUUCUUUCUUCAUA | 1986 |
| | GAAGGGUUCUCGUAUGUCA | 1987 |
| | GAAGAAGGAUGUGGUGAUU | 1988 |
| | GGACUGGGAUCGAACAACA | 1989 |
| MAP2K4 | GGACAGAAGUGGAAAUAUU | 1990 |
| | UCAAAGAGGUGAACAUUAA | 1991 |
| | GACCAAAUCUCAGUUGUUU | 1992 |
| | GGAGAAUGGUGCUGUUUAA | 1993 |
| MAP2K7 | GAAGAGACCAAAGUAUAAU | 1994 |
| | GAAGACCGGCCACGUCAUU | 1995 |
| | GGAAGAGACCAAAGUAUAA | 1996 |
| | GCAUUGAGAUUGACCAGAA | 1997 |
| | UGAGAGAACGAGAAAGUUG | 1998 |
| | GUGAAACCCUGUCUGCAUU | 1999 |
| | GGAUCUCUCUCAACAACUA | 2000 |
| | ACAACUAGGUGAACACAUA | 2001 |
| MAPK8 | UCACAGUCCUGAAACGAUA | 2002 |
| | GAUUGGAGAUUCUACAUUC | 2003 |
| | GCUCAUGGAUGCAAAUCUU | 2004 |
| | GAAGCUAAGCCGACCAUUU | 2005 |
| MAPK9 | AAAGAGAGCUUAUCGUGAA | 2006 |
| | GAUGAUAGGUUAGAAAUAG | 2007 |
| | ACAAAGAAGUCAUGGAUUG | 2008 |
| | GGAGCUGGAUCAUGAAAGA | 2009 |
| AIF1 | GAAAAGGGAUGAUGGGAUU | 2010 |
| | CCUAGACGAUCCCAAAUAU | 2011 |
| | GAGCCAAACCAGGGAUUUA | 2012 |
| | UGAAACGAAUGCUGGAGAA | 2013 |
| | UCACUCACCCAGAGAAAUA | 2014 |
| | CCAAGAAAGCUAUCUCUGA | 2015 |
| | AGACUCACCUAGAGCUAAA | 2016 |
| BBC3 | CCUGGAGGGUCCUGUACAA | 2017 |
| | GAGCAAAUGAGCCAAACGU | 2018 |
| | GGAGGGUCCUGUACAAUCU | 2019 |
| | GACUUUCUCUGCACCAUGU | 2020 |
| BCL2L1 | CCAGGGAGCUUGAAAGUUU | 2021 |
| | AAAGUGCAGUUCAGUAAUA | 2022 |
| | GAGAAUCACUAACCAGAGA | 2023 |
| | GAGCCCAUCCCUAUUAUAA | 2024 |
| BCL2L11 | GAGACGAGUUUAACGCUUA | 2025 |
| | AAAGCAACCUUCUGAUGUA | 2026 |
| | CCGAGAAGGUAGACAAUUG | 2027 |
| | GCAAAGCAACCUUCUGAUG | 2028 |
| | AGACAGAGCCACAAGGUAA | 2029 |
| | GCAAGGAGGUUAGAGAAAU | 2030 |
| | CAAGGAGGUUAGAGAAAUA | 2031 |
| | UCUUACGACUGUUACGUUA | 2032 |
| BID | GAAGACAUCAUCCGGAAUA | 2033 |
| | CAACAGCGUUCCUAGAGAA | 2034 |
| | GAAAUGGGAUGGACUGAAC | 2035 |
| | ACGAUGAGCUGCAGACUGA | 2036 |
| BIRC2 | GAAAGAAGCCUGCAUAUAA | 2037 |
| | GAAAUUGACUCUACAUUGU | 2038 |
| | ACAAAUAGCACUUAGGUUA | 2039 |
| | GAAUACACCUGUGGUUUAA | 2040 |
| BIRC3 | GGAGAUGCCUGCAUUAAAA | 2041 |
| | UCAUGAUCUUGUGUUAGA | 2042 |
| | GAAAGAACAUGUAAAGUGU | 2043 |
| | GAAGAAAGAACAUGUAAAG | 2044 |
| BIRC4 | GUAGAUAGAUGGCAAUAUG | 2045 |
| | GAGGAGGGCUAACUGAUUG | 2046 |
| | GAGGAACCCUGCCAUGUAU | 2047 |
| | GCACGGAUCUUUACUUUUG | 2048 |
| BIRC5 | GGCGUAAGAUGAUGGAUUU | 2049 |
| | GCAAAGGAAACCAACAAUA | 2050 |
| | GCACAAAGCCAUUCUAAGU | 2051 |
| | CAAAGGAAACCAACAAUAA | 2052 |
| BRCA1 | CCAUACAGCUUCAUAAAUA | 2053 |
| | GAAGAGAACUUAUCUAGUG | 2054 |
| | GAAGUGGGCUCCAGUAUUA | 2055 |
| | GCAAGAUGCUGAUUCAUUA | 2056 |
| | CCAUACAGCUUCAUAAAUA | 2057 |
| CARD4 | GAAAGUUAAUGUCAAGGAA | 2058 |
| | GAGCAACACUGGCAUAACA | 2059 |
| | UAACAGAGAAUUGCCUAAA | 2060 |
| | GCGAAGAGCUGACCAAAUA | 2061 |
| CASP10 | CAAAGGGUUUCUCUGUUUA | 2062 |
| | GAAAUGACCUCCCAAAGUA | 2063 |
| | GAAGGCAGCUGGUAUAUUC | 2064 |
| | GACAUGAUCUUCCUUCUGA | 2065 |
| | GCACUCUUCUGUUCCCUUA | 2066 |
| CASP2 | GUAUUAAACUCUCCUUUGA | 2067 |
| | GCAAGGAGAUGUCUGAAUA | 2068 |
| | CAACUUCCCUGAUCUUUAA | 2069 |
| | GCUCAAAGAUGUAAUGUAG | 2070 |
| CDKN1A | GAACAAGGAGUCAGACAUU | 2071 |
| | AAACUAGGCGGUUGAAUGA | 2072 |
| | GAUGGAACUUCGACUUUGU | 2073 |
| | GUAAACAGAUGGCACUUUG | 2074 |
| CFLAR | GAUGUGUCCUCAUUAAUUU | 2075 |
| | GAAGAGAGAUACAAGAUGA | 2076 |
| | GAGCAUACCUGGAGAGAGA | 2077 |
| | GCUAUGAAGUCCAGAAAUU | 2078 |
| CLK2 | GUGAAUAUGUGAAAUAGUG | 2079 |
| | AAAGCAUGCUAGAGUAUGA | 2080 |
| | UUAAGAUGUGGAGAAGUA | 2081 |
| | GAUAACAAGCUGACACAUA | 2082 |
| CLSPN | GGACGUAAUUGAUGAAGUA | 2083 |
| | GCAGAUGGGUUCUUAAAUG | 2084 |
| | CAAAUGAGGUUGAGGAAAU | 2085 |
| | GGAAAUACCUGGAGGAUGA | 2086 |
| CSNK2A1 | GAUCCACGUUUCAAUGAUA | 2087 |
| | GCAUUUAGGUGGAGACUUC | 2088 |
| | GAUGUACGAUUAUAGUUUG | 2089 |
| | UGAAUUGAUCCACGUUUC | 2090 |
| CTNNB1 | GCACAAGAAUGGAUCACAA | 2091 |
| | GCUGAAACAUGCAGUUGUA | 2092 |
| | GUACUACCAUGCAGAAUA | 2093 |
| | GAACUUGCAUUGUGAUUGG | 2094 |
| CXCR4 | GAAGCAUGACGGACAAGUA | 2095 |
| | GAACAUUCCAGAGCGUGUA | 2096 |
| | GUUCUUAGUUGCUGUAUGU | 2097 |
| | CAUCAUGGUUGGCCUUAUC | 2098 |
| CXCR6 | GGAACAAACUGGCAAAGCA | 2099 |
| | GAUCAGAGCAGCAGUGAAA | 2100 |
| | GGGCAAAACUGAAUUAUAA | 2101 |
| | GAUCUCAGGUUCUCCUUGA | 2102 |
| DAXX | CUACAGAUCUCCAAUGAAA | 2103 |
| | GCUACAGCUGGAGAAUGA | 2104 |
| | GGAAACAGCUAUGUGGAAA | 2105 |
| | GGAGUUGGAUCUCUCAGAA | 2106 |

TABLE X-continued

| Gene Symbol | Sense | SEQ ID NO. |
|---|---|---|
| GAS41 | GUAGUAAGCUAAACUGAAA | 2107 |
|  | GACAAUAUGUUCAAGAGAA | 2108 |
|  | GACAACAUCUCGUCAGCUA | 2109 |
|  | UAUAUGAUGUGUCCAGUAA | 2110 |
| GTSE1 | CAAAGAAGCUCACUUACUG | 2111 |
|  | GAACAGCCCUAAAGUGGUU | 2112 |
|  | GAACAUGGAUGACCCUAAG | 2113 |
|  | GGGCAAAGCUAAAUCAAGU | 2114 |
| HDAC3 | GGAAAGCGAUGUGGAGAUU | 2115 |
|  | CCAAGACCGUGGCCUAUUU | 2116 |
|  | AAAGCGAUGUGGAGAUUUA | 2117 |
|  | GUGAGGAGCUUCCCUAUAG | 2118 |
| HDAC5 | GAAUUCCUCUUUGUCGAAGU | 2119 |
|  | GUUAUUAGCACCUUUAAGA | 2120 |
|  | GGAGGGAGGCCAUGACUUG | 2121 |
|  | CAGGAGAGCUCAAGAAUGG | 2122 |
|  | GGAUAUGGAUUUCAGUUAA | 2123 |
|  | GGAAGUCGGUGCCUUGGUU | 2124 |
|  | GGAAGGAGAGGACUGGUUU | 2125 |
| HEC | GCAGAUACUUGCACGGUUU | 2126 |
|  | GAGUAGAACUAGAAUGUGA | 2127 |
|  | GCGAAUAAAUCAUGAAAGA | 2128 |
|  | GAAGAUGGAAUUAUGCAUA | 2129 |
| HIST1H2AA | GGCAAUGCGUCUCGCGAUA | 2130 |
|  | GAUCCGCAAUGAUGAGGAA | 2131 |
|  | GCAAUGCGUCUCGCGAUAA | 2132 |
|  | GAGGAACUCAAUAAGCUUU | 2133 |
| LMNB1 | AAUAGAAGCUGUGCAAUUA | 2134 |
|  | CAACUGACCUCACUCUGGAA | 2135 |
|  | GAAGGAAUCUGAUCUUAAU | 2136 |
|  | GGGAAGGGUUUCUCUAUUA | 2137 |
| LMNB2 | GGAGGUUCAUUGAGAAUUG | 2138 |
|  | GGCAAUAGCUCACCGUUUA | 2139 |
|  | CAAAUACGCUUAGCUGUGU | 2140 |
|  | GGAGAUCGCCUACAAGUUC | 2141 |
| MYB | GCAGAAACACUCCAAUUUA | 2142 |
|  | GUAAAUACGUGAAUGCAUU | 2143 |
|  | GCACUGAACUUUUGAGAUA | 2144 |
|  | GAAGAACAGUCAUUUGAUG | 2145 |
| MYT1 | GAGGUGAGCUGUUAAAAUCA | 2146 |
|  | GCAGGGUGAUUUCCUAAUA | 2147 |
|  | GGGAGAAGAUAUUUAAUUG | 2148 |
|  | CAACUUCUCUCCUGAACUU | 2149 |
| NFKBIB | GGACACGGCACUGCACUUG | 2150 |
|  | GCACUUGGCUGUGAUUCAU | 2151 |
|  | GAGACAGGGCGAUGAAUA | 2152 |
|  | CAUGAACCCUUCCUGGAUU | 2153 |
| NFKBIA | GAACAUGGACUUGUAUAUU | 2154 |
|  | GAUGUGGGGUGAAAAGUUA | 2155 |
|  | GGACGAGAAAGAUCAUUGA | 2156 |
|  | AGGACGAGCUGCCCUAUGA | 2157 |
| NFKBIE | GAAGGGAAGUUUCAGUAAC | 2158 |
|  | GGAGGGAAGUUUCAGUAA | 2159 |
|  | GGAAACUGCUGCUGUGUAC | 2160 |
|  | GAACCAACCACUCAUGGAA | 2161 |
| NUMA1 | GGGAACAGUUUGAAUAUAA | 2162 |
|  | GCAGUAGCCUGAAGCAGAA | 2163 |
|  | CGAAGGAUGCACAGAUA | 2164 |
|  | GCAAGAGGCUGAGAGGAAA | 2165 |
| NUP153 | GAAGACAAAUGAAAGCUAA | 2166 |
|  | GAUAAAGACUGCUGUUAGA | 2167 |
|  | GAGGAGAGCUCAAUAUAUA | 2168 |
|  | GAGGAAGCCUGAUUAAAGA | 2169 |
| OPA1 | GAAAGAGCAUGAUGACAUA | 2170 |
|  | GAGGAGAGCUCUAUUAUGU | 2171 |
|  | GAAACUGAAUGGAAGAAUA | 2172 |
|  | AAAGAAGGCUGUACCGUUA | 2173 |
| PARVA | CUACAUGUCUUUGCUCUUA | 2174 |
|  | GCUAAGUCCUGUAAGAAUA | 2175 |
|  | CAAAGGCAAUGUACUGUUU | 2176 |
|  | GAACAAUGGUGGAUCCAAA | 2177 |
| PIK3CG | AAGUUCAGCUUCUCUAUUA | 2178 |
|  | GAAGAAAUCUCUGAUGGAU | 2179 |
|  | GAACACCUUUACUCUAUAA | 2180 |
|  | GCAUGGAGCUGGAGAACUA | 2181 |
| PRKDC | GAUGAAAGCUCUAAAGAUG | 2182 |
|  | GAAAGGAGGUUCUAAACUA | 2183 |
|  | GGAAGAAGCUCAUUUGAUU | 2184 |
|  | GCAAAGAGGUGGCAGUUAA | 2185 |
| RASA1 | GGAAGAAGAUCCACAUGAA | 2186 |
|  | GAACAUACUUUCAGAGCUU | 2187 |
|  | GAACAAUCUUUGCUGUAUA | 2188 |
|  | UAACAGAACUGCUUCAACA | 2189 |
| SLC9A1 | GAAGAGAUCCACACACAGU | 2190 |
|  | UCAAUGAGCUGCUGCACAU | 2191 |
|  | GAAGAUAGGUUUCCAUGUG | 2192 |
|  | GAAUUACCCUUCCUCAUCU | 2193 |
| TEGT | CUACAGAGCUUCAGUGUGA | 2194 |
|  | GAACAUAUUUGAUCGAAAG | 2195 |
|  | GAGCAAACCUAGAUAAGGA | 2196 |
|  | GCAUUGAUCUCUUCUUAGA | 2197 |
| TERT | GGAAGACAGUGGUGAACUU | 2198 |
|  | GCAAAGCAUUGGAAUCAGA | 2199 |
|  | GAGCUGACGUGGAAGAUGA | 2200 |
|  | GAACGGGCCUGGAACCAUA | 2201 |
| TNFRSF6 | GAUACUAACUGCUCUCAGA | 2202 |
|  | GAAAGAAUGGUGUCAAUGA | 2203 |
|  | UCAAUAAUGUCCCAUGUAA | 2204 |
|  | UCAUGAAUCUCCAACCUUA | 2205 |
|  | GAUGUUGACUUGAGUAAAU | 2206 |
| TOP1 | GAAAGGAAAUGACUAAUGA | 2207 |
|  | GAAGAAGGCUGUUCAGAGA | 2208 |
|  | GGAAGUAGCUACGUUCUUU | 2209 |
|  | GGACAUAAGUGGAAAGAAG | 2210 |
| TOP2A | GAAAGAGUCCAUCAGAUUU | 2211 |
|  | CAAACUACAUUGGCAUUUA | 2212 |
|  | AAACAGACAUGGAUGGAUA | 2213 |
|  | CGAAAGGAAUGGUUAACUA | 2214 |
| TOP3A | CCAGAAAUCUUCCACAGAA | 2215 |
|  | GAAACUAUCUGGAUGUAUA | 2216 |
|  | CCACAAAGAUGGUAUCGUA | 2217 |
|  | GGAAAUGGCUGUGGUAACA | 2218 |
| TOP3B | GAGACAAGAUGAAGACUGU | 2219 |
|  | GCACAUGGGCUGCGUCUUU | 2220 |
|  | CCAGUGCGCUUCAAGAUGA | 2221 |
|  | GAACAUCUGCUUUGAGGUU | 2222 |
| WEE1 | GGUAUUGCCUUGUGAAUUU | 2223 |
|  | GCAGAACAAUUACGAAUAG | 2224 |
|  | GUACAUAGCUGUUUGAAAU | 2225 |
|  | GCUGUAAACUUGUAGCAUU | 2226 |

In addition, to identifying functional siRNA against gene families or pathways, it is possible to design duplexes against genes known to be involved in specific diseases. For example when dealing with human disorders associated with allergies, it will be beneficial to develop siRNA against a number of genes including but not limited to:

the interleukin 4 receptor gene
(SEQ. ID NO. 2227 UAGAGGUGCUCAUUCAUUU,
SEQ. ID NO. 2228 GGUAUAAGCCUUUCCAAGA,
SEQ. ID NO. 2229: ACACACAGCUGGAAGAAAU,
SEQ. ID NO. 2230: UAACAGAGCUUCCUUAGGU), the Beta-arrestin-2
(SEQ. ID NO. 2231: GGAUGAAGGAUGACGACUA,
SEQ. ID NO. 2232: ACACCAACCUCAUUGAAUU,
SEQ. ID NO. 2233: CGAACAAGAUGACCAGGUA,
SEQ. ID NO. 2234: GAUGAAGGAUGACGACUAU,), the interferon-gamma receptor 1 gene
(SEQ. ID NO. 2235: CAGCAUGGCUCUCCUCUUU,
SEQ. ID NO. 2236: GUAAAGAACUAUGGUGUUA,
SEQ. ID NO. 2237: GAAACUACCUGUUACAUUA,
SEQ. ID NO. 2238: GAAGUGAGAUCCAGUAUAA), the matrix metalloproteinase MMP-9
(SEQ. ID NO. 2239: GGAACCAGCUGUAUUUGUU,
SEQ. ID NO. 2240: GUUGGAGUGUUUCUAAUAA,
SEQ. ID NO. 2241: GCGCUGGGCUUUAGAUCAUU,
SEQ. ID NO. 2242: GGAGCCAGUUUGCCGGAUA), the Slc11a1 (Nramp1) gene
(SEQ. ID NO. 2243: CCAAUGGCCUGCUGAACAA,
SEQ. ID NO. 2244: GGGCCUGGCUUCCUCAUGA,
SEQ. ID NO. 2245: GGGCAGAGCUCCACCAUGA,
SEQ. ID NO. 2246: GCACGGCCAUUGCAUUCAA), SPINK5
(SEQ. ID NO. 2247: CCAACUGCCUGUUCAAUAA,
SEQ. ID NO. 2248: GGAUACAUGUGAUGAGUUU,
SEQ. ID NO. 2249: GGACGAAUGUGCUGAGUAU,
SEQ. ID NO. 2250 GAGCUUGUCUUAUUUGCUA,), the CYP1A2 gene
(SEQ. ID NO. 2251: GAAAUGCUGUGUCUUCGUA,
SEQ. ID NO. 2252: GGACAGCACUUCCCUGAGA,
SEQ. ID NO. 2253: GAAGACACCACCAUUCUGA,
SEQ. ID NO. 2254: GGCCAGAGCUUGACCUUCA), thymosin-beta4Y
(SEQ. ID NO. 2255: GGACAGGCCUGCGUUGUUU,
SEQ. ID NO. 2256: GGAAAGAGGAAGCUCAUGA,
SEQ. ID NO. 2257: GCAAACACGUUGGAUGAGU,
SEQ. ID NO. 2258: GGACUAUGCUGCCCUUUUG, activin A receptor IB
(SEQ. ID NO. 2259: ACAAGACGCUCCAGGAUCU,
SEQ. ID NO. 2260: GCAACAGGAUCGACUUGAG,
SEQ. ID NO. 2261: GAAGCUGCGUCCCAACAUC,
SEQ. ID NO. 2262: GCAUAGGCCUGUAAUCGUA,
SEQ. ID NO. 2263: UCAGAGAGUUCGAGACAAA,
SEQ. ID NO. 2264: UGCGAAAGGUUGUAUGUGA,
SEQ. ID NO. 2265: GCAACAGGAUCGACUUGAG,
SEQ. ID NO. 2266: GAAUAGCGUUGUGUGUUAU,
SEQ. ID NO. 2267: UGAAUAGCGUUGUGUGUUA,
SEQ. ID NO. 2268: GGGAUCAGUUUGUUGAAUA,
SEQ. ID NO. 2269: GAGCCUGAAUCAUCGUUUA,), ADAM33
(SEQ. ID NO. 2270: GGAAGUACCUGGAACUGUA,
SEQ. ID NO. 2271: GGACAGAGGGAACCAUUUA,
SEQ. ID NO. 2272: GGUGAGAGGUAGCUCCUAA,
SEQ. ID NO. 2273: AAAGACAGGUGGCCACUGA), the TAP1 gene
(SEQ. ID NO. 2274: GAAAGAUGAUCAGCUAUUU,
SEQ. ID NO. 2275: CAACAGAACCAGACAGGUA,
SEQ. ID NO. 2276: UGAGAAAUGUUCAGAAUGU,
SEQ. ID NO. 2277: UACCUUCACUCGAAACUUA, COX-2
(SEQ. ID NO. 2278: GAACGAAAGUAAAGAUGUU,
SEQ. ID NO. 2279: GGACUUAUGGGUAAUGUUA,
SEQ. ID NO. 2280: UGAAGGACUUAUGGGUAAA,
SEQ. ID NO. 2281: GAUCAGAGUUCACUUUCUU), ADPRT
(SEQ. ID NO. 2282: GGAAAGAUGUUAAGCAUUU,
SEQ. ID NO. 2283: CAUGGGAGCUCUUGAAAUA,
SEQ. ID NO. 2284: GAACAAGGAUGAAGUGAAG,
SEQ. ID NO. 2285: UGAAGAAGCUCACAGUAAA,), HDC
(SEQ. ID NO. 2286: CAGCAGACCUUCAGUGUGA,
SEQ. ID NO. 2287: GGAGAGAUGGUGGAUUA,
SEQ. ID NO. 2288: GUACAGAGCUGGAGAUGAA,
SEQ. ID NO. 2289: GAACGUCCCUUCAGUCUGU), HnmT
(SEQ. ID NO. 2290: CAAAUUCUCUCCAAAGUUC,
SEQ. ID NO. 2291: GGAUAUAUCUGACUGCUUU,
SEQ. ID NO. 2292: GAGCAGAGCUUGGGAAAGA,
SEQ. ID NO. 2293: GAUAUGAGAUGUAGCAAAU), GATA-3
(SEQ. ID NO. 2294: GAACUGCUUUCUUUCGUUU,
SEQ. ID NO. 2295: GCAGUAUCAUGAAGCCUAA,
SEQ. ID NO. 2296: GAAACUAGGUCUGAUAUUC,
SEQ. ID NO. 2297: GUACAGCUCCGGACUCUUC), Gab2
(SEQ. ID NO. 2298: GCACAACCAUUCUGAAGUU,
SEQ. ID NO. 2299: GGACUUAGAUGCCCAGAUG,
SEQ. ID NO. 2300: GAAGGUGGAUUCUAGGAAA,
SEQ. ID NO. 2301: GGACUAGCCCUGCUGUUUA),
and STAT6
(SEQ. ID NO. 2302 AUAGAAACUCCUGCUAAU,
SEQ. ID NO. 2303: GGACAUUUAUUCCCAGCUA,
SEQ. ID NO. 2304: GGACAGAGCUACAGACCUA,
SEQ. ID NO. 2305: GGAUGGCUCUCCACAGAUA).

In addition, rationally designed siRNA or siRNA pools can be directed against genes involved in anemia, hemophila or hypercholesterolemia. Such genes would include, but are not be limited to:

APOA5
(SEQ. ID NO. 2306: GAAAGACAGCCUUGAGCAA,
SEQ. ID NO. 2307: GGACAGGGAGGCCACCAAA,
SEQ. ID NO. 2308: GGACGAGGCUGGGCUUUG,
SEQ. ID NO. 2309: AGCAAGACCUCAACAAUAU),

HMG-CoA reductase
(SEQ. ID NO. 2310: GAAUGAAGCUUUGCCCUUU,
SEQ. ID NO. 2311: GAACACAGUUUAGUGCUUU,
SEQ. ID NO. 2312: UAUCGAGCUCUUUAAUGUU,
SEQ. ID NO. 2313: UGAAGAAUGUCUACAGAUA), NOS3
(SEQ. ID NO. 2314: UGAAGCACCUGGAGAAUGA,
SEQ. ID NO. 2315: CGGAACAGCACAAGAGUUA,
SEQ. ID NO. 2316: GGAAGAAGACCUUUAAAGA,
SEQ. ID NO. 2317: GCACAAGAGUUAUAAGAUC), ARH
(SEQ. ID NO. 2318: CGAUACAGCUUGGCACUUU,
SEQ. ID NO. 2319: GAGAAGCGCUGCCCUGUGA,
SEQ. ID NO. 2320: GAAUCAUGCUGUUCUCUUU,
SEQ. ID NO. 2321: GGAGUAACCGGACACCUUA), CYP7A1
(SEQ. ID NO. 2322: UAAGGUGACUCGAGUGUUU,
SEQ. ID NO. 2323: AAACGACACUUUCAUCAAA,
SEQ. ID NO. 2324: GGACUCAAGUUAAAGUAUU,
SEQ. ID NO. 2325: GUAAUGGACUCAAGUUAAA), FANCA
(SEQ. ID NO. 2326: GGACAUCACUGCCCACUUC,
SEQ. ID NO. 2327: AGAGGAAGAUGUUCACUUA,
SEQ. ID NO. 2328: GAUCGUGGCUCUUCAGGAA,
SEQ. ID NO. 2329: GGACAGAGGCAGAUAAGAA),

```
FANCG
(SEQ. ID NO. 2330: GCACUAAGCAGCCUUCAUG,
SEQ. ID NO. 2331: GCAAGCAGGUGCCUACAGA,
SEQ. ID NO. 2332: GGAAUUAGAUGCUCCAUUG,
SEQ. ID NO. 2333: GGACAUCUCUGCCAAAGUC),

ALAS
(SEQ. ID NO. 2334: CAAUAUGCCUGGAAACUAU,
SEQ. ID NO. 2335: GGUUAAGACUCACCAGUUC,
SEQ. ID NO. 2336: CAACAGGACUUUAGGUUCA,
SEQ. ID NO. 2337: GCAUAAGAUUGACAUCAUC),

PIGA
(SEQ. ID NO. 2338: GAAAGAGGGCAUAAGGUUA,
SEQ. ID NO. 2339: GGACUGAUCUUUAAACUAU,
SEQ. ID NO. 2340: UCAAUGGCUUACUUCAUC,
SEQ. ID NO. 2341: UCUAAGAACUGAUGUCUAA),
and factor VIII
(SEQ. ID NO. 2342: GCAAAUAGAUCUCCAUUAC,
SEQ. ID NO. 2343: CCAGAUAUGUCGUUCUUUA,
SEQ. ID NO. 2344: GAAAGGCUGUGCUCUCAAA,
SEQ. ID NO. 2345: GGAGAAACCUGCAUGAAAG,
SEQ. ID NO. 2346: CUUGAAGCCUCCUGAAUUA,
SEQ. ID NO. 2347: GAGGAAGCAUCCAAAGAUU,
SEQ. ID NO. 2348: GAUAGGAGAUACAAACUUU).
```

Furthermore, rationally designed siRNA or siRNA pools can be directed against genes involved in disorders of the brain and nervous system. Such genes would include, but are not be limited to:

```
APBB1
(SEQ. ID NO. 2349: CUACGUAGCUCGUGAUAAG,
SEQ. ID NO. 2350: GCAGAGAUGUCCACACGUU,
SEQ. ID NO. 2351: CAUGAGAUCUGCUCUAAGA,
SEQ. ID NO. 2352: GGGCACCUCUGCUGUAUUG),

BACE1
(SEQ. ID NO. 2353: CCACAGAGCAAGUGAUUUA,
SEQ. ID NO. 2354: GCAGAAAGGAGAUCAUUUA,
SEQ. ID NO. 2355: GUAGCAAGAUCUUUACAUA,
SEQ. ID NO. 2356: UGUCAGAGCUUGAUUAGAA),

PSEN1
(SEQ. ID NO. 2357: GAGCUGACAUUGAAAUAUG,
SEQ. ID NO. 2358: GUACAGAUUUCUCAUCA,
SEQ. ID NO. 2359: GAGGUUAGGUGAAGUGGUU,
SEQ. ID NO. 2360: GAAAGGGAGUCACAAGACA,
SEQ. ID NO. 2361: GAACUGGAGUGGAGUAGGA,
SEQ. ID NO. 2362: CAGCAGGCAUAUCUCAUUA,
SEQ. ID NO. 2363: UCAAGUACCUCCCUGAAUG),

PSEN2
(SEQ. ID NO. 2364: GCUGGGAAGUGGCUUAAUA,
SEQ. ID NO. 2365 CAUAUUCCCUGCCCUGAA,
SEQ. ID NO. 2366: GGGAAGUGCUCAAGACCUA,
SEQ. ID NO. 2367: CAUAGAAAGUGACGUGUUA),

MASS1
(SEQ. ID NO. 2368: GGAAGGAGCUGUUAUGAGA,
SEQ. ID NO. 2369: GAAAGGAGAAGCUAAAUUA,
SEQ. ID NO. 2370: GGAGGAAGGUCAAGAUUUA,
SEQ. ID NO. 2371: GGAAAUAGCUGAGAUAAUG,),

ARX
(SEQ. ID NO. 2372: CCAGACGCCUGAUAUUGAA,
SEQ. ID NO. 2373: CAGCACCACUCAAGACCAA,
SEQ. ID NO. 2374: CGCCUGAUAUUGAAGUAAA,
SEQ. ID NO. 2375: CAACAUCCACUCUCUCUUG)
and NNMT
(SEQ. ID NO. 2376: GGGCAGUGCUCCAGUGGUA,
SEQ. ID NO. 2377: GAAAGAGGCUGGCUACACA,
SEQ. ID NO. 2378: GUACAGAAGUGAGACAUAA,
SEQ. ID NO. 2379: GAGGUGAUCUCGCAAAGUU).
```

In addition, rationally designed siRNA or siRNA pools can be directed against genes involved in hypertension and related disorders. Such genes would include, but are not be limited to:

```
angiotensin II type 1 receptor
(SEQ. ID NO. 2380: CAAGAAGCCUGCACCAUGU,
SEQ. ID NO. 2381: GCACUUCACUACCAAAUGA,
SEQ. ID NO. 2382: GCACUGGUCCCAAGUAGUA,
SEQ. ID NO. 2383: CCAAAGGGCAGUAAAGUUU,
SEQ. ID NO. 2384: GCUCAGAGGAGGUGUAUUU,
SEQ. ID NO. 2385: GCACUUCACUACCAAAUGA,
SEQ. ID NO. 2386: AAAGGGCAGUAAAGUUU), AGTR2
(SEQ. ID NO. 2387: GAACAUCUCUGGCAACAAU,
SEQ. ID NO. 2388: GGUGAUAUAUCUCAAAUUG,
SEQ. ID NO. 2389: GCAAGCAUCUUAUAUAGUU,
SEQ. ID NO. 2390: GAACCAGUCUUUCAACUCA),
``` and other related targets.

Example XIII

Validation of Multigene Knockout Using Rab5 and Eps

Two or more genes having similar, overlapping functions often leads to genetic redundancy. Mutations that knockout only one of, e.g., a pair of such genes (also referred to as homologs) results in little or no phenotype due to the fact that the remaining intact gene is capable of fulfilling the role of the disrupted counterpart. To fully understand the function of such genes in cellular physiology, it is often necessary to knockout or knockdown both homologs simultaneously. Unfortunately, concomitant knockdown of two or more genes is frequently difficult to achieve in higher organisms (e.g., mice) thus it is necessary to introduce new technologies dissect gene function. One such approach to knocking down multiple genes simultaneously is by using siRNA. For example, FIG. 11 showed that rationally designed siRNA directed against a number of genes involved in the clathrin-mediated endocytosis pathway resulted in significant levels of protein reduction (e.g., >80%). To determine the effects of gene knockdown on clathrin-related endocytosis, internalization assays were performed using epidermal growth factor and transferrin. Specifically, mouse receptor-grade EGF (Collaborative Research Inc.) and iron-saturated human transferrin (Sigma) were iodinated as described previously (Jiang, X., Huang, F., Marusyk, A. & Sorkin, A. (2003) *Mol Biol Cell* 14, 858-70). HeLa cells grown in 12-well dishes were incubated with $^{125}$I-EGF (1 ng/ml) or $^{125}$I-transferrin (1 µg/ml) in binding medium (DMEM, 0.1% bovine serum albumin) at 37° C., and the ratio of internalized and surface radioactivity was determined during 5-min time course to calculate specific internalization rate constant $k_e$ as described previously (Jiang, X et al.). The measurements of the uptakes of radiolabeled transferrin and EGF were performed using short time-course assays to avoid influence of the recycling on the uptake kinetics, and using low ligand concentration to avoid saturation of the clathrin-dependent pathway (for EGF Lund, K. A., Opresko, L. K., Strarbuck, C., Walsh, B. J. & Wiley, H. S. (1990) *J. Biol. Chem.* 265, 15713-13723).

Figure 22:
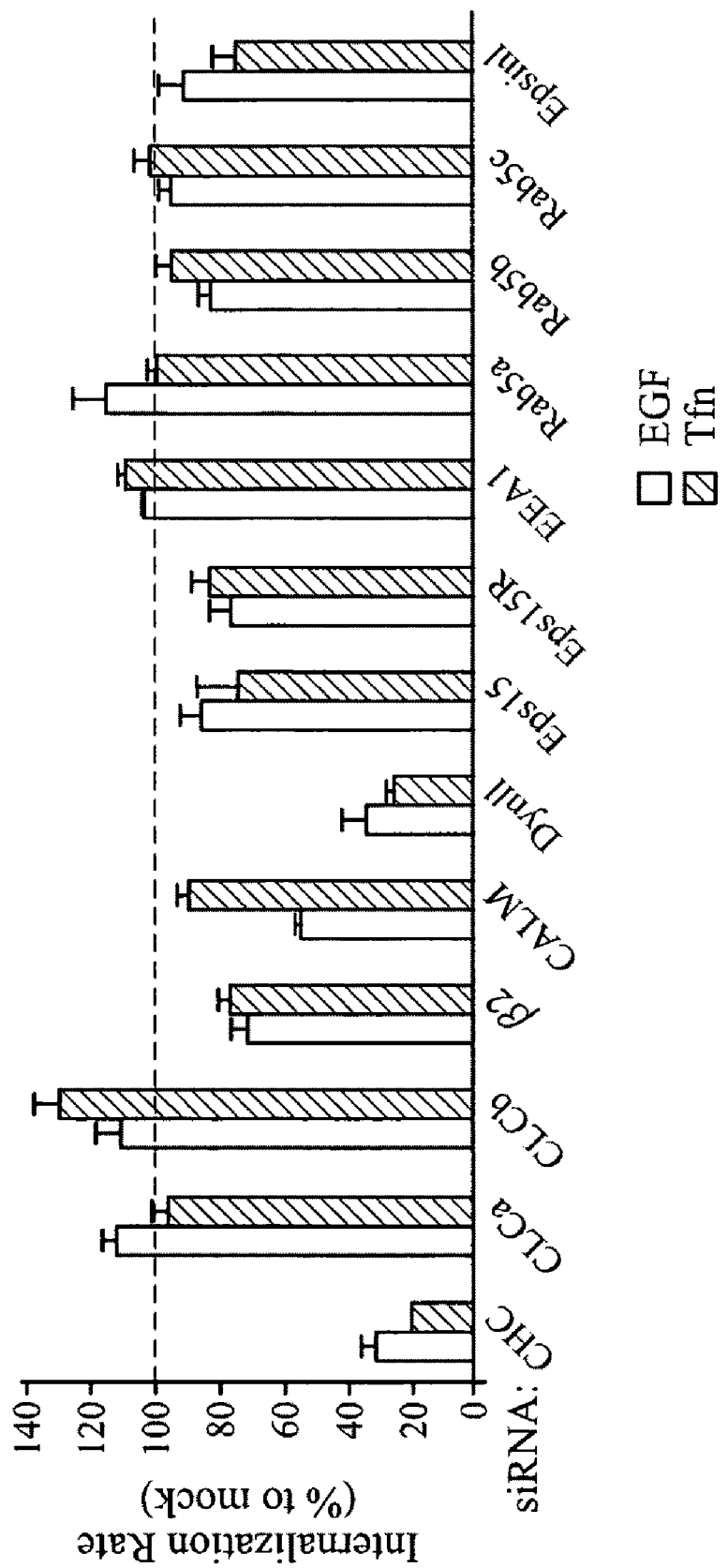
FIG. 22 shows the results of an EGFR and TfnR internalization assay when single gene knockdowns are performed. The Y-axis represents percent internalization relative to control.
Figure 23:
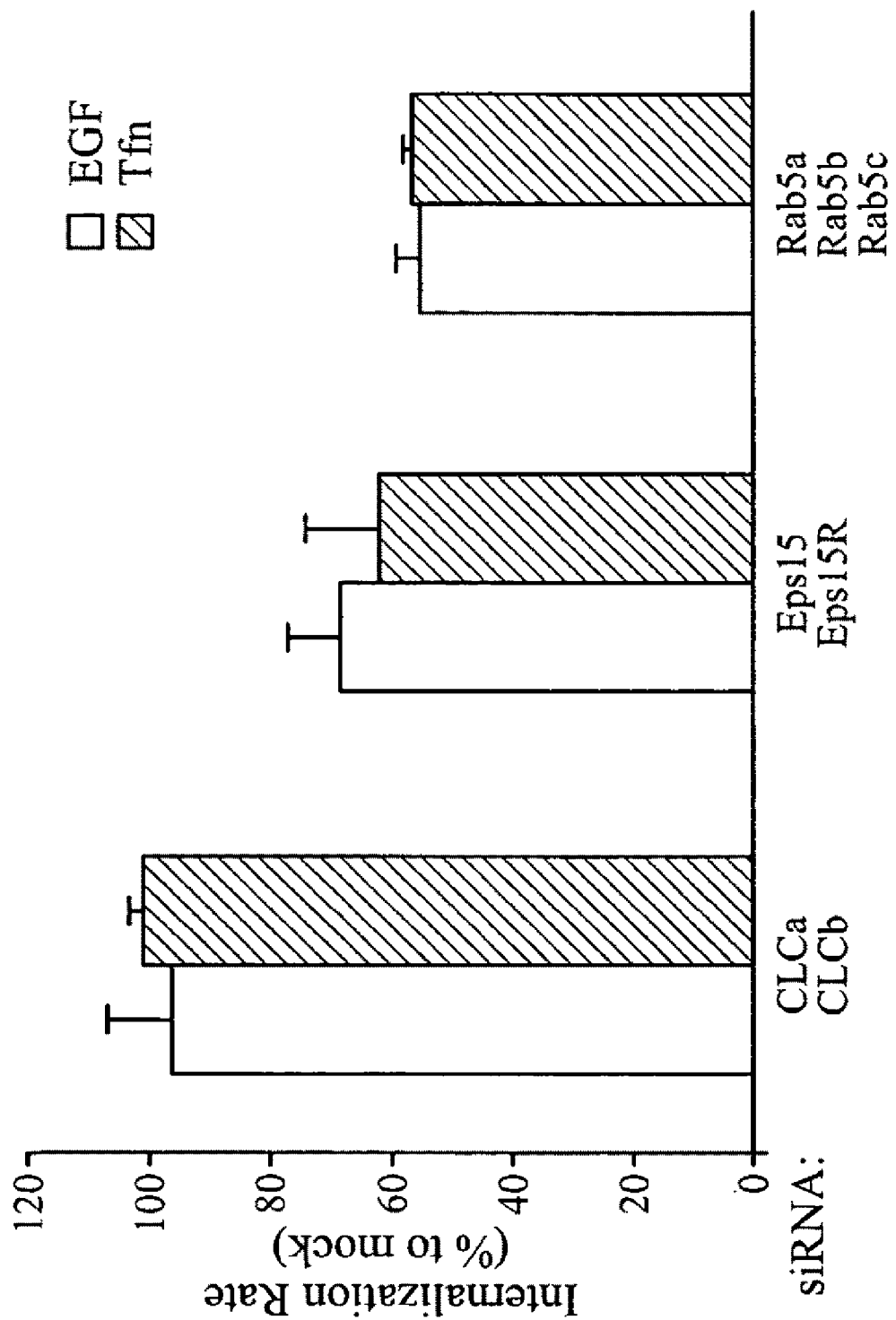
FIG. 23 shows the results of an EGFR and TfnR internalization assay when multiple genes are knocked down (e.g., Rab5a, b, c). The Y-axis represents the percent internalization relative to control.

The effects of knocking down Rab5a, 5b, 5c, Eps, or Eps 15R (individually) are shown in FIG. 22 and demonstrate that disruption of single genes has little or no effect on EGF or Tfn internalization. In contrast, simultaneous knock down of Rab5a, 5b, and 5c, or Eps and Eps 15R, leads to a distinct phenotype (note: total concentration of siRNA in these experiments remained constant with that in experiments in which a single siRNA was introduced, see FIG. 23). These experiments demonstrate the effectiveness of using rationally designed siRNA to knockdown multiple genes and validates the utility of these reagents to override genetic redundancy.

Example XIV

Validation of Multigene Targeting Using G6PD, GAPDH, PLK, and UQC

Figure 24:
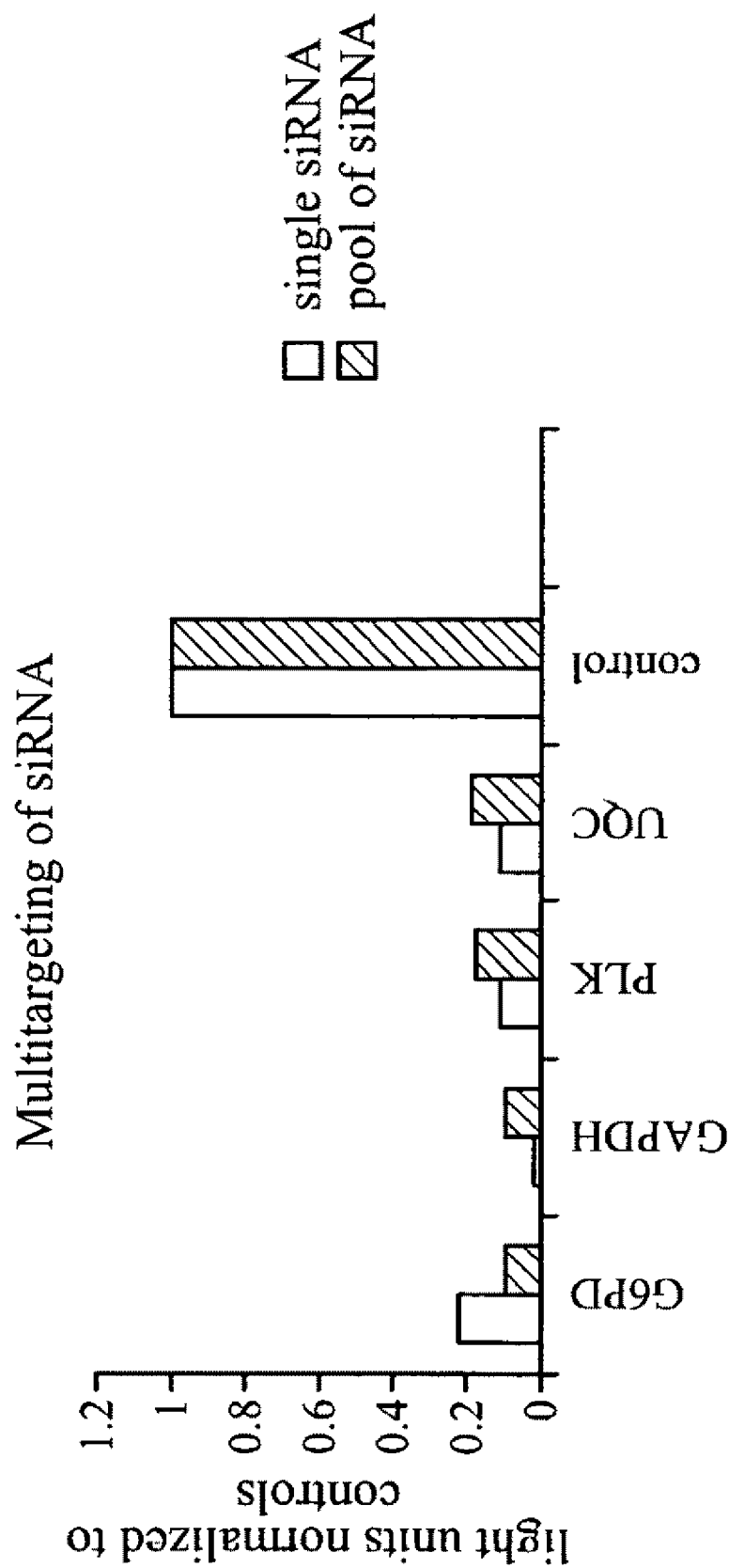
FIG. 24 shows the simultaneous knockdown of four different genes. siRNAs directed against G6PD, GAPDH, PLK, and UQC were simultaneously introduced into cells. Twenty-four hours later, cultures were harvested and assayed for mRNA target levels for each of the four genes. A comparison is made between cells transfected with individual siRNAs vs. a pool of siRNAs directed against all four genes.

Further demonstration of the ability to knock down expression of multiple genes using rationally designed siRNA was performed using pools of siRNA directed against four separate genes. To achieve this, siRNA were transfected into cells (total siRNA concentration of 100 nM) and assayed twenty-four hours later by B-DNA. Results shown in FIG. 24 show that pools of rationally designed molecules are capable of simultaneously silencing four different genes.

Example XV

Validation of Multigene Knockouts as Demonstrated by Gene Expression Profiling, a Prophetic Example To further demonstrate the ability to concomitantly knock-down the expression of multiple gene targets, single siRNA or siRNA pools directed against a collection of genes (e.g., 4, 8, 16, or 23 different targets) are simultaneously transfected into cells and cultured for twenty-four hours. Subsequently, mRNA is harvested from treated (and untreated) cells and labeled with one of two fluorescent probes dyes (e.g., a red fluorescent probe for the treated cells, a green fluorescent probe for the control cells.). Equivalent amounts of labeled RNA from each sample is then mixed together and hybridized to sequences that have been linked to a solid support (e.g., a slide, "DNA CHIP"). Following hybridization, the slides are washed and analyzed to assess changes in the levels of target genes induced by siRNA.

Example XVI

Identifying Hyperfunctional siRNA

Identification of Hyperfunctional Bcl-2 siRNA

Figure 25:
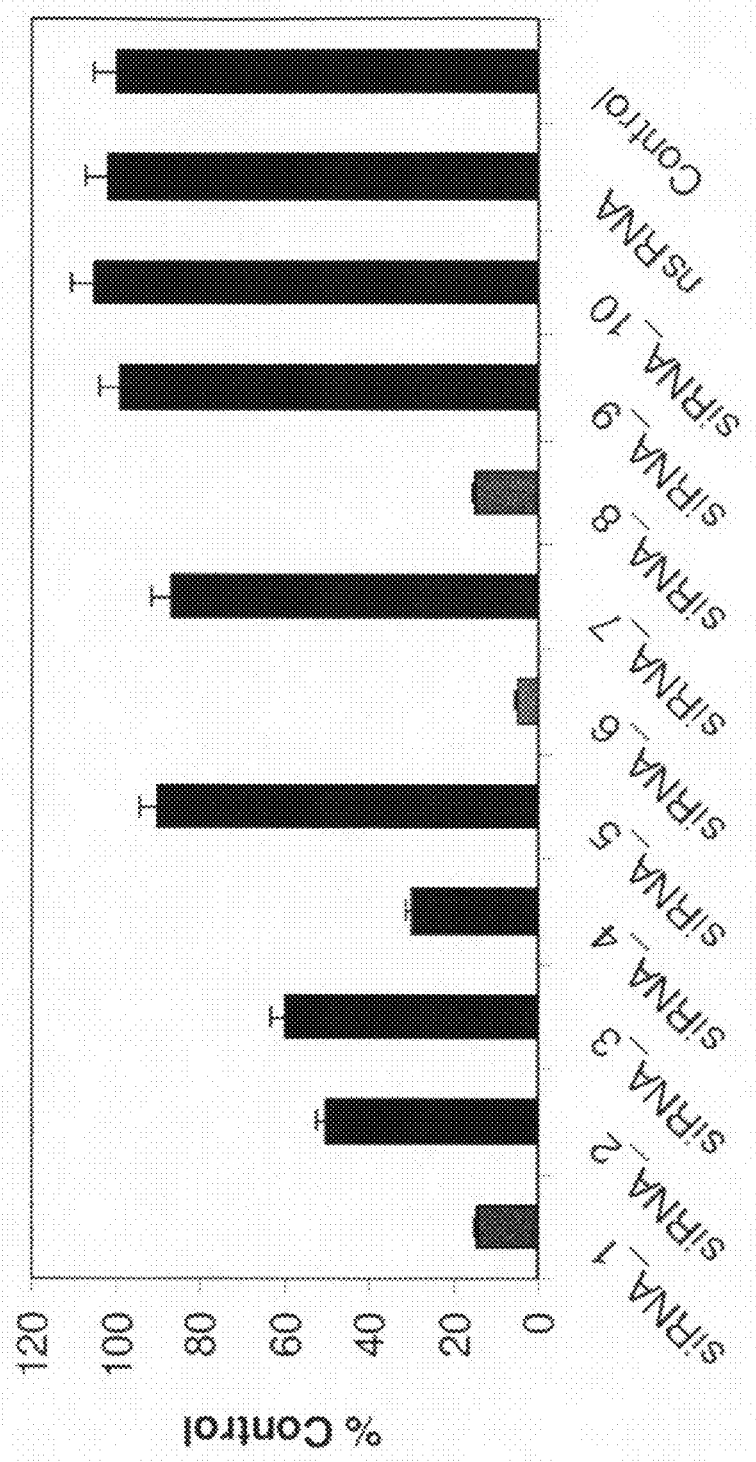
FIG. 25 shows the functionality of ten siRNAs at 0.3 nM concentrations.

The ten rationally designed Bcl2 siRNA (identified in FIG. 13, 14) were tested to identify hyperpotent reagents. To accomplish this, each of the ten Bcl-2 siRNA were individually transfected into cells at a 300 pM (0.3 nM) concentrations. Twenty-four hours later, transcript levels were assessed by B-DNA assays and compared with relevant controls. As shown in FIG. 25, while the majority of Bcl-2 siRNA failed to induce functional levels of silencing at this concentration, siRNA 1 and 8 induced >80% silencing, and siRNA 6 exhibited greater than 90% silencing at this subnanomolar concentration.

By way of prophetic examples, similar assays could be performed with any of the groups of rationally designed genes described in Example VII or Example VIII. Thus for instance, rationally designed siRNA sequences directed against

```
PDGFA
(SEQ. ID NO. 2391: GGUAAGAUAUUGUGCUUUA,
SEQ. ID NO. 2392: CCGCAAAUAUGCAGAAUUA,
SEQ. ID NO. 2393: GGAUGUACAUGGCGUGUUA,
SEQ. ID NO. 2394: GGUGAAGUUUGUAUGUUUA),
or
```

```
PDGFB
(SEQ. ID NO. 2395: GCUCCGCGCUUUCCGAUUU,
SEQ. ID NO. 2396: GAGCAGGAAUGGUGAGAUG,
SEQ. ID NO. 2397: GAACUUGGGAUAAGAGUGU,
SEQ. ID NO. 2398: CCGAGGAGCUUUAUGAGAU,
SEQ. ID NO. 2399: UUUAUGAGAUGCUGAGUGA)
``` could be introduced into cells at increasingly limiting concentrations to determine whether any of the duplexes are hyperfunctional. Similarly, rationally designed sequences directed against

```
HIF1 alpha
(SEQ. ID NO. 2400: GAAGGAACCUGAUGCUUUA,
SEQ. ID NO. 2401: GCAUAUAUCUAGAAGGUAU,
SEQ. ID NO. 2402: GAACAAAUACAUGGGAUUA,
SEQ. ID NO. 2403: GGACACAGAUUUAGACUUG),
or
```

```
VEGF
(SEQ. ID NO. 2404: GAACGUACUUGCAGAUGUG,
SEQ. ID NO. 2405: GAGAAAGCAUUUGUUUGUA,
SEQ. ID NO. 2406: GGAGAAAGCAUUUGUUUGU,
SEQ. ID NO. 0588: CGAGGCAGCUUGAGUUAAA)
``` could be introduced into cells at increasingly limiting concentrations and screened for hyperfunctional duplexes.

Example XVII

Gene Silencing: Prophetic Example

Below is an example of how one might transfect a cell.
a. Select a cell line. The selection of a cell line is usually determined by the desired application. The most important feature to RNAi is the level of expression of the gene of interest. It is highly recommended to use cell lines for which siRNA transfection conditions have been specified and validated.
b. Plate the cells. Approximately 24 hours prior to transfection, plate the cells at the appropriate density so that they will be approximately 70-90% confluent, or approximately $1 \times 10^5$ cells/ml at the time of transfection. Cell densities that are too low may lead to toxicity due to excess exposure and uptake of transfection reagent-siRNA complexes. Cell densities that are too high may lead to low transfection efficiencies and little or no silencing. Incubate the cells overnight. Standard incubation conditions for mammalian cells are 37° C. in 5% $CO_2$. Other cell types, such as insect cells, require different temperatures and $CO_2$ concentrations that are readily ascertainable by persons skilled in the art. Use conditions appropriate for the cell type of interest.
c. siRNA re-suspension. Add 20 µl siRNA universal buffer to each siRNA to generate a final concentration of 50 µM.
d. SiRNA-lipid complex formation. Use RNase-free solutions and tubes. Using the following table, Table XI:
e.

TABLE XI

|  | 96-well | 24-well |
|---|---|---|
| Mixture 1 (TransIT-TKO-Plasmid dilution mixture) | | |
| Opti-MEM | 9.3 µl | 46.5 µl |
| TransIT-TKO (1 µg/µl) | 0.5 µl | 2.5 µl |
| Mixture 1 Final Volume | 10.0 µl | 50.0 µl |

TABLE XI-continued

|  | 96-well | 24-well |
|---|---|---|
| Mixture 2 (siRNA dilution mixture) | | |
| Opti-MEM | 9.0 µl | 45.0 µl |
| siRNA (1 µM) | 1.0 µl | 5.0 µl |
| Mixture 2 Final Volume | 10.0 µl | 50.0 µl |
| Mixture 3 (siRNA-Transfection reagent mixture) | | |
| Mixture 1 | 10 µl | 50 µl |
| Mixture 2 | 10 µl | 50 µl |
| Mixture 3 Final Volume | 20 µl | 100 µl |
| Incubate 20 minutes at room temperature. | | |
| Mixture 4 (Media-siRNA/Transfection reagent mixture) | | |
| Mixture 3 | 20 µl | 100 µl |
| Complete media | 80 µl | 400 µl |
| Mixture 4 Final Volume | 100 µl | 500 µl |
| Incubate 48 hours at 37° C. | | |

Transfection. Create a Mixture 1 by combining the specified amounts of OPTI-MEM serum free media and transfection reagent in a sterile polystyrene tube. Create a Mixture 2 by combining specified amounts of each siRNA with OPTI-MEM media in sterile 1 ml tubes. Create a Mixture 3 by combining specified amounts of Mixture 1 and Mixture 2. Mix gently (do not vortex) and incubate at room temperature for 20 minutes. Create a Mixture 4 by combining specified amounts of Mixture 3 to complete media. Add appropriate volume to each cell culture well. Incubate cells with transfection reagent mixture for 24-72 hours at 37° C. This incubation time is flexible. The ratio of silencing will remain consistent at any point in the time period. Assay for gene silencing using an appropriate detection method such as RT-PCR, Western blot analysis, immunohistochemistry, phenotypic analysis, mass spectrometry, fluorescence, radioactive decay, or any other method that is now known or that comes to be known to persons skilled in the art and that from reading this disclosure would useful with the present invention. The optimal window for observing a knockdown phenotype is related to the mRNA turnover of the gene of interest, although 24-72 hours is standard. Final Volume reflects amount needed in each well for the desired cell culture format. When adjusting volumes for a Stock Mix, an additional 10% should be used to accommodate variability in pipetting, etc. Duplicate or triplicate assays should be carried out when possible.

While the invention has been described in connection with specific embodiments thereof, it will be understood that it is capable of further modifications and this application is intended to cover any variations, uses, or adaptations of the invention following, in general, the principles of the invention and including such departure from the present disclosure as come within known or customary practice within the art to which the invention pertains and as may be applied to the essential features hereinbefore set forth and as follows in the scope of the appended claims.

What is claimed is:

1. A method for obtaining an siRNA sequence, said method comprising:

(a) accessing a computer and causing said computer to apply a computer program product being embodied in a computer readable storage medium, wherein said computer program product comprises instructions for applying a formula to a set of at least two candidate siRNA sequences that are each between 19 and 30 bases in length and that each comprise a sense strand sequence of 19-30 bases, wherein said sense strand sequence of each siRNA sequence within said set of candidate siRNA sequences is at least 79% similar to a region of a target gene;

(b) determining a predicted relative functionality of at least two siRNA sequences within said set of candidate siRNA sequences, wherein said predicted relative functionality is measured by said computer applying said computer program product to said at least two siRNA sequences and said computer program product further comprises instructions for ascribing a value to each of said at least two siRNA sequences, and said value is generated by a formula, wherein said formula comprises:

$(-8)*A_1+(-1)*A_2+(12)*A_3+(7)*A_4+(18)*A_5+$
$(12)*A_6+(19)*A_7+(6)*A_8+(-4)*A_9+(-5)*A_{10}+$
$(-2)*A_{11}+(-5)*A_{12}+(17)*A_{13}+(-3)*A_{14}+$
$(4)*A_{15}+(2)*A_{16}+(8)*A_{17}+(11)*A_{18}+(30)*A_{19}+$
$(-13)*U_1+(-10)*U_2+(2)*U_3+(-2)*U_4+(-5)*U_5+$
$(5)*U_6+(-2)*U_7+(-10)*U_8+(-5)*U_9+(15)*U_{10}+$
$(-1)*U_{11}+(0)*U_{12}+(10)*U_{13}+(-9)*U_{14}+$
$(-13)*U_{15}+(-10)*U_{16}+(3)*U_{17}+(9)*U_{18}+$
$(9)*U_{19}+(7)*C_1+(3)*C_2+(-21)*C_3+(5)*C_4+$
$(-9)*C_5+(-20)*C_6+(-18)*C_7+(-5)*C_8+(5)*C_9+$
$(1)*C_{10}+(2)*C_{11}+(-5)*C_{12}+(-3)*C_{13}+$
$(-6)*C_{14}+(-2)*C_{15}+(-5)*C_{16}+(-3)*C_{17}+$
$(-12)*C_{18}+(-18)*C_{19}+(14)*G_1+(8)*G_2+$
$(7)*G_3+(-10)*G_4+(-4)*G_5+(2)*G_6+(1)*G_7+$
$(9)*G_8+(5)*G_9+(-11)*G_{10}+(1)*G_{11}+(9)*G_{12}+(-24)*G_{13}+(18)*G_{14}+(11)*G_{15}+(13)*G_{16}+$
$(-7)*G_{17}+(-9)*G_{18}\pm(-22)*G_{19}+6*($number of A+U in position 15-19$)-3*($number of G+C in whole siRNA$)$, and $A_1=1$ if A is the base at position 1 of the sense strand, otherwise its value is 0;
$A_2=1$ if A is the base at position 2 of the sense strand, otherwise its value is 0;
$A_3=1$ if A is the base at position 3 of the sense strand, otherwise its value is 0;
$A_4=1$ if A is the base at position 4 of the sense strand, otherwise its value is 0;
$A_5=1$ if A is the base at position 5 of the sense strand, otherwise its value is 0;
$A_6=1$ if A is the base at position 6 of the sense strand, otherwise its value is 0;
$A_7=1$ if A is the base at position 7 of the sense strand, otherwise its value is 0;
$A_8=1$ if A is the base at position 8 of the sense strand, otherwise its value is 0;
$A_9=1$ if A is the base at position 9 of the sense strand, otherwise its value is 0;
$A_{10}=1$ if A is the base at position 10 of the sense strand, otherwise its value is 0;
$A_{11}=1$ if A is the base at position 11 of the sense strand, otherwise its value is 0;
$A_{12}=1$ if A is the base at position 12 of the sense strand, otherwise its value is 0;
$A_{13}=1$ if A is the base at position 13 of the sense strand, otherwise its value is 0;
$A_{14}=1$ if A is the base at position 14 of the sense strand, otherwise its value is 0;
$A_{15}=1$ if A is the base at position 15 of the sense strand, otherwise its value is 0;
$A_{16}=1$ if A is the base at position 16 of the sense strand, otherwise its value is 0;
$A_{17}=1$ if A is the base at position 17 of the sense strand, otherwise its value is 0;
$A_{18}=1$ if A is the base at position 18 of the sense strand, otherwise its value is 0;
$A_{19}=1$ if A is the base at position 19 of the sense strand, otherwise its value is 0;
$C_1=1$ if C is the base at position 1 of the sense strand, otherwise its value is 0;

$C_2=1$ if C is the base at position 2 of the sense strand, otherwise its value is 0;
$C_3=1$ if C is the base at position 3 of the sense strand, otherwise its value is 0;
$C_4=1$ if C is the base at position 4 of the sense strand, otherwise its value is 0;
$C_5=1$ if C is the base at position 5 of the sense strand, otherwise its value is 0;
$C_6=1$ if C is the base at position 6 of the sense strand, otherwise its value is 0;
$C_7=1$ if C is the base at position 7 of the sense strand, otherwise its value is 0;
$C_8=1$ if C is the base at position 8 of the sense strand, otherwise its value is 0;
$C_9=1$ if C is the base at position 9 of the sense strand, otherwise its value is 0;
$C_{10}=1$ if C is the base at position 10 of the sense strand, otherwise its value is 0;
$C_{11}=1$ if C is the base at position 11 of the sense strand, otherwise its value is 0;
$C_{12}=1$ if C is the base at position 12 of the sense strand, otherwise its value is 0;
$C_{13}=1$ if C is the base at position 13 of the sense strand, otherwise its value is 0;
$C_{14}=1$ if C is the base at position 14 of the sense strand, otherwise its value is 0;
$C_{15}=1$ if C is the base at position 15 of the sense strand, otherwise its value is 0;
$C_{16}=1$ if C is the base at position 16 of the sense strand, otherwise its value is 0;
$C_{17}=1$ if C is the base at position 17 of the sense strand, otherwise its value is 0;
$C_{18}=1$ if C is the base at position 18 of the sense strand, otherwise its value is 0;
$C_{19}=1$ if C is the base at position 19 of the sense strand, otherwise its value is 0;
$G_1=1$ if G is the base at position 1 on the sense strand, otherwise its value is 0;
$G_2=1$ if G is the base at position 2 of the sense strand, otherwise its value is 0;
$G_3=1$ if G is the base at position 3 of the sense strand, otherwise its value is 0;
$G_4=1$ if G is the base at position 4 of the sense strand, otherwise its value is 0;
$G_5=1$ if G is the base at position 5 of the sense strand, otherwise its value is 0;
$G_6=1$ if G is the base at position 6 of the sense strand, otherwise its value is 0;
$G_7=1$ if G is the base at position 7 of the sense strand, otherwise its value is 0;
$G_8=1$ if G is the base at position 8 on the sense strand, otherwise its value is 0;
$G_9=1$ if G is the base at position 9 of the sense strand, otherwise its value is 0;
$G_{10}=1$ if G is the base at position 10 on the sense strand, otherwise its value is 0;
$G_{11}=1$ if G is the base at position 11 of the sense strand, otherwise its value is 0;
$G_{12}=1$ if G is the base at position 12 of the sense strand, otherwise its value is 0;
$G_{13}=1$ if G is the base at position 13 on the sense strand, otherwise its value is 0;
$G_{14}=1$ if G is the base at position 14 of the sense strand, otherwise its value is 0;
$G_{15}=1$ if G is the base at position 15 of the sense strand, otherwise its value is 0;
$G_{16}=1$ if G is the base at position 16 of the sense strand, otherwise its value is 0;
$G_{17}=1$ if G is the base at position 17 of the sense strand, otherwise its value is 0;
$G_{18}=1$ if G is the base at position 18 of the sense strand, otherwise its value is 0;
$G_{19}=1$ if G is the base at position 19 of the sense strand, otherwise its value is 0;
$U_1=1$ if U is the base at position 1 on the sense strand, otherwise its value is 0;
$U_2=1$ if U is the base at position 2 on the sense strand, otherwise its value is 0;
$U_3=1$ if U is the base at position 3 on the sense strand, otherwise its value is 0;
$U_4=1$ if U is the base at position 4 on the sense strand, otherwise its value is 0;
$U_5=1$ if U is the base at position 5 of the sense strand, otherwise its value is 0;
$U_6=1$ if U is the base at position 6 of the sense strand, otherwise its value is 0;
$U_7=1$ if U is the base at position 7 on the sense strand, otherwise its value is 0;
$U_8=1$ if U is the base at position 8 of the sense strand, otherwise its value is 0;
$U_9=1$ if U is the base at position 9 on the sense strand, otherwise its value is 0;
$U_{10}=1$ if U is the base at position 10 on the sense strand, otherwise its value is 0;
$U_{11}=1$ if U is the base at position 11 of the sense strand, otherwise its value is 0;
$U_{12}=1$ if U is the base at position 12 of the sense strand, otherwise its value is 0;
$U_{13}=1$ if U is the base at position 13 of the sense strand, otherwise its value is 0;
$U_{14}=1$ if U is the base at position 14 of the sense strand, otherwise its value is 0;
$U_{15}=1$ if U is the base at position 15 on the sense strand, otherwise its value is 0;
$U_{16}=1$ if U is the base at position 16 on the sense strand, otherwise its value is 0;
$U_{17}=1$ if U is the base at position 17 on the sense strand, otherwise its value is 0;
$U_{18}=1$ if U is the base at position 18 on the sense strand, otherwise its value is 0;
$U_{19}=1$ if U is the base at position 19 of the sense strand, otherwise its value is 0;
wherein
  (i) when there are nineteen bases present in said sense strand, positions 1-19 are defined relative to the 5' end of the sense strand, and
  (ii) when there are twenty to thirty bases present in said sense strand, positions 1-19 are the 3' most positions within the sense strand, wherein position 1 is the 5' most position within said positions 1-19 and position 19 is the 3' most position within said positions 1-19;
(c) selecting from said set of at least two candidate siRNA sequences, an siRNA sequence for gene silencing based on said predicted relative functionality, wherein a higher value generated by said formula is indicative of greater predicted functionality and said siRNA for gene silencing that is selected has the highest value from within said set of at least two siRNA sequences; and
(d) generating an output comprising said siRNA sequence for gene silencing that is selected, wherein said output is generated by said computer and is in a form that is readable by a user, thereby obtaining said siRNA sequence for gene silencing.

2. The method according to claim 1, further comprising selecting either for or against sequences that contain motifs that induce cellular stress.

3. The method according to claim 1, further comprising selecting either for or against sequences that have low or high internal thermodynamic stability.

4. A method of gene silencing, comprising obtaining an siRNA sequence for gene silencing according to the method of claim 1, synthesizing an siRNA molecule for gene silencing comprising said siRNA sequence for gene silencing and introducing into a cell said siRNA molecule for gene silencing.

5. The method according to claim 4, wherein said introducing is by allowing passive uptake of the siRNA molecule for gene silencing.

6. The method according to claim 4, wherein said siRNA molecule for gene silencing is unimolecular.

7. The method according to claim 4, wherein said siRNA molecule for gene silencing is comprised of two separate polynucleotide strands.

8. The method according to claim 4, wherein said siRNA molecule for gene silencing is expressed from one or more vectors.

9. The method according to claim 4, wherein two or more genes are silenced by a single administration of said siRNA molecule for gene silencing.

10. A method for obtaining an siRNA sequence for a target gene, wherein said siRNA sequence comprises 19-30 nucleotide bases, said method comprising the steps:
  (a) selecting a target gene;
  (b) generating a set of candidate siRNA sequences that are between 19 and 30 bases in length, wherein each of said candidate siRNA sequences comprises a sense region of 19-30 bases, wherein said sense region comprises a sense sequence of 19 bases that is at least 79% similar to a region of the target gene;
  (c) accessing a computer and causing said computer to apply a computer program product being embodied in a computer readable storage medium, wherein said computer program product comprises instructions for applying to said set of candidate siRNA sequences a set of one or more criteria selected from the group consisting of
    (i) a base other than an A at position 2 of the sense sequence,
    (ii) an A base at position 4 of the sense sequence,
    (iii) an A base at position 6 of the sense sequence,
    (iv) an A base at position 7 of the sense sequence,
    (v) an A base at position 8 of the sense sequence,
    (vi) a base other than an A at position 9 of the sense sequence,
    (vii) a base other than an A at position 12 of the sense sequence,
    (viii) a base other than a U at position 2 of the sense sequence,
    (ix) a U base at position 3 of the sense sequence,
    (x) a base other than a U at position 4 of the sense sequence,
    (xi) a U base at position 6 of the sense sequence,
    (xii) a base other than a U at position 7 of the sense sequence,
    (xiii) a base other than a U at position 8 of the sense sequence,
    (xiv) a base other than a U at position 9 of the sense sequence,
    (xv) a C base at position 2 of the sense sequence,
    (xvi) a C base at position 4 of the sense sequence,
    (xvii) a base other than a C at position 6 of the sense sequence,
    (xviii) a base other than a C at position 7 of the sense sequence,
    (xix) a base other than a C at position 8 of the sense sequence,
    (xx) a C base at position 9 of the sense sequence,
    (xxi) a C base at position 10 of the sense sequence,
    (xxii) a base other than a C at position 12 of the sense sequence,
    (xxiii) a G base at position 2 of the sense sequence,
    (xxiv) a G base at position 3 of the sense sequence,
    (xxv) a base other than a G at position 4 of the sense sequence,
    (xxvi) a G base at position 6 of the sense sequence,
    (xxvii) a G base at position 7 of the sense sequence,
    (xxviii) a G base at position 8 of the sense sequence,
    (xxix) a G base at position 9 of the sense sequence,
    (xxx) a G base at position 11 of the sense sequence,
    (xxxi) a G base at position 12 of the sense sequence,
    (xxxii) a G base at position 14 of the sense sequence,
    (xxxiii) a G base at position 15 of the sense sequence, and
    (xxxiv) a G base at position 16 of the sense sequence;
  (d) selecting an siRNA sequence from the set of candidate siRNA sequences of step (b) as a selected siRNA sequence for the target gene, wherein said selected siRNA for the target gene satisfies said one or more criteria, wherein said sense sequence occupies positions 1-19 of the sense region, and wherein when said candidate siRNA sequence is 20-30 bases, bases that are within the sense region that are not within said sense sequence occupy positions −1 to −11 of the sense region and positions −1 to −11 of the sense region are immediately 5' of the 5' end of the sense sequence; and
  (e) generating an output comprising said selected siRNA sequence for the target gene, wherein said generating is performed by said computer and said output is in a form that is readable by a user, thereby obtaining said siRNA sequence for the target gene.

11. The method according to claim 10, wherein in step (c) at least two of said criteria are applied and in step (d) said selected siRNA sequence for the target gene satisfies the at least two of said criteria.

12. The method according to claim 10, wherein in step (c) at least three of said criteria are applied and in step (d) said selected siRNA sequence for the target gene satisfies the at least three of said criteria.

13. The method according to claim 10, wherein in step (c) at least four of said criteria are applied and in step (d) said selected siRNA sequence for the target gene satisfies the at least four of said criteria.

14. The method according to claim 10, wherein in step (c) at least five of said criteria are applied and in step (d) said selected siRNA sequence for the target gene satisfies the at least five of said criteria.

15. The method according to claim 10 further comprising applying at least one additional criteria selected from the group consisting of the presence of A at position 19 of the sense sequence, the presence of A at position 3 of the sense sequence, the presence of U at position 10 of the sense sequence, the presence of A at position 14 of the sense sequence, the absence of C at position 19 of the sense sequence, the absence of G at position 13 of the sense sequence, the absence of U at position 5 of the sense sequence, the absence of A at position 1 of the sense sequence, the presence of A at position 5 of the sense sequence, the absence of A at position 10 of the sense sequence, the absence of A at position 11 of the sense sequence, the presence of A at position 13 of the sense sequence, the absence of A at position 14 of the sense sequence, the presence of A at position 15 of the sense sequence, the presence of A at position 16 of the sense sequence, the presence of A at position 17 of the sense sequence, the presence of A at position 18 of the sense sequence, the absence of U at position 1 of the sense sequence, the absence of U at position 5 of the sense sequence, the absence of U at position 11 of the sense sequence, the presence of U at position 13 of the sense sequence, the absence of U at position 14 of the sense sequence, the absence of U at position 15 of the sense sequence, the absence of U at position 16 of the sense sequence, the presence of U at position 17 of the sense sequence, the presence of U at position 18 of the sense sequence, the presence of U at position 19 of the sense sequence, the presence of C at position 1 of the sense sequence, the absence of C at position 3 of the sense sequence, the absence of C at position 5 of the sense sequence, the presence of C at position 11 of the sense sequence, the absence of C at position 13 of the sense sequence, the absence of C at position 14 of the sense sequence, the absence of C at position 15 of the sense sequence, the absence of C at position 16 of the sense sequence, the absence of C at position 17 of the sense sequence, the absence of C at position 18 of the sense sequence, the presence of G at position 1 of the sense sequence, the absence of G at position 5 of the sense sequence, the absence of G at position 10 of the sense sequence, the absence of G at position 17 of the sense sequence, the absence of G at position 18 of the sense sequence and the absence of G at position 19 of the sense sequence and wherein in step (d) said selected siRNA sequence for gene silencing satisfies the at least one additional criteria.

16. The method according to claim 15, wherein said at least one additional criteria comprises the presence of A at position 5 of the sense sequence.

17. The method according to claim 10, wherein the set of one or more criteria includes an A base at position 7 of the sense sequence.

18. The method according to claim 17, wherein said at least one additional criteria comprises the absence of C at position 3 of the sense sequence.

19. The method according to claim 10, wherein the set of one or more criteria includes a base other than C at position 6 of the sense sequence.

20. The method according to claim 10, wherein the set of one or more criteria includes a base other than C at position 7 of the sense sequence.

21. The method according to claim 10, wherein the set of one or more criteria includes the presence of G at position 14 of the sense sequence.

22. The method according to claim 1, wherein said output is displayed by a computer.

23. The method according to claim 4, wherein said output is displayed by a computer.

24. The method of claim 17, wherein said applying at least one additional criteria comprises applying at least two of said additional criteria.

25. The method of claim 17, wherein said applying at least one additional criteria comprises applying at least five of said additional criteria.

26. The method of claim 17, wherein said applying at least one additional criteria comprises applying at least ten of said additional criteria.

27. The method of claim 17, wherein said applying at least one additional criteria comprises applying at least fifteen of said additional criteria.

28. A method of gene silencing, comprising obtaining an siRNA sequence for gene silencing according to the method of claim 10, synthesizing an siRNA molecule for gene silencing comprising said siRNA sequence for gene silencing and introducing into a cell said siRNA molecule for gene silencing.

29. A method of gene silencing, comprising obtaining an siRNA sequence for gene silencing according to the method of claim 17, synthesizing an siRNA molecule for gene silencing comprising said siRNA sequence for gene silencing and introducing into a cell said siRNA molecule for gene silencing.

30. The method according to claim 10, wherein the sense region is 19 bases in length.

31. The method according to claim 10, wherein each sense region within said set of candidate siRNAs is 100% similar to said region of said target gene.

* * * * *